(12) United States Patent
Wang et al.

(10) Patent No.: US 9,249,152 B2
(45) Date of Patent: Feb. 2, 2016

(54) CYANO CONTAINING AZABENZOFURAN COMPOUNDS FOR THE TREATMENT OF HEPATITIS C

(71) Applicant: BRISTOL-MYERS SQUIBB COMPANY, Princeton, NJ (US)

(72) Inventors: Tao Wang, Farmington, CT (US); Kyle J. Eastman, Killingsworth, CT (US); Zhongxing Zhang, Madison, CT (US); Kyle E. Parcella, Wallingford, CT (US); Zhiwei Yin, Glastonbury, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/663,497

(22) Filed: Mar. 20, 2015

(65) Prior Publication Data
US 2015/0266886 A1  Sep. 24, 2015

Related U.S. Application Data

(60) Provisional application No. 61/968,763, filed on Mar. 21, 2014.

(51) Int. Cl.
*C07D 491/048* (2006.01)
*C07D 491/04* (2006.01)

(52) U.S. Cl.
CPC .......... *C07D 491/048* (2013.01); *C07D 491/04* (2013.01)

(58) Field of Classification Search
CPC .................................................. C07D 491/048
See application file for complete search history.

(56) References Cited

U.S. PATENT DOCUMENTS

| 7,265,152 | B2 | 9/2007 | Saha et al. | |
| 7,994,171 | B2 * | 8/2011 | Yeung et al. | 514/252.01 |
| 8,198,449 | B2 * | 6/2012 | Pracitto et al. | 546/121 |

FOREIGN PATENT DOCUMENTS

| WO | WO 2009/101022 | 8/2009 |
| WO | WO 2011/112186 | 9/2011 |
| WO | WO 2012/058125 | 5/2012 |

OTHER PUBLICATIONS

Nakamura "Imidazole derivatives as new potent and selective 20-HETE synthase inhibitors." Bioorganic & Medicinal Chemistry Letters 2004, 14, 333-336.*
Li "N-(Arylacetyl)-biphenylalanines as Potent VLA-4 Antagonists" Bioorganic & Medicinal Chemistry Letters 2002, 12, 2141-2144.*
Wermuth, Camille G. "Molecular Variation Based on Isosteric Replacements" in Chapter 13, The Practice of Medicinal Chemistry, Academic: 1996.*
George A. Patani "Bioisosterism: A Rational Approach in Drug Design" Chemical Reviews 1996, 96, 3147-3176.*
Bressanelli S. et al., "Structural Analysis of the Hepatitis C Virus RNA Polymerase in Complex with Ribonucleotides," Journal of Virology, pp. 3482-3492, Apr. 2002.
De Francesco R. et al., "New therapies on the horizon for hepatitis C: are we close?" Clinics in Liver Disease, pp. 211-242, 2003.
Lauer G.M. et al., "Hepatitis C Virus Infection," New England Journal of Medicine, vol. 345, No. 1, pp. 41-52, Jul. 5, 2001.
Poynard T. et al., "Randomised trial of interferon α2b plus ribavirin for 48 weeks or for 24 weeks versus interferon α2b plus placebo for 48 weeks for treatment of chronic infection with hepatitis C virus," The Lancet, vol. 352, pp. 1426-1432, Oct. 31, 1998.
Zeuzem S. et al., "Peginterferon alfa-2a in Patients with Chronic Hepatitis C," The New England Journal of Medicine, vol. 343, No. 23, pp. 1666-1672, Dec. 7, 2000.

* cited by examiner

*Primary Examiner* — David K O Dell
(74) *Attorney, Agent, or Firm* — John F. Levis

(57) ABSTRACT

Compounds of Formula I, including their salts, as well as compositions and methods of using the compounds are set forth. The compounds have activity against hepatitis C virus (HCV) and may be useful in treating those infected with HCV:

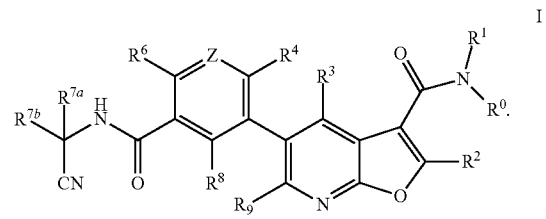

23 Claims, No Drawings

CYANO CONTAINING AZABENZOFURAN COMPOUNDS FOR THE TREATMENT OF HEPATITIS C

CROSS REFERENCE TO RELATED APPLICATION

This application claims the benefit of U.S. Provisional Application Ser. No. 61/968,763 filed Mar. 21, 2014, which is hereby incorporated by reference in its entirety.

FIELD OF THE INVENTION

The invention relates to novel compounds, including their salts, which have activity against hepatitis C virus (HCV) and which are useful in treating those infected with HCV. The invention also relates to compositions and methods of making and using these compounds.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.\

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242).

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, has shown an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed; see for example, WO2009/101022, as well as WO 2012/058125.

What is therefore needed in the art are additional compounds which are novel and effective against hepatitis C. Additionally, these compounds should provide advantages for pharmaceutical uses, for example, with regard to one or more of their mechanism of action, binding, inhibition efficacy, target selectivity, solubility, safety profiles, or bioavailability. Also needed are new formulations and methods of treatment which utilize these compounds.

SUMMARY OF THE INVENTION

One aspect of the invention is a compound of Formula I, including pharmaceutically acceptable salts thereof:

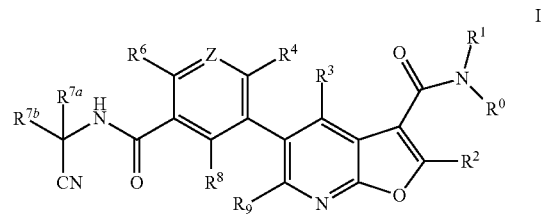

wherein
Z is C—$R^5$ or N;
$R^0$ is hydrogen;
$R^1$ is methyl;
$R^2$ is phenyl that is independently substituted with 0-2 halo or methoxy, or is para substituted with W—Ar;
W is —O— or —NH—;
Ar is phenyl or para-halophenyl;
$R^3$ is hydrogen, fluoro, or chloro;

$R^4$, $R^5$, and $R^6$ are independently selected from the group of hydrogen, halo, alkyl, haloalkyl, alkoxy, and perdeuteroalkoxy;

$R^{7a}$, $R^{7b}$ are each independently selected from the group of hydrogen, alkyl, cycloalkyl, and $Ar^1$, or together $R^{7a}$ and $R^{7b}$ form a 3-7 membered carbocyclic ring;

$R^8$ is hydrogen, $Ar^1$ is phenyl, a 5-membered heteroaromatic ring or a 6-membered heteroaromatic ring;

$R^9$ is selected from the group of hydrogen, halo, $R^{201}$, $OR^{202}$ and $NR^{203}R^{204}$;

$R^{201}$ is alkyl, alkenyl, or $C_1$-$C_4$ alkyl with between one to all of the hydrogens replaced by fluoro;

$R^{202}$ is $C_1$-$C_3$ alkyl, or $C_1$-$C_3$ alkyl with between one to all of the hydrogens replaced by fluoro;

$R^{203}$ is hydrogen; and $R^{204}$ is $C_1$-$C_3$ alkyl, $C_1$-$C_3$ hydroxyalkyl, or is $C_1$-$C_3$ alkyl with between one to all of the hydrogens replaced by fluoro.

The invention also relates to pharmaceutical compositions comprising a compound of Formula I, including pharmaceutically acceptable salts thereof, and a pharmaceutically acceptable carrier, excipient, and/or diluent.

In addition, the invention provides one or more methods of treating hepatitis C infection comprising administering a therapeutically effective amount of a compound of Formula I to a patient.

Also provided as part of the invention are one or more methods for making the compounds of Formula I.

The present invention is directed to these, as well as other important ends, hereinafter described.

DETAILED DESCRIPTION OF THE EMBODIMENTS

The singular forms "a", "an", and "the" include plural reference unless the context clearly dictates otherwise.

Unless otherwise specifically set forth elsewhere in the application, the following terms may be used herein and shall have the following meanings: "Hydrogen" or "H" refers to hydrogen, including its isotopes, such as deuterium which may be represented herein by the letter "D". "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to one or more compounds of Formula I, including pharmaceutically acceptable salts thereof:

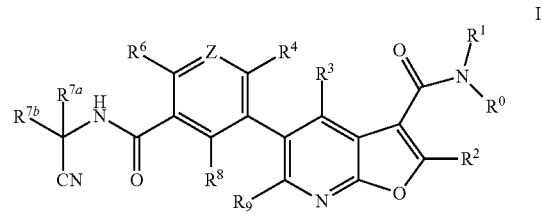

wherein

Z is C—$R^5$ or N;

$R^0$ is hydrogen;

$R^1$ is methyl;

$R^2$ is phenyl that is independently substituted with 0-2 halo or methoxy, or is para substituted with W—Ar;

W is —O— or —NH—;

Ar is phenyl or para-halophenyl;

$R^3$ is hydrogen, fluoro, or chloro;

$R^4$, $R^5$, and $R^6$ are independently selected from the group of hydrogen, halo, alkyl, haloalkyl, alkoxy, and perdeuteroalkoxy;

$R^{7a}$, $R^{7b}$ are each independently selected from the group of hydrogen, alkyl, cycloalkyl, and $Ar^1$, or together $R^{7a}$ and $R^{7b}$ form a 3-7 membered carbocyclic ring;

$R^8$ is hydrogen;

$Ar^1$ is phenyl, a 5-membered heteroaromatic ring or a 6-membered heteroaromatic ring:

$R^9$ is selected from the group of hydrogen, halo, $R^{201}$, $OR^{202}$, and $NR^{203}R^{204}$;

$R^{201}$ is alkyl, alkenyl, or $C_1$-$C_4$ alkyl with between one to all of the hydrogens replaced by fluoro.

$R^{202}$ is $C_1$-$C_3$ alkyl, or $C_1$-$C_3$ alkyl with between one to all of the hydrogens replaced by fluoro;

$R^{203}$ is hydrogen; and $R^{204}$ is $C_1$-$C_3$ alkyl, $C_1$-$C_3$ hydroxyalkyl, or is $C_1$-$C_3$ alkyl with between one to all of the hydrogens replaced by fluoro.

It is preferred in the compound of Formula I above that $R^2$ is para-fluorophenyl.

It is also preferred that $R^3$ is hydrogen.

In addition, it is preferred that $R^4$, $R^5$, and $R^6$ are each independently selected from the group of hydrogen, fluoro, —$OCH_3$, and —$OCD_3$.

It is further preferred that $R^{7a}$ is selected from the group of hydrogen, methyl, fluoromethyl, and cyclopropyl.

It is also preferred that $R^{7b}$ is selected from the group of hydrogen, methyl, fluoromethyl, cyclopropy, and $Ar^1$.

In certain embodiments, it is also preferred that together $R^{7a}$ and $R^{7b}$ form a cyclopropyl or cyclobutyl ring.

It is further preferred that $Ar^1$ is phenyl or pyrimidyl.

It is also preferred that $R^9$ is $R^{201}$ or $NR^{203}R^{204}$.

In addition, it is preferred that $R^{201}$ is —$CH_2CH_2CF_3$ or vinyl.

It is also preferred that $R^{204}$ is —$CH_2CF_3$, —$CH_2CF_2CF_3$ or —$CH_2CH_2OH$.

In a further embodiment of the invention, it is preferred that $R^2$ is para-fluorophenyl, $R^3$ is hydrogen, $R^4$, $R^5$, and $R^6$ are each independently selected from the group of hydrogen, fluoro, —$OCH_3$, and —$OCD_3$, $R^{7a}$ is selected from the group of hydrogen, methyl, fluoromethyl, and cyclopropyl, $R^{7b}$ is selected from the group of hydrogen, methyl, fluoromethyl, cyclopropy, and $Ar^1$, or together $R^{7a}$ and $R^{7b}$ form a cyclopropyl or cyclobutyl ring;

$Ar^1$ is phenyl or pyrimidyl, $R^9$ is $R^{201}$ or $NR^{203}R^{204}$;

$R^{201}$ is —$CH_2CH_2CF_3$ or vinyl; and $R^{204}$ is —$CH_2CF_3$, —$CH_2CF_2CF_3$ or —$CH_2CH_2OH$.

In a further embodiment of the invention, it is preferred that $R^4$ is hydrogen, $R^5$ is hydrogen or fluoro, $R^{7a}$ is selected from the group of hydrogen, methyl, fluoromethyl, and cyclopropyl, or together $R^{7a}$ and $R^{7b}$ form a cyclopropyl or cyclobutyl ring; and $R^{201}$ is —$CH_2CH_2CF_3$.

In certain embodiments of the compound of Formula I above, it is preferred that Z is N.

Also preferred are compounds wherein Z is N, $R^4$ is hydrogen, and $R^6$ is —$OCD_3$.

In certain embodiments of the compound of Formula I above, it is preferred that Z is $CR^5$.

Other preferred compounds include those wherein Z is $CR^5$, $R^4$ is hydrogen, $R^5$ is hydrogen or fluoro, $R^6$ is hydrogen, fluoro, or —$OCH_3$, $R^{7a}$ is selected from hydrogen, methyl, fluoromethyl, or cyclopropyl $R^{7b}$ is selected from hydrogen, methyl, fluoromethyl, or cyclopropyl or together $R^{7a}$ and $R^{7b}$ form a cyclopropyl or cyclobutyl ring; and $R^{201}$ is —$CH_2CH_2CF_3$.

Also preferred are compounds of Formula I wherein $R^5$ is hydrogen, $R^6$ is fluoro, $R^{7a}$ is methyl, $R^{7b}$ is cyclopropyl, and $R^9$ is $R^{201}$.

Other preferred compounds include those wherein the compound exists as a single enantiomer which is: (R)-5-(3-((1-cyano-1-cyclopropylethyl)carbamoyl)-4-fluorophenyl)-2-(4-fluorophenyl)-N-methyl-6-(3,3,3-trifluoropropyl)furo[2,3-b]pyridine-3-carboxamide, or the other single enantiomer which is: (S)-5-(3-((1-cyano-1-cyclopropylethyl)carbamoyl)-4-fluorophenyl)-2-(4-fluorophenyl)-N-methyl-6-(3,3,3-trifluoropropyl)furo[2,3-b]pyridine-3-carboxamide.

Even more preferred is the compound from the two pure enantiomers above wherein the compound exists as the single enantiomer that exhibits a minus rotation when optical rotation is measured via standard methods in a polarimeter.

Preferred compounds of the invention, including pharmaceutically acceptable salts thereof, are selected from the group of:

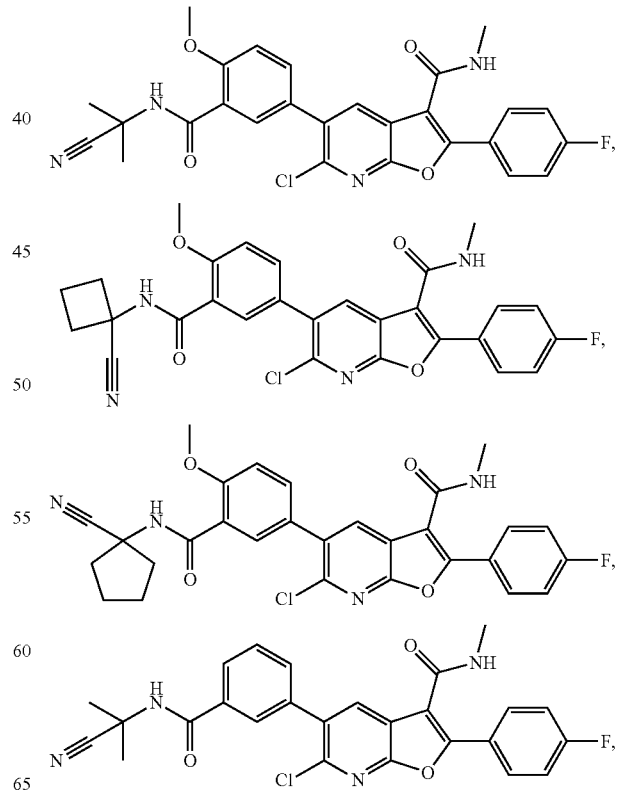

US 9,249,152 B2
7
-continued
8
-continued
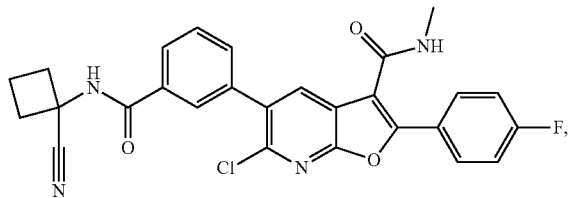
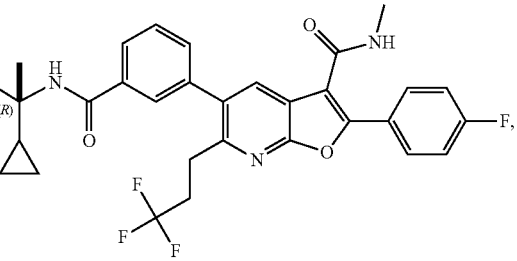

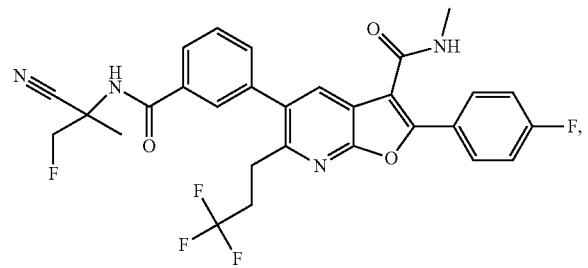
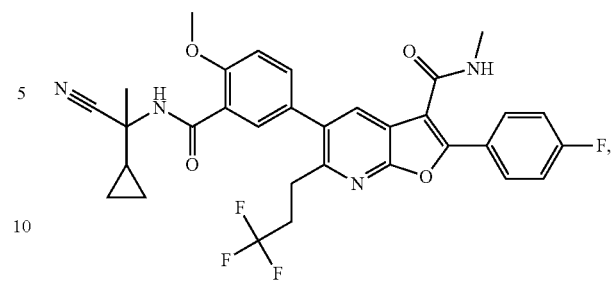
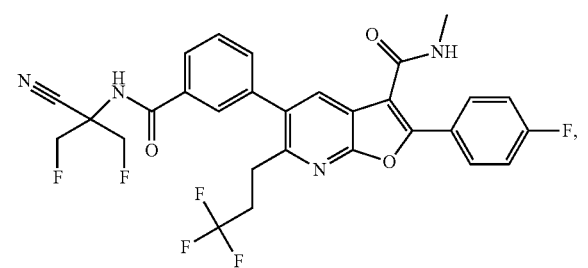
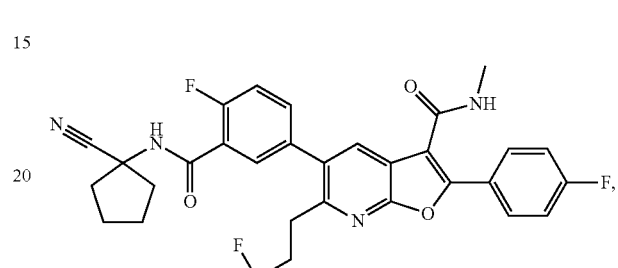
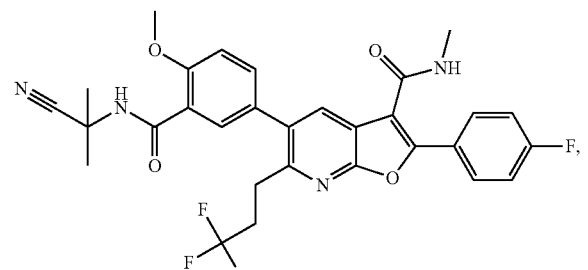
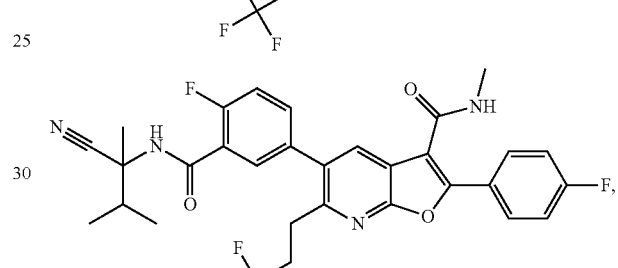
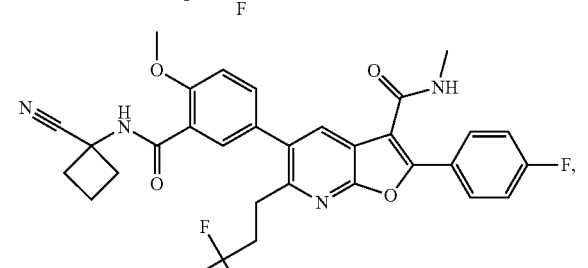
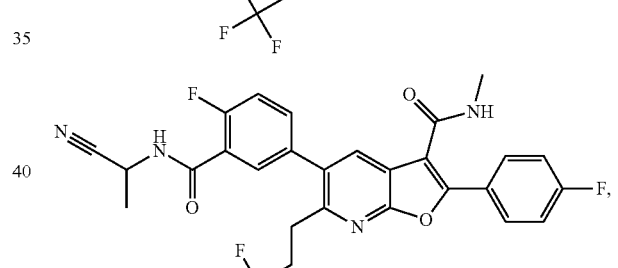
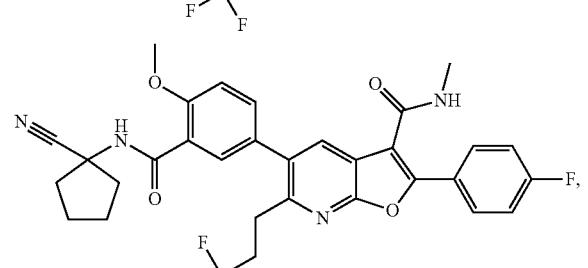
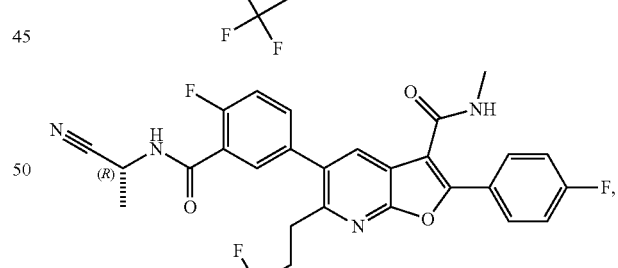
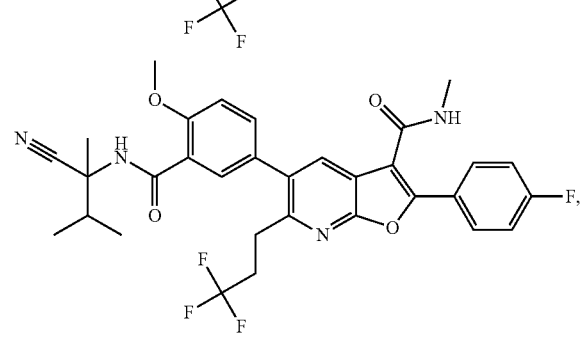
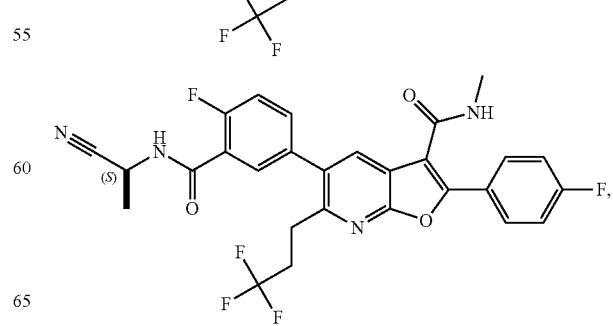

| 11 -continued | 12 -continued |
|---|---|
| 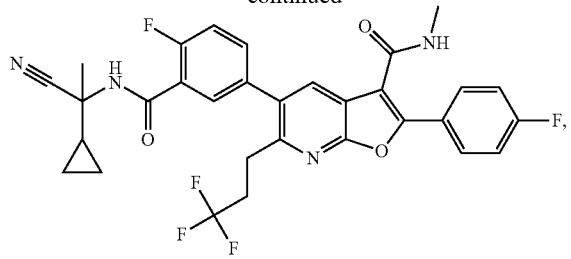 | 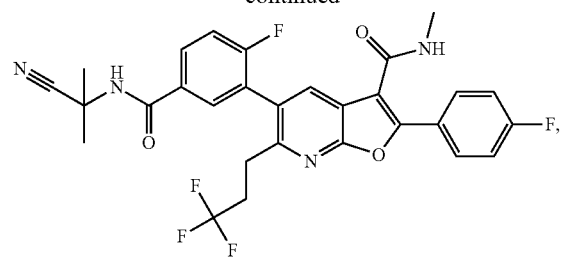 |
| 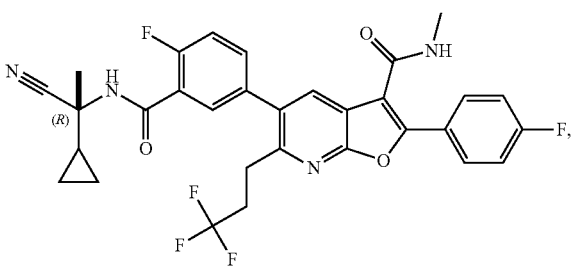 | 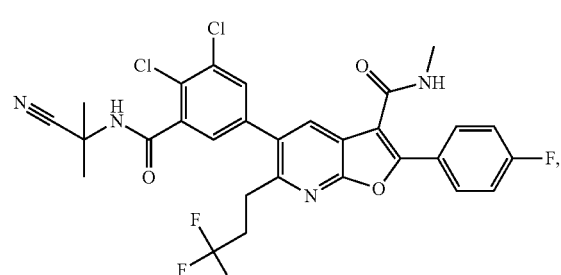 |
| 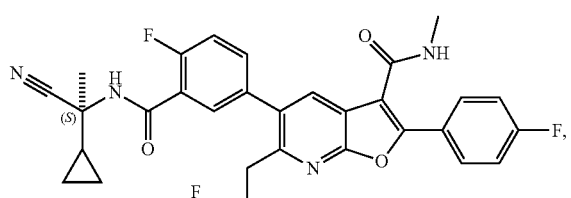 | 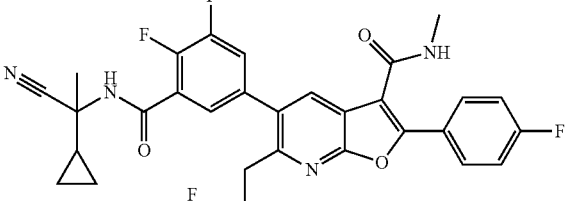 |
| 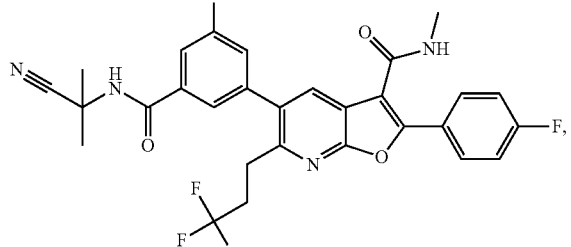 | 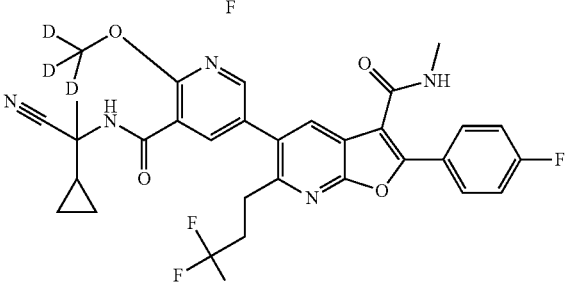 |
| 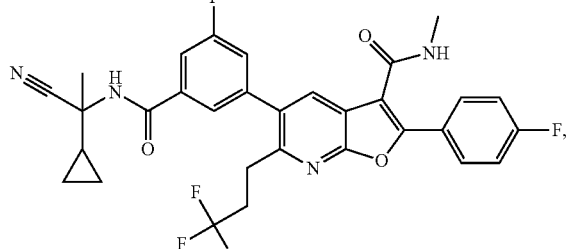 | 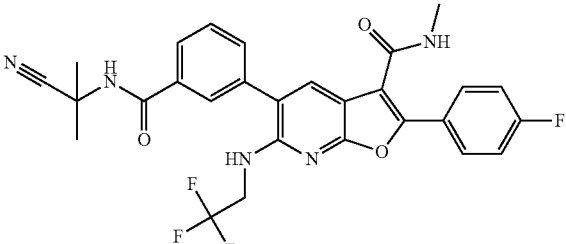 |
| 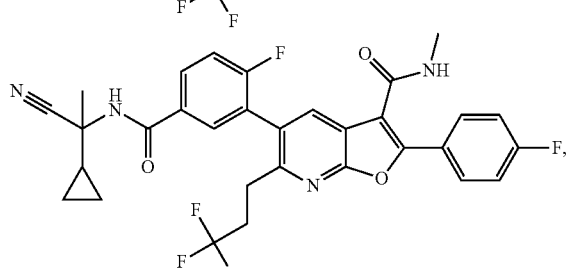 | 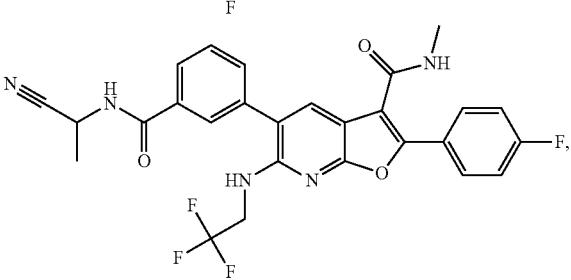 |

-continued
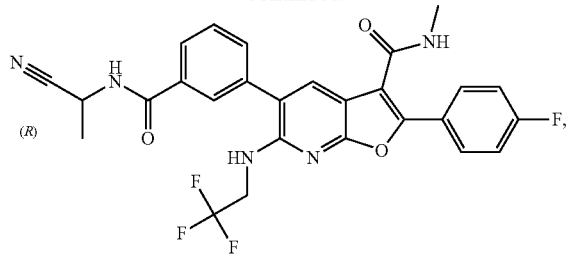
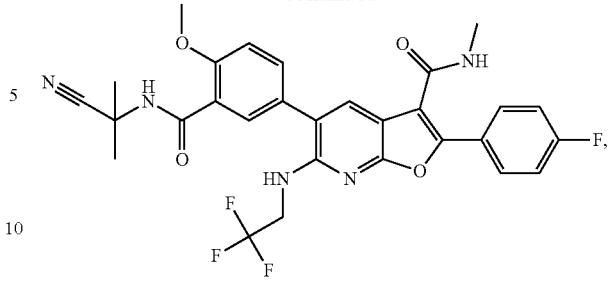
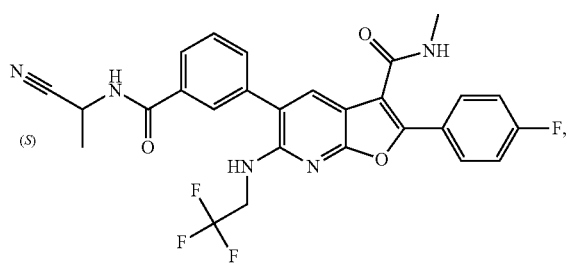
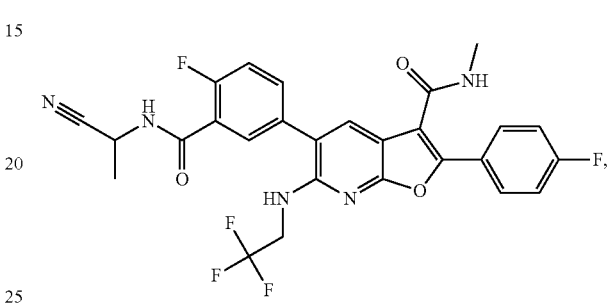
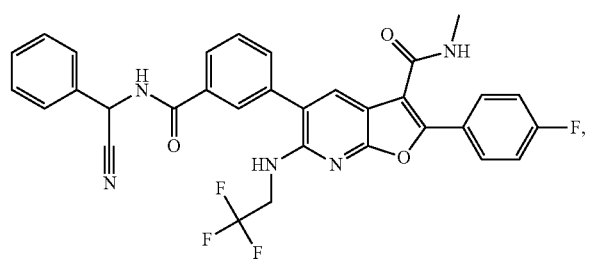
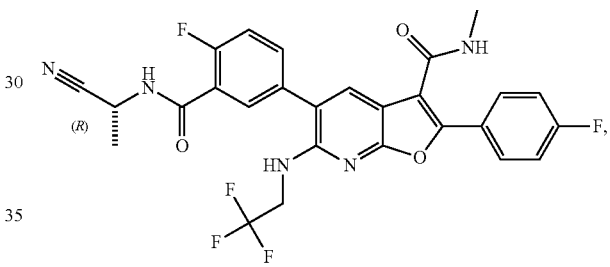
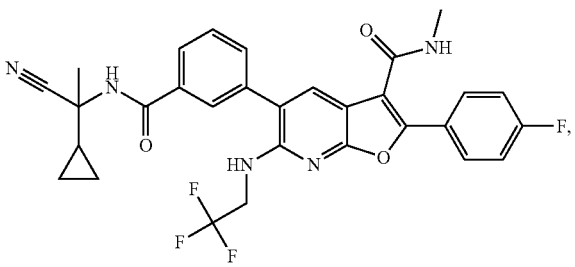
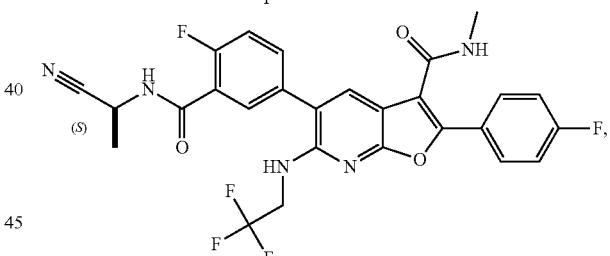
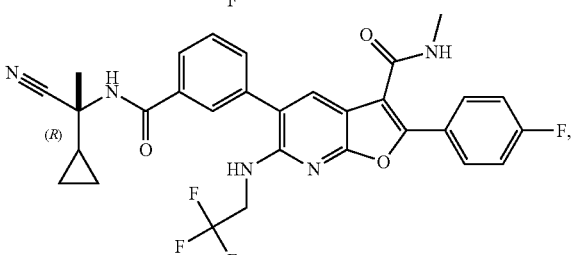
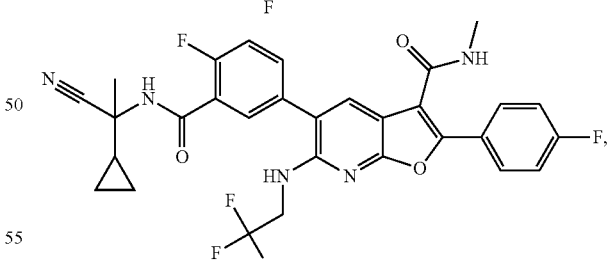
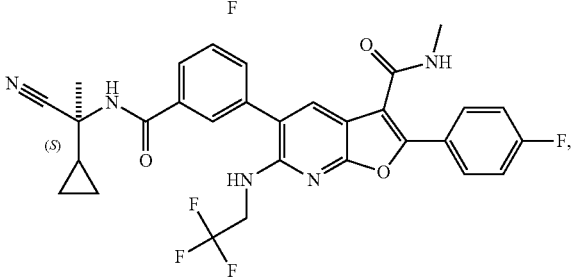
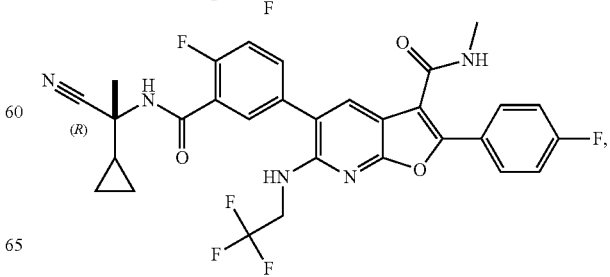

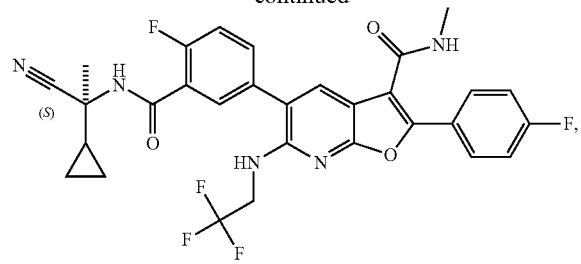
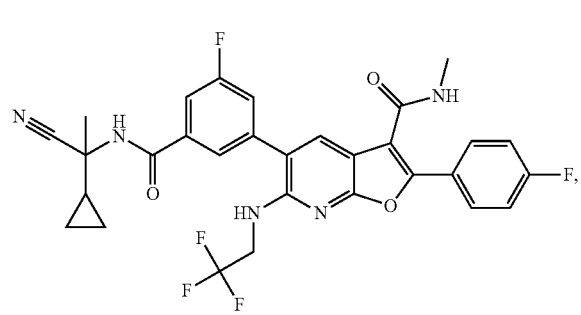
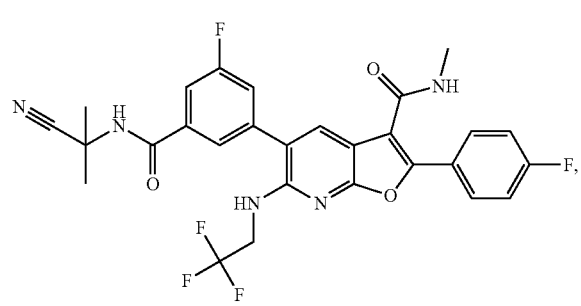
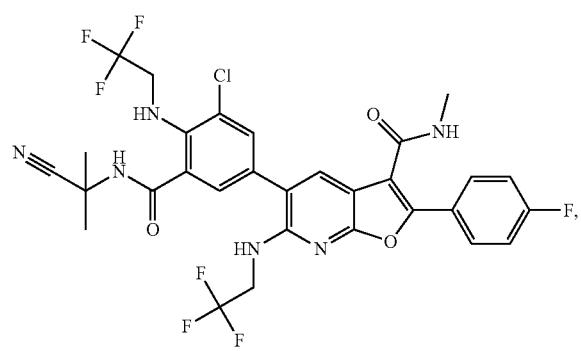
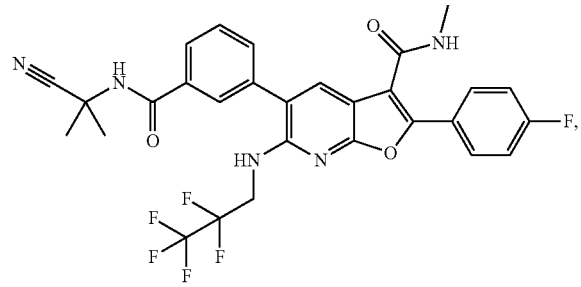
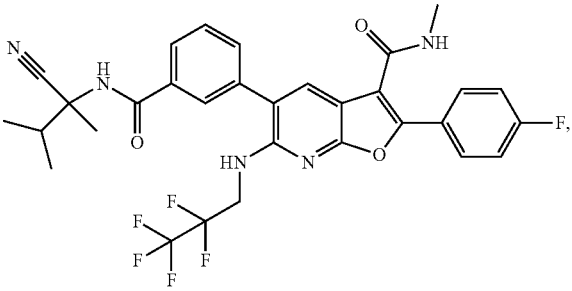
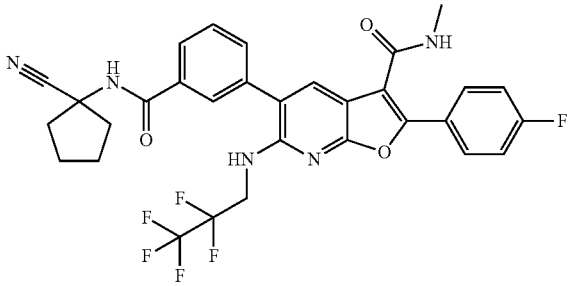
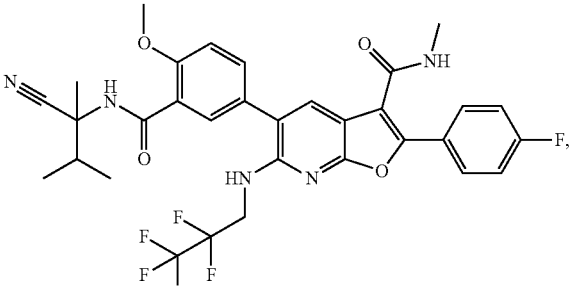
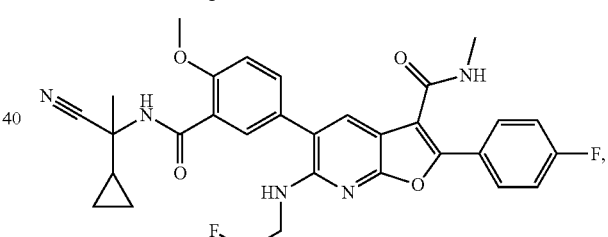
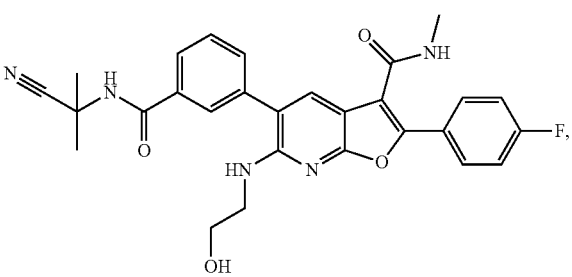
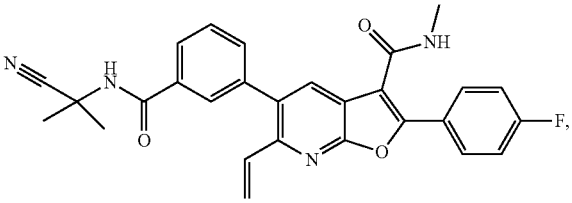

17
-continued
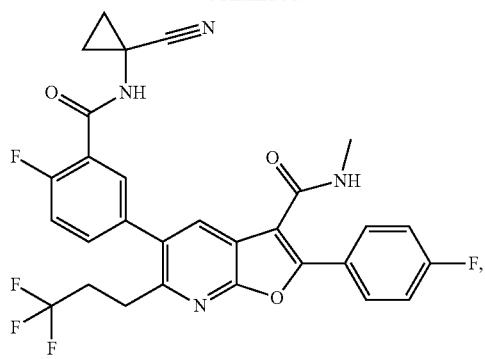
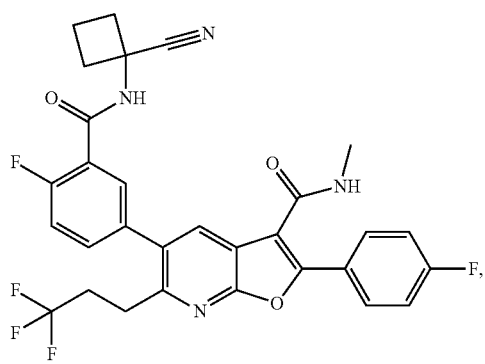
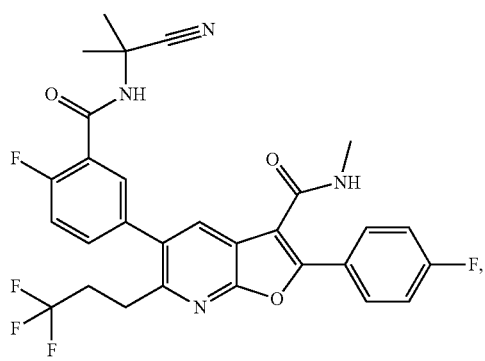
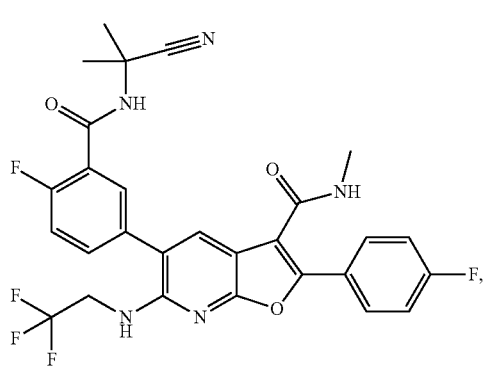
18
-continued
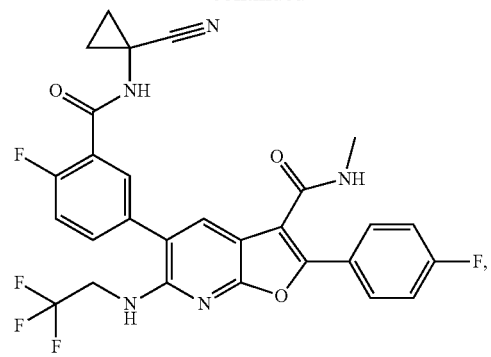
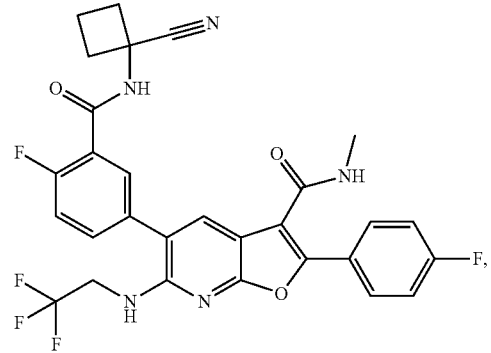
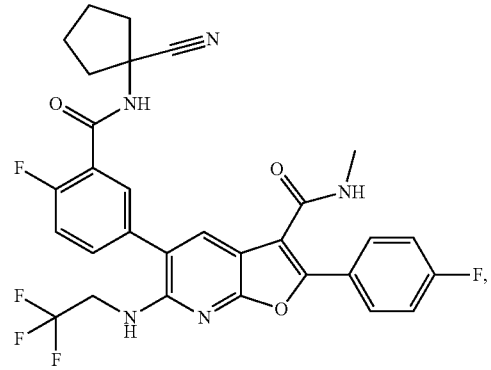
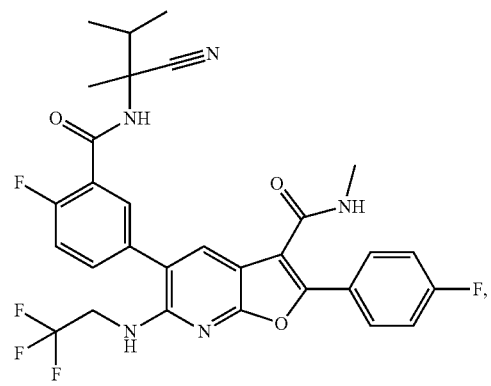

-continued
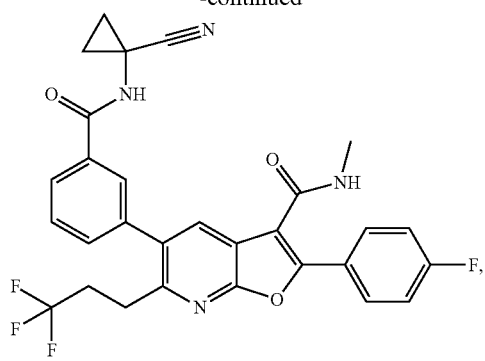
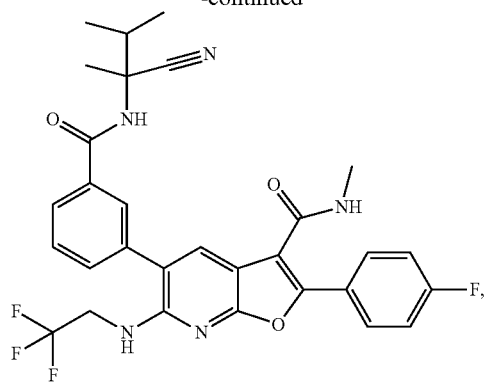
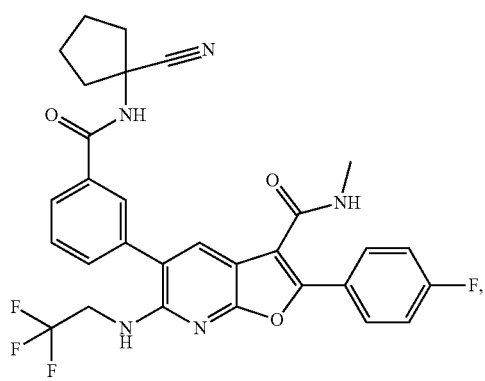
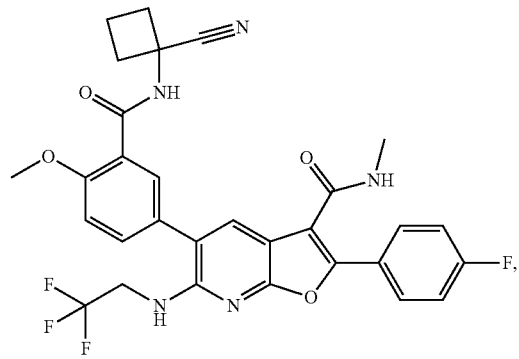
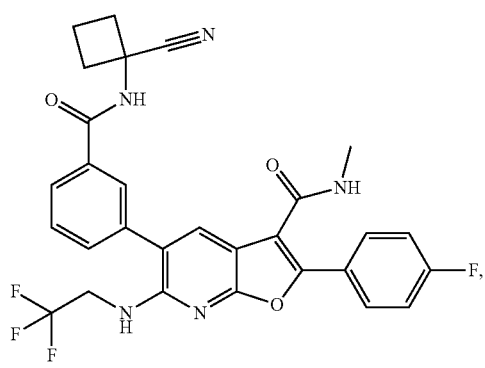
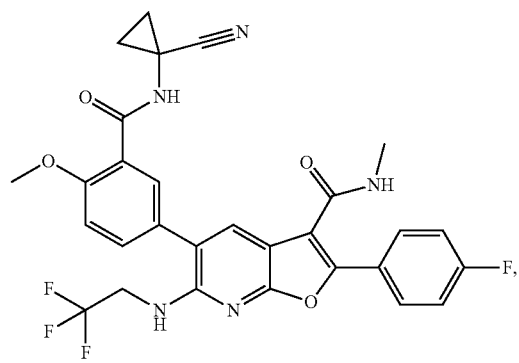
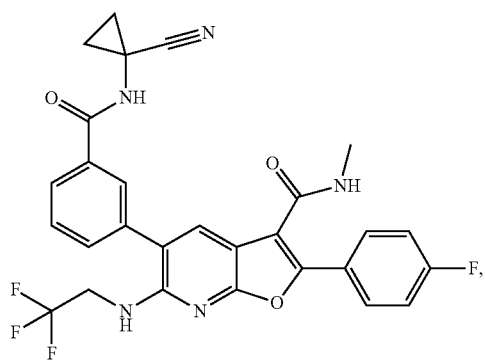
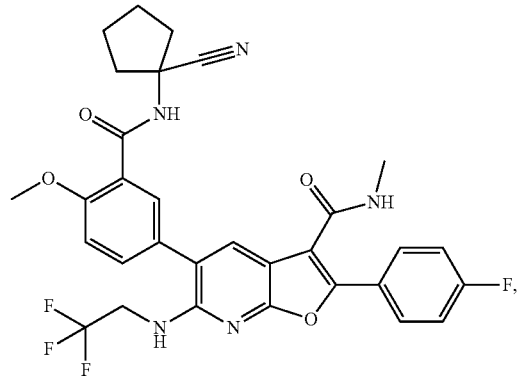

21
-continued
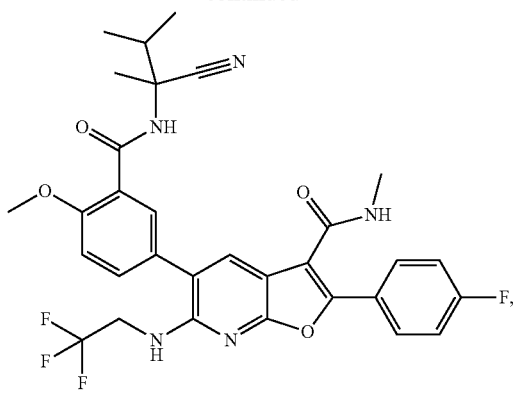
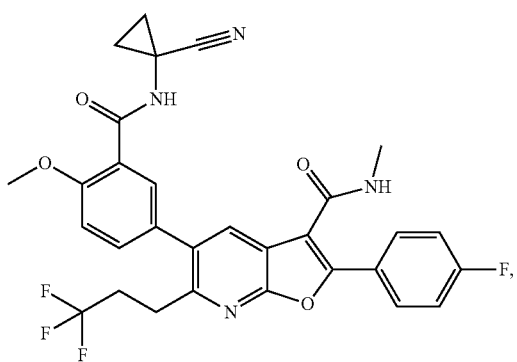
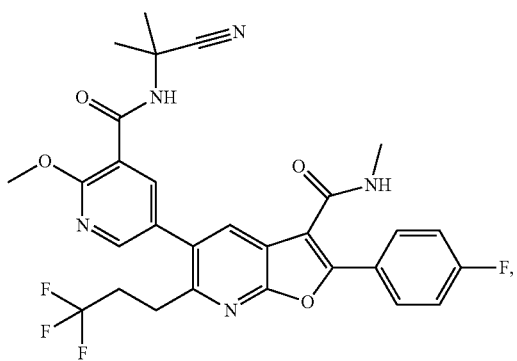
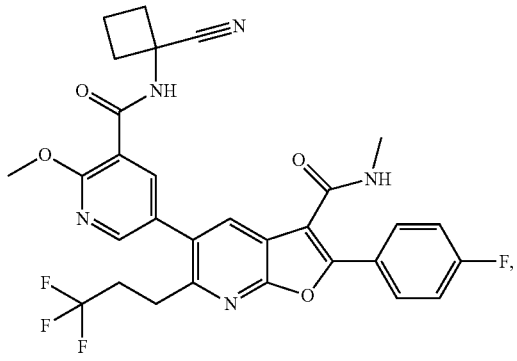
22
-continued
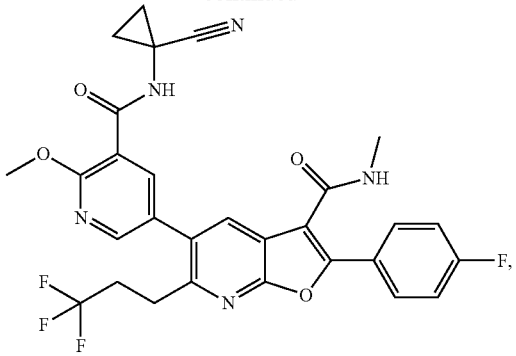
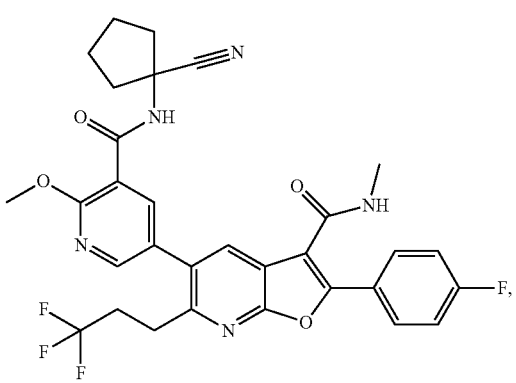
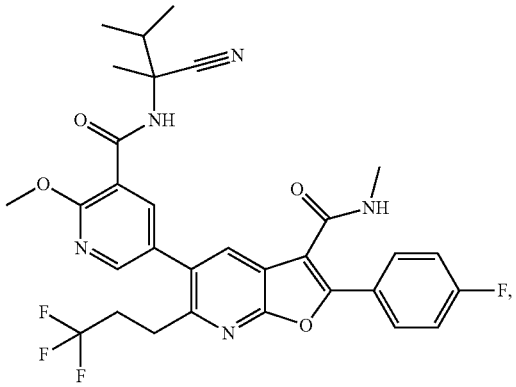
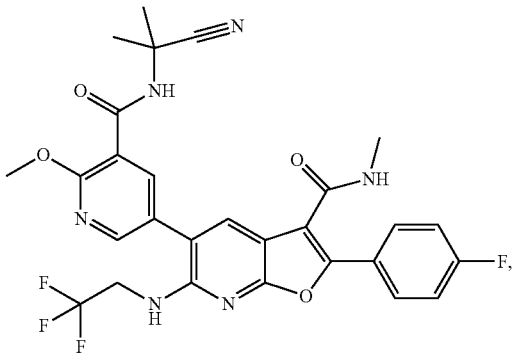

-continued
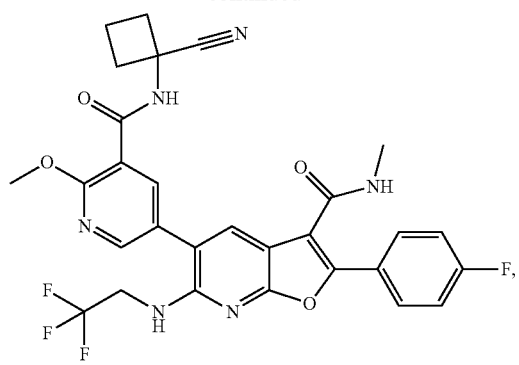
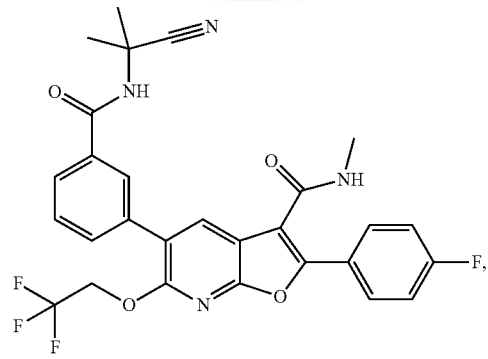
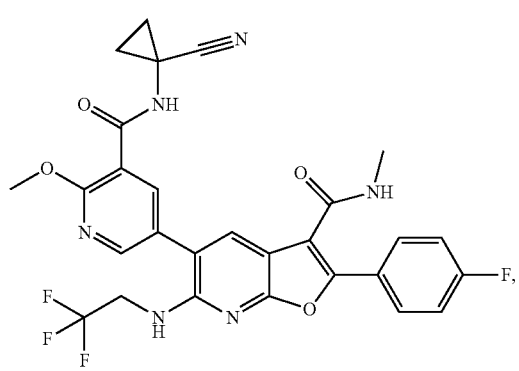
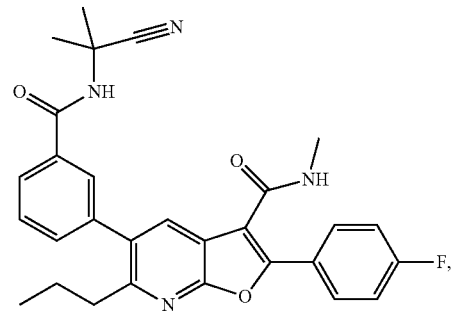
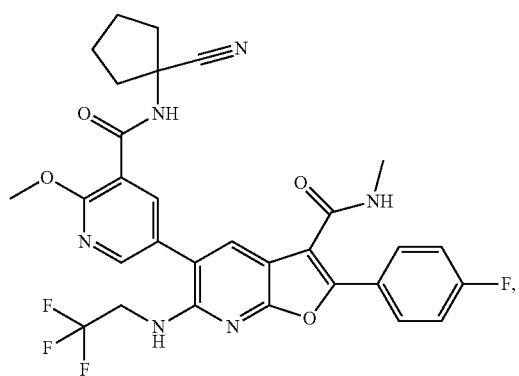
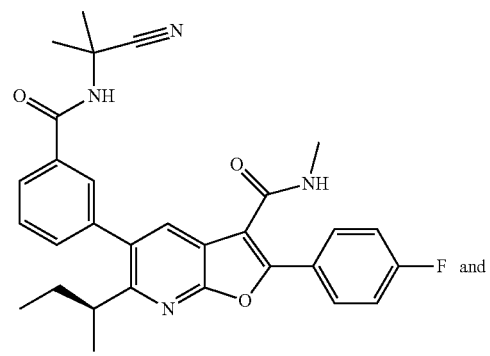
first eluting isomer
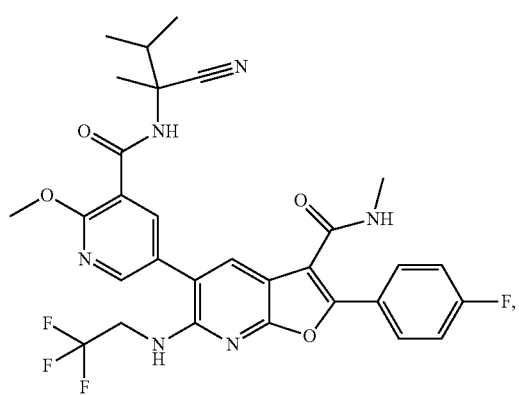
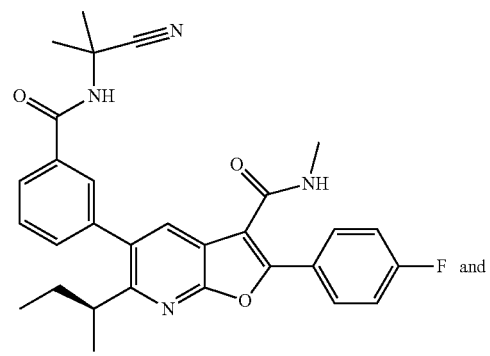
second eluting isomer
Also preferred are compounds, including pharmaceutically acceptable salts thereof, which are selected from the group of:

25
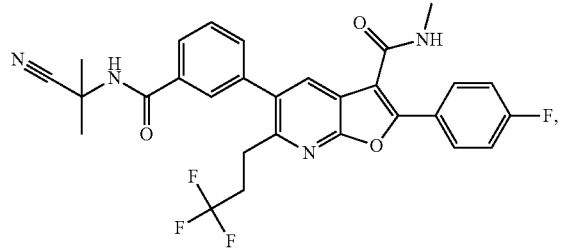
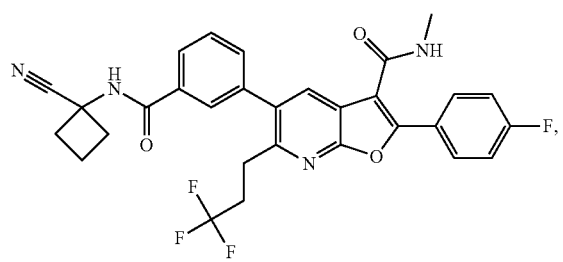
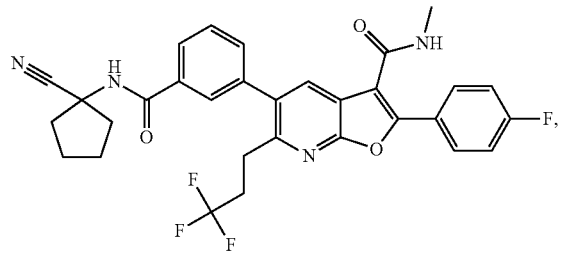
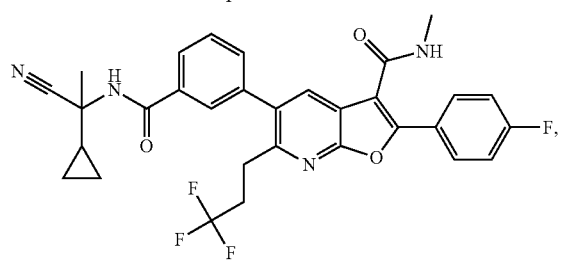
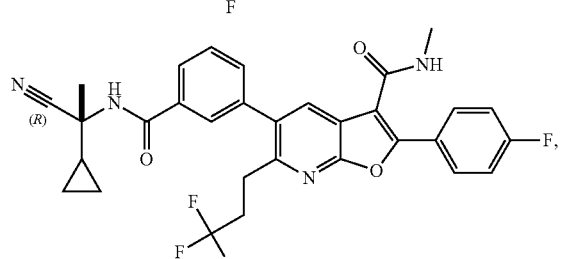
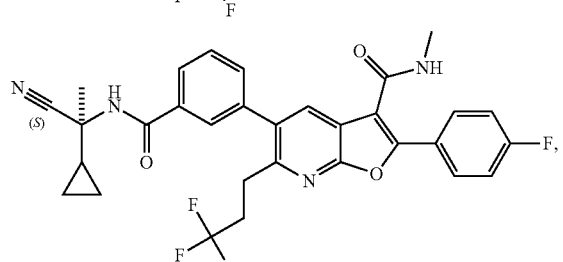
26
-continued
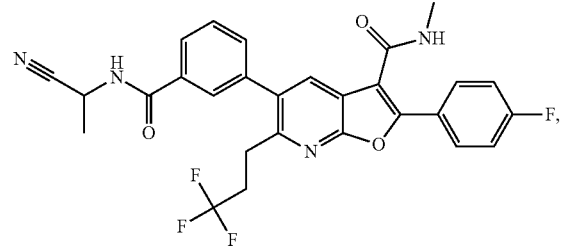
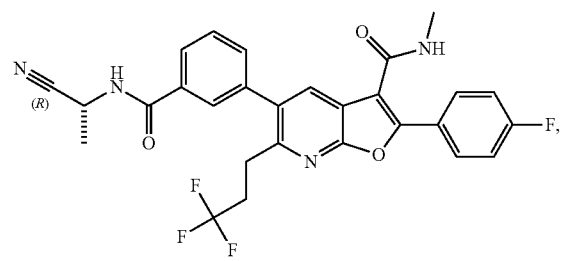
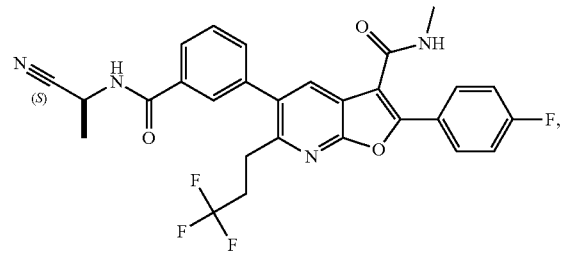
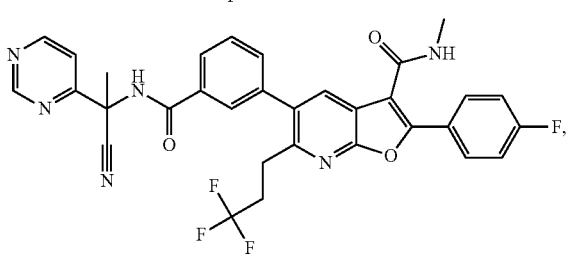
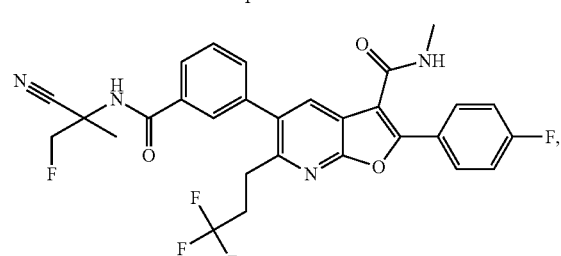
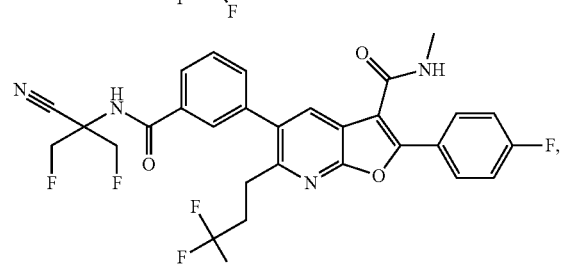

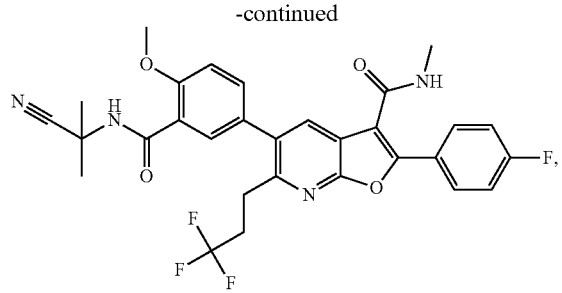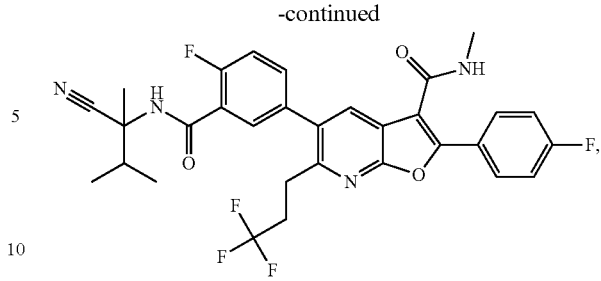

29
-continued
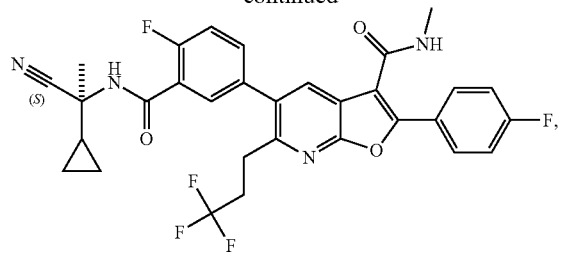
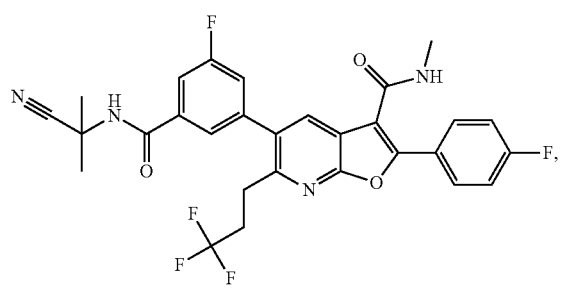
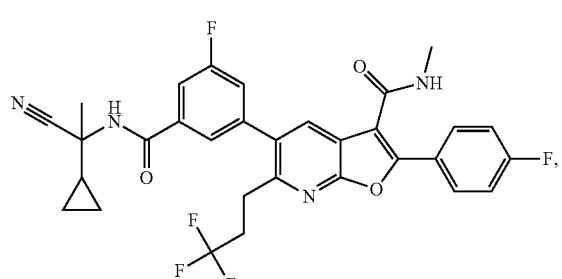
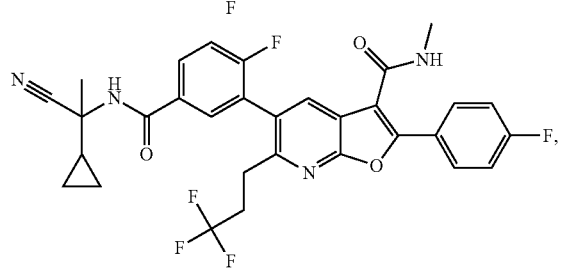
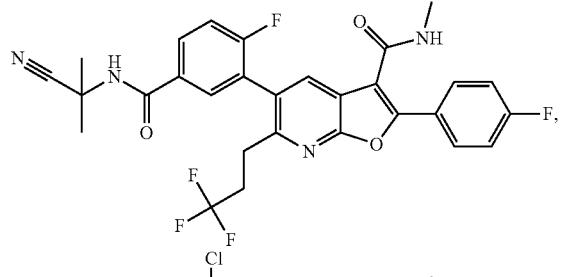
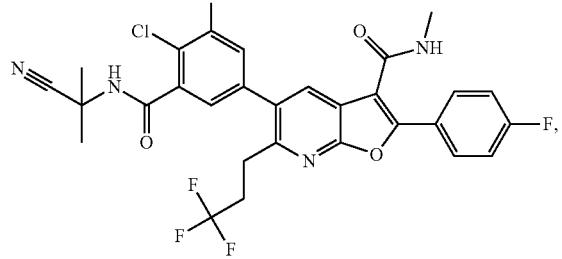
30
-continued
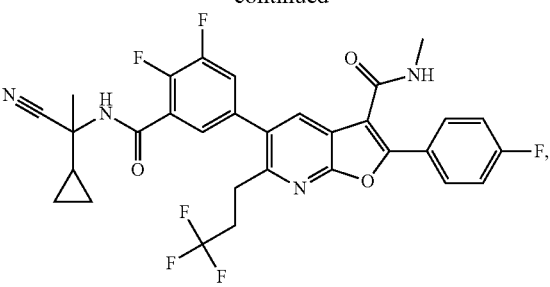
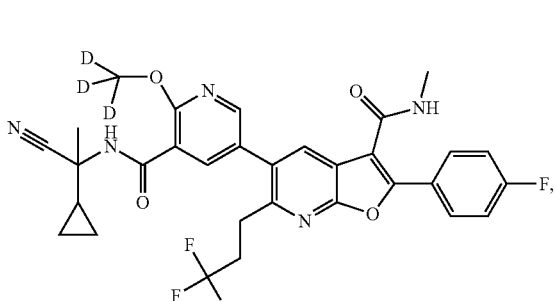
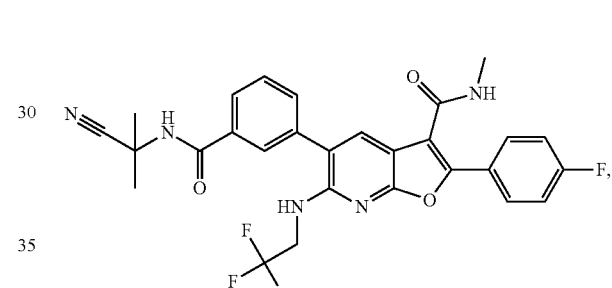
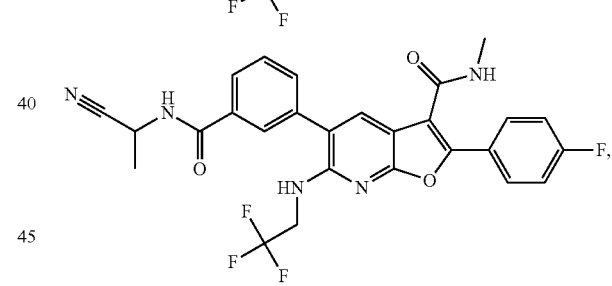
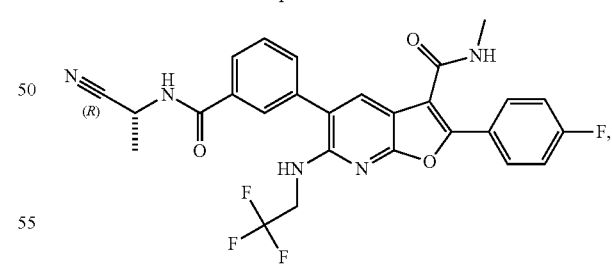
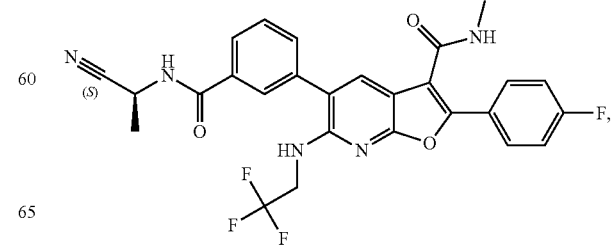

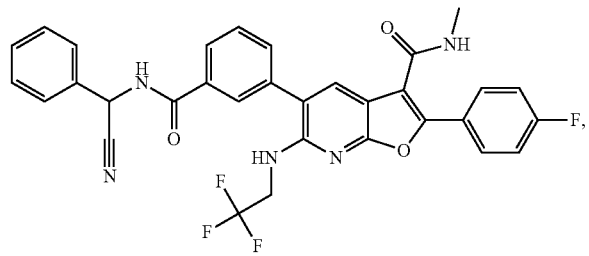
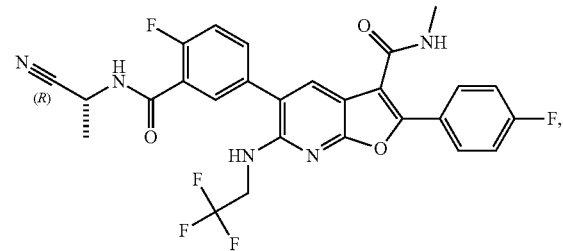
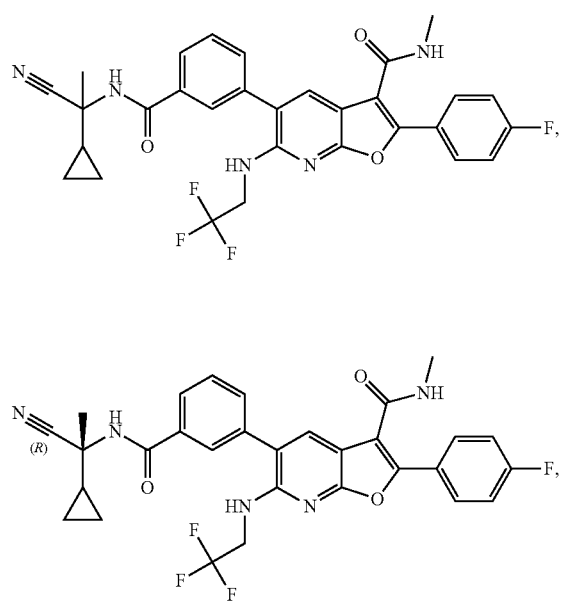
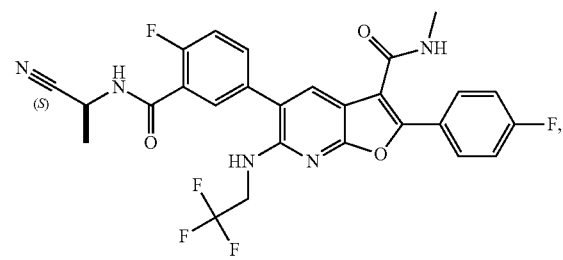
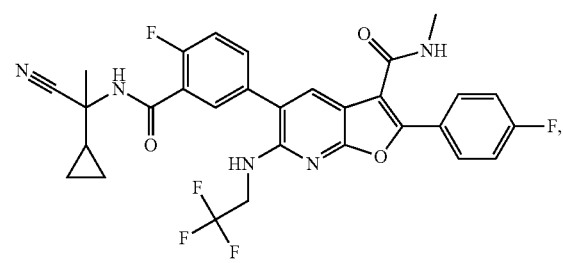
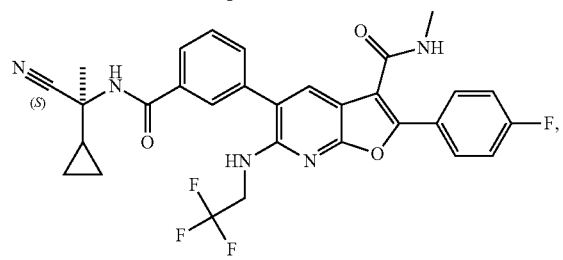
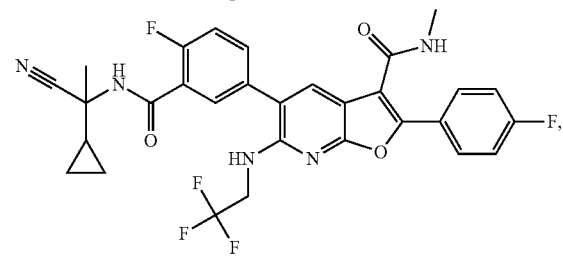
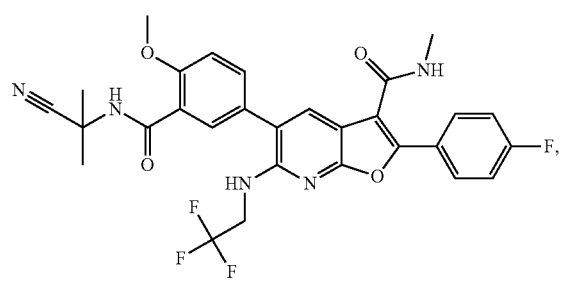
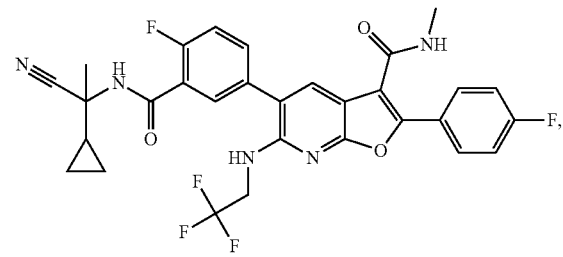
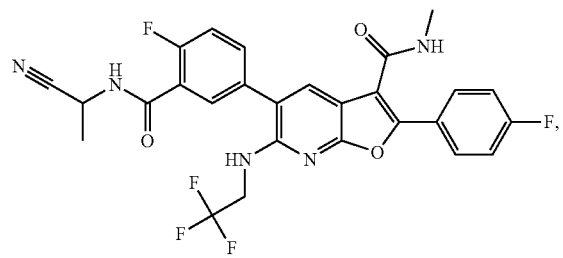
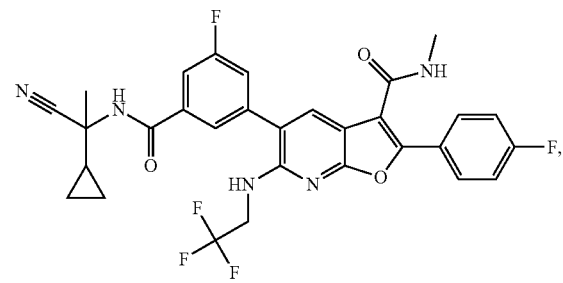

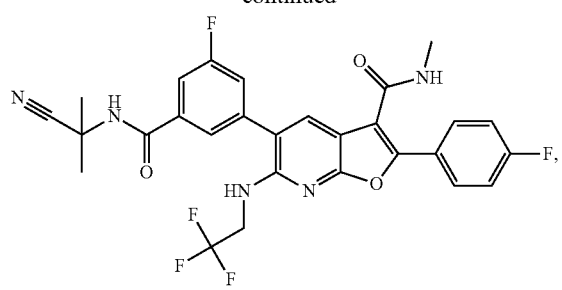
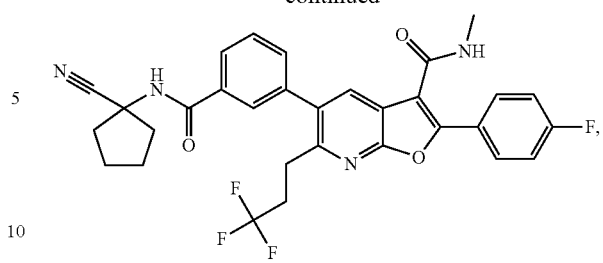
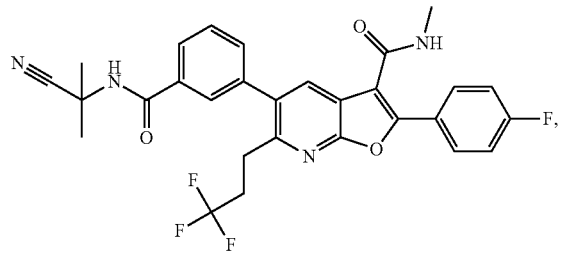
first eluting isomer and
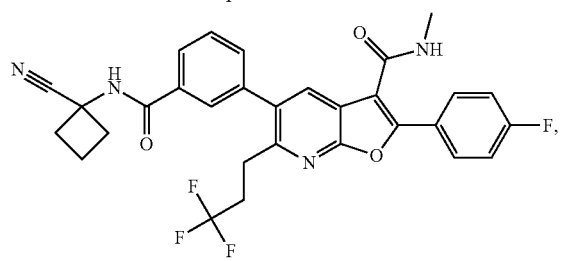
second eluting isomer
Further preferred are compounds, including pharmaceutically acceptable salts thereof, which are selected from the group of:
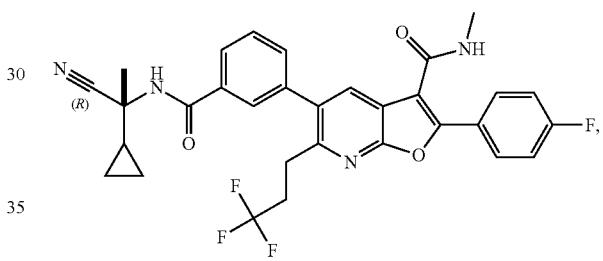
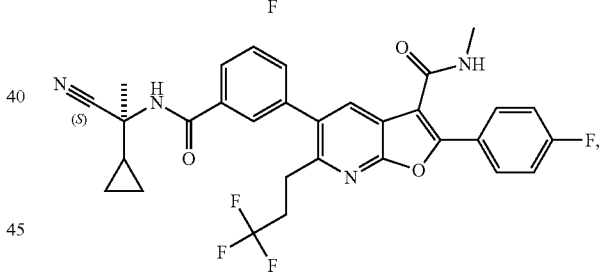
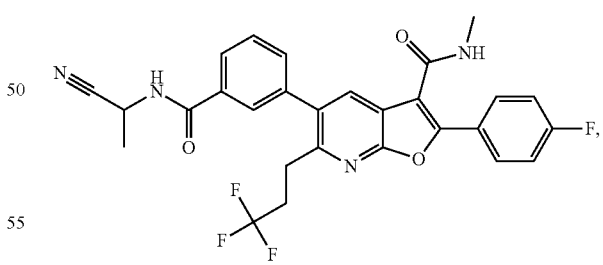
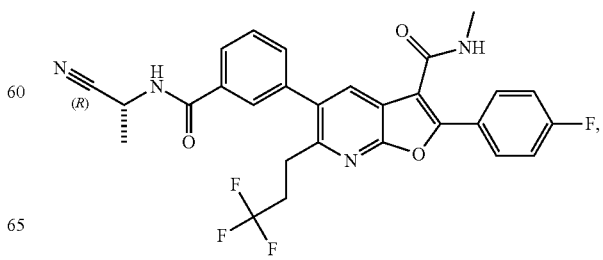

35
-continued
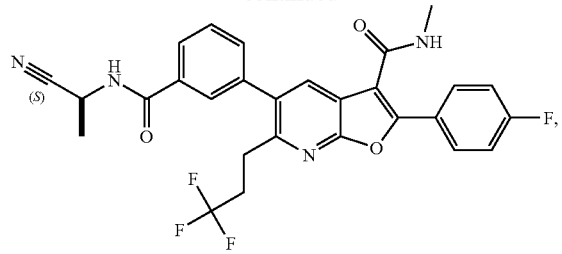
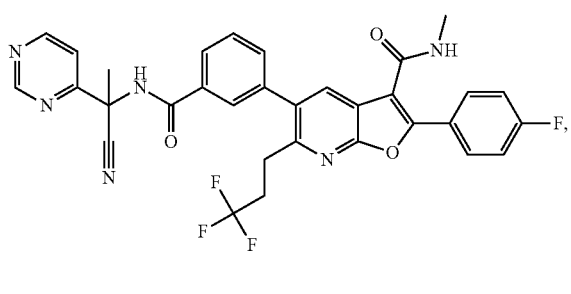
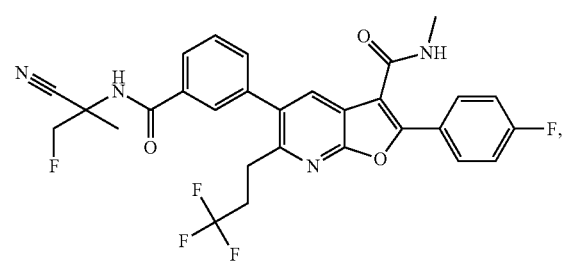
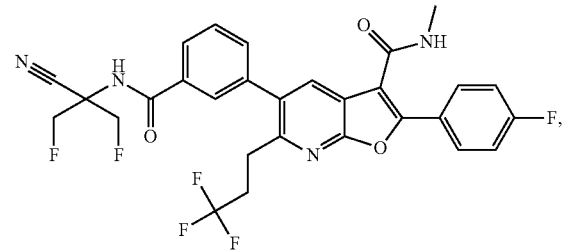
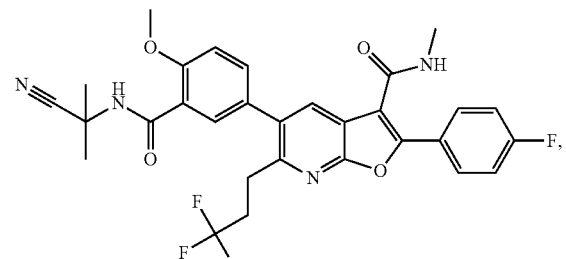
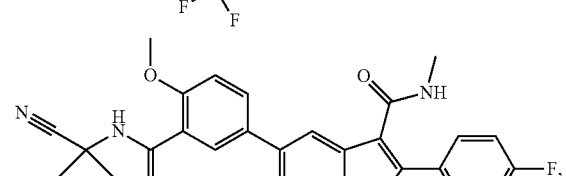
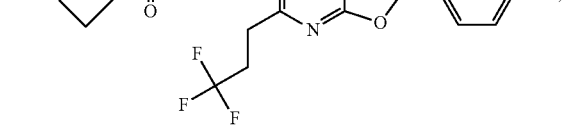
36
-continued
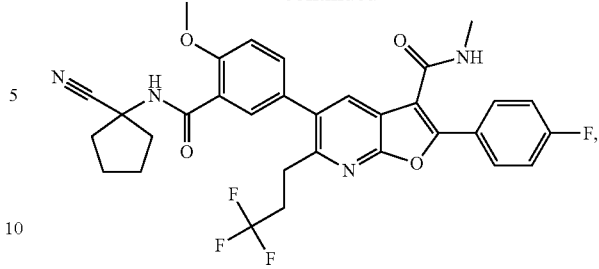
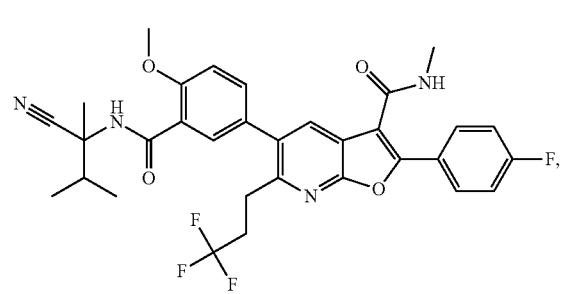
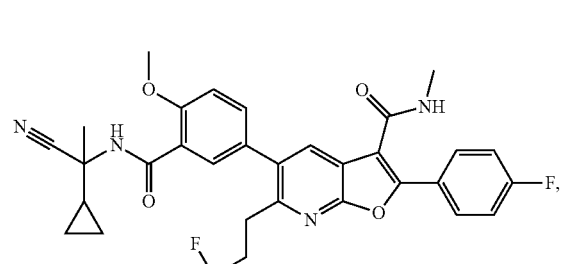
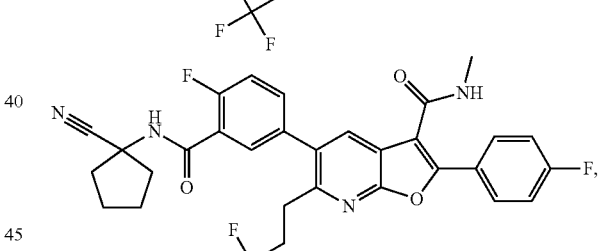
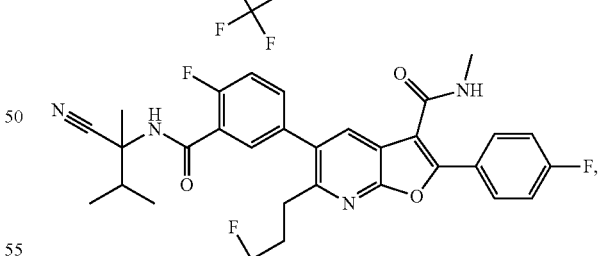
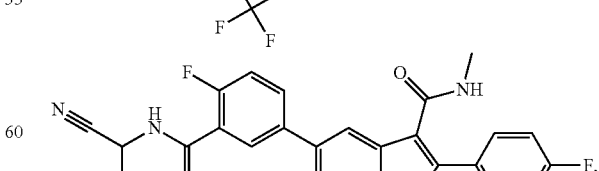
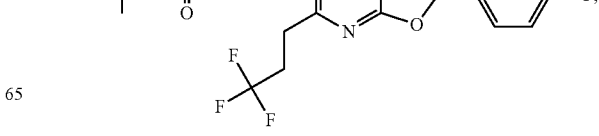

37
-continued
38
-continued
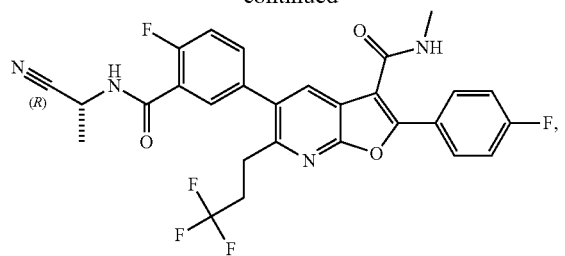
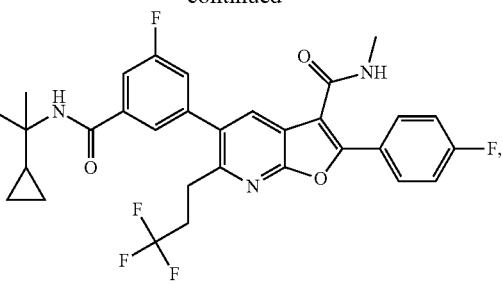
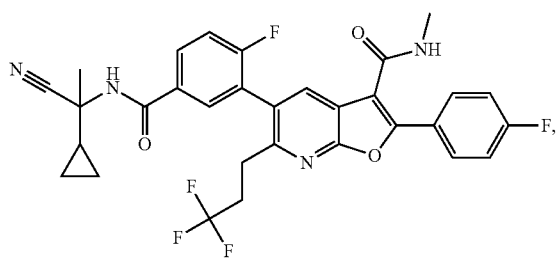
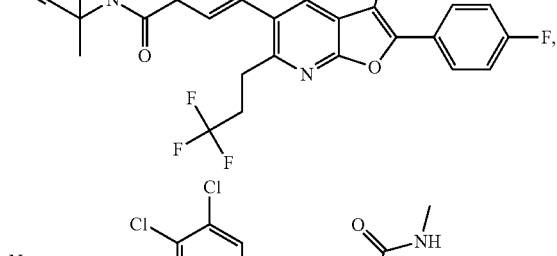
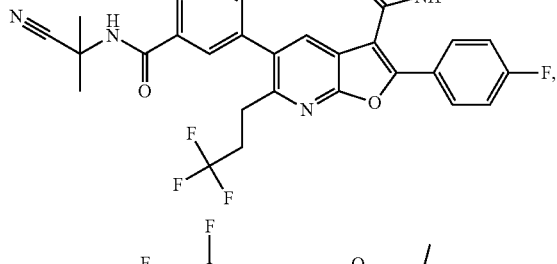
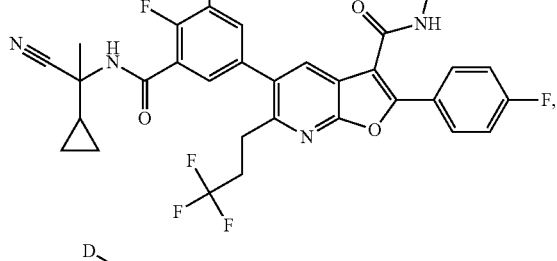
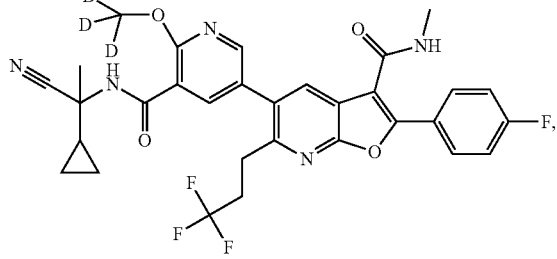

-continued
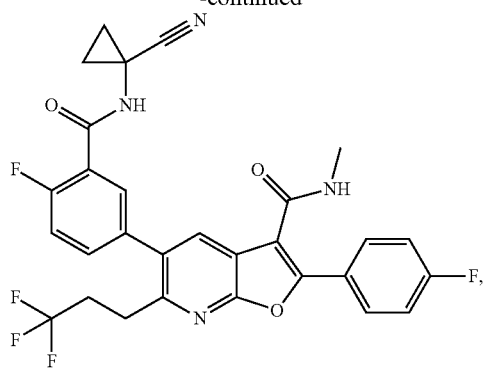
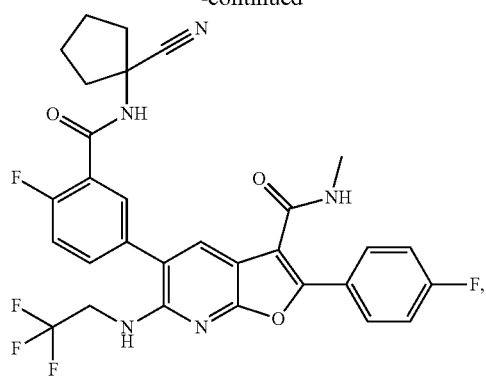

41
-continued
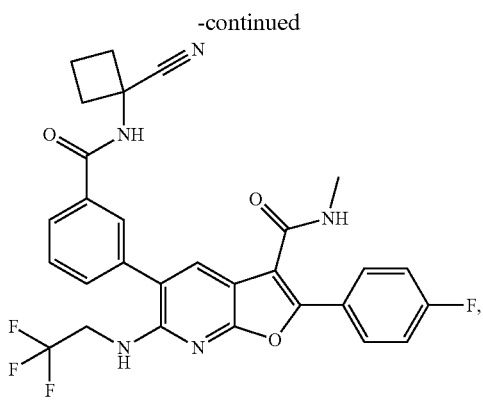
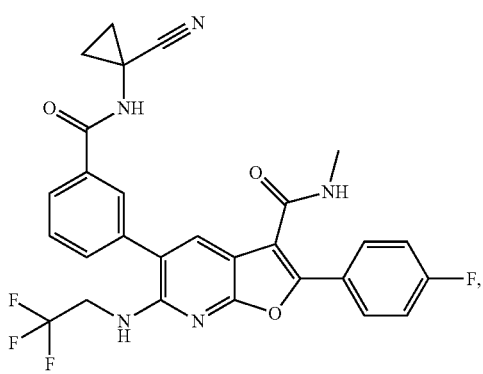
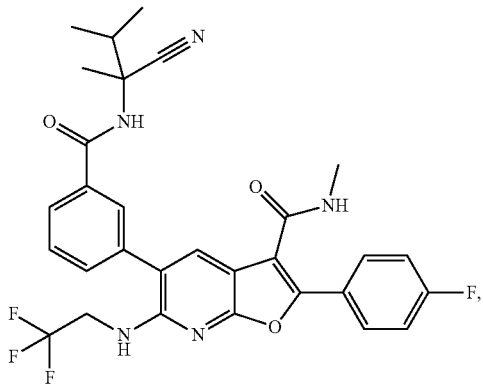
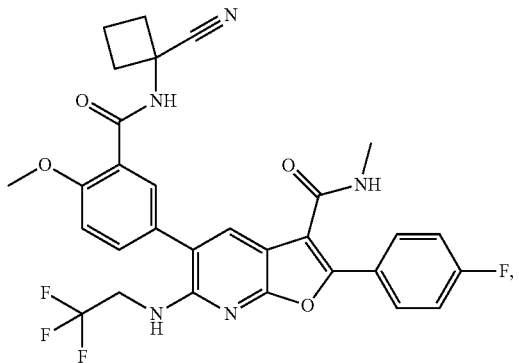
42
-continued
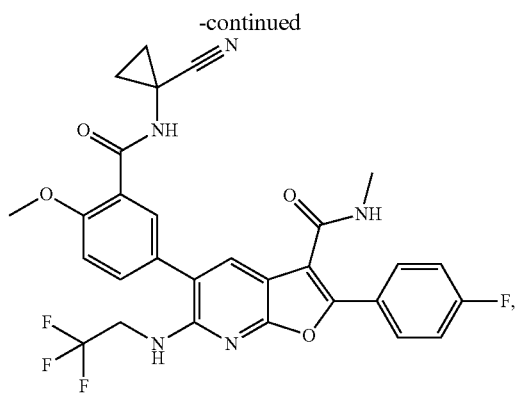
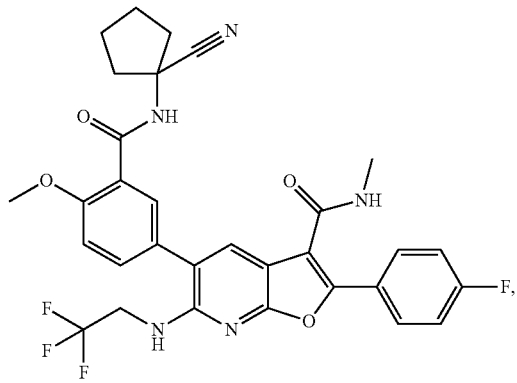
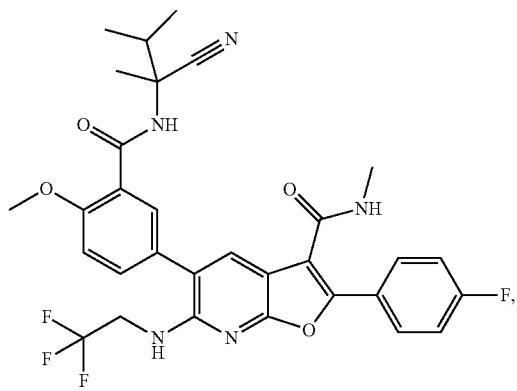
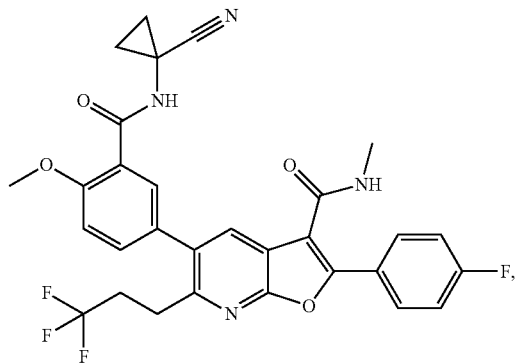

-continued
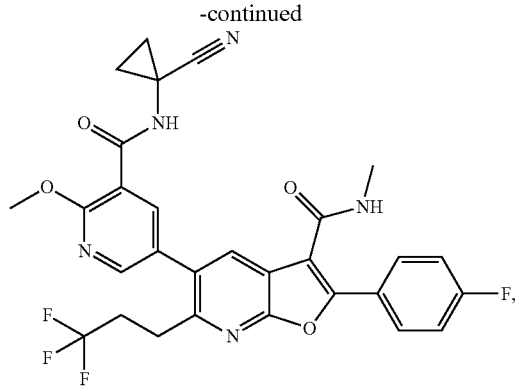
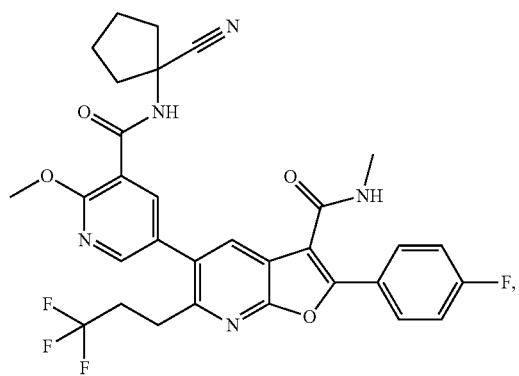
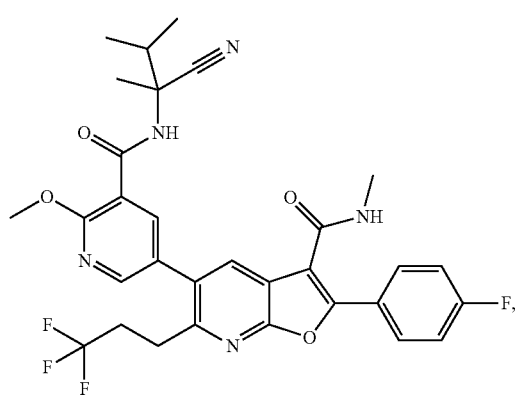
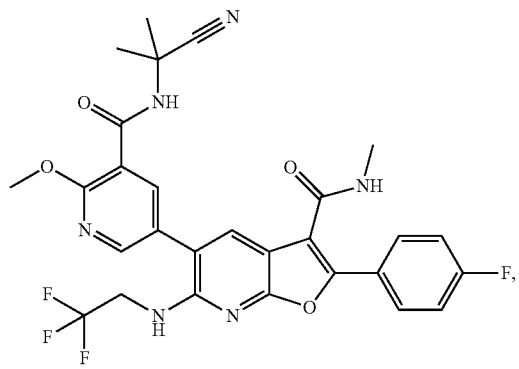
-continued
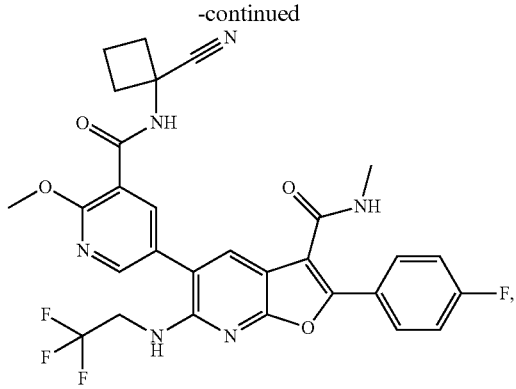
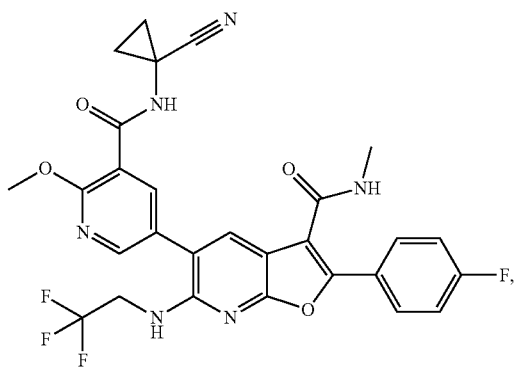
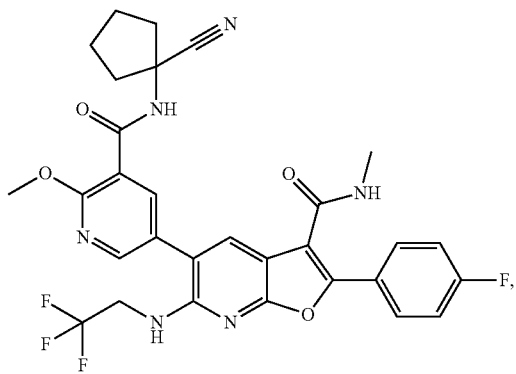
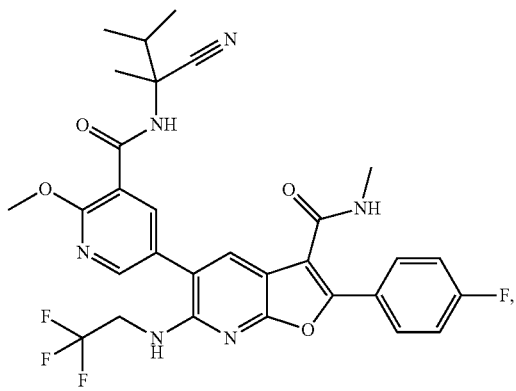

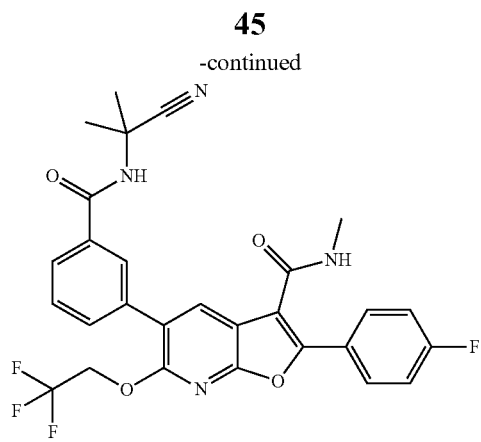
and
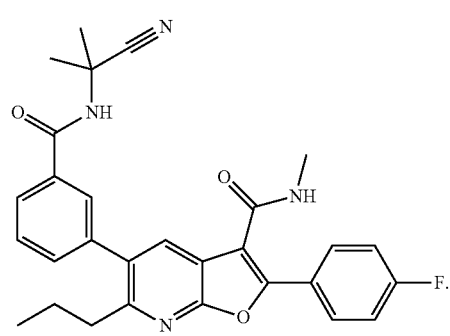 [SMILES: CCCc1nc2oc(-c3ccc(F)cc3)c(C(=O)NC)c2cc1-c1cccc(C(=O)NC(C)(C)C#N)c1]
More preferred compounds, including pharmaceutically acceptable salts thereof, are selected from the group of:
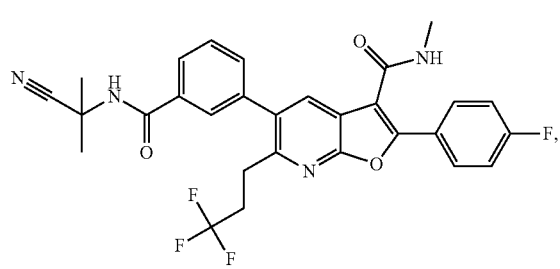
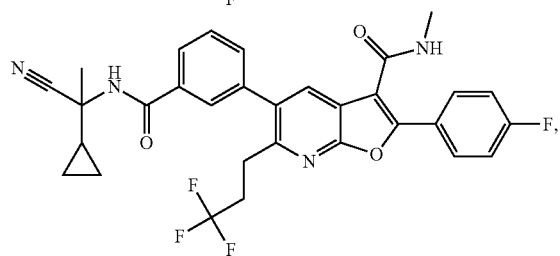
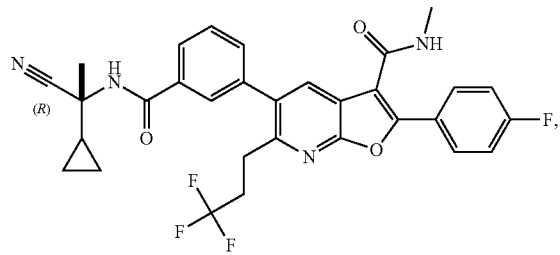
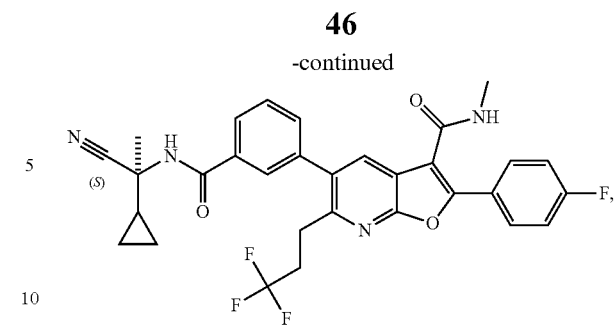
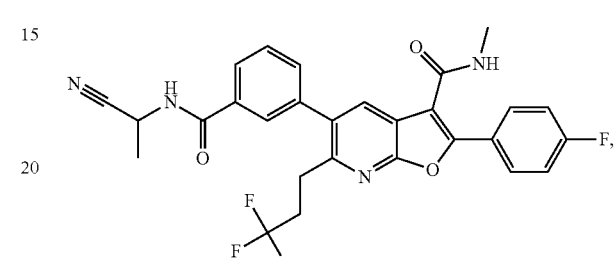
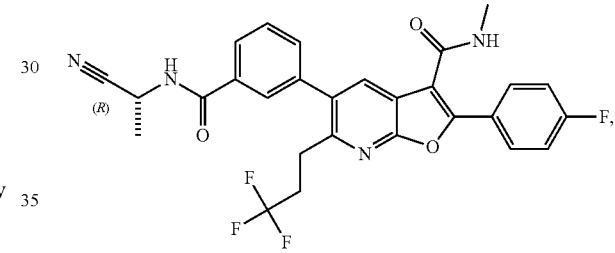
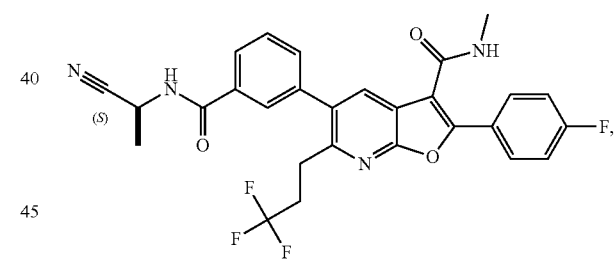
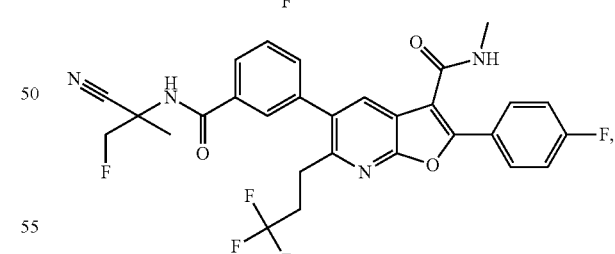
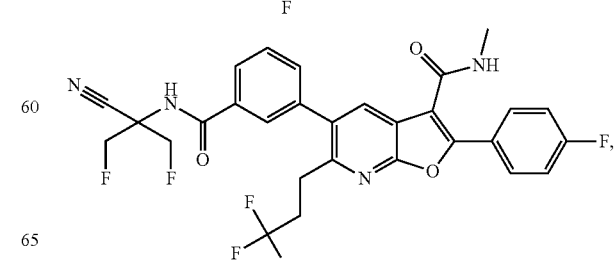

47
-continued
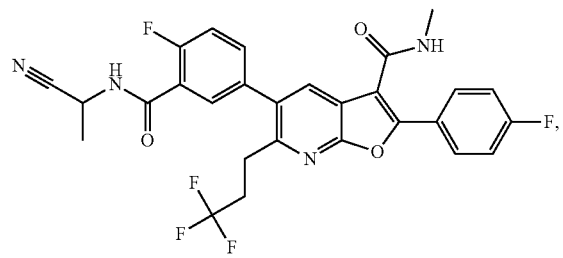
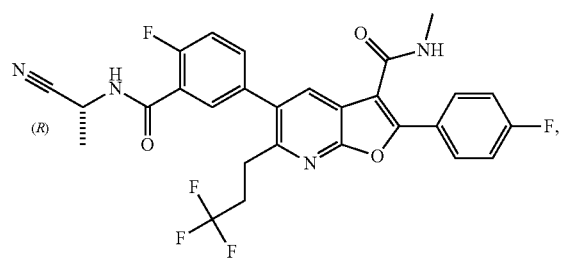
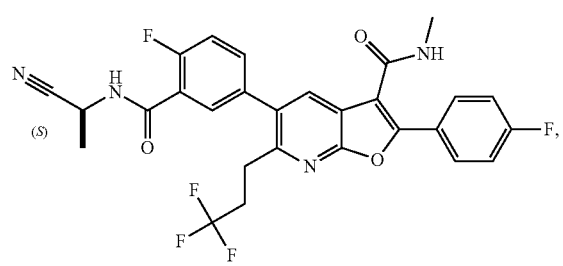
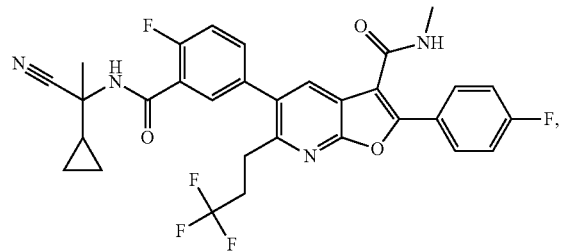
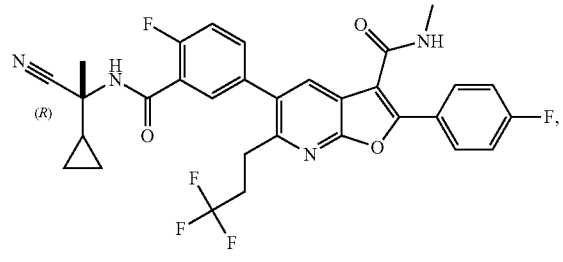
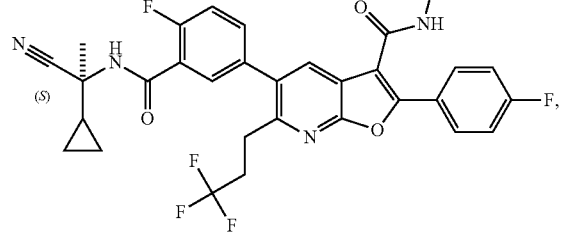
48
-continued
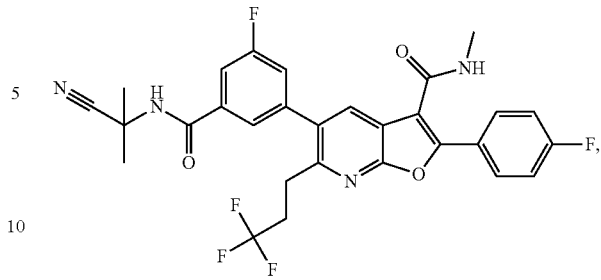
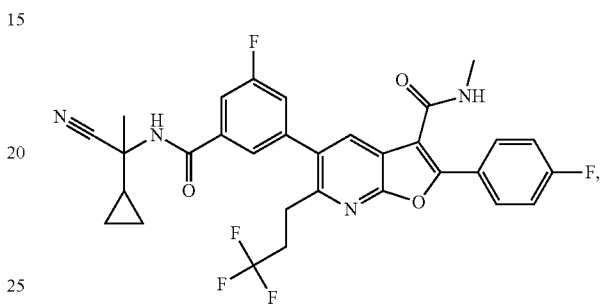
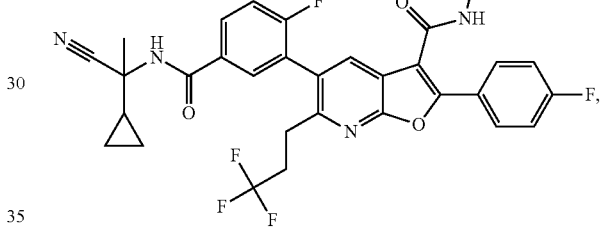
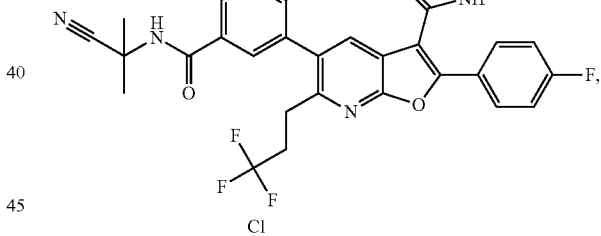
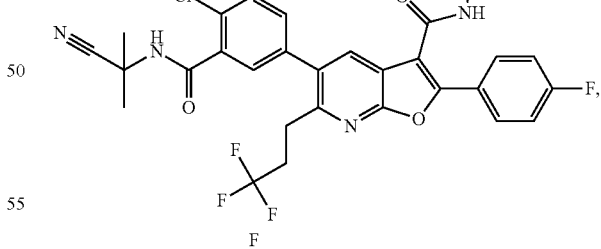
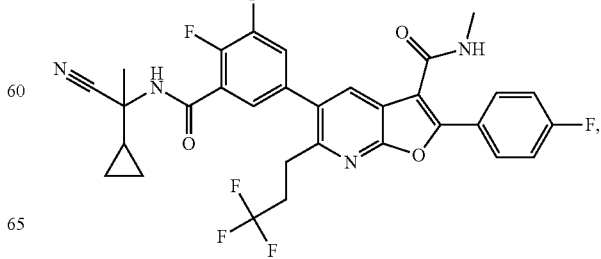

-continued
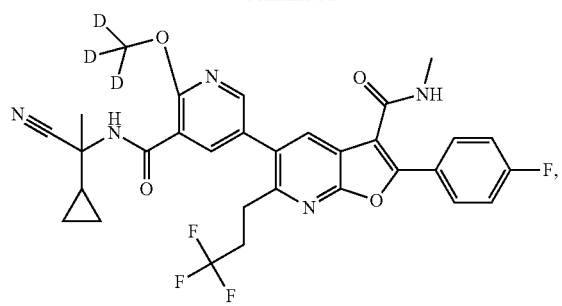
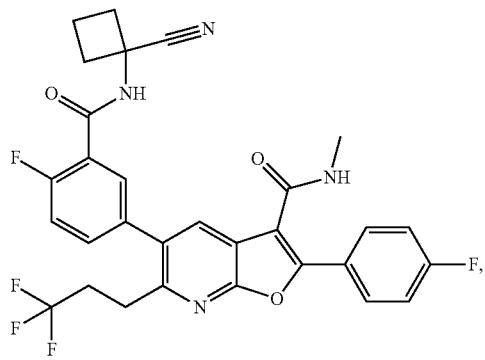
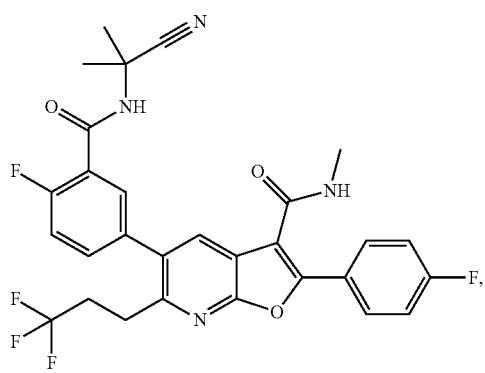
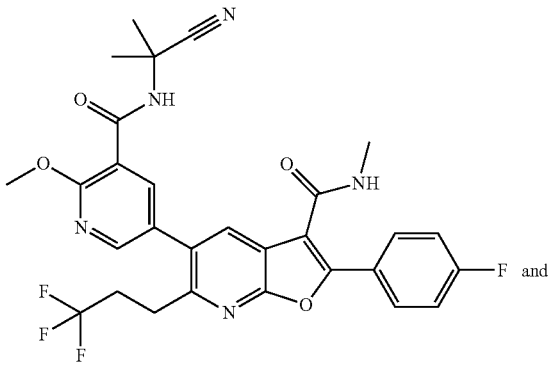
and
-continued
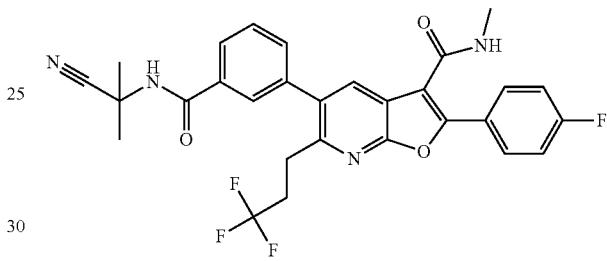
Other more preferred compounds, including pharmaceutically acceptable salts thereof, are selected from the group of:
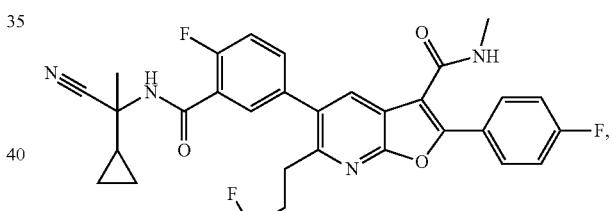
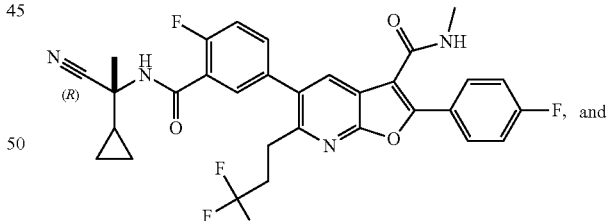
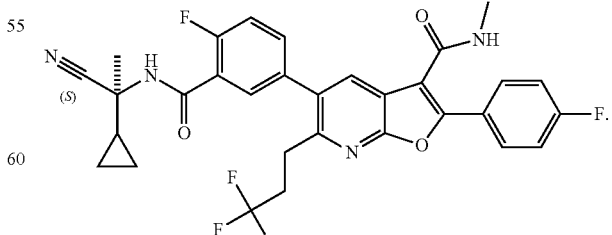
, and
Further preferred is the compound, including pharmaceutically acceptable salts thereof, which is identified as:

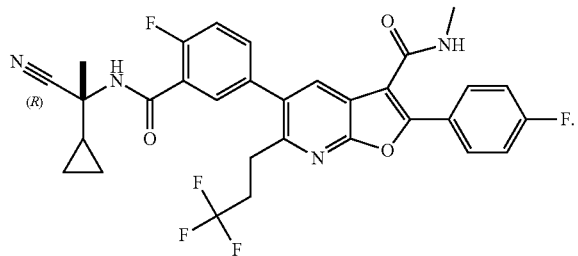

In addition, the compound, including pharmaceutically acceptable salts thereof, which is identified as:

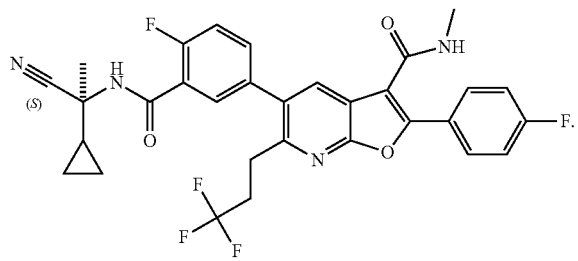

Pharmaceutical Compositions and Methods of Treatment

The compounds according to the various embodiments herein set forth demonstrate activity against HCV NS5B, and can be useful in treating HCV and HCV infection. Therefore, another aspect of the invention is a composition comprising a compound of Formula I, including pharmaceutically acceptable salts thereof, and a pharmaceutically acceptable carrier, excipient and/or diluent.

Another aspect of the invention is a composition further comprising an additional compound having anti-HCV activity.

Another aspect of the invention is a composition wherein the additional compound having anti-HCV activity is an interferon or a ribavirin. Another aspect of the invention is wherein the interferon is selected from interferon alpha 2B, pegylated interferon alpha, consensus interferon, interferon alpha 2A, interferon lambda, and lymphoblastoid interferon tau.

Another aspect of the invention is a composition wherein the compound having additional anti-HCV activity is a cyclosporin. Another aspect of the invention is where the cyclosporin is cyclosporin A.

Another aspect of the invention is a composition wherein the additional compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition wherein the additional compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of Formula I, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of Formula I or a pharmaceutically acceptable salt thereof.

Another aspect of the invention is a method of inhibiting the function of the HCV NS5B protein comprising contacting the HCV NS5B protein with a compound of Formula I or a pharmaceutically acceptable salt thereof.

Another aspect of the invention is a method of treating an HCV infection in a patient comprising administering to the patient a therapeutically effective amount of a compound of Formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of Formula I, or a pharmaceutically acceptable salt thereof, in conjunction with (prior to, after, or concurrently) another compound having anti-HCV activity.

Another aspect of the invention is the method wherein the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method wherein the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method wherein the other compound having anti-HCV activity is effective to inhibit the function of target in the HCV life cycle other than the HCV NS5B protein. "Therapeutically effective" means the amount of agent required to provide a meaningful patient benefit, e.g., inhibiting, ameliorating, or healing of acute conditions caused by HCV infection and/or inhibiting, ameliorating, or healing of the HCV infection itself, when applied to an individual so infected, as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Bio-pharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |

TABLE 1-continued

| Brand Name | Physiological Class | Type of Inhibitor or Target | Source Company |
|---|---|---|---|
| CellCept | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/ α1-thymosin | RegeneRx Biopharma. Inc., Bethesda, MD/ SciClone Pharmaceuticals Inc, San Mateo, CA |
| Rebetron | Interferon | IFN-α2b/ ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lambda | Antiviral | Interferon | ZymoGenetics/Bristol-Myers Squibb |

Synthesis Methods

The compounds may be made by methods available in the art, as well as those described below. Some reagents and intermediates are available in the art. Other reagents and intermediates can be made by methods available in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine.

For the section of compounds in the 0000 series all Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., Compound Isolation).

Compounds purified by preparative HPLC were diluted in methanol (1.2 mL) and purified using a Shimadzu LC-8A or LC-10A or Dionex APS-3000 or Waters Acquity™ automated preparative HPLC system.

Examples

Preparation of Compounds 10001

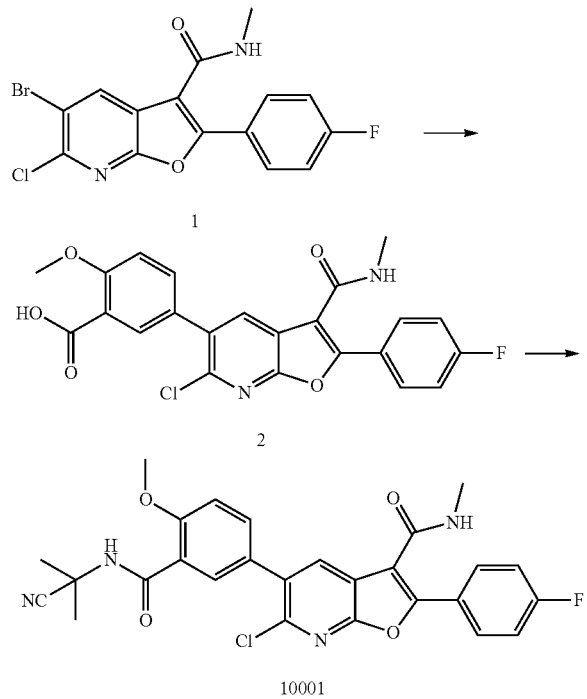

Step 1: To a mixture of Compound 1 (5 g), 5-borono-2-methoxybenzoic acid (3.07 g) and $Cs_2CO_3$ (8.49 g) in dioxane (120 mL) and water (20 mL) was added $Pd(PPh_3)_4$ (1.51 g). The mixture was flushed with nitrogen and then heated at 85° C. for 16 hours. The mixture was diluted with water and acidified with 1N HCl to pH ~3 and then extracted with EtOAc (2×150 mL). The organic layers were combined, washed with brine, dried over $MgSO_4$ and concentrated under vacuum. The residue was purified by titration with EtOAc to give Compound 2.

| Compound 2 | |
|---|---|
| MS (MHZ)$^+$ Calcd. | 455.1 |
| MS (MHZ)$^+$ Observ. | 454.9 |
| Retention Time | 1.84 min |
| LC Condition | |
| Solvent A | 90% Water -10% Methanol-0.1% TFA |
| Solvent B | 10% Water -90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 2: To a solution of Compound 2 (300 mg), 2-amino-2-methylpropanenitrile (66.6 mg) and HATU (376 mg) in DMF (5 mL) was added $iPr_2NEt$ (0.46 mL). The mixture was stirred at room temperature for 4 hours. The mixture was diluted with EtOAc (200 mL), washed water (50 mL), brine (50 mL), dried over $MgSO_4$ and concentrated under vacuum. The residue was purified by titration with EtOAc to give Compound 10001.

| 10001 | |
|---|---|
| MS (MHZ)$^+$ Calcd. | 521.1 |
| MS (MHZ)$^+$ Observ. | 521.2 |
| Retention Time | 1.85 min |
| LC Condition | |
| Solvent A | 90% Water -10% Methanol-0.1% TFA |
| Solvent B | 10% Water -90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 10002

Compound 10002 was prepared via the same procedure towards compound 10001, using 1-aminocyclobutanecarbonitrile as the starting material.

| 10002 | |
|---|---|

[Structure of compound 10002]

| MS (MHZ)$^+$ Calcd. | 533.1 |
|---|---|
| MS (MHZ)$^+$ Observ. | 533.1 |
| Retention Time | 1.90 min |
| LC Condition | |
| Solvent A | 90% Water −10% Methanol-0.1% TFA |
| Solvent B | 10% Water −90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 10003

Compound 10003 was prepared via the same procedure towards compound 10001, using 1-aminocyclopentanecarbonitrile hydrochloride as the starting material.

10003

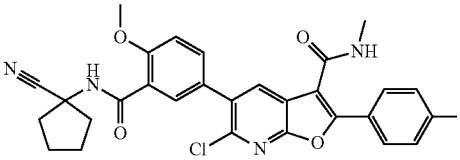

| | |
|---|---|
| MS (MHZ)+ Calcd. | 547.2 |
| MS (MHZ)+ Observ. | 547.1 |
| Retention Time | 1.65 min |
| | LC Condition |
| Solvent A | 90% Water –10% Methanol-0.1% TFA |
| Solvent B | 10% Water –90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 10004

Compound 10004 was prepared via the same procedure towards compound 10001 from Compound 1, using 3-borono-benzoic acid as the starting material in the Step 1.

10004

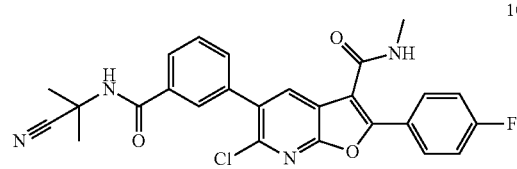

| | |
|---|---|
| MS (MHZ)+ Calcd. | 491.1 |
| MS (MHZ)+ Observ. | 491.1 |
| Retention Time | 1.85 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 10005

Compound 10005 was prepared via the same procedure towards compound 10002 from Compound 1, using 3-borono-benzoic acid as the starting material in the Step 1.

10005

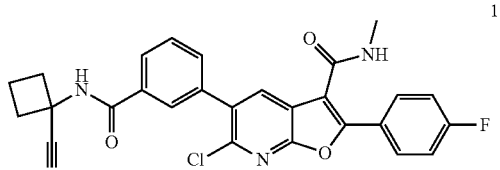

| | |
|---|---|
| MS (MHZ)+ Calcd. | 503.1 |
| MS (MHZ)+ Observ. | 503.1 |

10005

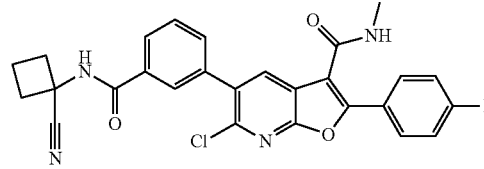

| | |
|---|---|
| Retention Time | 1.89 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 10006

Compound 10006 was prepared via the same procedure towards compound 10003 from Compound 1, using 3-borono-benzoic acid as the starting material in the Step 1.

10006

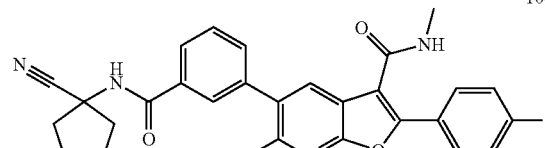

| | |
|---|---|
| MS (MHZ)+ Calcd. | 517.1 |
| MS (MHZ)+ Observ. | 517.1 |
| Retention Time | 1.60 min |
| | LC Condition |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 11001

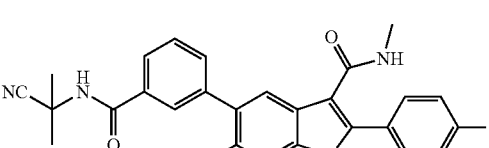

10004

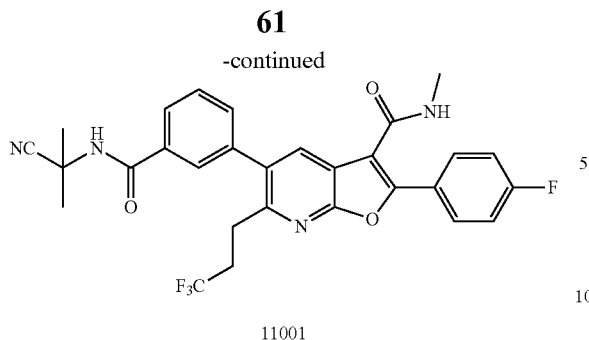

11001

A mixture of Compound 10004 (30 mg), CF$_3$CH$_2$CH$_2$BF$_3$K (43.6 mg), cesium carbonate (59.7 mg), dicyclohexyl(2',6'-diisopropoxy-[1,1'-biphenyl]-2-yl)phosphine (11.41 mg) and diacetoxypalladium (2.74 mg) in toluene (3 mL) and water (0.3 mL) was heated at 80° C. for 16 hours. The mixture was diluted with EtOAc (20 mL), washed with water (20 mL), brine (20 mL), dried over MgSO$_4$ and concentrated under vacuum. The residue was purified by preparative HPLC system.

| 11001 | |
|---|---|
| MS (MHZ)$^+$ Calcd. | 553.2 |
| MS (MHZ)$^+$ Observ. | 553.2 |
| Retention Time | 1.79 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Preparation of Compound 11002

Compound 11002 was prepared via the same procedure towards compound 11001, using Compound 10005 as the starting material.

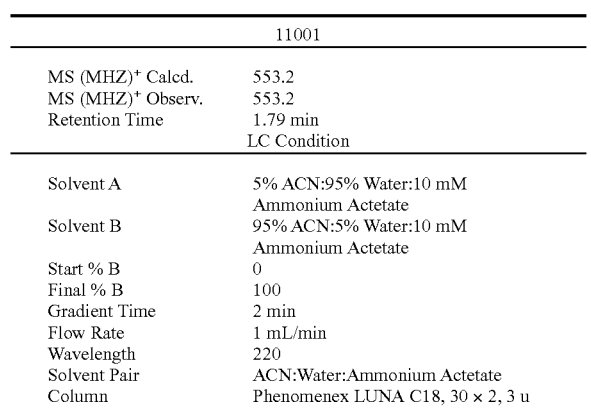

11002

| MS (MHZ)$^+$ Calcd. | 565.2 |
|---|---|
| MS (MHZ)$^+$ Observ. | 565.3 |
| Retention Time | 1.82 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Preparation of Compound 11003

Compound 11003 was prepared via the same procedure towards compound 11001, using Compound 10006 as the starting material.

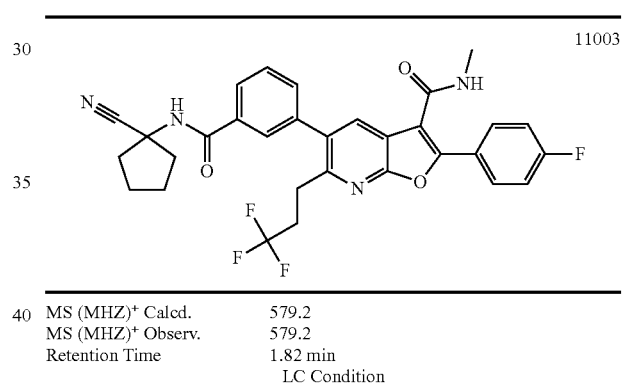

11003

| MS (MHZ)$^+$ Calcd. | 579.2 |
|---|---|
| MS (MHZ)$^+$ Observ. | 579.2 |
| Retention Time | 1.82 min |
| | LC Condition |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Intermediate 5

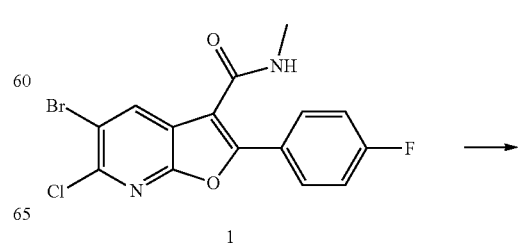

1

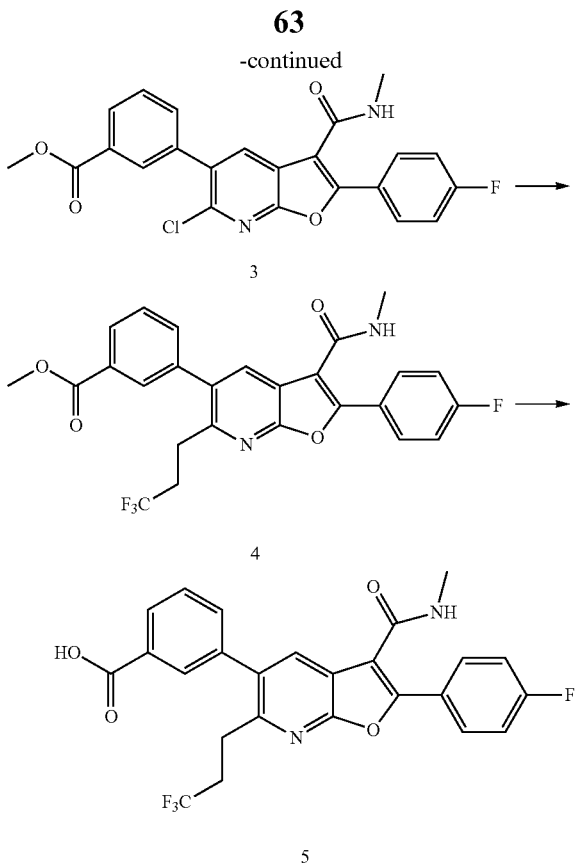

| Compound 4 | |
|---|---|
| MS (MHZ)⁺ Calcd. | 501.1 |
| MS (MHZ)⁺ Observ. | 501.1 |
| Retention Time | 1.88 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 3: A mixture of Compound 4 (400 mg) and NaOH (4.0 mL, 1N) in THF (30 mL) and water (15 mL) was heated at 80° C. for 6 hours. The mixture was acidified by 1N HCl to pH ~5 and extracted with EtOAc (2×50 mL). The organic layers were combined, washed with brine (2×50 mL), dried over MgSO$_4$ and concentrated under vacuum to give Compound 5 which was used as was.

| Compound 5 | |
|---|---|
| MS (MHZ)⁺ Calcd. | 487.1 |
| MS (MHZ)⁺ Observ. | 487.0 |
| Retention Time | 1.64 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 1: To a mixture of Compound 1 (100 mg), (3-(methoxycarbonyl)phenyl)boronic acid (46.9 mg) and Cs$_2$CO$_3$ (170 mg) in dioxane (4 mL) and water (1 mL) was added Pd(PPh$_3$)$_4$ (30.1 mg). The mixture was flushed with nitrogen and then heated at 85° C. for 4 hours. The mixture was diluted with water and extracted with EtOAc (2×10 mL). The organic layers were combined, washed with brine (2×10 mL), dried over MgSO$_4$ and concentrated under vacuum. The residue was purified by titration with EtOAc to give Compound 3.

| Compound 3 | |
|---|---|
| MS (MHZ)⁺ Calcd. | 439.1 |
| MS (MHZ)⁺ Observ. | 439.0 |
| Retention Time | 1.76 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 2: A mixture of Compound 3 (1 g), CF$_3$CH$_2$CH$_2$BF$_3$K (1.63 g), Cs$_2$CO$_3$ (2.23 g), dicyclohexyl(2',6'-diisopropoxy-[1,1'-biphenyl]-2-yl)phosphine (0.43 g) and diacetoxypalladium (0.10 g) in toluene (50 mL) and water (5.0 mL) was heated at 90° C. for 16 hours. The mixture was diluted with EtOAc (250 mL), washed with water (100 mL), brine (100 mL), dried over MgSO$_4$ and concentrated under vacuum. The residue was purified by silica gel column (hexanes:EtOAc=1:1 to 1:2) to give Compound 4.

Preparation of Compounds 11004, 11005, 11008, 11011, 11012 and 11013 iPr$_2$NEt or Et$_3$N (2 eq.) and HATU or HCTU or DEBPT (1.3 eq.) were added into a solution of Compound 5 (1 eq.) and amine (1.3 eq.) in DMF or THF. The reaction was stirred at room temperature or 85° C. for 30 minutes to 72 hours. The desired product was isolated by preparative HPLC system.

| LC Condition A | |
|---|---|
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| LC Condition B | |
|---|---|
| Solvent A | 5% ACN:95% Water:10 mM Ammonium Actetate |
| Solvent B | 95% ACN:5% Water:10 mM Ammonium Actetate |
| Start % B | 0 |

65
-continued

LC Condition B

| | |
|---|---|
| Final % B | 100 |
| Gradient Time | 2 min |
| Flow Rate | 1 mL/min |
| Wavelength | 220 |

66
-continued

LC Condition B

| | |
|---|---|
| Solvent Pair | ACN:Water:Ammonium Actetate |
| Column | Phenomenex LUNA C18, 30 × 2, 3 u |

| Cmpd # | LC Method | Structure | MS (MHZ)+ Calcd. | MS (MHZ)+ Observ. | Retention Time (min) |
|---|---|---|---|---|---|
| 11004 | A | 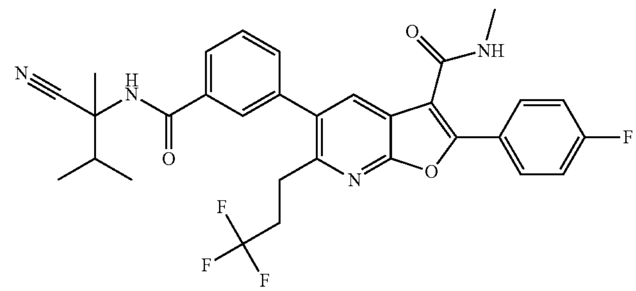 [SMILES: CNC(=O)c1c(-c2ccc(F)cc2)oc2nc(CCC(F)(F)F)c(-c3cccc(C(=O)NC(C)(C#N)C(C)C)c3)cc12] | 581.2 | 581.2 | 1.88 |
| 11005 | B | 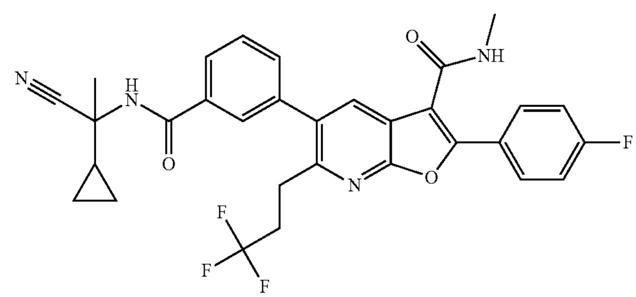 [SMILES: CNC(=O)c1c(-c2ccc(F)cc2)oc2nc(CCC(F)(F)F)c(-c3cccc(C(=O)NC(C)(C#N)C4CC4)c3)cc12] | 579.2 | 579.3 | 1.92 |
| 11008 | A | 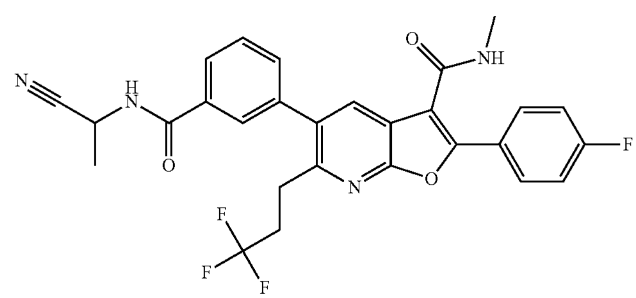 [SMILES: CNC(=O)c1c(-c2ccc(F)cc2)oc2nc(CCC(F)(F)F)c(-c3cccc(C(=O)NC(C)C#N)c3)cc12] | 539.2 | 539.1 | 1.67 |
| 11011 | A | 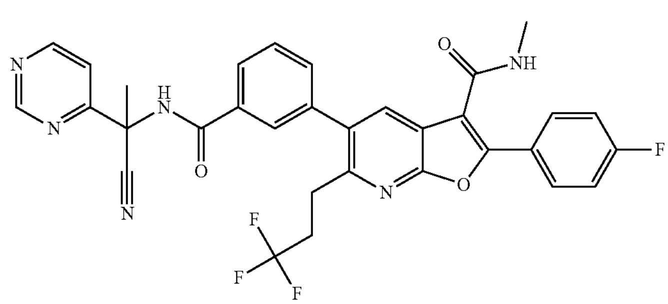 [SMILES: CNC(=O)c1c(-c2ccc(F)cc2)oc2nc(CCC(F)(F)F)c(-c3cccc(C(=O)NC(C)(C#N)c4ccncn4)c3)cc12] | 617.2 | 617.3 | 1.50 |

-continued
| Cmpd # | LC Method | Structure | MS (MHZ)+ Calcd. | MS (MHZ)+ Observ. | Retention Time (min) |
|---|---|---|---|---|---|
| 11012 | B | 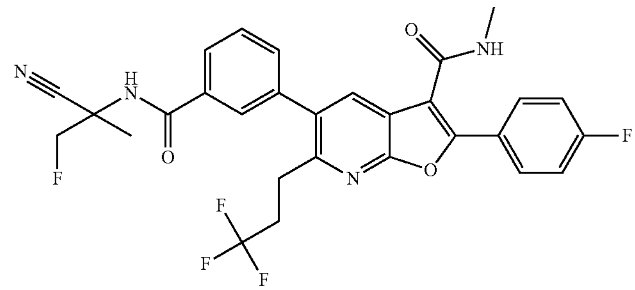 [SMILES: CNC(=O)c1c(-c2ccc(F)cc2)oc2nc(CCC(F)(F)F)c(-c3cccc(C(=O)NC(C)(C#N)CF)c3)cc12] | 571.2 | 571.4 | 1.83 |
| 11013 | B | 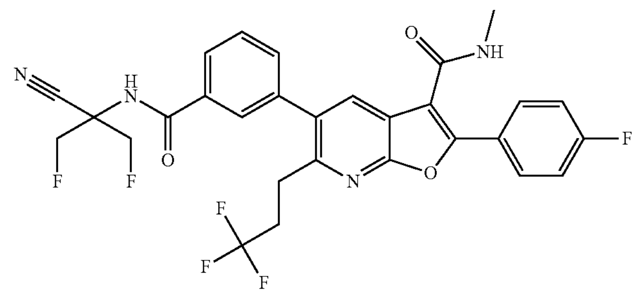 [SMILES: CNC(=O)c1c(-c2ccc(F)cc2)oc2nc(CCC(F)(F)F)c(-c3cccc(C(=O)NC(C#N)(CF)CF)c3)cc12] | 589.2 | 589.4 | 1.86 |
Preparation of Compounds 11006 and 11007
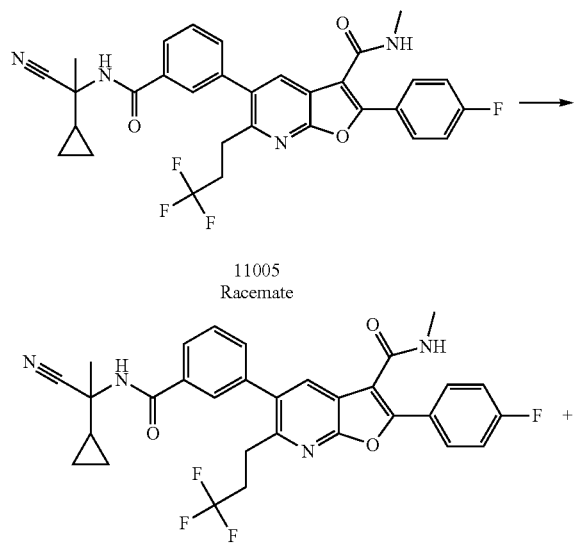
11005
Racemate
11006
Enantiomer A
11007
Enantiomer B
Compounds 11006 and 11007 were two enantiomers separated from sample 11005. The absolute stereochemistry is not determined.
Preparation of Compounds 11009 and 11010
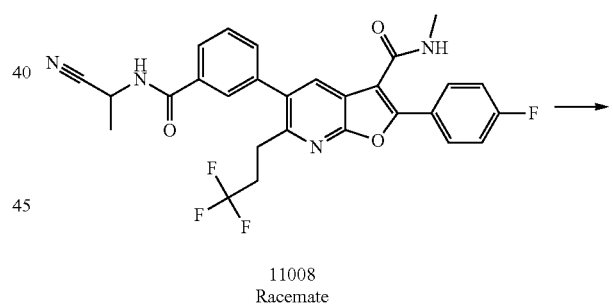
11008
Racemate
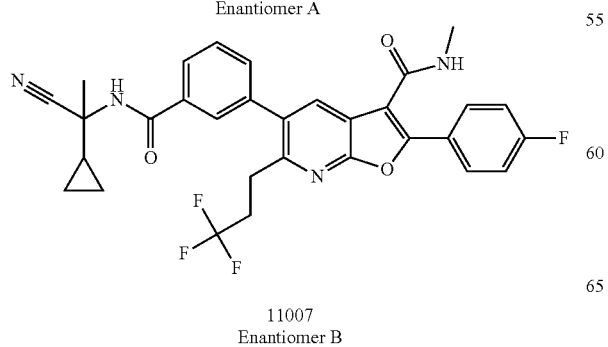
11009
Enantiomer A

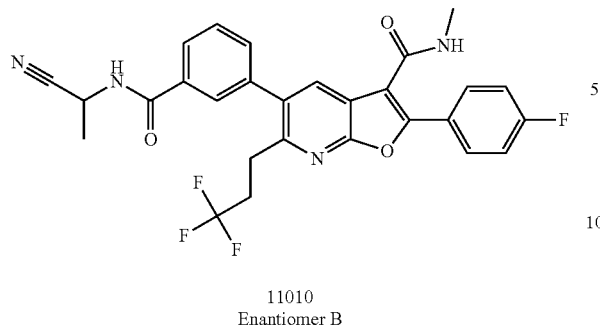

11010
Enantiomer B

Compounds 11009 and 11010 were two enantiomers separated from sample 11008. The absolute stereochemistry is not determined.

Preparation of Compound 12001

Compound 12001 was prepared via the same procedure towards compound 11001, using Compound 10001 as the starting material.

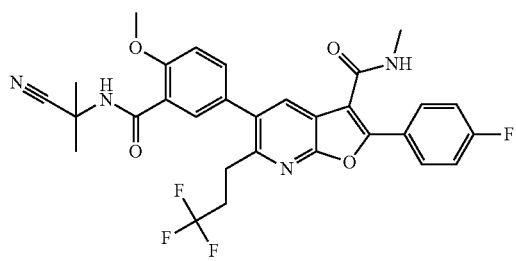 [SMILES: CNC(=O)c1c(-c2ccc(F)cc2)oc2nc(CCC(F)(F)F)c(-c3ccc(OC)c(C(=O)NC(C)(C)C#N)c3)cc12]

12001

| | |
|---|---|
| MS (MHZ)⁺ Calcd. | 583.2 |
| MS (MHZ)⁺ Observ. | 583.1 |
| Retention Time | 1.69 min |
| | LC Condition |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 12002

Compound 12002 was prepared via the same procedure towards compound 11001, using Compound 10002 as the starting material.

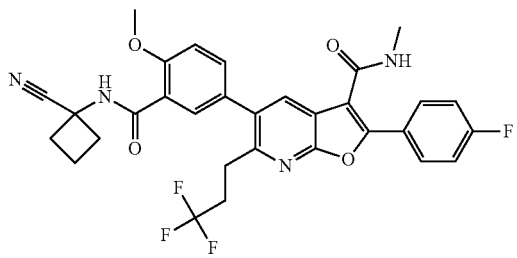 [SMILES: CNC(=O)c1c(-c2ccc(F)cc2)oc2nc(CCC(F)(F)F)c(-c3ccc(OC)c(C(=O)NC4(C#N)CCC4)c3)cc12]

12002

| | |
|---|---|
| MS (MHZ)⁺ Calcd. | 595.2 |
| MS (MHZ)⁺ Observ. | 595.3 |
| Retention Time | 1.93 min |
| | LC Condition |
| Solvent A | 5% ACN:95% Water:10mM Ammonium Actetate |
| Solvent B | 95% ACN:5% Water:10mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Preparation of Compound 12003

Compound 12003 was prepared via the same procedure towards compound 11001, using Compound 10003 as the starting material.

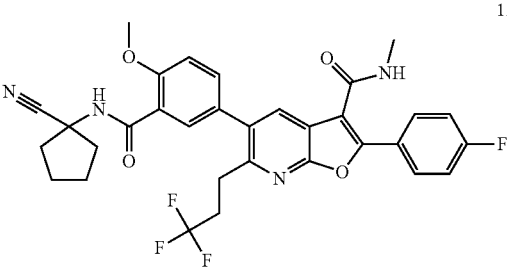

12003

| | |
|---|---|
| MS (M-H)+Calcd. | 609.2 |
| MS (M-H)+Observ. | 609.3 |
| Retention Time | 1.95 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Preparation of Intermediate 6

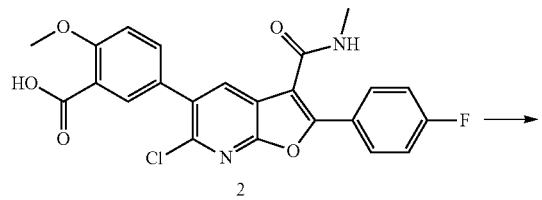

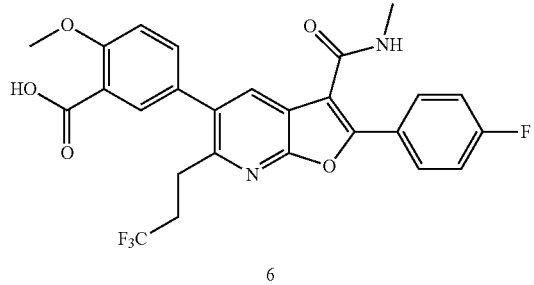

Intermediate 6 was prepared via the same procedure towards compound 11001, using Intermediate 2 as the starting material.

| | Compound 6 |
|---|---|
| MS (MHZ)+ Calcd. | 517.1 |
| MS (MHZ)+ Observ. | 517.0 |
| Retention Time | 1.63 min |
| | LC Condition |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 12004 and 12005

$iPr_2NEt$ or $Et_3N$ (2 eq.) and HATU or HCTU or DEBPT (1.3 eq.) were added into a solution of Compound 6 (1 eq.) and amine (1.3 eq.) in DMF or THF. The reaction was stirred at room temperature or 85° C. for 30 minutes to 72 hours. The desired product was isolated by preparative HPLC system.

| | LC Condition |
|---|---|
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Structure | MS (MHZ)+ Calcd. | MS (MHZ)+ Observ. | Retention Time (min) |
|---|---|---|---|---|
| 12004 | 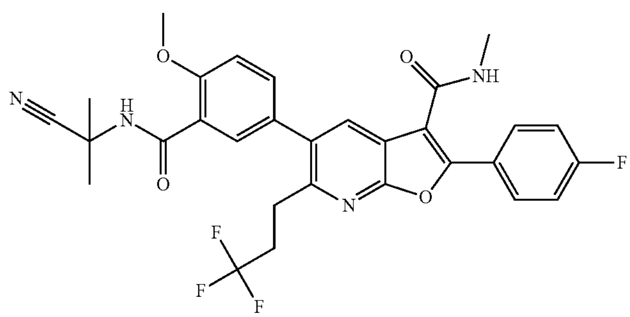 [SMILES: CNC(=O)c1c(-c2ccc(F)cc2)oc2nc(CCC(F)(F)F)c(-c3ccc(OC)c(C(=O)NC(C)(C)C#N)c3)cc12] | 611.2 | 611.2 | 1.88 |
| 12005 | 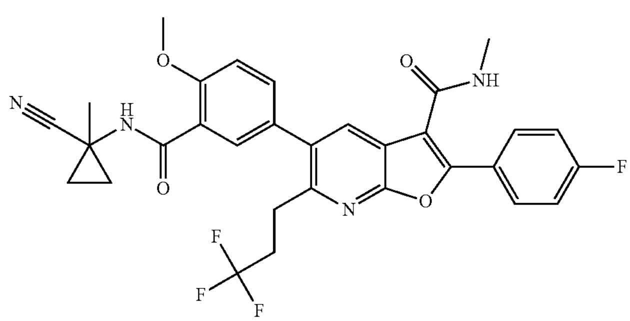 | 609.2 | 609.1 | 1.82 |

Preparation of Intermediate 9

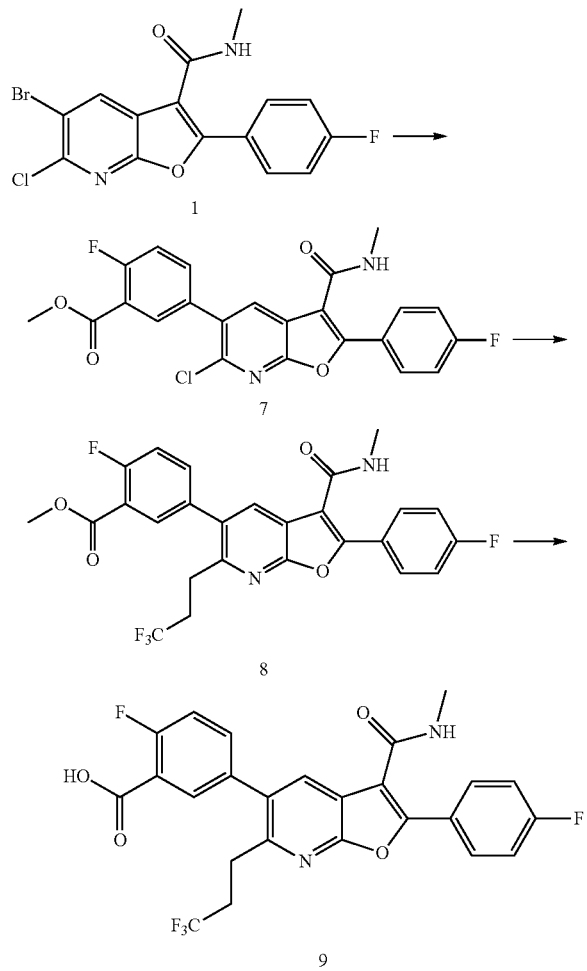

Step 1: To a mixture of Compound 1 (1 g), (4-fluoro-3-(methoxycarbonyl)phenyl)boronic acid (0.62 g) and $Cs_2CO_3$ (1.70 g) in dioxane (40 mL) and water (4 mL) was added $Pd(PPh_3)_4$ (0.30 g). The mixture was flushed with nitrogen and then heated at 85° C. for 16 hours. The mixture was diluted with water and then extracted with EtOAc (2×100 mL). The organic layers were combined, washed with brine (100 mL), dried over $MgSO_4$ and concentrated under vacuum. The residue was purified by titration with EtOAc to give Compound 7.

| Compound 7 | |
|---|---|
| MS (MHZ)$^+$ Calcd. | 457.1 |
| MS (MHZ)$^+$ Observ. | 457.0 |
| Retention Time | 1.76 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 2: A mixture of Compound 7 (270 mg), potassium trifluoro(3,3,3-trifluoropropyl)borate (422 mg), cesium carbonate (578 mg), dicyclohexyl(2',6'-diisopropoxy-[1,1'-biphenyl]-2-yl)phosphine (110 mg) and diacetoxypalladium (26.5 mg) in toluene (10 mL) and water (1.0 mL) was heated at 80° C. for 16 hours. The mixture was diluted with EtOAc (20 mL), washed with water (20 mL), brine (20 mL), dried over $MgSO_4$ and concentrated under vacuum to give Compound 8 which was used as was.

| Compound 8 | |
|---|---|
| MS (MHZ)$^+$ Calcd. | 519.1 |
| MS (MHZ)$^+$ Observ. | 519.1 |
| Retention Time | 1.94 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 3: To a suspension of Compound 8 (50 mg) in acetone (3 mL) and water (1 mL) was added NaOH (1.93 mL, 1N). The mixture was heated at 80° C. for 4 hours. The mixture was acidified by 1N HCl to pH ~3. The precipitate was collected by filtration to give Compound 9 which was used as was.

| Compound 9 | |
|---|---|
| MS (MHZ)$^+$ Calcd. | 505.1 |
| MS (MHZ)$^+$ Observ. | 505.0 |
| Retention Time | 1.64 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 11004, 11005, 11008, 11011, 11012 and 11013

$iPr_2NEt$ or $Et_3N$ (2 eq.) and HATU or HCTU or DEBPT (1.3 eq.) were added into a solution of Compound 9 (1 eq.) and amine (1.3 eq.) in DMF or THF. The reaction was stirred at room temperature or 85° C. for 30 minutes to 72 hours. The desired product was isolated by preparative HPLC system.

| LC Condition A | |
|---|---|
| Solvent A | 90% Water -10% Methanol-0.1% TFA |
| Solvent B | 10% Water -90% Methanol-0.1% TFA |

-continued

| LC Condition A | |
|---|---|
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| LC Condition B | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

| Cmpd # | LC Method | Structure | Coupling/ Base Agent Used | MS (MHZ)+ Calcd. | MS (MHZ)+ Observ. | Retention Time (min) |
|---|---|---|---|---|---|---|
| 13001 | B | 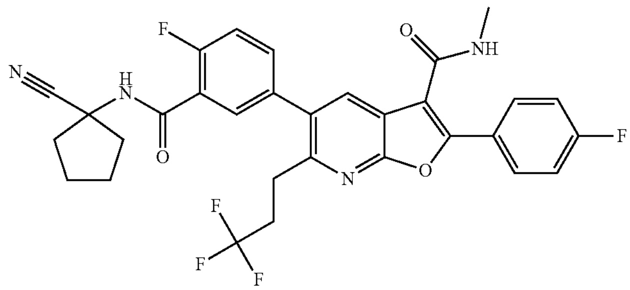 [SMILES: CNC(=O)c1c(-c2ccc(F)cc2)oc2nc(CCC(F)(F)F)c(-c3ccc(F)c(C(=O)NC4(C#N)CCCC4)c3)cc12] | HATU/ iPr$_2$NEt | 597.2 | 597.3 | 1.94 |
| 13002 | B | 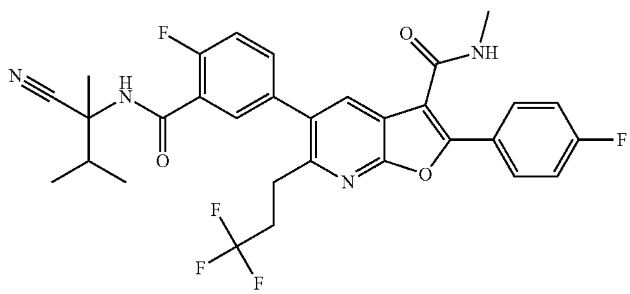 [SMILES: CNC(=O)c1c(-c2ccc(F)cc2)oc2nc(CCC(F)(F)F)c(-c3ccc(F)c(C(=O)NC(C)(C#N)C(C)C)c3)cc12] | HATU/ iPr$_2$NEt | 599.2 | 599.3 | 1.96 |
| 13003 | A | 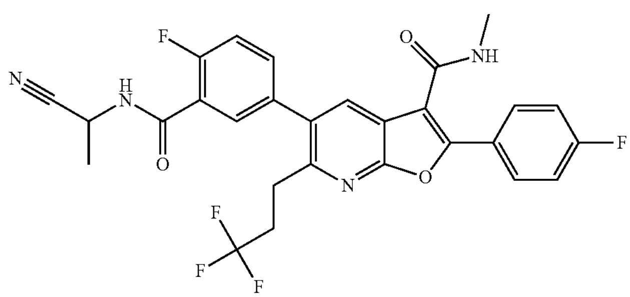 [SMILES: CNC(=O)c1c(-c2ccc(F)cc2)oc2nc(CCC(F)(F)F)c(-c3ccc(F)c(C(=O)NC(C)C#N)c3)cc12] | HATU/ iPr$_2$NEt | 557.2 | 557.0 | 1.57 |
| 13006 | B | 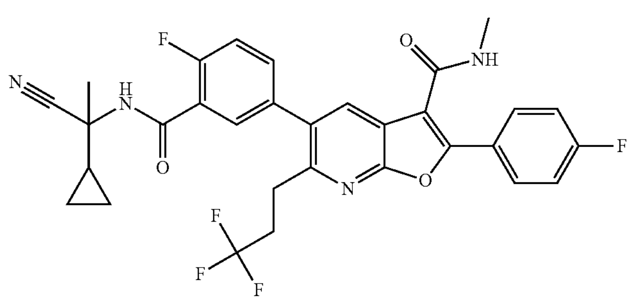 [SMILES: CNC(=O)c1c(-c2ccc(F)cc2)oc2nc(CCC(F)(F)F)c(-c3ccc(F)c(C(=O)NC(C)(C#N)C4CC4)c3)cc12] | HATU/ iPr$_2$NEt | 597.2 | 597.4 | 1.91 |

Preparation of Compounds 13004 and 13005

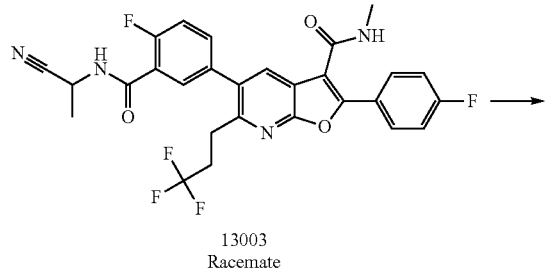

13003
Racemate

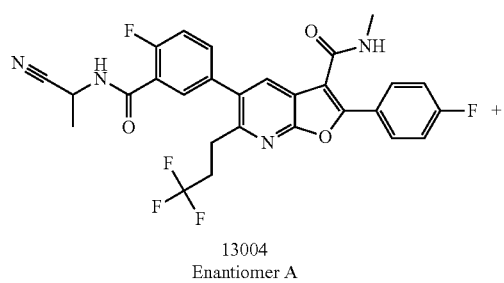

13004
Enantiomer A

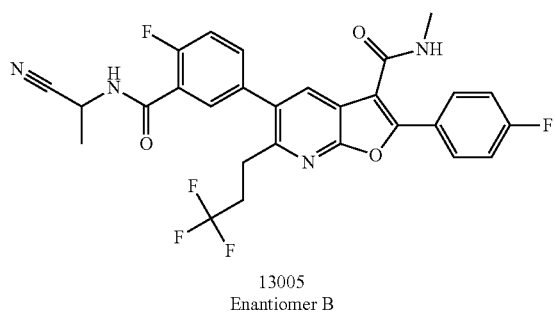

13005
Enantiomer B

Compounds 13004 and 13005 were two enantiomers separated from sample 13003. The absolute stereochemistry is not determined.

Preparation of Compounds 13007 and 13008

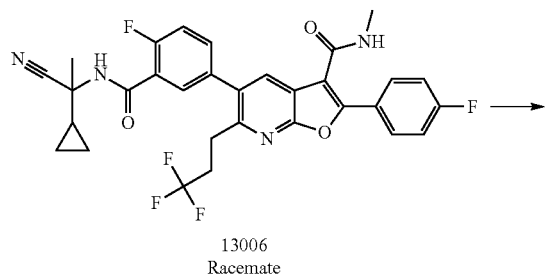

13006
Racemate

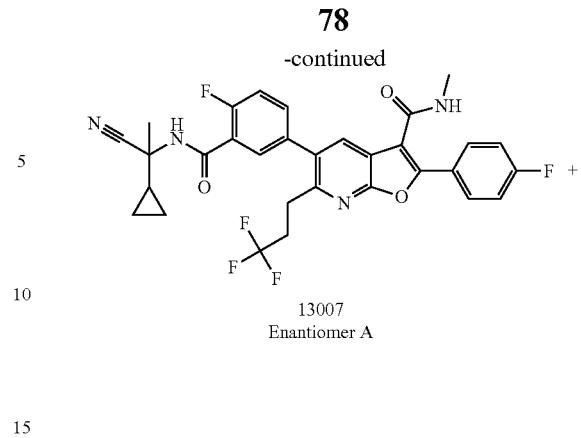

13007
Enantiomer A

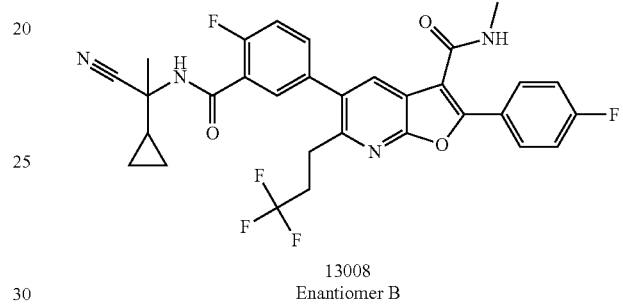

13008
Enantiomer B

Compounds 13007 and 13008 were two enantiomers separated from sample 13006. The absolute stereochemistry is not determined.

Chiral separation and purity analysis of Compounds 13007 and 13008:

Chiralcel OD-H preparative column, 30×250 mm, 5 μm

Mobile Phase: 10% MeOH (0.1% DEA) in $CO_2$, 150 bar

Temp: 35° C.

Flow rate: 70.0 mL/min. for 22 min.

UV monitored @316 nm

Injection: 0.5 ml of ~40 mg/mL solution in 1:1 MeOH:CHCl3

Retention Time: 15.25 minutes (Compound 13007) and 17.68 minutes (Compound 13008)

Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Compound 13308 was further recrystallized from a mixed solution of EtOH and $H_2O$ to give a white solid.

Characterization of Compound 13308 a. Optical rotation
   Result: $[\alpha]_d^{20°\,C.}=-33.48°$ (3.435 mg/ml, CHCl$_3$)
b. Mass spectrum:
   Mass Range: m/z 120-1200
   Ionization and Mode: Electrospray ionization, positive ion mode
   Result: ES$^+$=597.3
c. Elemental Analysis: % composition difference ($\Delta$)=experimental−theoretical (Acceptance criterion: $\Delta\leq\pm0.4$)
   Result: C$_{31}$H$_{25}$F$_5$N$_4$O$_3$.0.06H$_2$O: $\Delta$C=−0.09%; $\Delta$H=−0.19%; $\Delta$N=+0.06%
d. Proton Spectrum:
   Experimental: 7.3 mg sample dissolved in 600 μl DMSO-4d, 4 scans, 32K points at room temperature. The $^1$H chemical shifts are referenced to TMS at 0.0 ppm.
$^1$H NMR (500 MHz, DMSO-d$_6$) δ 9.06 (s, 1H), 8.54 (q, J=4.4 Hz, 1H), 8.07 (dd, J=9.0, 5.5 Hz, 2H), 7.97 (s, 1H), 7.69 (m, 1H), 7.66 (m, 1H), 7.48 (t, J=8.5 Hz, 1H), 7.43 (dd, J=8.8, 7.3 Hz, 2H), 3.03 (dd, J=9.1, 6.6 Hz, 2H), 2.83 (d, J=4.7 Hz, 3H), 2.79 (m, 2H), 1.67 (s, 3H), 1.50 (m, 1H), 0.64 (m, 3H), 0.53 (m, 1H)
e. Carbon Spectrum:
   Experimental: 7.3 mg sample dissolved in 600 μl DMSO-d$_6$. Carbon resonance frequency is 125.73 MHz. 1024 scans, 32K points at room temperature. The $^{13}$C chemical shifts are referenced to TMS at 0.0 ppm.
$^{13}$C NMR (125.73 MHz, DMSO-d$_6$) δ 163.4, 162.4, 163.0 (d, J=248.9 Hz), 158.8, 158.7 (d, J=250.7 Hz), 152.0, 151.4, 135.0 (d, J=3.6 Hz), 133.6 (d, J=8.2 Hz), 131.9, 131.8, 130.8, 129.9 (d, J=9.1 Hz), 127.5 (q, J=277.0 Hz), 125.2 (d, J=2.7 Hz), 123.9 (d, J=15.4 Hz), 118.8, 117.5, 116.4 (d, J=22.7 Hz), 116.1 (d, J=22.7 Hz), 112.6, 52.2, 31.3 (q, J=27.3 Hz), 27.1, 26.2, 23.8, 18.6, 2.9, 1.7.
f. Fluorine Spectrum
   Experimental: 7.3 mg sample dissolved in 600 μl DMSO-d$_6$, fluorine resonance frequency is 470.45 MHz, 16 scans, 64K points at room temperature. The $^{19}$F chemical shifts are referenced to CFCl$_3$ at 0.0 ppm.

$^{19}$F NMR (470.45 MHz, DMSO-d$_6$) δ −64.74, −109.85, −115.68.

Preparation of Intermediate 10

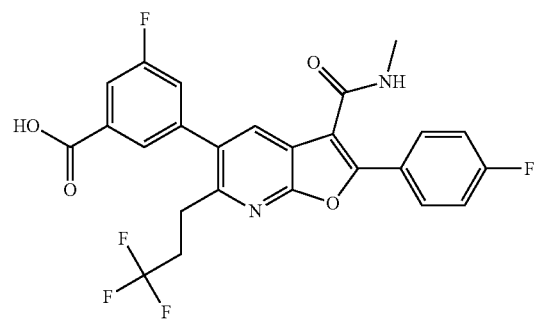

Intermediate 10 was prepared via the same procedure towards Intermediate 9, using methyl 3-fluoro-5-(4,4,5,5-tetramethyl-1,3,2-dioxaborolan-2-yl)benzoate as the starting material in Step 1.

Preparation of Compounds 14001 and 14002 iPr$_2$NEt or Et$_3$N (2 eq.) and HATU or HCTU or DEBPT (1.3 eq.) were added into a solution of Compound 10 (1 eq.) and amine (1.3 eq.) in DMF or THF. The reaction was stirred at room temperature or 85° C. for 30 minutes to 72 hours. The desired product was isolated by preparative HPLC system.

| LC Condition | |
|---|---|
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | Structure | MS (MHZ)$^+$ Calcd. | MS (MHZ)$^+$ Observ. | Retention Time (min) |
|---|---|---|---|---|
| 14001 | 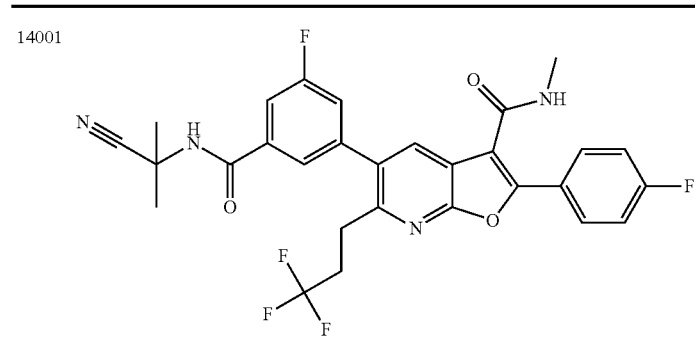 | 571.2 | 571.1 | 1.89 |

-continued

| Cmpd # | Structure | MS (MHZ)+ Calcd. | MS (MHZ)+ Observ. | Retention Time (min) |
|---|---|---|---|---|
| 14002 | 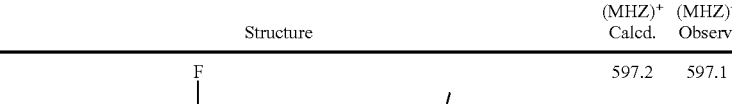 | 597.2 | 597.1 | 1.98 |

Preparation of Intermediate 14

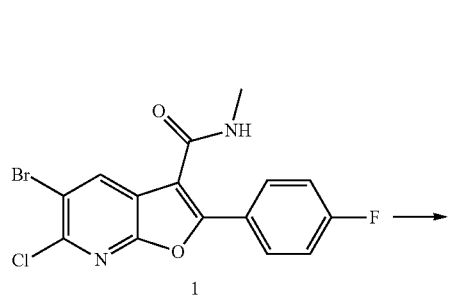

1

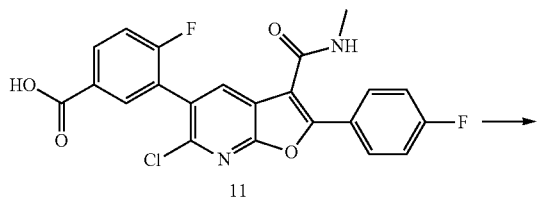

11

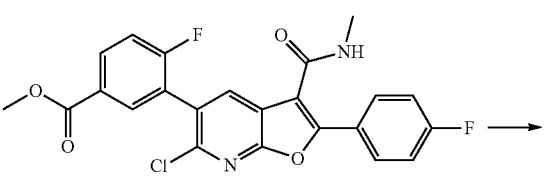

12

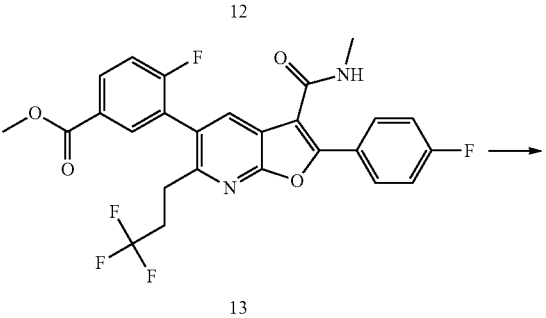

13

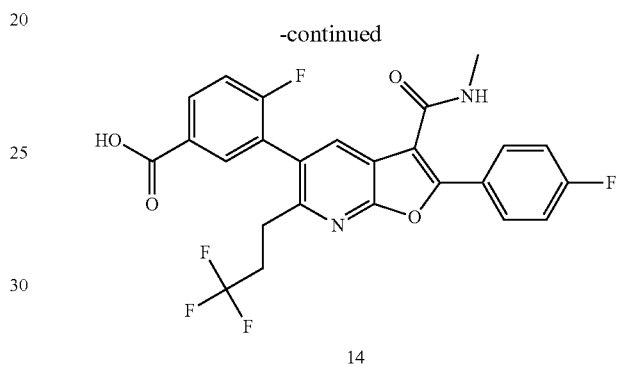

14

Step 1: To a mixture of Compound 1 (500 mg), 3-borono-4-fluorobenzoic acid (264 mg) and Cs2CO3 (849 mg) in DMF (15 mL) and water (1.5 mL) was added Pd(PPh₃)₄ (151 mg). The mixture was flushed with nitrogen and then heated at 85° C. for 6 hours. The mixture was diluted with water and then extracted with EtOAc (2×50 mL). The organic layers were combined, washed with brine (50 mL) and concentrated under vacuum. The residue was purified by titration with EtOAc to give Compound 11.

| Compound 11 | |
|---|---|
| MS (MHZ)+ Calcd. | 443.1 |
| MS (MHZ)+ Observ. | 442.9 |
| Retention Time | 1.67 min |
| | LC Condition |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 2: A mixture of Compound 2 (70 mg), iodomethane (0.049 mL) and $Cs_2CO_3$ (103 mg) in MeOH (3 mL) in a sealed tube was heated at 80° C. for 6 hours. The mixture was diluted with MeOH. The solid was removed by filtration. The filtrate was concentrated to give a residue which was purified by preparative HPLC system.

| Compound 12 | |
|---|---|
| MS (MHZ)+ Calcd. | 457.1 |
| MS (MHZ)+ Observ. | 456.9 |
| Retention Time | 1.91 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 3: A mixture of Compound 12 (25 mg), potassium trifluoro(3,3,3-trifluoropropyl)borate (39.1 mg), cesium carbonate (53.5 mg), dicyclohexyl(2',6'-diisopropoxy-[1,1'-biphenyl]-2-yl)phosphine (10.21 mg) and diacetoxypalladium (2.46 mg) in toluene (2 mL)/water (0.2 mL) was degassed and heated at 80° C. for 16 hours. The mixture was diluted with EtOAc (10 mL), then washed with water (10 mL) and brine (10 mL). The organic layer was separated and concentrated under vacuum. The residue was purified by titration with EtOAc to Compound 13.

| Compound 13 | |
|---|---|
| MS (MHZ)+ Calcd. | 519.1 |
| MS (MHZ)+ Observ. | 519.0 |
| Retention Time | 2.09 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 4: To a suspension of Compound 13 (15 mg) in THF (3 mL) and water (0.3 mL) was added NaOH (0.5 mL, 1N). The mixture was heated at 80° C. for 4 hours. The mixture was acidified with 1N HCl to pH ~3. All solvents were removed under vacuum to give Compound 14 which was used as was.

| Compound 14 | |
|---|---|
| MS (MHZ)+ Calcd. | 505.1 |
| MS (MHZ)+ Observ. | 505.0 |
| Retention Time | 1.98 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 15001 and 15002 iPr$_2$NEt or Et$_3$N (2 eq.) and HATU or HCTU or DEBPT (1.3 eq.) were added into a solution of Compound 14 (1 eq.) and amine (1.3 eq.) in DMF or THF. The reaction was stirred at room temperature or 85° C. for 30 minutes to 72 hours. The desired product was isolated by preparative HPLC system.

| LC Condition | |
|---|---|
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

| Cmpd # | Structure | MS (MHZ)+ Calcd. | MS (MHZ)+ Observ. | Retention Time (min) |
|---|---|---|---|---|
| 15001 | 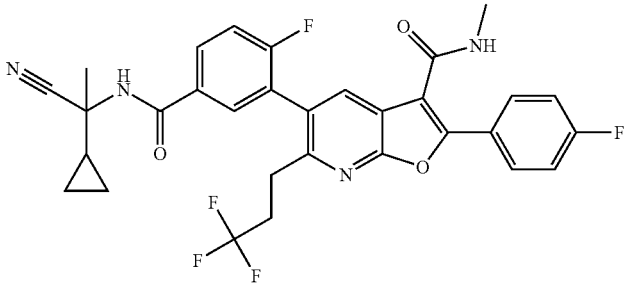 [SMILES: CNC(=O)c1c(-c2ccc(F)cc2)oc2nc(CCC(F)(F)F)c(-c3cc(C(=O)NC(C)(C#N)C4CC4)ccc3F)cc12] | 597.2 | 597.1 | 2.00 |

| Cmpd # | Structure | MS (MHZ)+ Calcd. | MS (MHZ)+ Observ. | Retention Time (min) |
|---|---|---|---|---|
| 15002 | 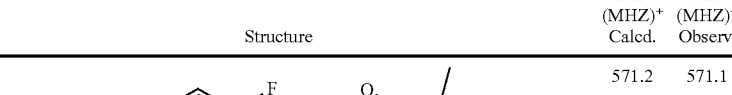 | 571.2 | 571.1 | 1.71 |

Preparation of Intermediate 15

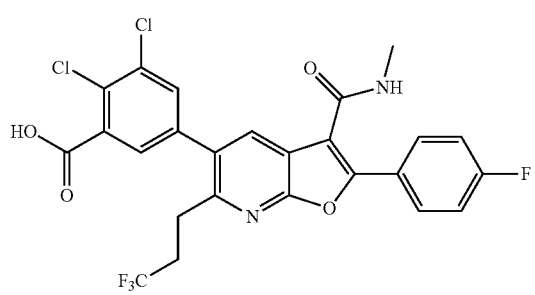

Intermediate 15 was prepared via the same procedure towards Intermediate 9, using methyl 2,3-dichloro-5-(4,4,5,5-tetramethyl-1,3,2-dioxaborolan-2-yl)benzoate as the starting material in Step 1.

| Compound 15 | |
|---|---|
| MS (MHZ)+ Calcd. | 555.0 |
| MS (MHZ)+ Observ. | 555.0 |
| Retention Time | 1.97 min |
| LC Condition | |
| Solvent A | 90% Water-10% Methanol-0.1% TFA |
| Solvent B | 10% Water-90% Methanol-0.1% TFA |
| Start % B | 60 |
| Final % B | 90 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 16001

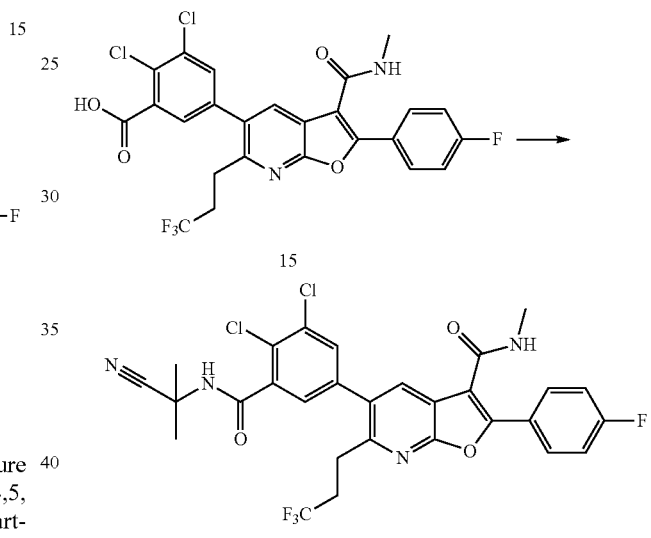

To a solution of Compound 15 (8 mg), 2-amino-2-methylpropanenitrile (2.424 mg, 0.029 mmol) and HATU (8.22 mg, 0.022 mmol) in DMF (1 mL) was added iPr$_2$NEt (10.06 μl). The mixture was stirred at room temperature for 4 hours. The product was isolated by preparative HPLC system.

| Compound 16001 | |
|---|---|
| MS (MHZ)+ Calcd. | 621.1 |
| MS (MHZ)+ Observ. | 621.1 |
| Retention Time | 1.59 min |
| LC Condition | |
| Solvent A | 90% Water-10% Methanol-0.1% TFA |
| Solvent B | 10% Water-90% Methanol-0.1% TFA |
| Start % B | 60 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Intermediate 16

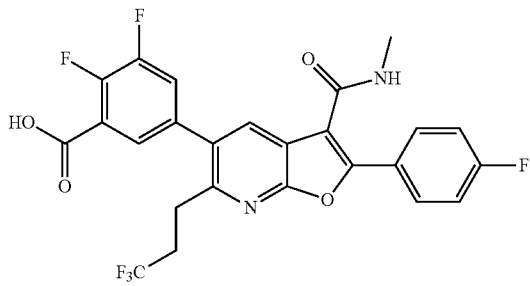

Intermediate 16 was prepared via the same procedure towards Intermediate 9, using (3,4-difluoro-5-(methoxycarbonyl)phenyl)boronic acid as the starting material in Step 1.

| Compound 16 | |
|---|---|
| MS (MHZ)+ Calcd. | 523.1 |
| MS (MHZ)+ Observ. | 523.4 |
| Retention Time | 1.41 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Preparation of Compound 17001

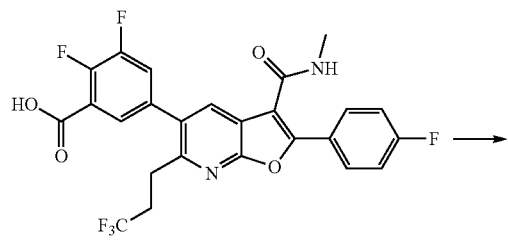

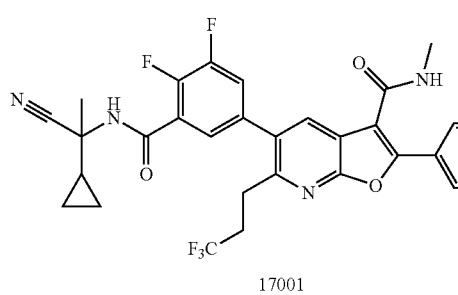

| Compound 18001 | |
|---|---|
| MS (MHZ)+ Calcd. | 615.2 |
| MS (MHZ)+ Observ. | 615.1 |
| Retention Time | 1.84 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 18001

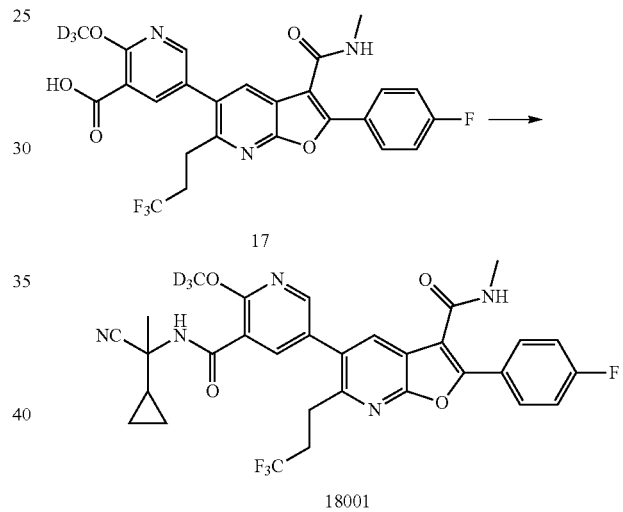

To a solution of Compound 17 (15 mg), 2-amino-2-cyclopropylpropanenitrile (9.52 mg) and HATU (16.44 mg) in DMF (1 mL) was added iPr$_2$NEt (0.02 mL). The mixture was stirred at room temperature for 4 hours. The product was isolated by preparative HPLC system.

| Compound 18001 | |
|---|---|
| MS (MHZ)+ Calcd. | 613.2 |
| MS (MHZ)+ Observ. | 613.2 |
| Retention Time | 2.00 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Intermediate 19

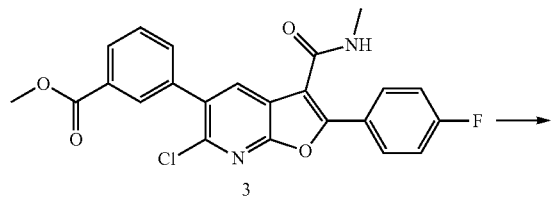

3

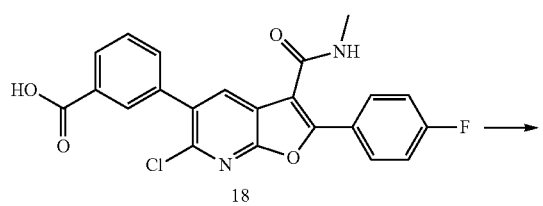

18

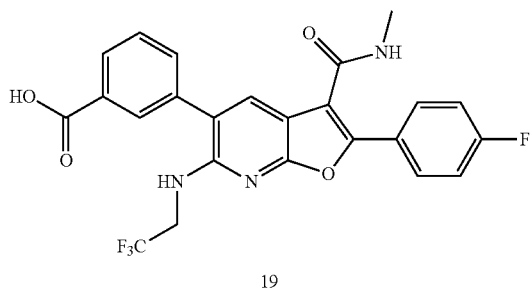

19

Step 1: A mixture of Compound 3 (800 mg) and NaOH (9.12 mL, 1N) in THF (30 mL) and water (15 mL) was heated at 80° C. for 6 hours. The mixture was acidified by 1N HCl to pH ~5 and extracted with EtOAc (2×50 mL). The organic layers were combined, washed with brine (50 mL), dried over MgSO₄ and concentrated under vacuum to give Compound 18.

| Compound 18 | |
|---|---|
| MS (MHZ)⁺ Calcd. | 425.1 |
| MS (MHZ)⁺ Observ. | 425.0 |
| Retention Time | 1.49 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 2: A mixture of Compound 18 (175 mg), chloro[2-(dicyclohexylphosphino)-3,6-dimethoxy-2',4',6'-tri-i-propyl-1,1'-biphenyl][2-(2-aminoethyl)phenyl]palladium (II) (28.2 mg) and sodium 2-methylbutan-2-olate (194 mg) in dioxane (10 mL) was heated at 90° C. for 30 minutes. The mixture was diluted with EtOAc (20 mL), washed with water (20 mL), brine (20 mL), dried over MgSO₄ and concentrated under vacuum. The residue was purified by preparative HPLC system.

| Compound 19 | |
|---|---|
| MS (MHZ)⁺ Calcd. | 488.1 |
| MS (MHZ)⁺ Observ. | 488.0 |
| Retention Time | 1.91 min |
| LC Condition | |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 20001, 20002, 20005 and 20006 iPr₂NEt or Et₃N (2 eq.) and HATU or HCTU or DEBPT (1.3 eq.) were added into a solution of Compound 19 (1 eq.) and amine (1.3 eq.) in DMF or THF. The reaction was stirred at room temperature or 85° C. for 30 minutes to 72 hours. The desired product was isolated by preparative HPLC system.

| LC Condition A | |
|---|---|
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

| LC Condition B | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

| Cmpd # | LC Method | Structure | MS (MHZ)+ Calcd. | MS (MHZ)+ Observ. | Retention Time (min) |
|---|---|---|---|---|---|
| 20001 | B | 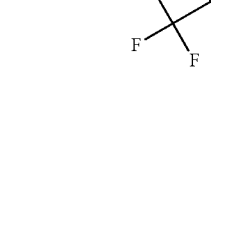 | 554.2 | 554.3 | 1.85 |
| 20002 | A | 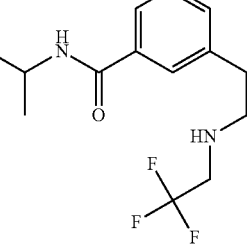 | 540.2 | 540.1 | 1.59 |
| 20005 | A | 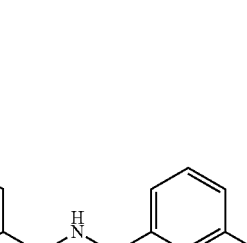 | 602.2 | 602.2 | 1.77 |
| 20006 | A | 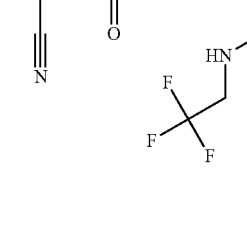 | 580.2 | 580.1 | 1.71 |

Preparation of Compounds 20003 and 20004

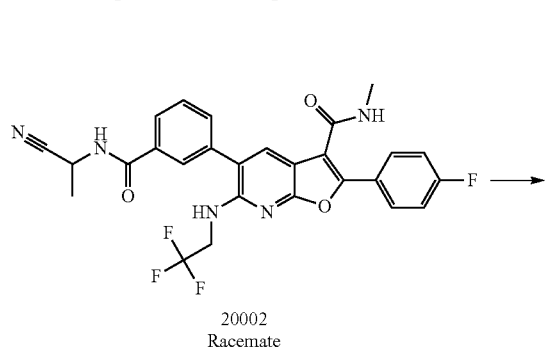

20002
Racemate

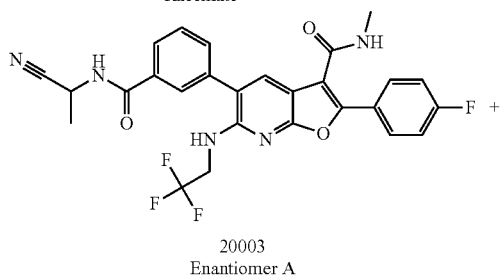

20003
Enantiomer A

+

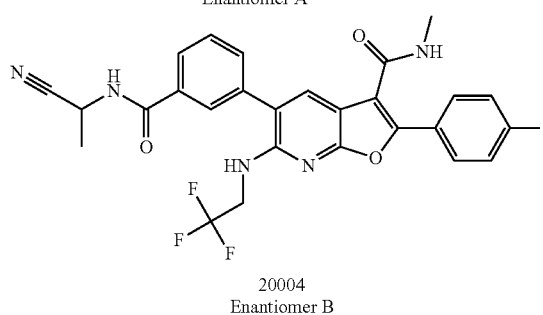

20004
Enantiomer B

Compounds 20003 and 20004 were two enantiomers separated from sample 20002. The absolute stereochemistry is not determined.

Preparation of Compounds 20007 and 20008

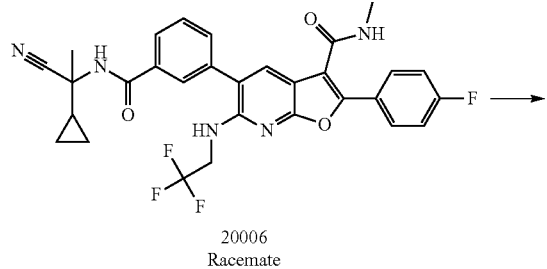

20006
Racemate

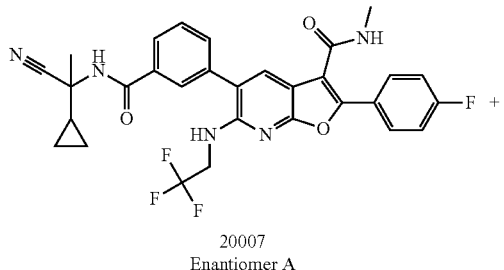

20007
Enantiomer A

+

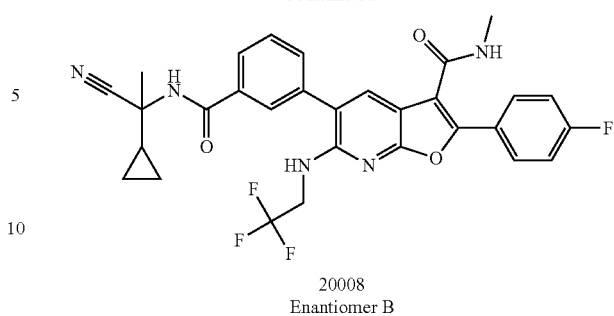

20008
Enantiomer B

Compounds 20007 and 20008 were two enantiomers separated from sample 20006. The absolute stereochemistry is not determined.

Preparation of Intermediate 20

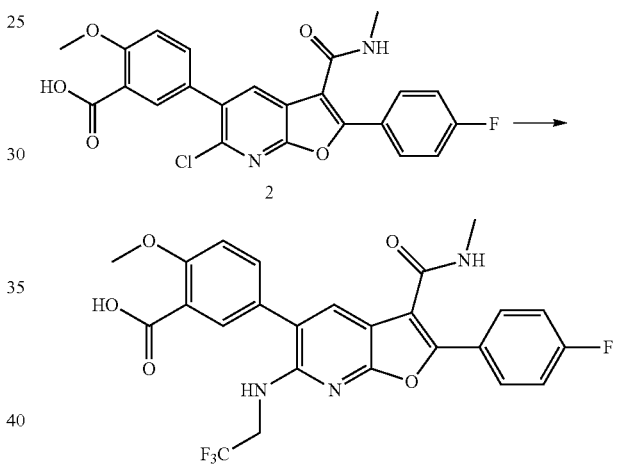

Intermediate 20 was prepared via the same procedure towards Intermediate 19 from Compound 18, using Compound 2 as the starting material.

| | Compound 20 |
|---|---|
| MS (MHZ)+ Calcd. | 518.1 |
| MS (MHZ)+ Observ. | 518.0 |
| Retention Time | 1.89 min |
| | LC Condition |
| Solvent A | 90% Water-10% Methanol-0.1% TFA |
| Solvent B | 10% Water-90% Methanol-0.1% TFA |
| Start % B | 30 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compound 21001

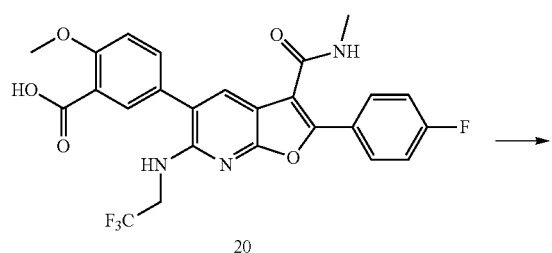

20

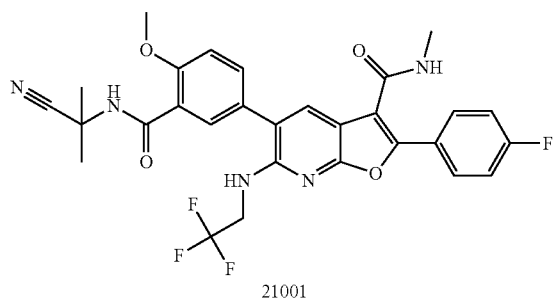

21001

To a solution of Compound 20 (20 mg), 2-amino-2-methyl-propanenitrile hydrochloride (9.32 mg, 0.077 mmol) and HATU (22.05 mg) in DMF (2 mL) was added iPr₂NEt (0.027 mL). The mixture was stirred at room temperature for 4 hours. The product was isolated by preparative HPLC system.

| Compound 21001 | |
|---|---|
| MS (MHZ)⁺ Calcd. | 584.2 |
| MS (MHZ)⁺ Observ. | 584.3 |
| Retention Time | 1.87 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Preparation of Intermediate 21

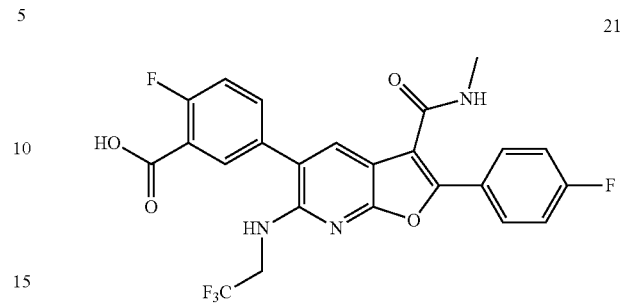

21

Intermediate 21 was prepared via the same procedure towards Intermediate 19, using Compound 7 as the starting material at step 1.

| Compound 21 | |
|---|---|
| MS (MHZ)⁺ Calcd. | 506.1 |
| MS (MHZ)⁺ Observ. | 506.0 |
| Retention Time | 1.60 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Preparation of Compounds 22001 and 22004 iPr₂NEt or Et₃N (2 eq.) and HATU or HCTU or DEBPT (1.3 eq.) were added into a solution of Compound 21 (1 eq.) and amine (1.3 eq.) in DMF or THF. The reaction was stirred at room temperature or 85° C. for 30 minutes to 72 hours. The desired product was isolated by preparative HPLC system.

| LC Condition | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

| Cmpd # | Structure | MS (MHZ)+ Calcd. | MS (MHZ)+ Observ. | Retention Time (min) |
|---|---|---|---|---|
| 22001 | 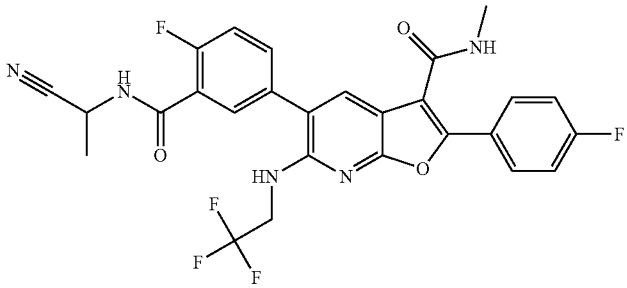 [SMILES: CNC(=O)c1c(-c2ccc(F)cc2)oc2nc(NCC(F)(F)F)c(-c3ccc(F)c(C(=O)NC(C)C#N)c3)cc12] | 558.2 | 558.3 | 1.77 |
| 22004 | 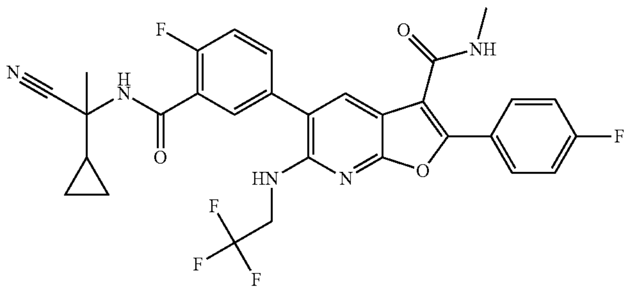 [SMILES: CNC(=O)c1c(-c2ccc(F)cc2)oc2nc(NCC(F)(F)F)c(-c3ccc(F)c(C(=O)NC(C)(C#N)C4CC4)c3)cc12] | 598.2 | 598.4 | 1.86 |
Preparation of Compounds 22002 and 22003
Compounds 22002 and 22003 were two enantiomers separated from sample 22001. The absolute stereochemistry is not determined.
Preparation of Compounds 22005 and 22006
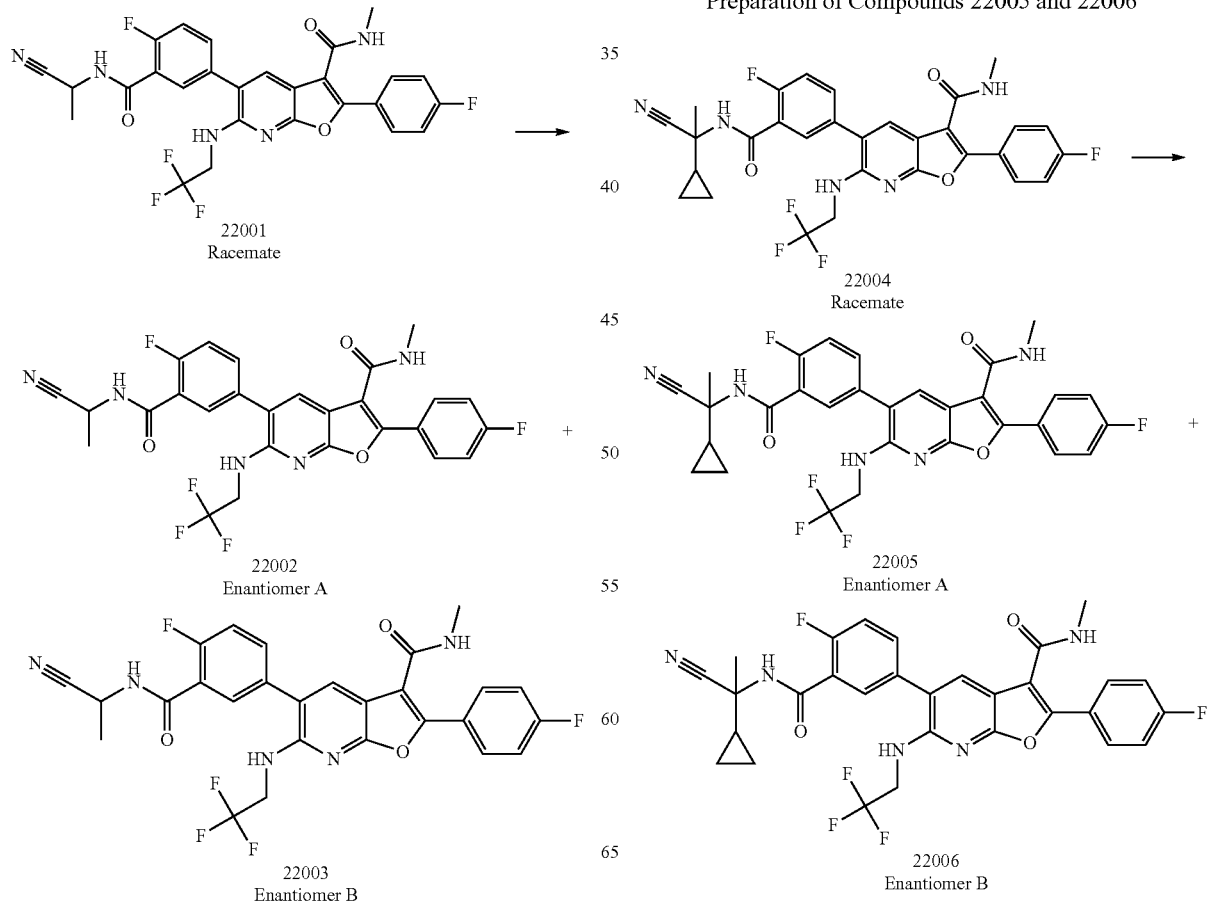

Compounds 22005 and 22006 were two enantiomers separated from sample 22004. The absolute stereochemistry is not determined.

Preparation of Intermediate 23

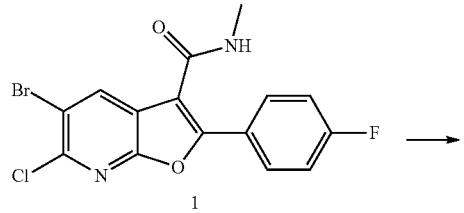

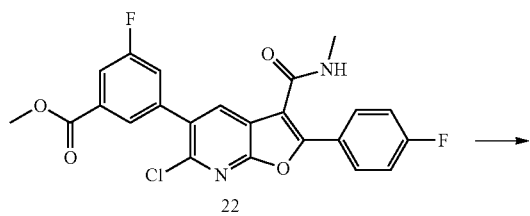

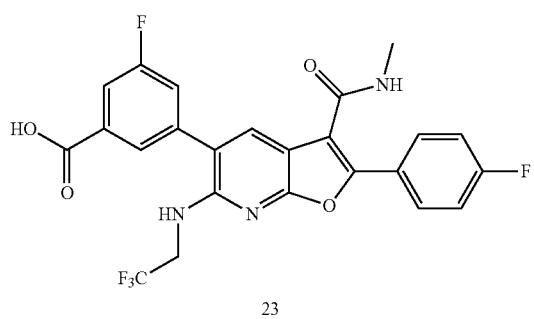

Step 1: Intermediate 22 was prepared via the same procedure towards Intermediate 7, using methyl 3-fluoro-5-(4,4,5,5-tetramethyl-1,3,2-dioxaborolan-2-yl)benzoate as the starting material.

| Compound 22 | |
|---|---|
| MS (MHZ)+ Calcd. | 457.1 |
| MS (MHZ)+ Observ. | 456.9 |
| Retention Time | 2.01 min |
| LC Condition | |
| Solvent A | 90% Water-10% Methanol-0.1% TFA |
| Solvent B | 10% Water-90% Methanol-0.1% TFA |
| Start % B | 50 |
| Final % B | 100 |

| Compound 22 | |
|---|---|
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Step 2: A mixture of Compound 22 (50 mg), 2,2,2-trifluoroethanamine (54.2 mg), chloro[2-(dicyclohexylphosphino)-3,6-dimethoxy-2',4',6'-tri-i-propyl-1,1'-biphenyl][2-(2-aminoethyl)phenyl]palladium (II) (17.49 mg) and sodium 2-methylbutan-2-olate (48.2 mg) in dioxane (3 mL) was heated at 65° C. for 20 minutes. The mixture was diluted with EtOAc (20 mL), washed with 1N HCl (20 mL) and brine (20 mL). The organic layer was dried over MgSO₄ and concentrated under vacuum. The residue was purified by preparative HPLC system to Compound 23.

| Compound 23 | |
|---|---|
| MS (MHZ)+ Calcd. | 506.1 |
| MS (MHZ)+ Observ. | 506.0 |
| Retention Time | 1.60 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 23001 and 23002 iPr₂NEt or Et₃N (2 eq.) and HATU or HCTU or DEBPT (1.3 eq.) were added into a solution of Compound 23 (1 eq.) and amine (1.3 eq.) in DMF or THF. The reaction was stirred at room temperature or 85° C. for 30 minutes to 72 hours. The desired product was isolated by preparative HPLC system.

| LC Condition | |
|---|---|
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |
| Column | Phenomenex LUNA C18, 30 × 2, 3 u |

| Cmpd # | Structure | MS (MHZ)+ Calcd. | MS (MHZ)+ Observ. | Retention Time (min) |
|---|---|---|---|---|
| 23001 | 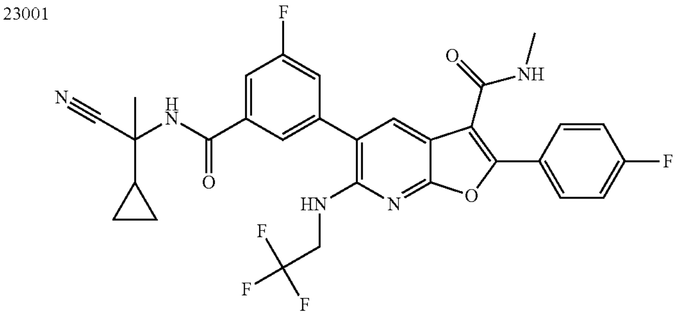 | 598.2 | 598.1 | 1.73 |
| 23002 | 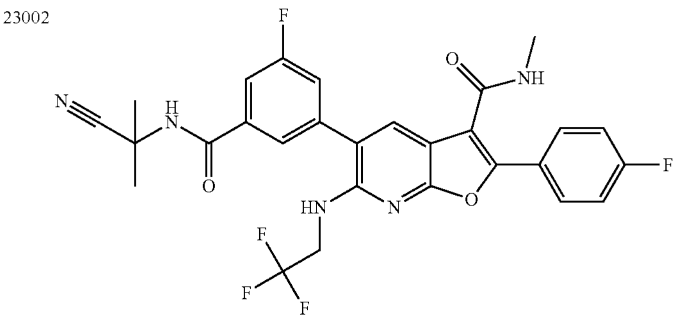 | 572.2 | 572.1 | 1.60 |

Preparation of Intermediate 26

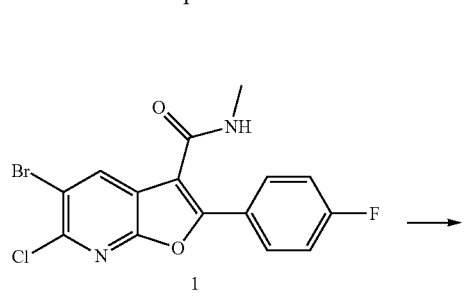

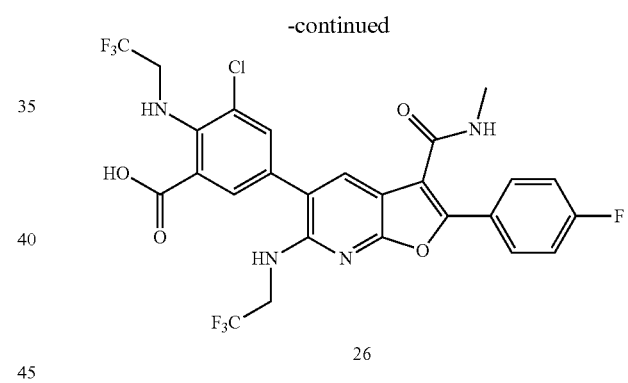

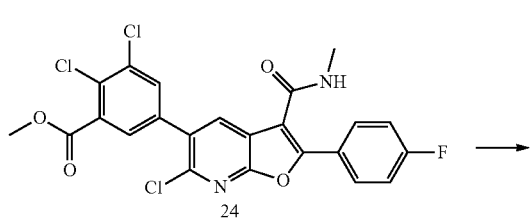

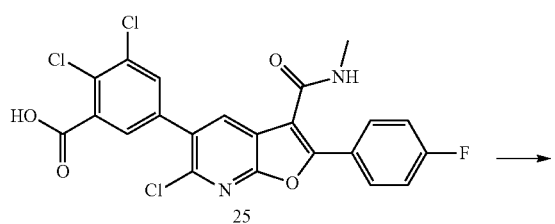

Step 1: Intermediate 24 was prepared via the same procedure towards Intermediate 7, using methyl 2,3-dichloro-5-(4,4,5,5-tetramethyl-1,3,2-dioxaborolan-2-yl)benzoate as the starting material.

| | Compound 24 |
|---|---|
| MS (MHZ)+ Calcd. | 507.0 |
| MS (MHZ)+ Observ. | 507.0 |
| Retention Time | 2.07 min |
| | LC Condition |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Step 2: To a suspension of Compound 24 (40 mg) in THF (3 mL) and water (1 mL) was added NaOH (1 mL, 1 N). The mixture was heated at 80° C. for 4 hours. The mixture was acidified with 1N HCl to pH ~3. The solid was collected by filtration to give Compound 25.

| Compound 25 | |
| --- | --- |
| MS (MHZ)+ Calcd. | 493.0 |
| MS (MHZ)+ Observ. | 493.2 |
| Retention Time | 1.38 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: A mixture of Compound 25 (37 mg), 2,2,2-trifluoroethanamine (37.1 mg), chloro[2-(dicyclohexylphosphino)-3,6-dimethoxy-2',4',6'-tri-i-propyl-1,1'-biphenyl][2-(2-aminoethyl)phenyl]palladium (II) (11.97 mg) and sodium 2-methylbutan-2-olate (33.0 mg) in dioxane (5 mL) was heated at 80° C. for 20 minutes. The mixture was diluted with EtOAc (20 mL), washed with 1N HCl (20 mL) and brine (20 mL). The organic layer was dried over MgSO₄ and concentrated under vacuum. The residue was purified by preparative HPLC system to Compound 26.

| Compound 26 | |
| --- | --- |
| MS (MHZ)+ Calcd. | 619.1 |
| MS (MHZ)+ Observ. | 619.1 |
| Retention Time | 1.69 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compound 24001

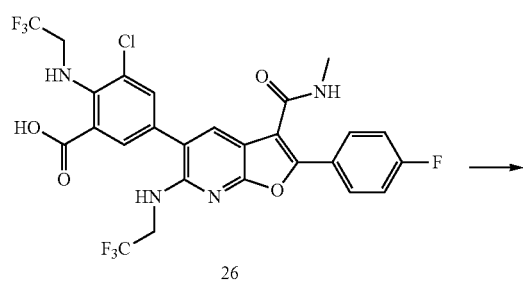

26

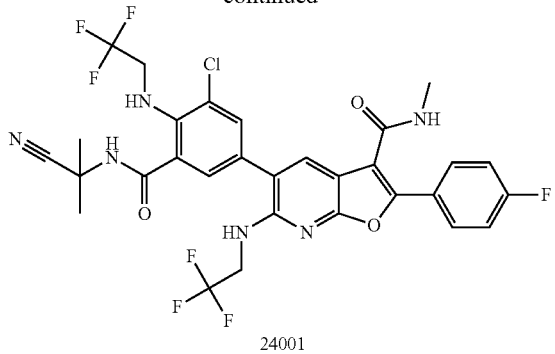

24001

To a solution of Compound 26 (15 mg), 2-amino-2-methylpropanenitrile (4.08 mg) and HATU (13.82 mg) in DMF (2 mL) was added iPr₂NEt (0.017 mL). The mixture was stirred at room temperature for 4 hours. The product was isolated by preparative HPLC system.

| Compound 24001 | |
| --- | --- |
| MS (MHZ)+ Calcd. | 685.2 |
| MS (MHZ)+ Observ. | 685.3 |
| Retention Time | 1.89 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Preparation of Intermediate 27

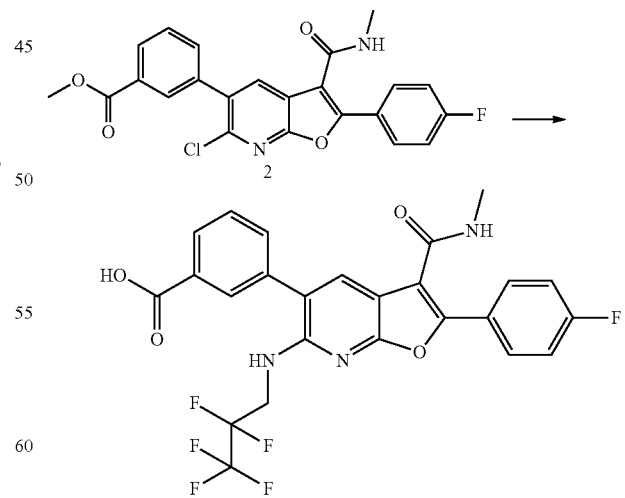

27

A mixture of Compound 2 (460 mg), 2,2,3,3,3-pentafluoropropan-1-amine (781 mg), chloro[2-(dicyclohexylphosphino)-3,6-dimethoxy-2',4',6'-tri-i-propyl-1,1'-biphenyl][2-

(2-aminoethyl)phenyl]palladium (II) (84 mg) and sodium 2-methylbutan-2-olate (577 mg) in dioxane (25 mL) was heated at 85° C. for 30 minutes. The mixture was diluted with EtOAc (100 mL), washed with water (100 mL) and brine (100 mL), dried over MgSO$_4$ and concentrated under vacuum to give Compound 27.

| Compound 27 | |
|---|---|
| MS (MHZ)$^+$ Calcd. | 538.1 |
| MS (MHZ)$^+$ Observ. | 538.0 |
| Retention Time | 1.79 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 30001-30003 iPr$_2$NEt or Et$_3$N (2 eq.) and HATU or HCTU or DEBPT (1.3 eq.) were added into a solution of Compound 27 (1 eq.) and amine (1.3 eq.) in DMF or THF. The reaction was stirred at room temperature or 85° C. for 30 minutes to 72 hours. The desired product was isolated by preparative HPLC system.

| LC Condition A | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 0.5 min hold at 0% B, 0-100% B over 4 minutes, then a 0.5-minute hold at 100% B |
| Flow Rate | 1 mL/min |
| Wavelength | 220 |
| Solvent Pair | ACN:Water:Ammonium Actetate |
| Column | Waters BEH C18, 2.0 × 50 mm, 1.7-μm particles |

| LC Condition B | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

| Cmpd # | LC Method | Structure | MS (MHZ)$^+$ Calcd. | MS (MHZ)$^+$ Observ. | Retention Time (min) |
|---|---|---|---|---|---|
| 30001 | B | 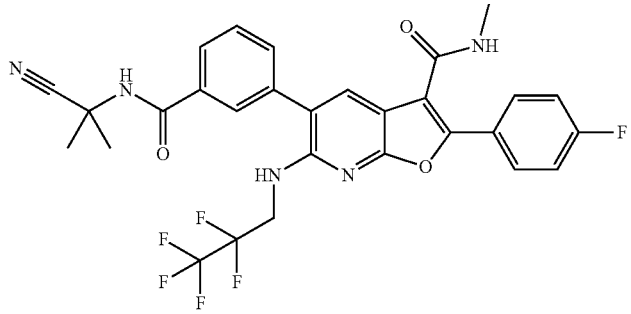 [SMILES: CNC(=O)c1c(-c2ccc(F)cc2)oc2nc(NCC(F)(F)C(F)(F)F)c(-c3cccc(C(=O)NC(C)(C)C#N)c3)cc12] | 604.2 | 604.3 | 1.84 |
| 30002 | A | 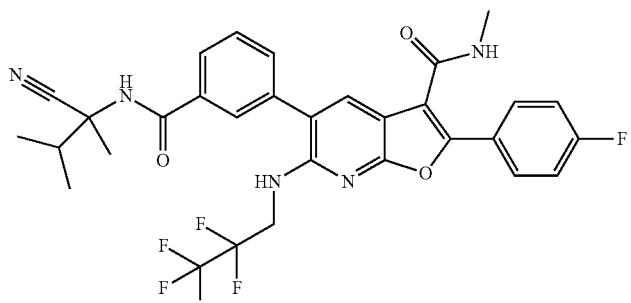 | 632.2 | 632.4 | 3.29 |

| Cmpd # | LC Method | Structure | MS (MHZ)+ Calcd. | MS (MHZ)+ Observ. | Retention Time (min) |
|---|---|---|---|---|---|
| 30003 | A | 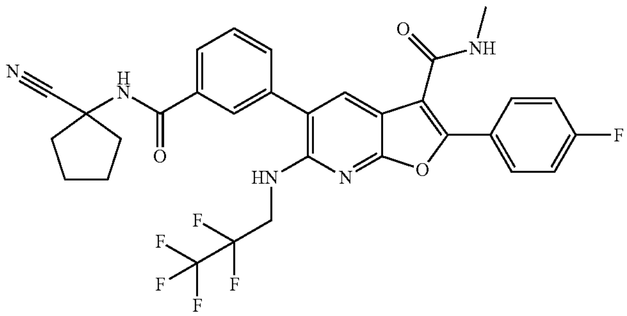 [SMILES: CNC(=O)c1c(-c2ccc(F)cc2)oc2nc(NCC(F)(F)C(F)(F)F)c(-c3cccc(C(=O)NC4(C#N)CCCC4)c3)cc12] | 630.2 | 630.4 | 3.24 |

Preparation of Intermediate 28

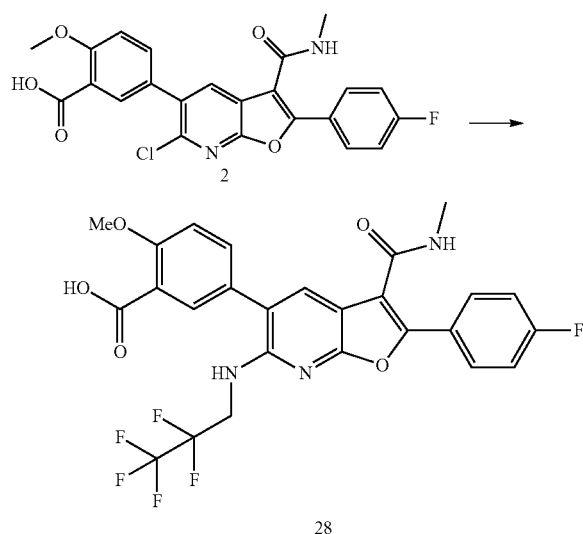

Intermediate 28 was prepared via the same procedure towards Intermediate 20 from Compound 2, using 2,2,3,3,3-pentafluoropropan-1-amine as the starting material.

Compound 28

| | |
|---|---|
| MS (MHZ)+ Calcd. | 568.1 |
| MS (MHZ)+ Observ. | 568.1 |
| Retention Time | 1.74 min |

LC Condition

| | |
|---|---|
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compounds 31001 and 31002 iPr$_2$NEt or Et$_3$N (2 eq.) and HATU or HCTU or DEBPT (1.3 eq.) were added into a solution of Compound 28 (1 eq.) and amine (1.3 eq.) in DMF or THF. The reaction was stirred at room temperature or 85° C. for 30 minutes to 72 hours. The desired product was isolated by preparative HPLC system.

LC Condition A

| | |
|---|---|
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 0.5 min hold at 0% B, 0-100% B over 4 minutes, then a 0.5-minute hold at 100% B |
| Flow Rate | 1 mL/min |
| Wavelength | 220 |
| Solvent Pair | ACN:Water:Ammonium Actetate |
| Column | Waters BEH C18, 2.0 × 50 mm, 1.7-μm particles |

LC Condition B

| | |
|---|---|
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

| Cmpd # | LC Method | Structure | MS (MHZ)+ Calcd. | MS (MHZ)+ Observ. | Retention Time (min) |
|---|---|---|---|---|---|
| 31001 | B | 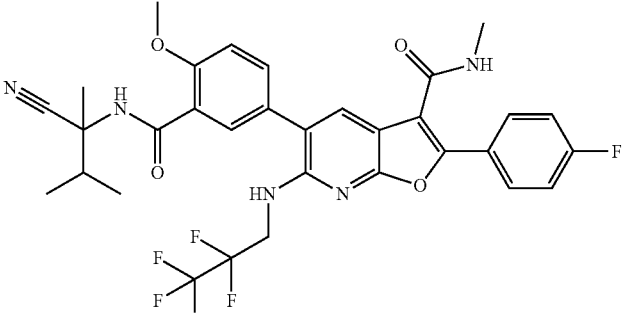 | 662.2 | 662.2 | 1.97 |
| 31002 | A | 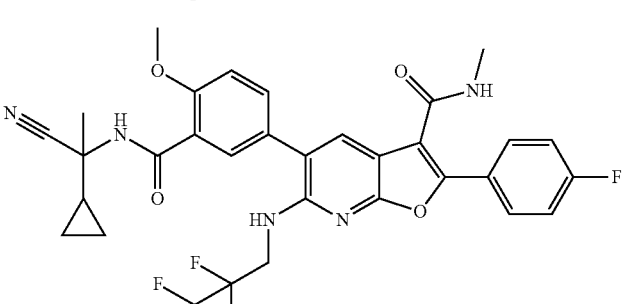 | 660.2 | 660.3 | 3.39 |

Preparation of Intermediate 29

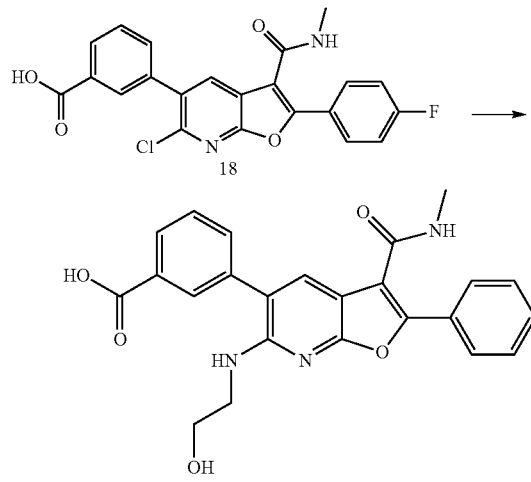

Intermediate 29 was prepared via the same procedure towards Intermediate 19 from Compound 18, using 2-aminoethanol as the starting material.

| Compound 29 | |
|---|---|
| MS (MHZ)+ Calcd. | 450.1 |
| MS (MHZ)+ Observ. | 450.1 |
| Retention Time | 1.88 min |

| -continued | |
|---|---|
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compound 40001

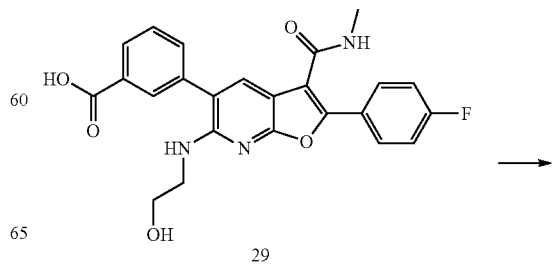

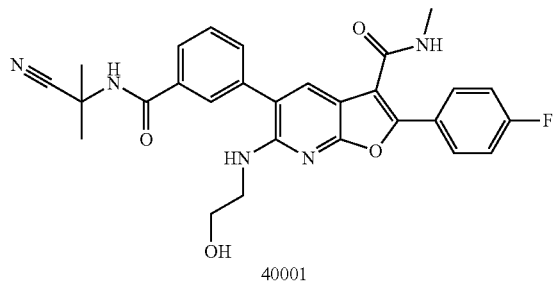

40001

To a solution of Compound 29 (10 mg), 2-amino-2-methylpropanenitrile (3.74 mg) and HATU (12.69 mg) in DMF (1.5 mL) was added iPr₂NEt (0.016 mL). The mixture was stirred at room temperature for 4 hours. The product was isolated by preparative HPLC system.

| Compound 40001 | |
|---|---|
| MS (MHZ)⁺ Calcd. | 516.2 |
| MS (MHZ)⁺ Observ. | 516.1 |
| Retention Time | 1.87 min |
| LC Condition | |
| Solvent A | 90% Water -10% Methanol-0.1% TFA |
| Solvent B | 10% Water -90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

Preparation of Compound 50001

A mixture of Compound 10004 (80 mg), potassium vinyltrifluoroborate (76 mg), cesium carbonate (159 mg), dicyclohexyl(2',6'-diisopropoxy-[1,1'-biphenyl]-2-yl)phosphine (30.4 mg) and diacetoxypalladium (7.32 mg) in toluene (8 mL) and water (0.8 mL) was heated at 80° C. for 16 hours. The mixture was diluted with EtOAc (20 mL), washed with water (20 mL) and brine (20 mL), dried over MgSO₄ and concentrated under vacuum. The residue purified by preparative HPLC.

| Compound 50001 | |
|---|---|
| MS (MHZ)⁺ Calcd. | 483.2 |
| MS (MHZ)⁺ Observ. | 483.2 |
| Retention Time | 2.49 min |
| LC Condition | |
| Solvent A | 90% Water -10% Methanol-0.1% TFA |
| Solvent B | 10% Water -90% Methanol-0.1% TFA |
| Start % B | 50 |
| Final % B | 100 |
| Gradient Time | 2 min |
| Flow Rate | 1 mL/min |
| Wavelength | 220 |
| Solvent Pair | Water - Methanol- TFA |
| Column | PHENOMENEX-LUNA 2.0 × 30 mm 3 um |

General Procedure for the Preparation of Compounds K1001-K1003 iPr₂NEt (3 eq.) and HATU (1.5 eq.) were added into a solution of 2-fluoro-5-(2-(4-fluorophenyl)-3-(methylcarbamoyl)-6-(3,3,3-trifluoropropyl)furo[2,3-b]pyridin-5-yl)benzoic acid (1 eq.) and amine (2 eq.) in DMF. The reaction mixture was stirred at room temperature for 1 hour. The entire reaction mixture was purified via preparative HPLC to obtain the desired product.

Compound K1001

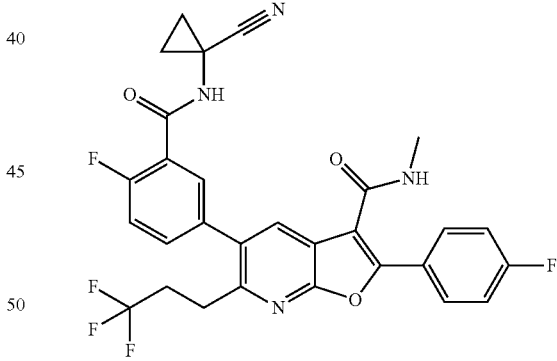

Amine nucleophile=1-aminocyclopropanecarbonitrile hydrochloride. LCMS: Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.90 min, (M+H)⁺: 569. Injection 2 conditions:Column: Waters BEH C18, 2.0×50 mm, 1.7-μm particles; Mobile Phase A: 5:95 methanol:water with 10 mM ammonium acetate; Mobile-Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.91 min, (M+H)+: 569.

Compound K1002

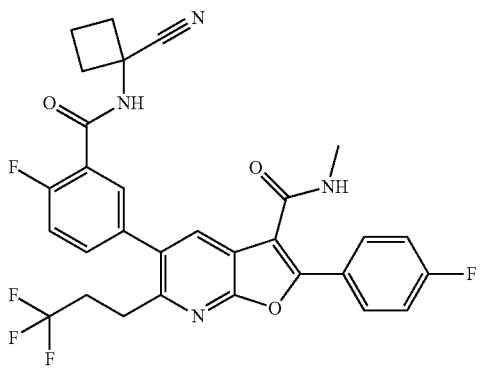 [SMILES: CNC(=O)c1c(-c2ccc(F)cc2)oc2nc(CCC(F)(F)F)c(-c3ccc(F)c(C(=O)NC4(C#N)CCC4)c3)cc12]

Amine nucleophile=1-aminocyclobutanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.11 min, (M+H)+: 583. Injection 2 conditions:Column: Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 4.01 min, (M−H)+: 581. 1H NMR (500 MHz, DMSO-d6) δ 9.43 (s, 1H), 8.54-8.48 (m, 1H), 8.06 (dd, J=8.9, 5.5 Hz, 2H), 7.97 (s, 1H), 7.74-7.65 (m, 2H), 7.49 (t, J=9.3 Hz, 1H), 7.41 (t, J=8.9 Hz, 2H), 3.05-2.97 (m, 2H), 2.85-2.64 (m, 7H), 2.47 (d, J=11.3 Hz, 2H), 2.11-2.00 (m, 2H).

Compound K1003

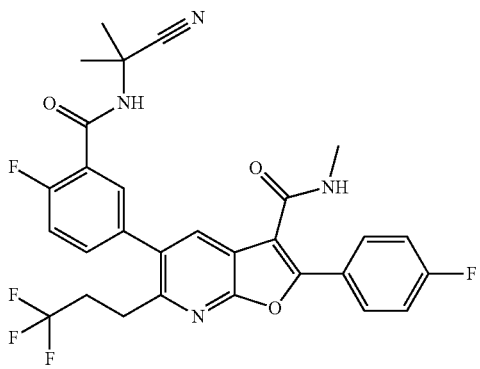 [SMILES: CNC(=O)c1c(-c2ccc(F)cc2)oc2nc(CCC(F)(F)F)c(-c3ccc(F)c(C(=O)NC(C)(C)C#N)c3)cc12]

Amine nucleophile=2-amino-2-methylpropanenitrile hydrochloride. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Retention time: 4.06 min, (M+H)+: 571. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min. Retention time: 3.08 min, (M+H)+: 571. 1H NMR (500 MHz, DMSO-d6) δ 8.98 (s, 1H), 8.54-8.45 (m, 1H), 8.06 (dd, J=8.4, 5.6 Hz, 2H), 7.96 (s, 1H), 7.69-7.63 (m, 2H), 7.47 (s, 1H), 7.41 (t, J=8.7 Hz, 2H), 3.06-2.98 (m, 2H), 2.85-2.72 (m, 5H), 1.73-1.65 (m, 6H).

General Procedure for the Preparation of Compounds K2001-K2005 iPr$_2$NEt (8 eq.) and HATU (1.5 eq.) were added into a solution of 2-fluoro-5-(2-(4-fluorophenyl)-3-(methylcarbamoyl)-6-((2,2,2-trifluoroethyl)amino)furo[2,3-b]pyridin-5-yl)benzoic acid (1 eq.) and amine (1 eq.) in DMF. The reaction mixture was stirred at room temperature for 1 hour. The entire reaction mixture was purified via preparative HPLC to obtain the desired product.

Compound K2001

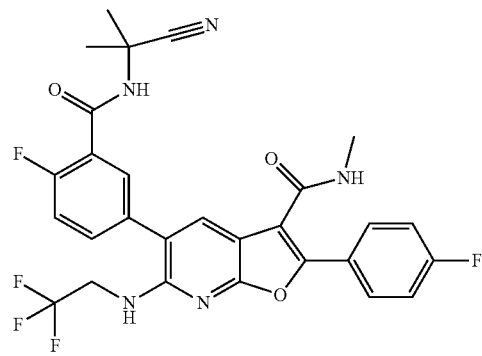 [SMILES: CNC(=O)c1c(-c2ccc(F)cc2)oc2nc(NCC(F)(F)F)c(-c3ccc(F)c(C(=O)NC(C)(C)C#N)c3)cc12]

Amine nucleophile=2-amino-2-methylpropanenitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.92 min, (M+H)+: 572. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.86 min, (M+H)+: 572.

Compound K2002

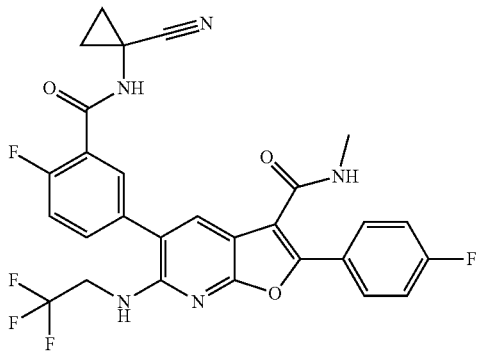 [SMILES: CNC(=O)c1c(-c2ccc(F)cc2)oc2nc(NCC(F)(F)F)c(-c3ccc(F)c(C(=O)NC4(C#N)CC4)c3)cc12]

Amine nucleophile=1-aminocyclopropanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.86 min, $(M+H)^+$: 570. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.81 min, $(M+H)^+$: 570.

Compound K2003

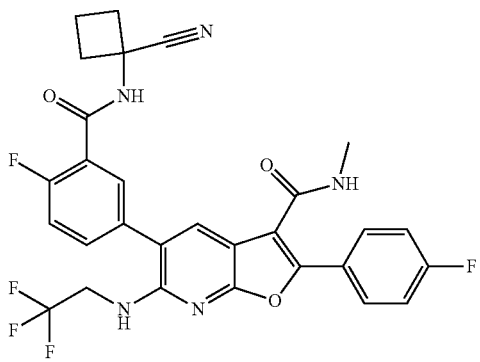 [SMILES: CNC(=O)c1c(-c2ccc(F)cc2)oc2nc(NCC(F)(F)F)c(-c3ccc(F)c(C(=O)NC4(C#N)CCC4)c3)cc12]

Amine nucleophile=1-aminocyclobutanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.96 min, $(M+H)^+$: 584. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.90 min, $(M+H)^+$: 584.

Compound K2004

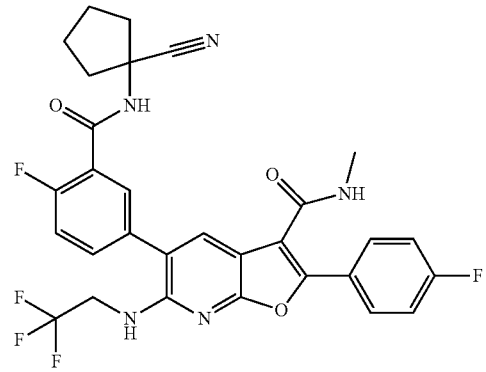 [SMILES: CNC(=O)c1c(-c2ccc(F)cc2)oc2nc(NCC(F)(F)F)c(-c3ccc(F)c(C(=O)NC4(C#N)CCCC4)c3)cc12]

Amine nucleophile=1-aminocyclopentanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 3.05 min, $(M+H)^+$: 598. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.98 min, $(M+H)^+$: 598.

Compound K2005

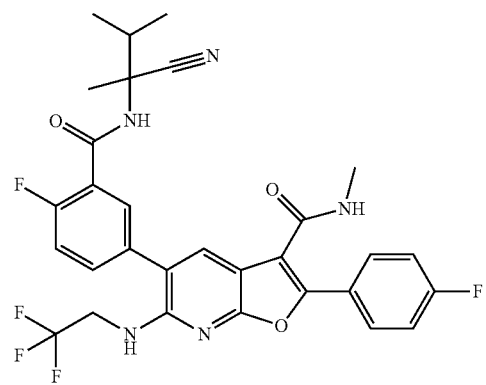 [SMILES: CNC(=O)c1c(-c2ccc(F)cc2)oc2nc(NCC(F)(F)F)c(-c3ccc(F)c(C(=O)NC(C)(C#N)C(C)C)c3)cc12]

Amine nucleophile=2-amino-2,3-dimethylbutanenitrile. Injection 1 conditions: Column: Waters BEH C18, 2.0×50 mm, 1.7-μm particles; Mobile Phase A: 5:95 water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 3.10 min, (M+H)⁺: 600. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm.

Retention time: 4.02 min, (M+H)⁺: 600.

General Procedure for the Preparation of Compound K3001 iPr₂NEt (3 eq.) and HATU (1.5 eq.) were added into a solution of 3-(2-(4-fluorophenyl)-3-(methylcarbamoyl)-6-(3,3,3-trifluoropropyl)furo[2,3-b]pyridin-5-yl)benzoic acid (1 eq.) and amine (2 eq.) in DMF. The reaction mixture was stirred at room temperature for 1 hour. The entire reaction mixture was purified via preparative HPLC to obtain the desired product.

Compound K3001

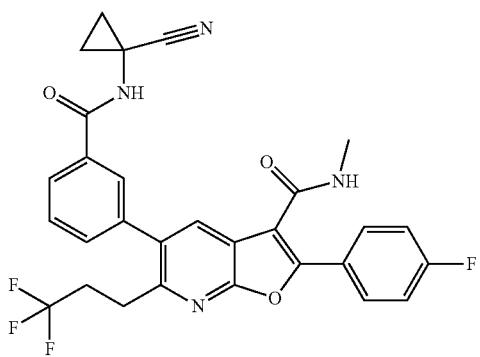 [SMILES: CNC(=O)c1c(-c2ccc(F)cc2)oc2nc(CCC(F)(F)F)c(-c3cccc(C(=O)NC4(C#N)CC4)c3)cc12]

Amine nucleophile=1-aminocyclopropanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.87 min, (M+H)⁺: 551. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.93 min, (M+H)⁺: 551. 1H NMR (500 MHz, DMSO-d6) δ 9.43 (s, 1H), 8.54-8.44 (m, 1H), 8.10-8.00 (m, 2H), 7.97 (s, 2H), 7.90 (s, 1H), 7.74-7.60 (m, 2H), 7.42 (s, 2H), 3.05-2.96 (m, 2H), 2.84-2.69 (m, 5H), 1.63-1.52 (m, 2H), 1.34-1.26 (m, 2H).

General Procedure for the Preparation of Compounds K4001-K4003 iPr₂NEt (8 eq.) and HATU (1.5 eq.) were added into a solution of 3-(2-(4-fluorophenyl)-3-(methylcarbamoyl)-6-((2,2,2-trifluoroethyl)amino)furo[2,3-b]pyridin-5-yl)benzoic acid (1 eq.) and amine (1 eq.) in DMF. The reaction mixture was stirred at room temperature for 1 hour. The entire reaction mixture was purified via preparative HPLC to obtain the desired product.

Compound K4001

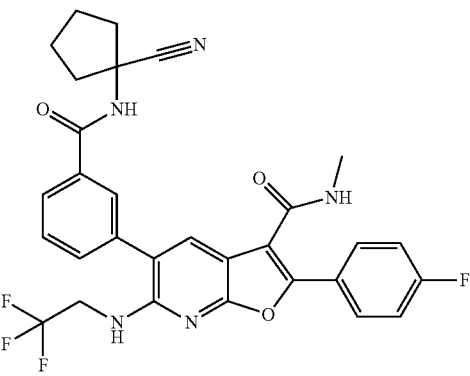 [SMILES: CNC(=O)c1c(-c2ccc(F)cc2)oc2nc(NCC(F)(F)F)c(-c3cccc(C(=O)NC4(C#N)CCCC4)c3)cc12]

Amine nucleophile=1-aminocyclopentanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.94 min, (M+H)⁺: 580. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.98 min, (M+H)⁺: 580.

Compound K4002

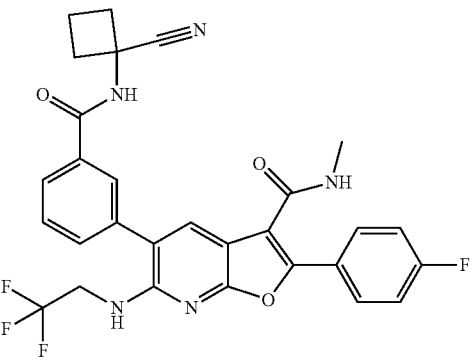 [SMILES: CNC(=O)c1c(-c2ccc(F)cc2)oc2nc(NCC(F)(F)F)c(-c3cccc(C(=O)NC4(C#N)CCC4)c3)cc12]

1-aminocyclobutanecarbonitrile hydrochloride was the amine used. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time:

2.86 min, (M+H)⁺: 566. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.91 min, (M+H)⁺: 566.

Compound K4003

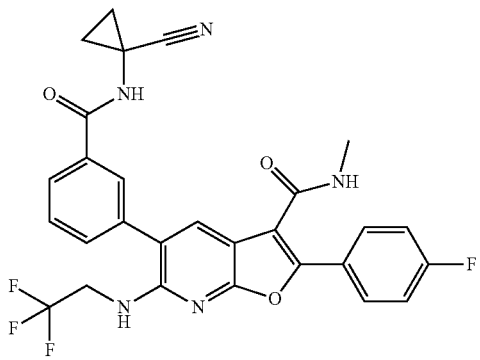 [SMILES: CNC(=O)c1c(-c2ccc(F)cc2)oc2nc(NCC(F)(F)F)c(-c3cccc(C(=O)NC4(C#N)CC4)c3)cc12]

Amine nucleophile=1-aminocyclopropanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.99 min, (M+H)⁺: 552. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.78 min, (M+H)⁺: 552.

Compound K4004

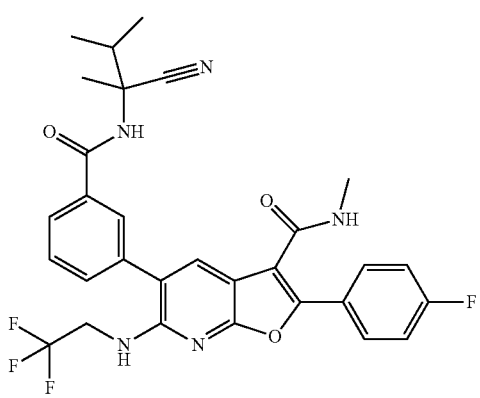 [SMILES: CNC(=O)c1c(-c2ccc(F)cc2)oc2nc(NCC(F)(F)F)c(-c3cccc(C(=O)NC(C)(C#N)C(C)C)c3)cc12]

Amine nucleophile=2-amino-2,3-dimethylbutanenitrile. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 3.18 min, (M+H)⁺: 582. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm.

Retention time: 3.97 min, (M+H)⁺: 582.

General Procedure for the Preparation of Compounds K5001-K5004 iPr₂NEt (8 eq.) and HATU (1.5 eq.) were added into a solution of 5-(2-(4-fluorophenyl)-3-(methylcarbamoyl)-6-((2,2,2-trifluoroethyl)amino)furo[2,3-b]pyridin-5-yl)-2-methoxybenzoic acid (1 eq.) and amine (1 eq.) in DMF. The reaction mixture was stirred at room temperature for 1 hour. The entire reaction mixture was purified via preparative HPLC to obtain the desired product.

Compound K5001

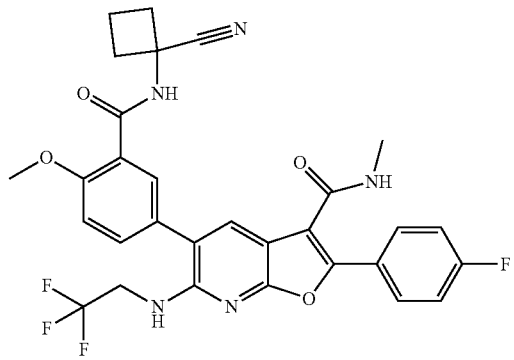 [SMILES: CNC(=O)c1c(-c2ccc(F)cc2)oc2nc(NCC(F)(F)F)c(-c3ccc(OC)c(C(=O)NC4(C#N)CCC4)c3)cc12]

Amine nucleophile=1-aminocyclobutanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 3.15 min, (M+H)⁺: 596. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.88 min, (M+H)⁺: 596.

Compound K5002

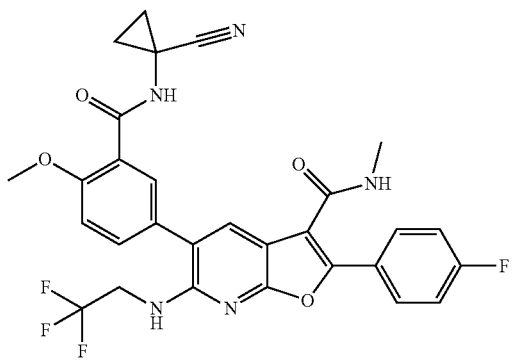 [SMILES: CNC(=O)c1c(-c2ccc(F)cc2)oc2nc(NCC(F)(F)F)c(-c3ccc(OC)c(C(=O)NC4(C#N)CC4)c3)cc12]

Amine nucleophile=1-aminocyclopropanecarbonitrile hydrochloride. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.91 min, (M+H)$^+$: 582. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.81 min, (M+H)$^+$: 582.

Compound K5003

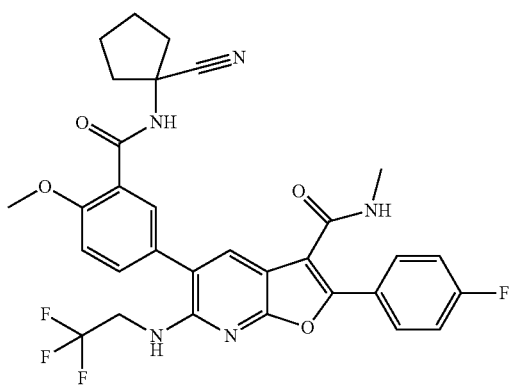 [SMILES: CNC(=O)c1c(-c2ccc(F)cc2)oc2nc(NCC(F)(F)F)c(-c3ccc(OC)c(C(=O)NC4(C#N)CCCC4)c3)cc12]

Amine nucleophile=1-aminocyclopentanecarbonitrile hydrochloride. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 3.01 min, (M+H)$^+$: 610. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 3.98 min, (M+H)$^+$: 610.

Compound K5004

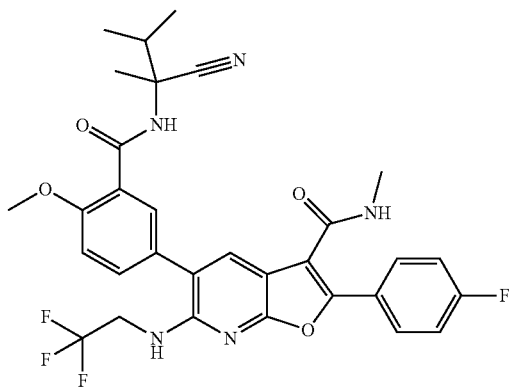 [SMILES: CNC(=O)c1c(-c2ccc(F)cc2)oc2nc(NCC(F)(F)F)c(-c3ccc(OC)c(C(=O)NC(C)(C#N)C(C)C)c3)cc12]

Amine nucleophile=2-amino-2,3-dimethylbutanenitrile. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 3.20 min, (M+H)$^+$: 612. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm.

Retention time: 4.03 min, (M+H)$^+$: 612.

General Procedure for the Preparation of Compounds K6001 iPr$_2$NEt (8 eq.) and HATU (1.5 eq.) were added into a solution of 5-(2-(4-fluorophenyl)-3-(methylcarbamoyl)-6-(3,3,3-trifluoropropyl)furo[2,3-b]pyridin-5-yl)-2-methoxybenzoic acid (1 eq.) and amine (1 eq.) in DMF. The reaction mixture was stirred at room temperature for 1 hour. The entire reaction mixture was purified via preparative HPLC to obtain the desired product.

Compound K6001

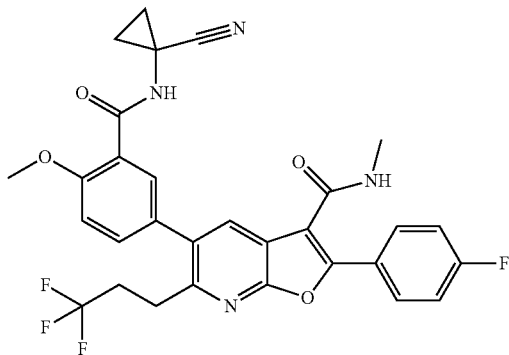 [SMILES: CNC(=O)c1c(-c2ccc(F)cc2)oc2nc(CCC(F)(F)F)c(-c3ccc(OC)c(C(=O)NC4(C#N)CC4)c3)cc12]

Amine nucleophile=1-aminocyclopropanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.95 min, (M+H)$^+$: 581. Injection 2 conditions:Column: Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.93 min, (M+H)$^+$: 581.

General Procedure for the Preparation of Compounds K7001-K7005 iPr$_2$NEt (8 eq.) and HATU (1.5 eq.) were added into a solution of 5-(2-(4-fluorophenyl)-3-(methylcarbamoyl)-6-(3,3,3-trifluoropropyl)furo[2,3-b]pyridin-5-yl)-2-methoxynicotinic acid (1 eq.) and amine (1 eq.) in DMF. The reaction mixture was stirred at room temperature for 1 hour. The entire reaction mixture was purified via preparative HPLC to obtain the desired product.

Compound K7001

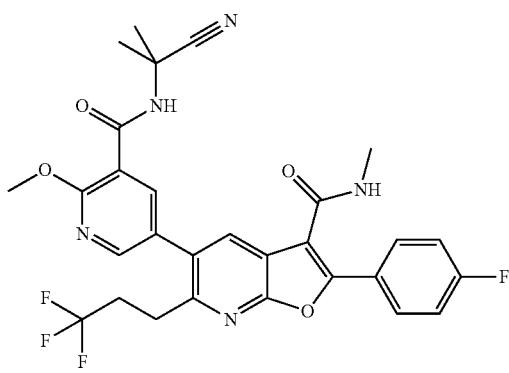 [SMILES: CNC(=O)c1c(-c2ccc(F)cc2)oc2nc(CCC(F)(F)F)c(-c3cnc(OC)c(C(=O)NC(C)(C)C#N)c3)cc12]

Amine nucleophile=2-amino-2-methylpropanenitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 3.17 min, (M+H)$^+$: 584. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 4.09 min, (M+H)$^+$: 584.

Compound K7002

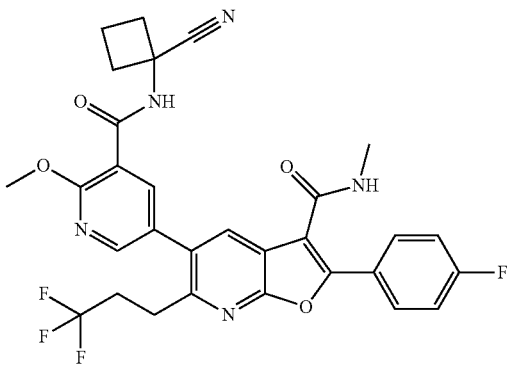 [SMILES: CNC(=O)c1c(-c2ccc(F)cc2)oc2nc(CCC(F)(F)F)c(-c3cnc(OC)c(C(=O)NC4(C#N)CCC4)c3)cc12]

Amine nucleophile=1-aminocyclobutanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 3.20 min, (M+H)$^+$: 596. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 4.11 min, (M+H)$^+$: 596.

Compound K7003

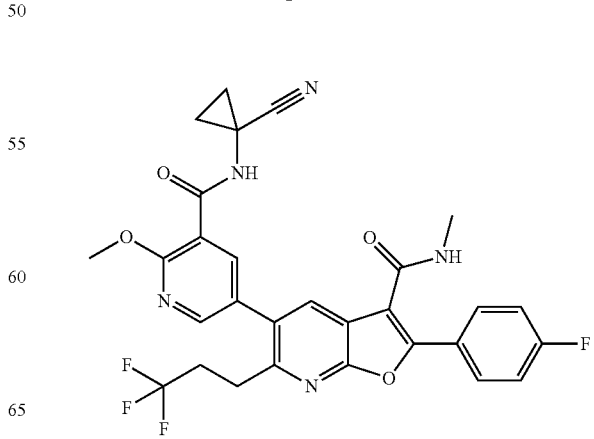

Amine nucleophile=1-aminocyclopropanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.94 min, (M+H)⁺: 582. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.99 min, (M+H)⁺: 582.

Compound K7004

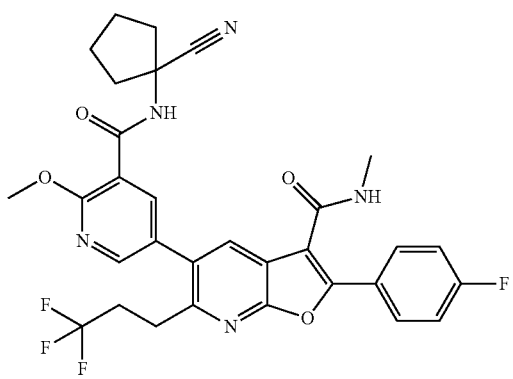 [SMILES: CNC(=O)c1c(-c2ccc(F)cc2)oc2nc(CCC(F)(F)F)c(-c3cnc(OC)c(C(=O)NC4(C#N)CCCC4)c3)cc12]

Amine nucleophile=1-aminocyclopentanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 3.18 min, (M+H)⁺: 610. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 4.16 min, (M+H)⁺: 610.

Compound K7005

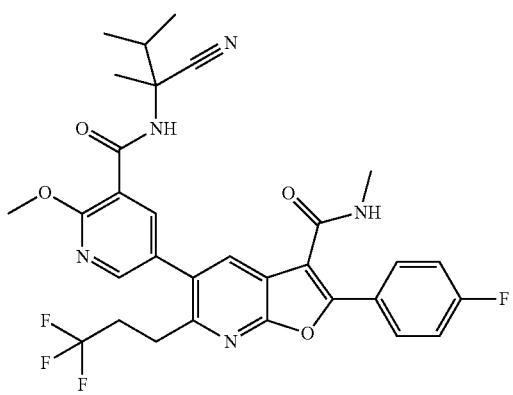 [SMILES: CNC(=O)c1c(-c2ccc(F)cc2)oc2nc(CCC(F)(F)F)c(-c3cnc(OC)c(C(=O)NC(C)(C#N)C(C)C)c3)cc12]

Amine nucleophile=2-amino-2,3-dimethylbutanenitrile. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Retention time: 3.33 min, (M+H)⁺: 612. Injection 2 conditions: Column: Waters Acquity UPLC BEH C18, 2.1× 50 mm, 1.7-μm particles; Mobile Phase A: 5:95 acetonitrile: water with 0.05% TFA; Mobile Phase B: 95:5 acetonitrile: water with 0.1% TFA; Temperature: 50° C.; Gradient: 0-100% B over 3 minutes, then a 0.75-minute hold at 100% B; Flow: 1.11 mL/min. Retention time: 4.31 min, (M+H)⁺: 612.

General Procedure for the Preparation of Compounds K8001-K8005 iPr₂NEt (8 eq.) and HATU (1.5 eq.) were added into a solution of 5-(2-(4-fluorophenyl)-3-(methylcarbamoyl)-6-((2,2,2-tri-fluoroethyl)amino)furo[2,3-b]pyridin-5-yl)-2-methoxynico-tinic acid (1 eq.) and amine (1 eq.) in DMF. The reaction mixture was stirred at room temperature for 1 hour. The entire reaction mixture was purified via preparative HPLC to obtain the desired product.

Compound K8001

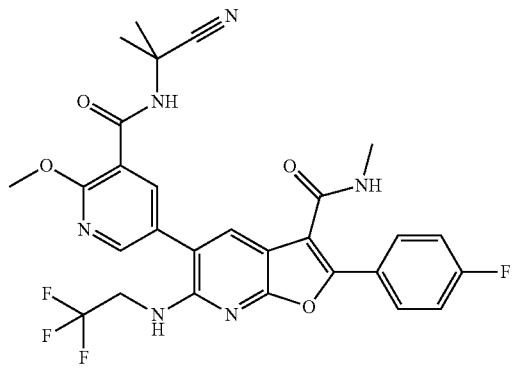 [SMILES: CNC(=O)c1c(-c2ccc(F)cc2)oc2nc(NCC(F)(F)F)c(-c3cnc(OC)c(C(=O)NC(C)(C)C#N)c3)cc12]

Amine nucleophile=2-amino-2-methylpropanenitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.92 min, (M+H)⁺: 585. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.88 min, (M+H)⁺: 585.

Compound K8002

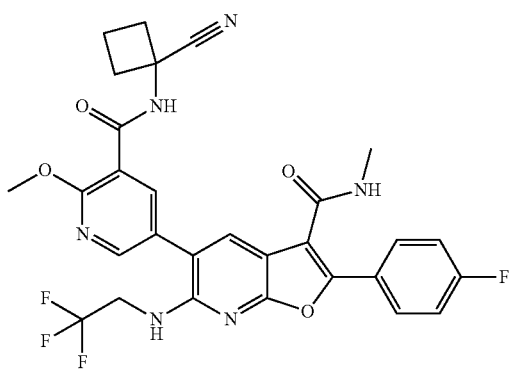 [SMILES: CNC(=O)c1c(-c2ccc(F)cc2)oc2nc(NCC(F)(F)F)c(-c3cnc(OC)c(C(=O)NC4(C#N)CCC4)c3)cc12]

Amine nucleophile=1-aminocyclobutanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 3.05 min, (M+H)$^+$: 597. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.87 min, (M+H)$^+$: 597.

Compound K8003

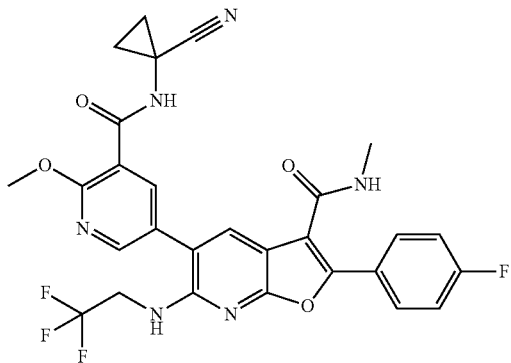

Amine nucleophile=1-aminocyclopropanecarbonitrile hydrochloride. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 2.82 min, (M+H)$^+$: 583. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 3.83 min, (M+H)$^+$: 583.

Compound K8004

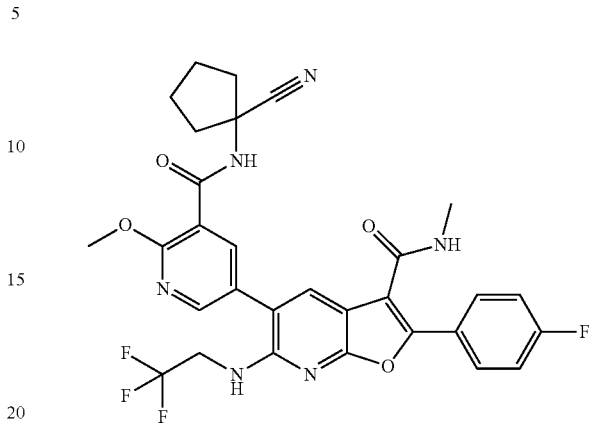

Amine nucleophile=1-aminocyclopentanecarbonitrile hydrochloride. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. Retention time: 3.14 min, (M+H)$^+$: 611. Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min. Retention time: 4.15 min, (M+H)$^+$: 611.

Compound K8005

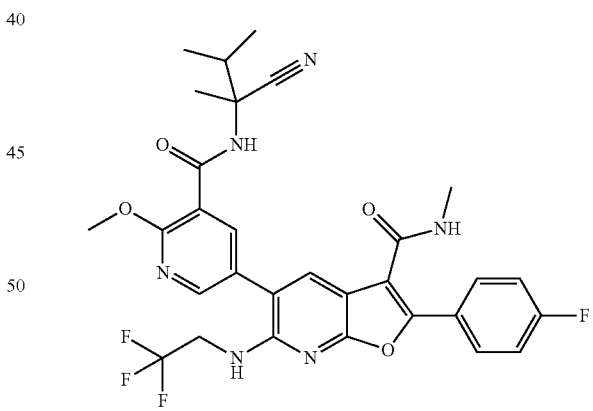

Amine nucleophile=2-amino-2,3-dimethylbutanenitrile was. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Retention time: 3.11 min, (M+H)$^+$: 613. Injection 2 conditions:Column: Waters BEH C18, 2.0×50 mm, 1.7-μm particles; Mobile Phase A: 5:95 methanol:water with 10 mM ammonium acetate; MobilePhase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. Retention time: 4.04 min, (M+H)+: 613.

Preparation of Compound K9001

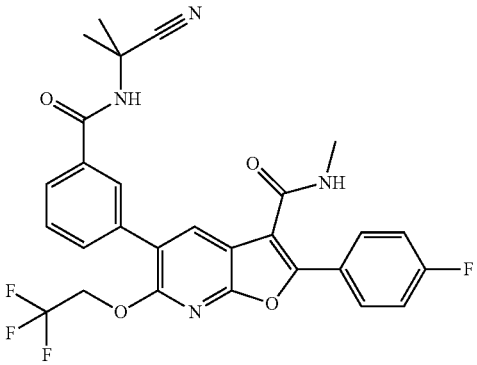 [SMILES: CNC(=O)c1c(-c2ccc(F)cc2)oc2nc(OCC(F)(F)F)c(-c3cccc(C(=O)NC(C)(C)C#N)c3)cc12]

A mixture of Chloro[2-(dicyclohexylphosphino)-3,6-dimethoxy-2',4',6'-triisopropyl-1,1'-biphenyl][2-(2-aminoethyl)phenyl]palladium(II) (4.5 mg, 5.6 µmol), 5-(3-((2-(1,2,4-oxadiazol-3-yl)propan-2-yl)carbamoyl)phenyl)-6-chloro-2-(4-fluorophenyl)-N-methylfuro[2,3-b]pyridine-3-carboxamide (30 mg, 0.056 mmol), di-tert-butyl(2',4',6'-triisopropyl-3-methoxy-6-methyl-[1,1'-biphenyl]-2-yl)phosphine (2.6 mg, 5.6 µmol), sodium 2-methylbutan-2-olate (30 mg, 0.28 mmol) were combined in trifluoroethanol and heated to 65° C. for 2 hours and then at 90° C. for 16 hours. The reaction mixture was purified by preparative reverse phase HPLC on a C18 column using a suitably buffered H₂O/CH₃CN gradient, and concentrated. The minor product is consistent with: 5-(3-((2-cyanopropan-2-yl)carbamoyl)phenyl)-2-(4-fluorophenyl)-N-methyl-6-(2,2,2-trifluoroethoxy)furo[2,3-b]pyridine-3-carboxamide (1.0 mg, 1.7 µmol, 3.0% yield) by LCMS and NMR. ¹H NMR (400 MHz, CDCl₃) δ 8.31-8.28 (m, 1H), 7.96-7.89 (m, 4H), 7.77-7.73 (m, 1H), 7.61-7.55 (m, 1H), 7.26-7.21 (m, 2H), 6.22-6.17 (m, 1H), 5.88-5.80 (m, 1H), 4.95-4.86 (m, 2H), 3.01 (d, J=5.0 Hz, 3H), 1.85 (s, 6H). LC-MS retention time: 1.76 min; m/z (M+H)+: 555. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% acetonitrile/90% H2O/0.1% trifluoroacetic acid and solvent B was 10% H2O/90% acetonitrile/0.1% trifluoroacetic acid. MS data was determined using a Micromass Platform for LC in electrospray mode.

Preparation of Compound K10001

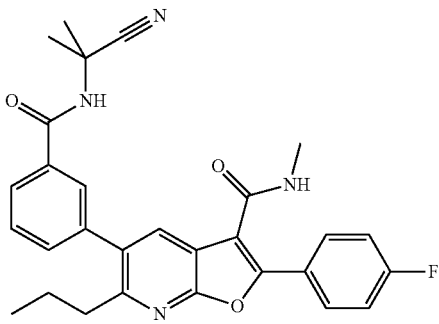 [SMILES: CCCc1nc2oc(-c3ccc(F)cc3)c(C(=O)NC)c2cc1-c1cccc(C(=O)NC(C)(C)C#N)c1]

Pd/C (9.0 mg, 8.5 µmol) was added to a stirring solution of (E)-5-(3-((2-(1,2,4-oxadiazol-3-yl)propan-2-yl)carbamoyl)phenyl)-2-(4-fluorophenyl)-N-methyl-6-(prop-1-en-1-yl)furo[2,3-b]pyridine-3-carboxamide (23 mg, 0.043 mmol) in MeOH (853 µl) at room temperature. The reaction mixture was placed in a Parr bomb and charged with 25 PSI of H₂ (g) and the reaction mixture was allowed to stir for 4 hours. LCMS indicated no conversion. Pd/C (9.0 mg, 8.5 µmol) was added and the reaction mixture was placed in a Parr bomb and charged with 50 PSI of H₂ (g) and the reaction mixture was allowed to stir for 16 hours. The reaction mixture was filtered and purified by preparative reverse phase HPLC on a C18 column using a suitably buffered H₂O/CH₃CN gradient, and concentrated to give 5-(3-((2-cyanopropan-2-yl)carbamoyl)phenyl)-2-(4-fluorophenyl)-N-methyl-6-propylfuro[2,3-b]pyridine-3-carboxamide (2.5 mg, 4.7 µmol, 11% yield) consistent by LCMS and NMR. ¹H NMR (400 MHz, CDCl₃) δ 8.01-7.95 (m, 2H), 7.94 (s, 1H), 7.82 (d, J=7.5 Hz, 1H), 7.70 (s, 1H), 7.56-7.45 (m, 2H), 7.22 (t, J=8.7 Hz, 2H), 6.58 (s, 1H), 6.09-6.01 (m, 1H), 2.99 (d, J=5.0 Hz, 3H), 2.74-2.67 (m, 2H), 1.86 (s, 6H), 1.71-1.65 (m, 2H), 0.85 (t, J=7.4 Hz, 3H). LC-MS retention time: 2.05 min; m/z (M+H)+: 499. LC data was recorded on a Shimadzu LC-10AS liquid chromatograph equipped with a Phenomenex-Luna 3u C18 2.0×30 mm column using a SPD-10AV UV-Vis detector at a detector wave length of 220 nM. The elution conditions employed a flow rate of 1 mL/min, a gradient of 100% solvent A/0% solvent B to 0% solvent A/100% solvent B, a gradient time of 2 min, a hold time of 1 min, and an analysis time of 3 min where solvent A was 10% methanol/90% H2O/0.1% trifluoroacetic acid and solvent B was 10% H2O/90% methanol/0.1% trifluoroacetic acid. MS data was determined using a Micromass Platform for LC in electrospray mode.

Preparation of Compounds K11001 and K11002

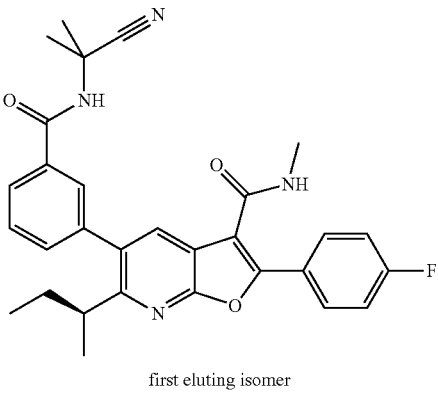

first eluting isomer

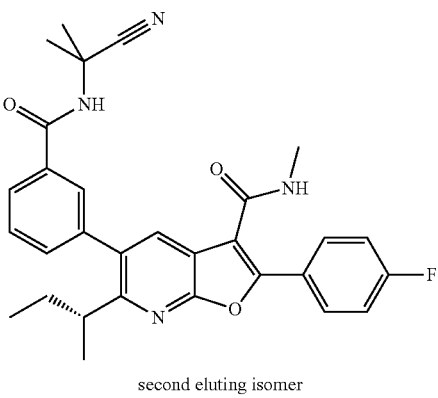

second eluting isomer 2-(3H-[1,2,3]triazolo[4,5-b]pyridin-3-yl)-1,1,3,3-tetramethylisouronium hexafluorophosphate (V) (45 mg, 0.12 mmol) was added to stirring solution of 3-(6-(sec-butyl)-2-(4-fluorophenyl)-3-(methylcarbamoyl)furo[2,3-b]pyridin-5-yl)benzoic acid (35 mg, 0.078 mmol), N-ethyl-N-isopropylpropan-2-amine (41 μl, 0.24 mmol) and 2-amino-2-methylpropanenitrile hydrochloride (11 mg, 0.094 mmol) in DMF (0.8 μl) at room temperature. The mixture was allowed to stir at room temperature for 30 minutes. The entire reaction mixture was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammoniumacetate; Gradient: 40-80% B over 20 minutes, then a 7-minute hold at 100% B; Flow: 20 mL/min. Fractions containing the desired product were combined and dried via centrifugal evaporation. The material was further purified through chiral separation.

First eluting isomer: The yield of the product was 8.9 mg, and its purity was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.99 min, (M+H)$^+$: 513 Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 4.04 min, (M+H)$^+$: 513. 1H NMR (500 MHz, DMSO-d6) δ 8.86 (s, 1H), 8.55-8.47 (m, 1H), 8.10-8.02 (m, 2H), 7.98-7.94 (m, 1H), 7.90 (s, 2H), 7.66-7.61 (m, 1H), 7.59-7.55 (m, 1H), 7.43-7.36 (m, 1H), 2.93-2.86 (m, 1H), 2.81 (d, J=4.3 Hz, 3H), 1.83-1.74 (m, 1H), 1.71 (s, 6H), 1.58-1.47 (m, 1H), 1.19 (d, J=6.7 Hz, 3H), 0.65 (s, 3H).

Second eluting isomer: The yield of the product was 9.5 mg, and its purity was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min; Detection: UV at 220 nm. Retention time: 2.99 min, (M+H)$^+$: 513. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min; Detection: UV at 220 nm. Retention time: 4.04 min, (M+H)$^+$: 513. 1H NMR (500 MHz, DMSO-d6) δ 8.82 (s, 1H), 8.50-8.45 (m, J=4.3 Hz, 1H), 8.06 (dd, J=8.9, 5.5 Hz, 2H), 7.96 (d, J=7.9 Hz, 1H), 7.92-7.85 (m, 2H), 7.67-7.60 (m, 1H), 7.60-7.54 (m, 1H), 7.41 (t, J=8.9 Hz, 2H), 2.93-2.86 (m, 1H), 2.81 (d, J=4.6 Hz, 2H), 1.84-1.75 (m, 1H), 1.71 (s, 6H), 1.58-1.49 (m, 1H), 1.20 (d, J=6.7 Hz, 3H), 0.66 (t, J=7.3 Hz, 3H).

Biological Methods

The compound demonstrated activity against HCV NS5B as determined in the following HCV RdRp assays.

HCV NS5B RdRp cloning, expression, and purification. The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 g/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl$_2$, 15 ug/mL deoxyribonuclease I, and Complete™ protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl$_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is ≥90% based on SDS-PAGE analysis. The enzyme was aliquoted and stored at −80° C.

HCV NS5B RdRp enzyme assay. An on-bead solid phase homogeneous assay was used in a 384-well format to assess NS5B inhibitors (Wang Y-K, Rigat K, Roberts S, and Gao M (2006) Anal Biochem, 359: 106-111). The biotinylated oligo dT$_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 μL) of water, 3× reaction mix, and enzyme in 3× assay buffer (60 mM Hepes buffer, pH 7.5, 7.5 mM MgCl$_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 μM $^3$H-UTP (0.3 μCi), 1.6 U/μL RNAse inhibitor, 7 nM NS5B enzyme, 0.01 mg/mL BSA, 1 mM DTT, and 0.33 μg/μL beads, 20 mM Hepes buffer, pH 7.5, 2.5 mM MgCl$_2$, 2.5 mM KCl, and 0.1% DMSO.

Reactions were allowed to proceed for 24 hours at 30° C. and terminated by the addition of 50 mM EDTA (5 μL). After incubating for at least 15 minutes, plates were read on an Amersham LEADseeker multimodality imaging system.

IC$_{50}$ values for compounds were determined using ten different [I]. IC$_{50}$ values were calculated from the inhibition using the four-parameter logistic formula y=A+((B−A)/(1+((C/x)^D))), where A and B denote minimal and maximal % inhibition, respectively, C is the IC$_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a *Renilla luciferase* reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 μL at a density of 2.4×10$^3$ cells/well) in DMEM containing 4% FBS (final DMSO concentration at 0.5%). After 3 days incubation at 37° C., cells were analyzed for *Renilla Luciferase* activity using the EnduRen substrate (Promega cat #E6485) according to the manufacturer's directions. Briefly, the EnduRen substrate was diluted in DMEM and then added to the plates to a final concentration of 7.5 μM. The plates were incubated for at least 1 h at 37° C. then read on a Viewlux Imager (PerkinElmer) using a luminescence program. The 50% effective concentration (EC$_{50}$) was calculated using the four-parameter logistic formula noted above.

To assess cytotoxicity of compounds, Cell Titer-Blue (Promega) was added to the EnduRen-containing plates and incubated for at least 4 hrs at 37° C. The fluorescence signal from each well was read using a Viewlux Imager. All CC$_{50}$ values were calculated using the four-parameter logistic formula.

Compound EC$_{50}$ data is expressed as A: <100 nM; B=100-1000 nM; C>1000 nM). Representative data for compounds are reported in Table 2.

TABLE 2

| Cmpd# | Structure | EC$_{50}$ (uM) 1b |
|---|---|---|
| 10001 | (structure) | 0.0738 A |
| 10002 | (structure) | A |
| 10003 | (structure) | A |
| 10004 | (structure) | 0.1051 B |

TABLE 2-continued

| Cmpd# | Structure | EC$_{50}$ (uM) 1b |
|---|---|---|
| 10005 | 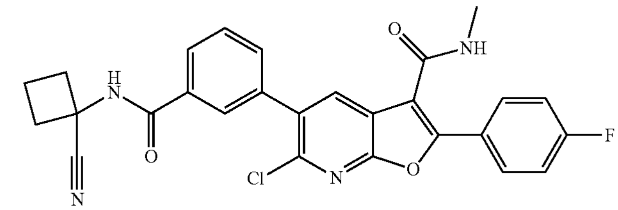 [SMILES: CNC(=O)c1c(-c2ccc(F)cc2)oc2nc(Cl)c(-c3cccc(C(=O)NC4(C#N)CCC4)c3)cc12] | A |
| 10006 | 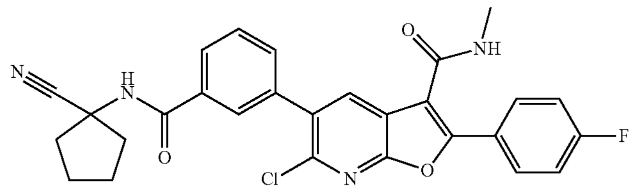 [SMILES: CNC(=O)c1c(-c2ccc(F)cc2)oc2nc(Cl)c(-c3cccc(C(=O)NC4(C#N)CCCC4)c3)cc12] | 0.0760 A |
| 11001 | 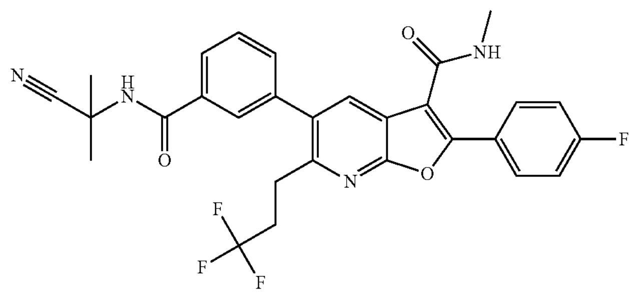 [SMILES: CNC(=O)c1c(-c2ccc(F)cc2)oc2nc(CCC(F)(F)F)c(-c3cccc(C(=O)NC(C)(C)C#N)c3)cc12] | A |
| 11002 | 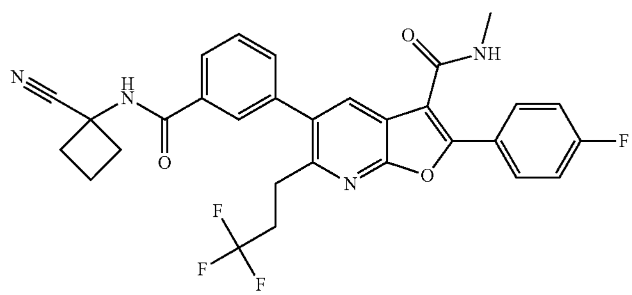 [SMILES: CNC(=O)c1c(-c2ccc(F)cc2)oc2nc(CCC(F)(F)F)c(-c3cccc(C(=O)NC4(C#N)CCC4)c3)cc12] | A |
| 11003 | 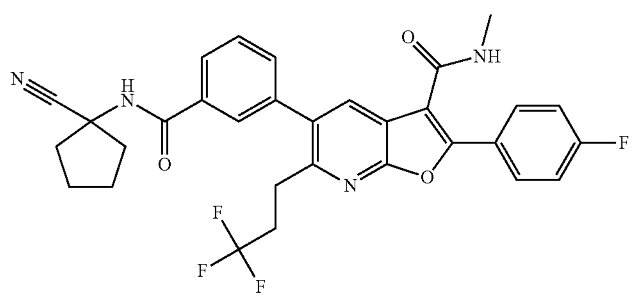 [SMILES: CNC(=O)c1c(-c2ccc(F)cc2)oc2nc(CCC(F)(F)F)c(-c3cccc(C(=O)NC4(C#N)CCCC4)c3)cc12] | 0.0046 A |
| 11004 | 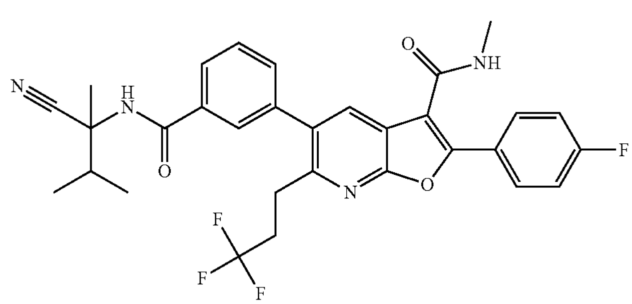 [SMILES: CNC(=O)c1c(-c2ccc(F)cc2)oc2nc(CCC(F)(F)F)c(-c3cccc(C(=O)NC(C)(C#N)C(C)C)c3)cc12] | A |

TABLE 2-continued
| Cmpd# | Structure | EC$_{50}$ (uM) 1b |
|---|---|---|
| 11005 | 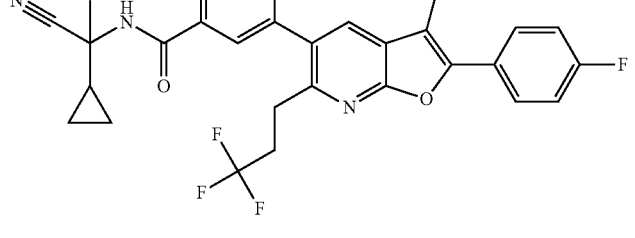 | A |
| 11006 Chiral | 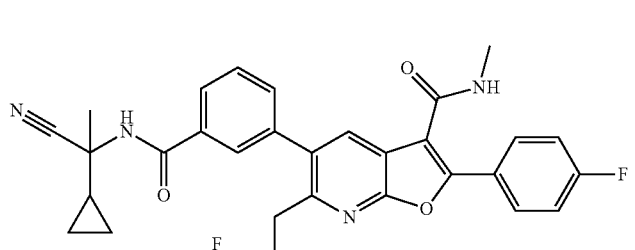 | 0.0022 A |
| 11007 Chiral | 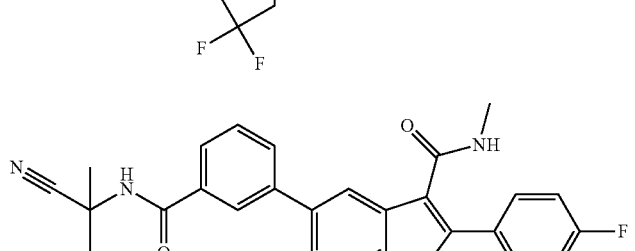 | 0.0027 A |
| 11008 | 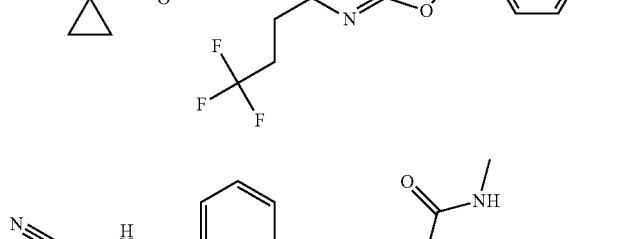 | A |
| 11009 Chiral | 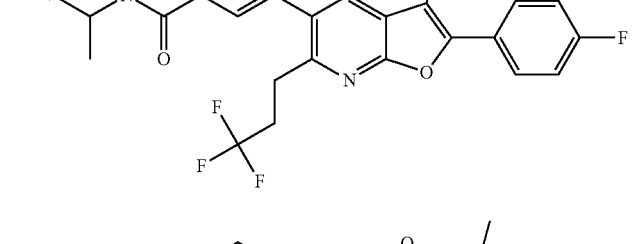 | A |

TABLE 2-continued
| Cmpd# | Structure | EC$_{50}$ (uM) 1b |
|---|---|---|
| 11010 Chiral | 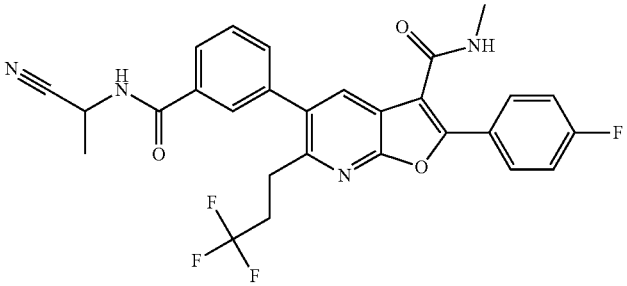 [SMILES: CNC(=O)c1c(-c2ccc(F)cc2)oc2nc(CCC(F)(F)F)c(-c3cccc(C(=O)NC(C)C#N)c3)cc12] | A |
| 11011 | 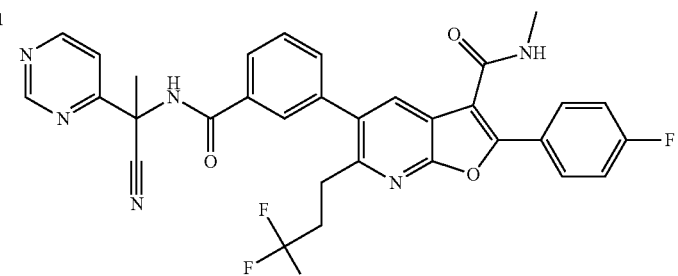 | 0.0075 A |
| 11012 | 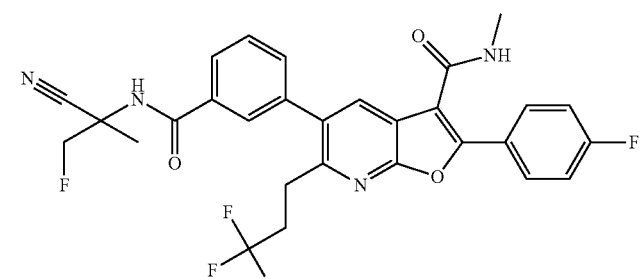 | A |
| 11013 | 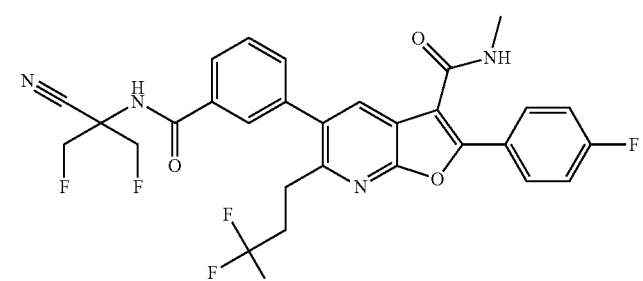 | N/A |
| 12001 | 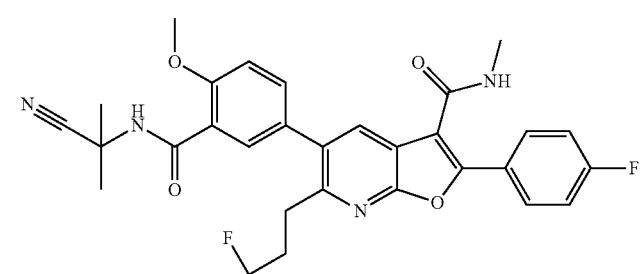 | 0.0025 A |

TABLE 2-continued

| Cmpd# | Structure | EC$_{50}$ (uM) 1b |
|---|---|---|
| 12002 | 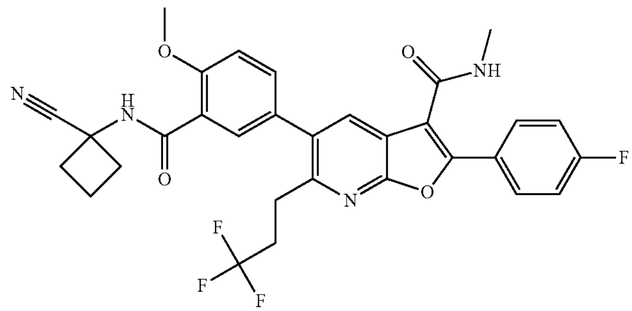 [SMILES: CNC(=O)c1c(-c2ccc(F)cc2)oc2nc(CCC(F)(F)F)c(-c3ccc(OC)c(C(=O)NC4(C#N)CCC4)c3)cc12] | A |
| 12003 | 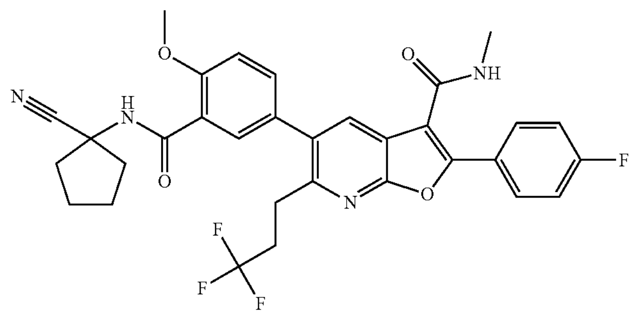 [SMILES: CNC(=O)c1c(-c2ccc(F)cc2)oc2nc(CCC(F)(F)F)c(-c3ccc(OC)c(C(=O)NC4(C#N)CCCC4)c3)cc12] | A |
| 12004 | 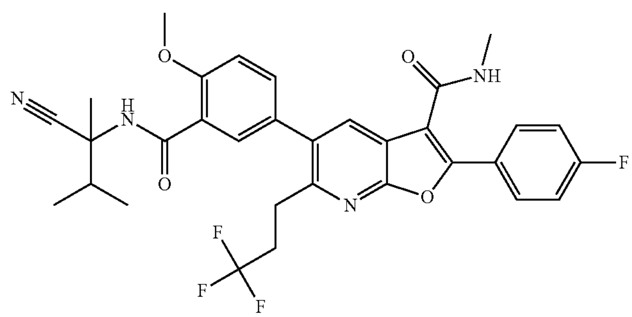 [SMILES: CNC(=O)c1c(-c2ccc(F)cc2)oc2nc(CCC(F)(F)F)c(-c3ccc(OC)c(C(=O)NC(C)(C#N)C(C)C)c3)cc12] | 0.0033 A |
| 12005 | 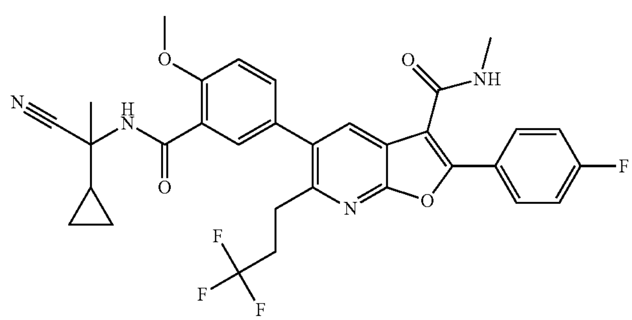 [SMILES: CNC(=O)c1c(-c2ccc(F)cc2)oc2nc(CCC(F)(F)F)c(-c3ccc(OC)c(C(=O)NC(C)(C#N)C4CC4)c3)cc12] | N/A |
| 13001 | 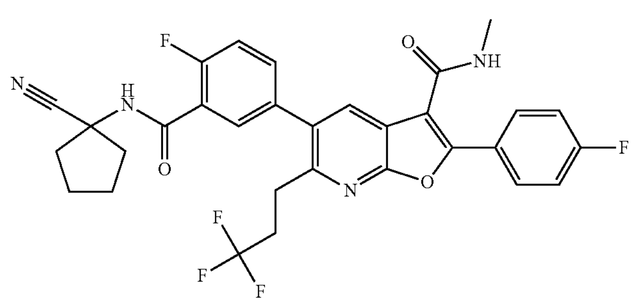 [SMILES: CNC(=O)c1c(-c2ccc(F)cc2)oc2nc(CCC(F)(F)F)c(-c3ccc(F)c(C(=O)NC4(C#N)CCCC4)c3)cc12] | N/A |

TABLE 2-continued

| Cmpd# | Structure | EC$_{50}$ (uM) 1b |
|---|---|---|
| 13002 | 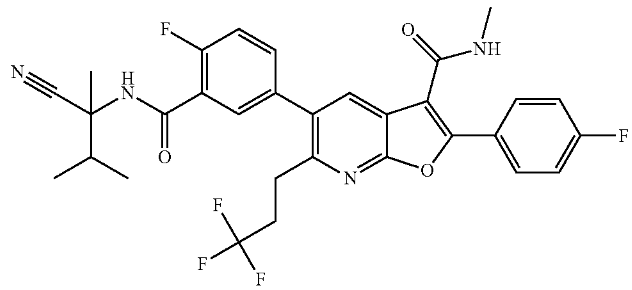 [SMILES: CNC(=O)c1c(-c2ccc(F)cc2)oc2nc(CCC(F)(F)F)c(-c3ccc(F)c(C(=O)NC(C)(C#N)C(C)C)c3)cc12] | 0.0024 A |
| 13003 | 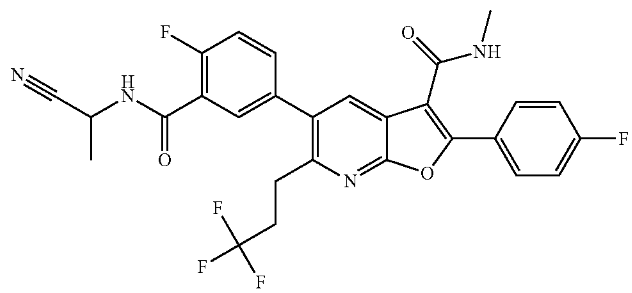 [SMILES: CNC(=O)c1c(-c2ccc(F)cc2)oc2nc(CCC(F)(F)F)c(-c3ccc(F)c(C(=O)NC(C)C#N)c3)cc12] | A |
| 13004 Chiral | 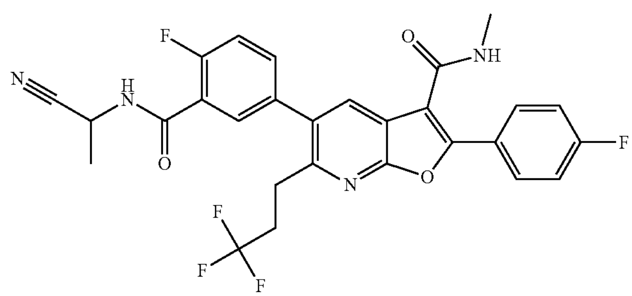 [SMILES: CNC(=O)c1c(-c2ccc(F)cc2)oc2nc(CCC(F)(F)F)c(-c3ccc(F)c(C(=O)NC(C)C#N)c3)cc12] | A |
| 13005 Chiral | 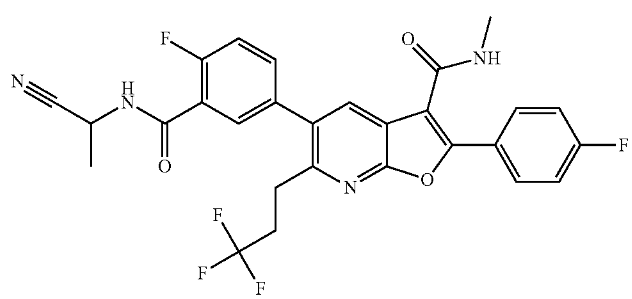 [SMILES: CNC(=O)c1c(-c2ccc(F)cc2)oc2nc(CCC(F)(F)F)c(-c3ccc(F)c(C(=O)NC(C)C#N)c3)cc12] | A |
| 13006 | 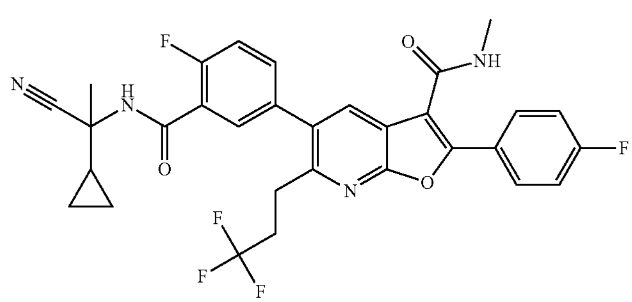 [SMILES: CNC(=O)c1c(-c2ccc(F)cc2)oc2nc(CCC(F)(F)F)c(-c3ccc(F)c(C(=O)NC(C)(C#N)C4CC4)c3)cc12] | 0.0036 A |

TABLE 2-continued

| Cmpd# | Structure | EC$_{50}$ (uM) 1b |
|---|---|---|
| 13007 Chiral | 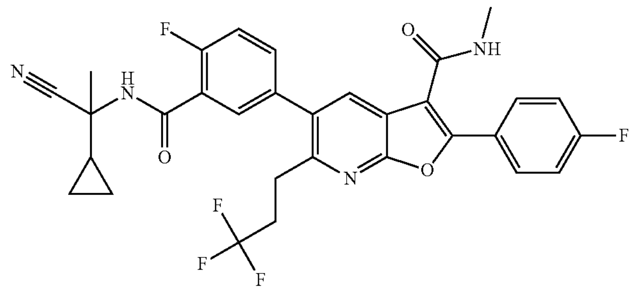 [SMILES: CNC(=O)c1c(-c2ccc(F)cc2)oc2nc(CCC(F)(F)F)c(-c3ccc(F)c(C(=O)NC(C)(C#N)C4CC4)c3)cc12] | A |
| 13008 Chiral | 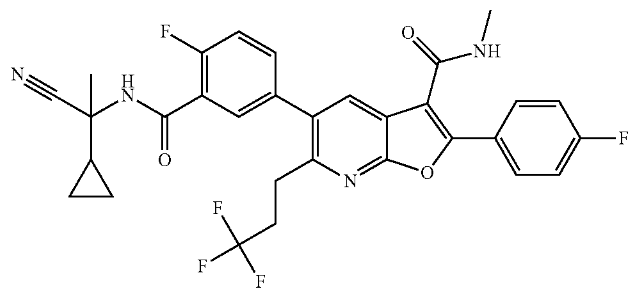 [SMILES: CNC(=O)c1c(-c2ccc(F)cc2)oc2nc(CCC(F)(F)F)c(-c3ccc(F)c(C(=O)NC(C)(C#N)C4CC4)c3)cc12] | A |
| 14001 | 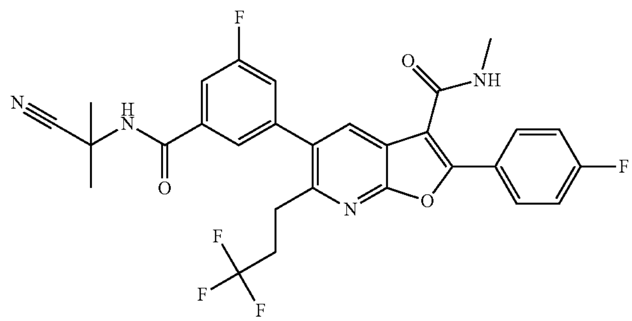 [SMILES: CNC(=O)c1c(-c2ccc(F)cc2)oc2nc(CCC(F)(F)F)c(-c3cc(F)cc(C(=O)NC(C)(C)C#N)c3)cc12] | 0.0022 A |
| 14002 | 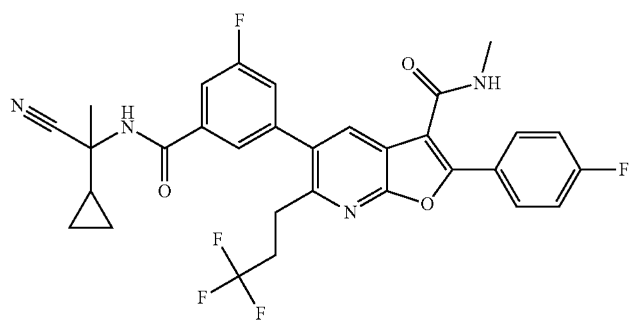 [SMILES: CNC(=O)c1c(-c2ccc(F)cc2)oc2nc(CCC(F)(F)F)c(-c3cc(F)cc(C(=O)NC(C)(C#N)C4CC4)c3)cc12] | A |
| 15001 | 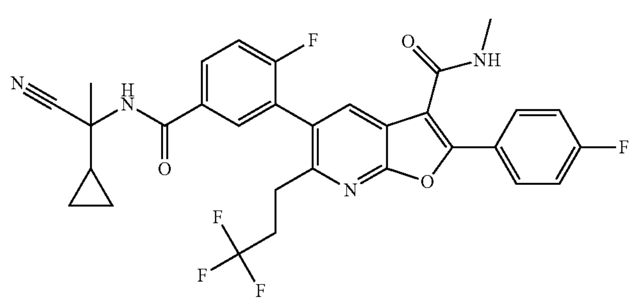 [SMILES: CNC(=O)c1c(-c2ccc(F)cc2)oc2nc(CCC(F)(F)F)c(-c3cc(C(=O)NC(C)(C#N)C4CC4)ccc3F)cc12] | A |

TABLE 2-continued

| Cmpd# | Structure | EC$_{50}$ (uM) 1b |
|---|---|---|
| 15002 | 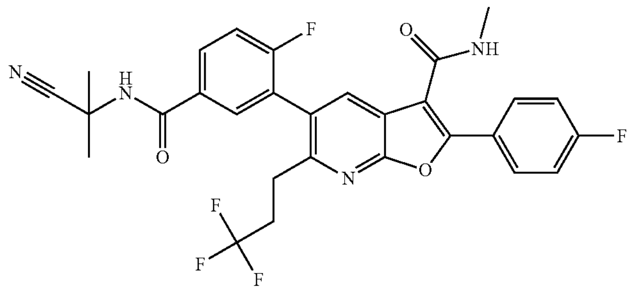 [SMILES: CNC(=O)c1c(-c2ccc(F)cc2)oc2nc(CCC(F)(F)F)c(-c3cc(C(=O)NC(C)(C)C#N)ccc3F)cc12] | 0.0042 A |
| 16001 | 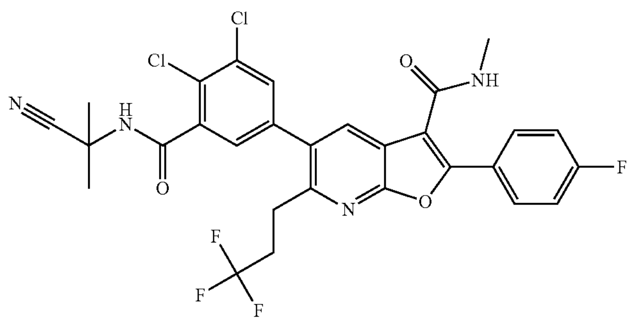 [SMILES: CNC(=O)c1c(-c2ccc(F)cc2)oc2nc(CCC(F)(F)F)c(-c3cc(Cl)c(Cl)c(C(=O)NC(C)(C)C#N)c3)cc12] | A |
| 17001 | 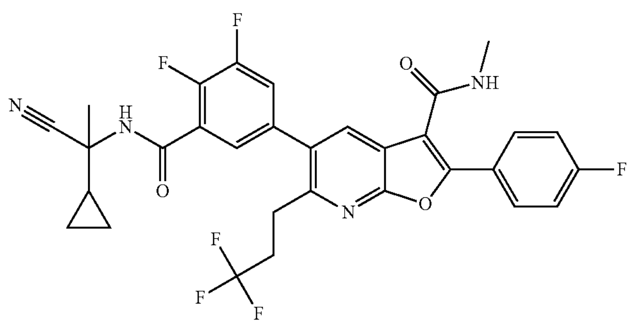 [SMILES: CNC(=O)c1c(-c2ccc(F)cc2)oc2nc(CCC(F)(F)F)c(-c3cc(F)c(F)c(C(=O)NC(C)(C#N)C4CC4)c3)cc12] | 0.0018 A |
| 18001 | 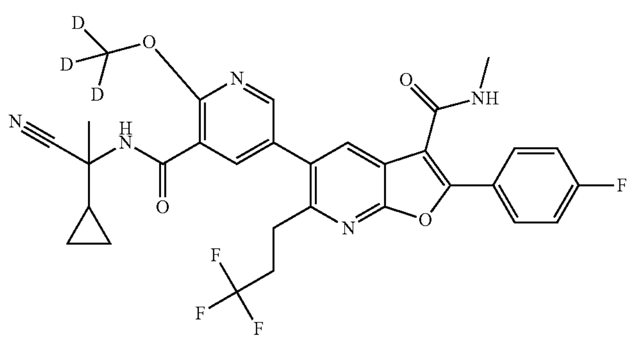 [SMILES: [2H]C([2H])([2H])Oc1ncc(-c2cc3c(C(=O)NC)c(-c4ccc(F)cc4)oc3nc2CCC(F)(F)F)cc1C(=O)NC(C)(C#N)C1CC1] | 0.0037 A |
| 20001 | 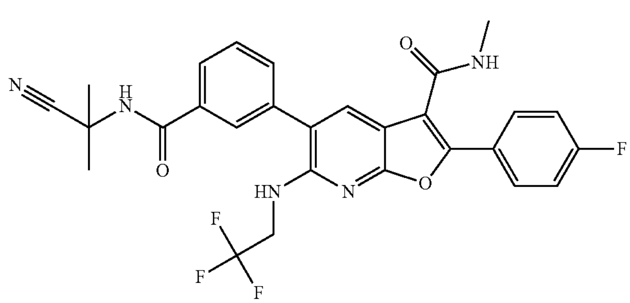 [SMILES: CNC(=O)c1c(-c2ccc(F)cc2)oc2nc(NCC(F)(F)F)c(-c3cccc(C(=O)NC(C)(C)C#N)c3)cc12] | A |

TABLE 2-continued

| Cmpd# | Structure | EC$_{50}$ (uM) 1b |
|---|---|---|
| 20002 | 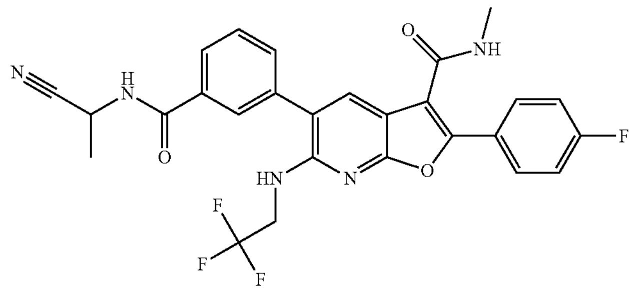 [SMILES: CNC(=O)c1c(-c2ccc(F)cc2)oc2nc(NCC(F)(F)F)c(-c3cccc(C(=O)NC(C)C#N)c3)cc12] | A |
| 20003 Chiral | 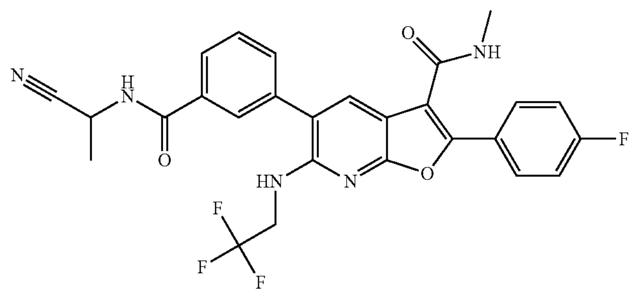 [SMILES: CNC(=O)c1c(-c2ccc(F)cc2)oc2nc(NCC(F)(F)F)c(-c3cccc(C(=O)NC(C)C#N)c3)cc12] | A |
| 20004 Chiral | 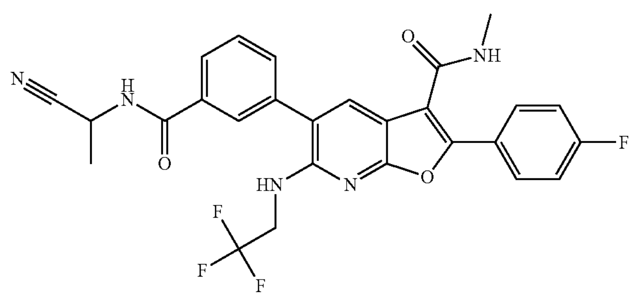 [SMILES: CNC(=O)c1c(-c2ccc(F)cc2)oc2nc(NCC(F)(F)F)c(-c3cccc(C(=O)NC(C)C#N)c3)cc12] | A |
| 20005 | 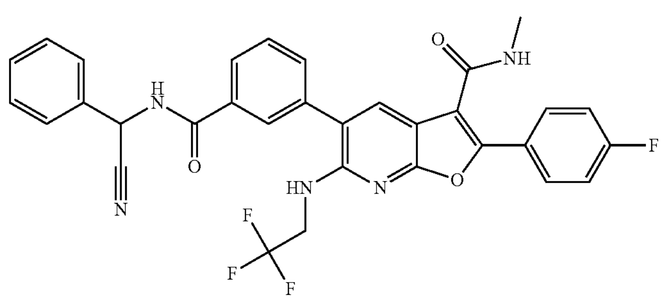 [SMILES: CNC(=O)c1c(-c2ccc(F)cc2)oc2nc(NCC(F)(F)F)c(-c3cccc(C(=O)NC(C#N)c4ccccc4)c3)cc12] | 0.0140 A |
| 20006 | 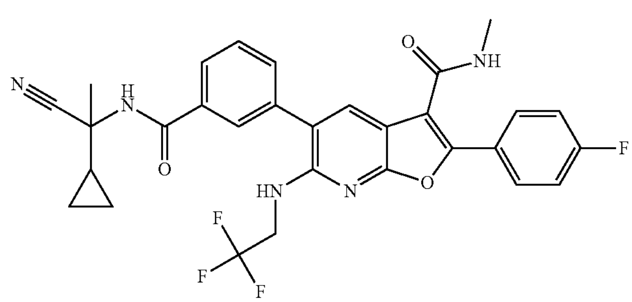 [SMILES: CNC(=O)c1c(-c2ccc(F)cc2)oc2nc(NCC(F)(F)F)c(-c3cccc(C(=O)NC(C)(C#N)C4CC4)c3)cc12] | 0.0031 A |

TABLE 2-continued

| Cmpd# | Structure | EC$_{50}$ (uM) 1b |
|---|---|---|
| 20007 Chiral | 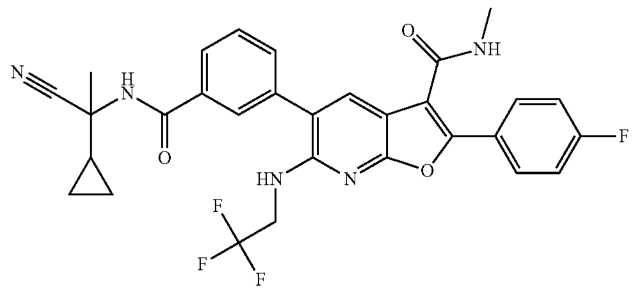 [SMILES: CNC(=O)c1c(-c2ccc(F)cc2)oc2nc(NCC(F)(F)F)c(-c3cccc(C(=O)NC(C)(C#N)C4CC4)c3)cc12] | A |
| 20008 Chiral | 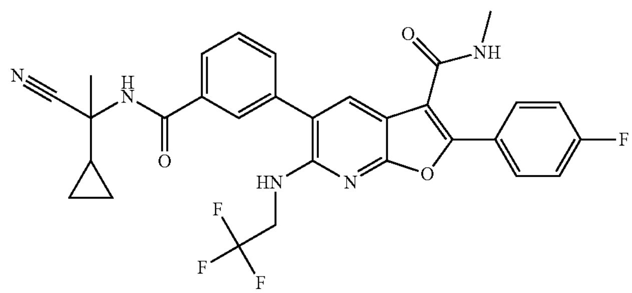 [SMILES: CNC(=O)c1c(-c2ccc(F)cc2)oc2nc(NCC(F)(F)F)c(-c3cccc(C(=O)NC(C)(C#N)C4CC4)c3)cc12] | A |
| 21001 | 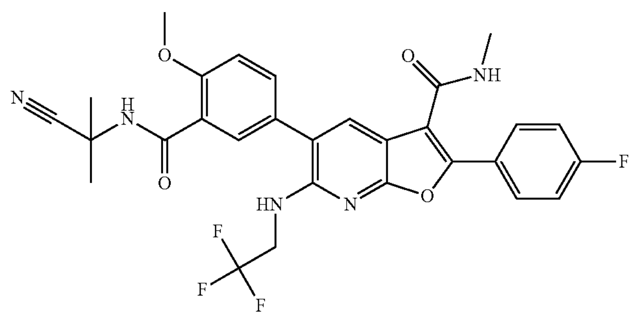 [SMILES: CNC(=O)c1c(-c2ccc(F)cc2)oc2nc(NCC(F)(F)F)c(-c3ccc(OC)c(C(=O)NC(C)(C)C#N)c3)cc12] | A |
| 22001 | 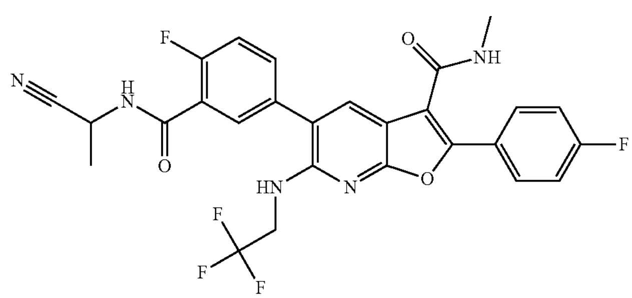 [SMILES: CNC(=O)c1c(-c2ccc(F)cc2)oc2nc(NCC(F)(F)F)c(-c3ccc(F)c(C(=O)NC(C)C#N)c3)cc12] | 0.0055 A |
| 22002 Chiral | 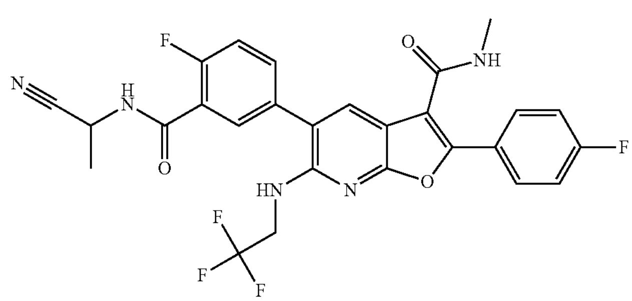 [SMILES: CNC(=O)c1c(-c2ccc(F)cc2)oc2nc(NCC(F)(F)F)c(-c3ccc(F)c(C(=O)NC(C)C#N)c3)cc12] | A |

TABLE 2-continued
| Cmpd# | Structure | EC$_{50}$ (uM) 1b |
|---|---|---|
| 22003 Chiral | 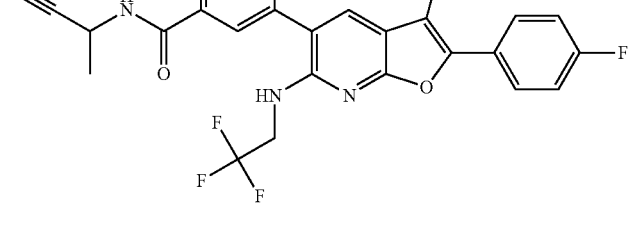 | A |
| 22004 | 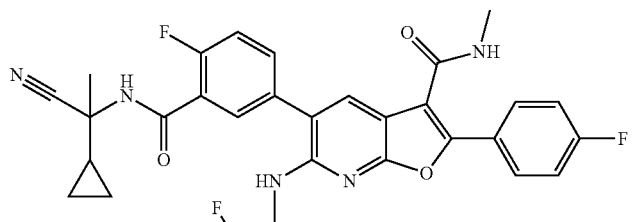 | 0.0040 A |
| 22005 Chiral | 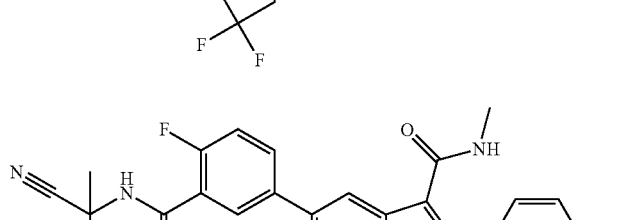 | A |
| 22006 Chiral | 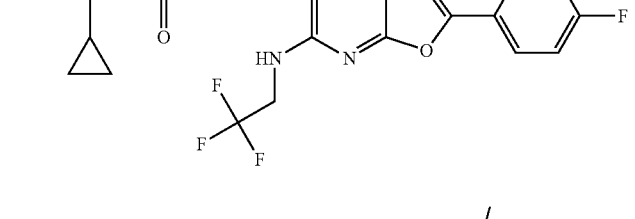 | A |
| 23001 | 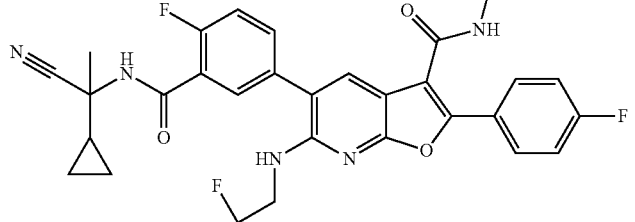 | A |

TABLE 2-continued

| Cmpd# | Structure | EC$_{50}$ (uM) 1b |
|---|---|---|
| 23002 | 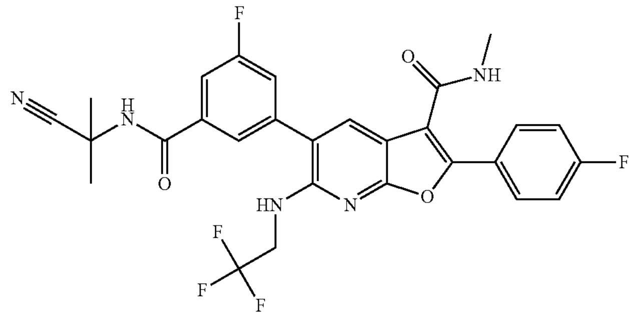 [SMILES: CNC(=O)c1c(-c2ccc(F)cc2)oc2nc(NCC(F)(F)F)c(-c3cc(F)cc(C(=O)NC(C)(C)C#N)c3)cc12] | 0.0072 A |
| 24001 | 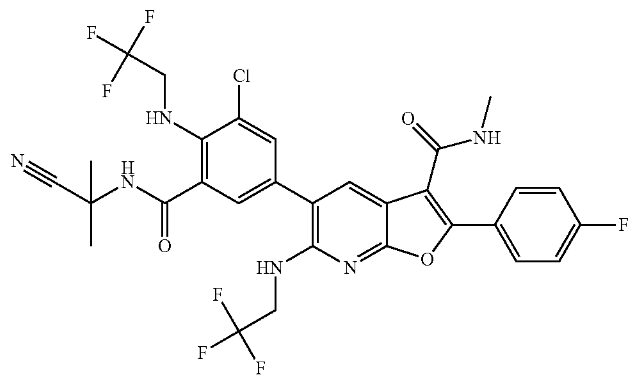 [SMILES: CNC(=O)c1c(-c2ccc(F)cc2)oc2nc(NCC(F)(F)F)c(-c3cc(Cl)c(NCC(F)(F)F)c(C(=O)NC(C)(C)C#N)c3)cc12] | 0.0539 A |
| 30001 | 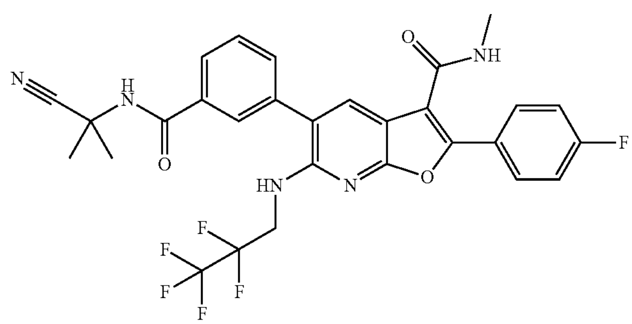 [SMILES: CNC(=O)c1c(-c2ccc(F)cc2)oc2nc(NCC(F)(F)C(F)(F)F)c(-c3cccc(C(=O)NC(C)(C)C#N)c3)cc12] | A |
| 30002 | 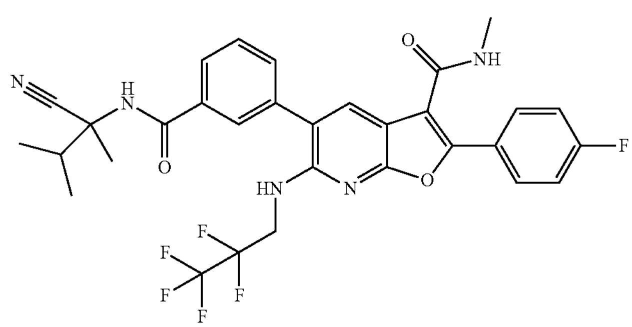 [SMILES: CNC(=O)c1c(-c2ccc(F)cc2)oc2nc(NCC(F)(F)C(F)(F)F)c(-c3cccc(C(=O)NC(C)(C#N)C(C)C)c3)cc12] | 0.0394 A |

TABLE 2-continued

| Cmpd# | Structure | EC$_{50}$ (uM) 1b |
|---|---|---|
| 30003 | 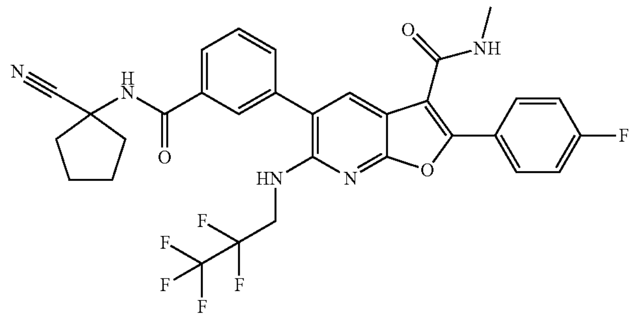 [SMILES: CNC(=O)c1c(-c2ccc(F)cc2)oc2nc(NCC(F)(F)C(F)(F)F)c(-c3cccc(C(=O)NC4(C#N)CCCC4)c3)cc12] | A |
| 31001 | 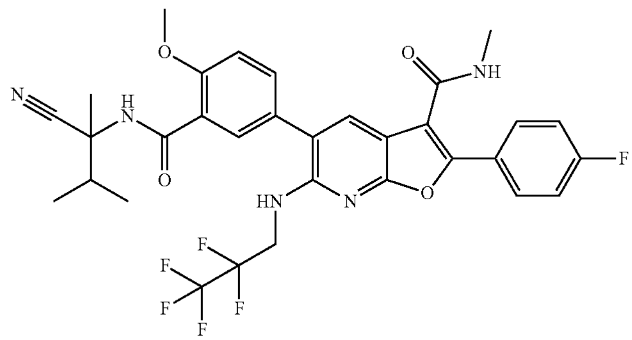 [SMILES: CNC(=O)c1c(-c2ccc(F)cc2)oc2nc(NCC(F)(F)C(F)(F)F)c(-c3ccc(OC)c(C(=O)NC(C)(C#N)C(C)C)c3)cc12] | A |
| 31002 | 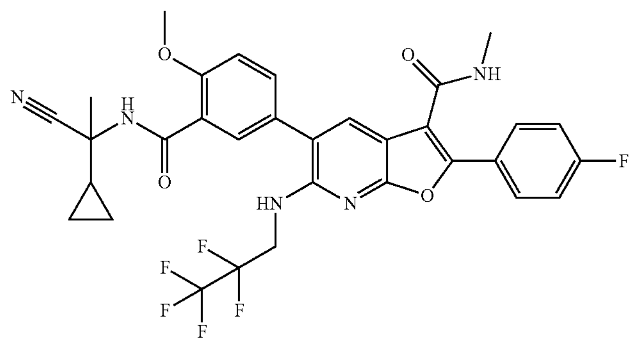 [SMILES: CNC(=O)c1c(-c2ccc(F)cc2)oc2nc(NCC(F)(F)C(F)(F)F)c(-c3ccc(OC)c(C(=O)NC(C)(C#N)C4CC4)c3)cc12] | 0.0061 A |
| 40001 | 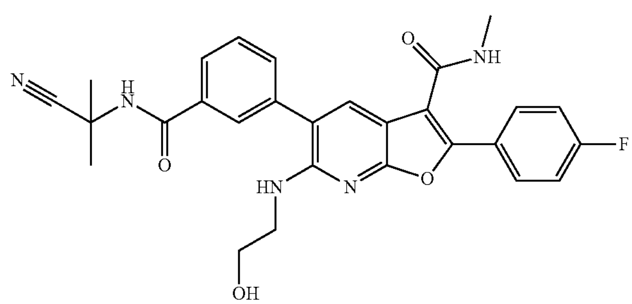 [SMILES: CNC(=O)c1c(-c2ccc(F)cc2)oc2nc(NCCO)c(-c3cccc(C(=O)NC(C)(C)C#N)c3)cc12] | A |
| 50001 | 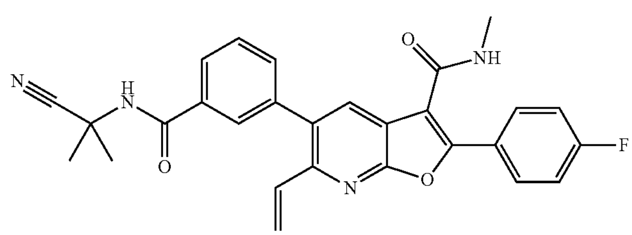 [SMILES: C=Cc1nc2oc(-c3ccc(F)cc3)c(C(=O)NC)c2cc1-c1cccc(C(=O)NC(C)(C)C#N)c1] | 0.0107 A |

TABLE 2-continued
| Cmpd# | Structure | EC$_{50}$ (uM) 1b |
|---|---|---|
| K1001 | 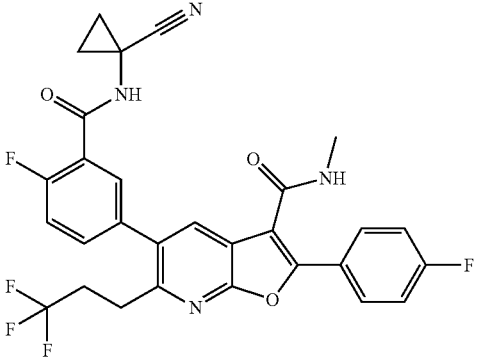 [SMILES: CNC(=O)c1c(-c2ccc(F)cc2)oc2nc(CCC(F)(F)F)c(-c3ccc(F)c(C(=O)NC4(C#N)CC4)c3)cc12] | 0.0061 A |
| K1002 | 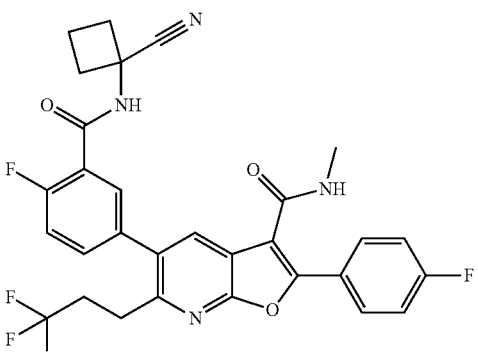 | A |
| K1003 | 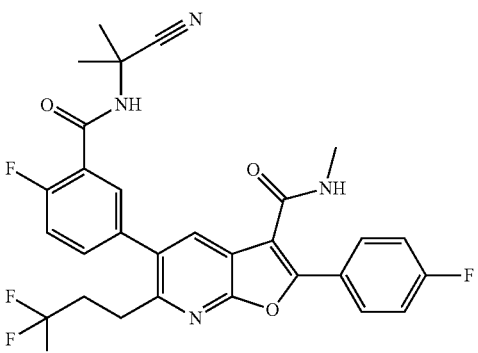 | A |
| K2001 | 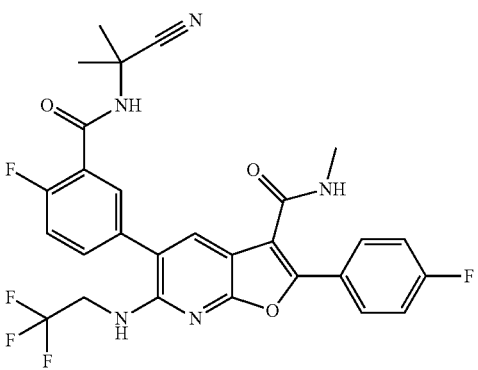 [SMILES: CNC(=O)c1c(-c2ccc(F)cc2)oc2nc(NCC(F)(F)F)c(-c3ccc(F)c(C(=O)NC(C)(C)C#N)c3)cc12] | A |

TABLE 2-continued

| Cmpd# | Structure | EC$_{50}$ (uM) 1b |
|---|---|---|
| K2002 | 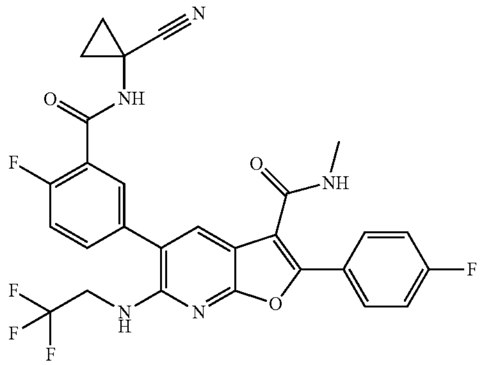 | 0.0034 A |
| K2003 | 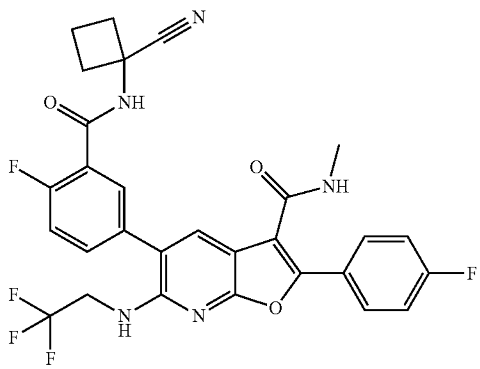 [SMILES: CNC(=O)c1c(-c2ccc(F)cc2)oc2nc(NCC(F)(F)F)c(-c3ccc(F)c(C(=O)NC4(C#N)CCC4)c3)cc12] | A |
| K2004 | 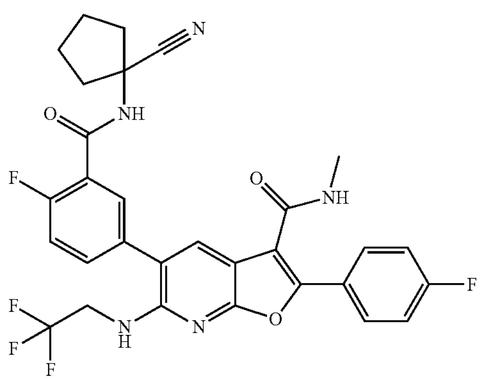 [SMILES: CNC(=O)c1c(-c2ccc(F)cc2)oc2nc(NCC(F)(F)F)c(-c3ccc(F)c(C(=O)NC4(C#N)CCCC4)c3)cc12] | A |
| K2005 | 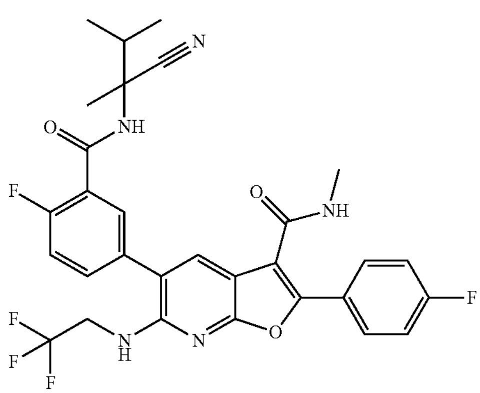 [SMILES: CNC(=O)c1c(-c2ccc(F)cc2)oc2nc(NCC(F)(F)F)c(-c3ccc(F)c(C(=O)NC(C)(C#N)C(C)C)c3)cc12] | A |

TABLE 2-continued

| Cmpd# | Structure | EC$_{50}$ (uM) 1b |
|---|---|---|
| K3001 | 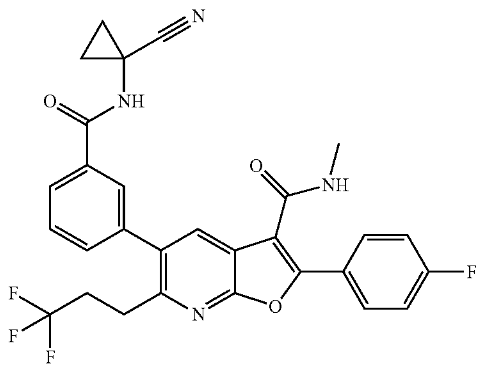 [SMILES: CNC(=O)c1c(-c2ccc(F)cc2)oc2nc(CCC(F)(F)F)c(-c3cccc(C(=O)NC4(C#N)CC4)c3)cc12] | A |
| K4001 | 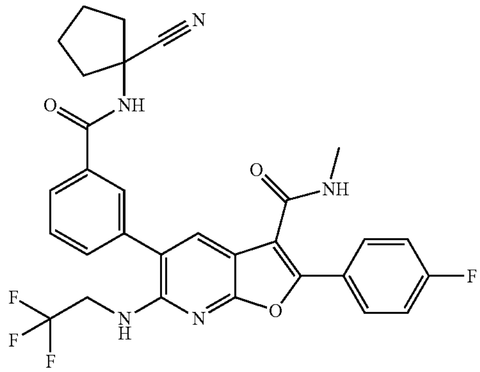 [SMILES: CNC(=O)c1c(-c2ccc(F)cc2)oc2nc(NCC(F)(F)F)c(-c3cccc(C(=O)NC4(C#N)CCCC4)c3)cc12] | A |
| K4002 | 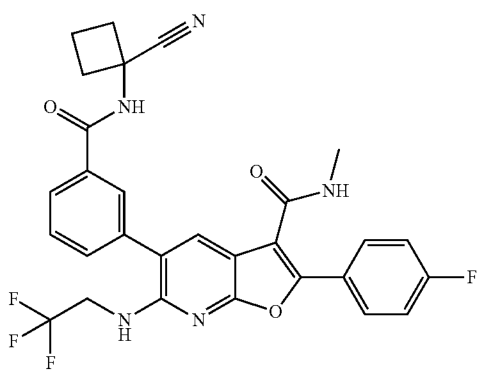 [SMILES: CNC(=O)c1c(-c2ccc(F)cc2)oc2nc(NCC(F)(F)F)c(-c3cccc(C(=O)NC4(C#N)CCC4)c3)cc12] | A |
| K4003 | 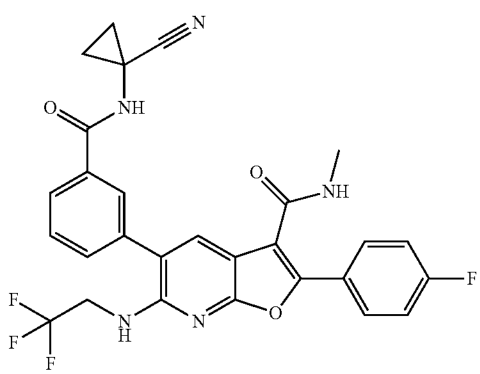 [SMILES: CNC(=O)c1c(-c2ccc(F)cc2)oc2nc(NCC(F)(F)F)c(-c3cccc(C(=O)NC4(C#N)CC4)c3)cc12] | 0.0043 A |

TABLE 2-continued

| Cmpd# | Structure | EC$_{50}$ (uM) 1b |
|---|---|---|
| K4004 | 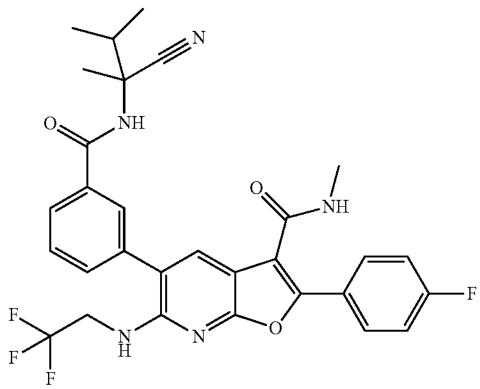 [SMILES: CNC(=O)c1c(-c2ccc(F)cc2)oc2nc(NCC(F)(F)F)c(-c3cccc(C(=O)NC(C)(C#N)C(C)C)c3)cc12] | 0.0040 A |
| K5001 | 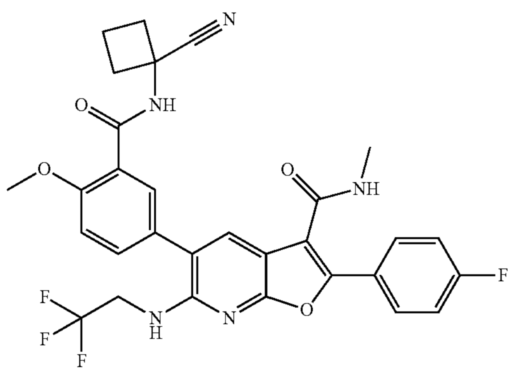 [SMILES: CNC(=O)c1c(-c2ccc(F)cc2)oc2nc(NCC(F)(F)F)c(-c3ccc(OC)c(C(=O)NC4(C#N)CCC4)c3)cc12] | A |
| K5002 | 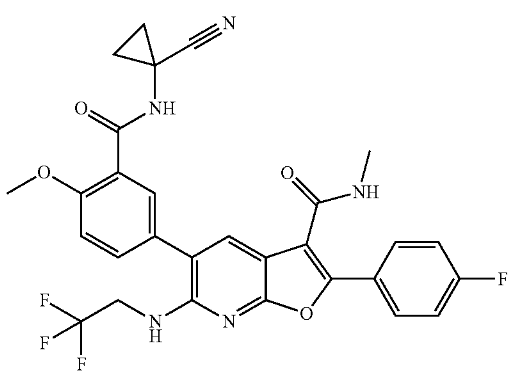 | A |
| K5003 | 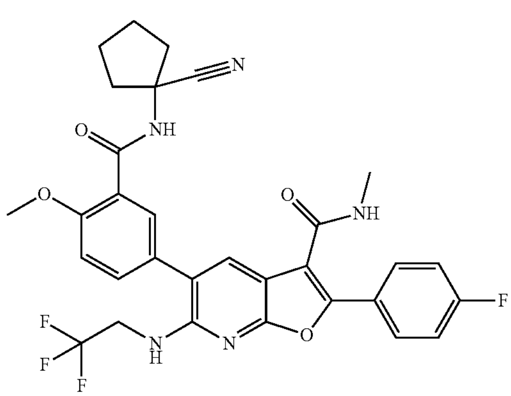 [SMILES: CNC(=O)c1c(-c2ccc(F)cc2)oc2nc(NCC(F)(F)F)c(-c3ccc(OC)c(C(=O)NC4(C#N)CCCC4)c3)cc12] | A |

TABLE 2-continued

| Cmpd# | Structure | EC$_{50}$ (uM) 1b |
|---|---|---|
| K5004 | 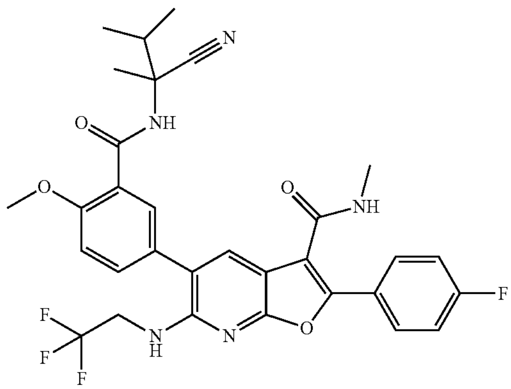 [SMILES: CNC(=O)c1c(-c2ccc(F)cc2)oc2nc(NCC(F)(F)F)c(-c3ccc(OC)c(C(=O)NC(C)(C#N)C(C)C)c3)cc12] | 0.0028 A |
| K6001 | 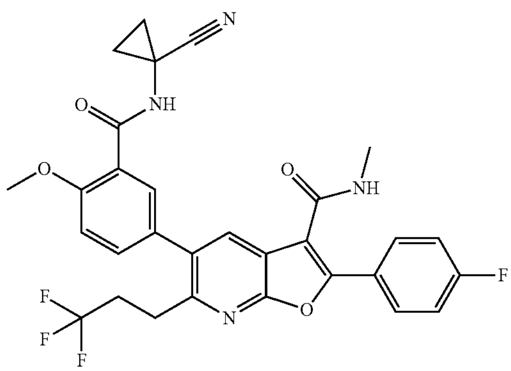 | A |
| K7001 | 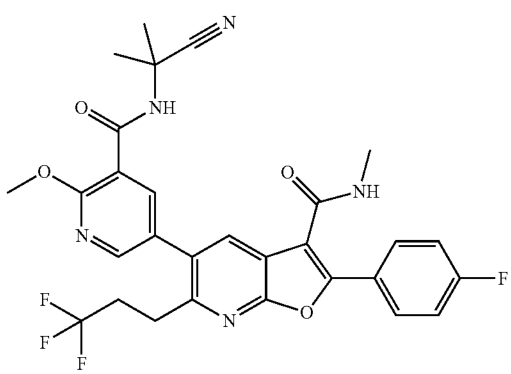 [SMILES: CNC(=O)c1c(-c2ccc(F)cc2)oc2nc(CCC(F)(F)F)c(-c3cnc(OC)c(C(=O)NC(C)(C)C#N)c3)cc12] | A |
| K7002 | 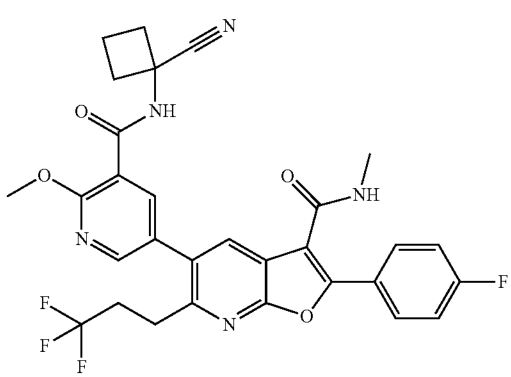 [SMILES: CNC(=O)c1c(-c2ccc(F)cc2)oc2nc(CCC(F)(F)F)c(-c3cnc(OC)c(C(=O)NC4(C#N)CCC4)c3)cc12] | A |

TABLE 2-continued
| Cmpd# | Structure | EC$_{50}$ (uM) 1b |
|---|---|---|
| K7003 | 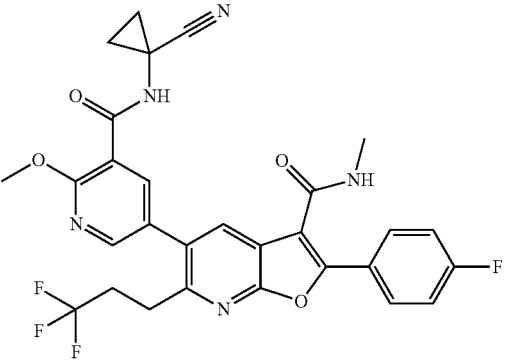 [SMILES: CNC(=O)c1c(-c2ccc(F)cc2)oc2nc(CCC(F)(F)F)c(-c3cnc(OC)c(C(=O)NC4(C#N)CC4)c3)cc12] | A |
| K7004 | 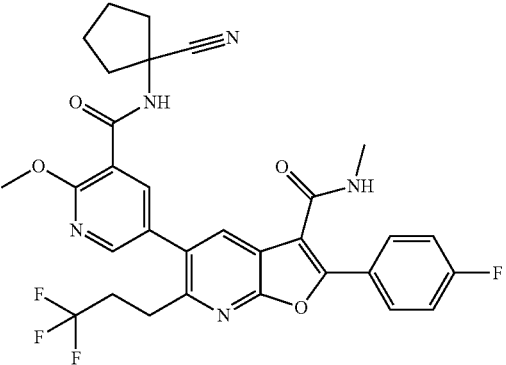 [SMILES: CNC(=O)c1c(-c2ccc(F)cc2)oc2nc(CCC(F)(F)F)c(-c3cnc(OC)c(C(=O)NC4(C#N)CCCC4)c3)cc12] | A |
| K7005 | 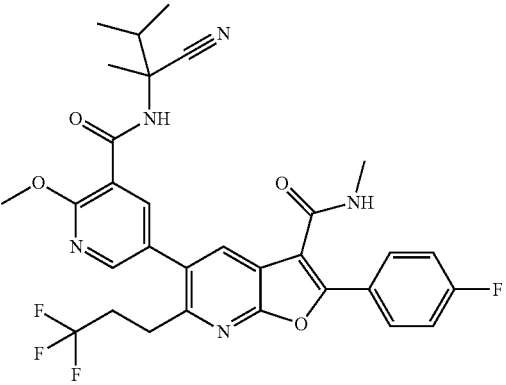 [SMILES: CNC(=O)c1c(-c2ccc(F)cc2)oc2nc(CCC(F)(F)F)c(-c3cnc(OC)c(C(=O)NC(C)(C#N)C(C)C)c3)cc12] | 0.0028 A |
| K8001 | 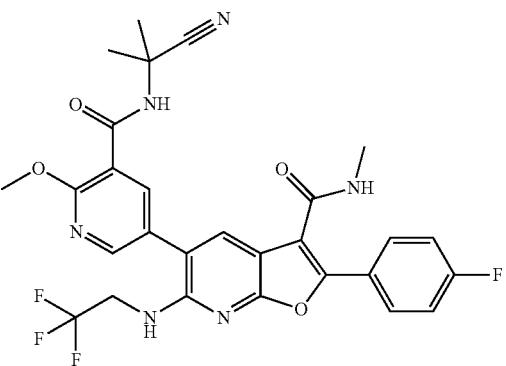 [SMILES: CNC(=O)c1c(-c2ccc(F)cc2)oc2nc(NCC(F)(F)F)c(-c3cnc(OC)c(C(=O)NC(C)(C)C#N)c3)cc12] | A |

TABLE 2-continued
| Cmpd# | Structure | EC$_{50}$ (uM) 1b |
|---|---|---|
| K8002 | 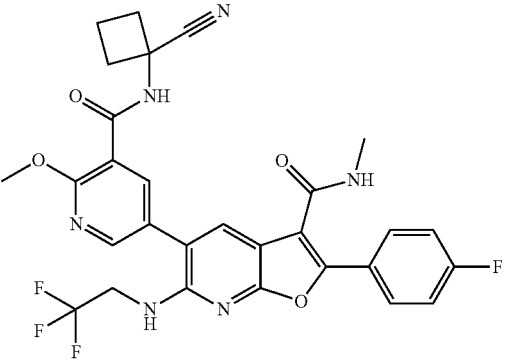 [SMILES: CNC(=O)c1c(-c2ccc(F)cc2)oc2nc(NCC(F)(F)F)c(-c3cnc(OC)c(C(=O)NC4(C#N)CCC4)c3)cc12] | A |
| K8003 | 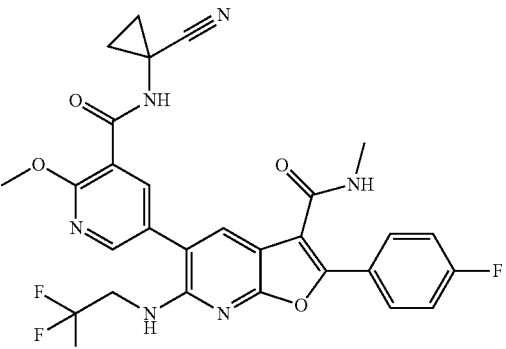 | A |
| K8004 | 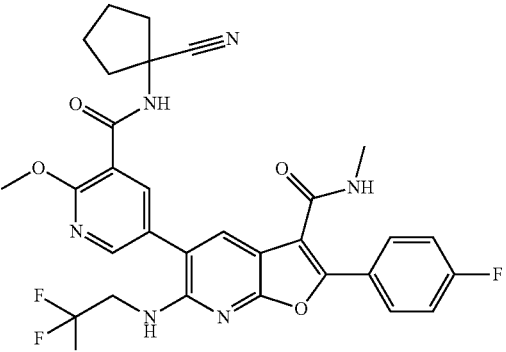 | A |
| K8005 | 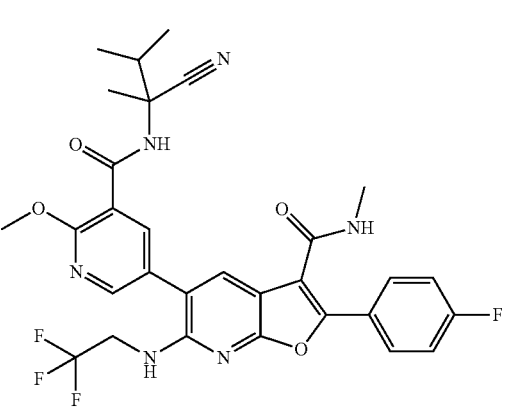 [SMILES: CNC(=O)c1c(-c2ccc(F)cc2)oc2nc(NCC(F)(F)F)c(-c3cnc(OC)c(C(=O)NC(C)(C#N)C(C)C)c3)cc12] | 0.0036 A |

TABLE 2-continued

| Cmpd# | Structure | EC$_{50}$ (uM) 1b |
|---|---|---|
| K9001 | 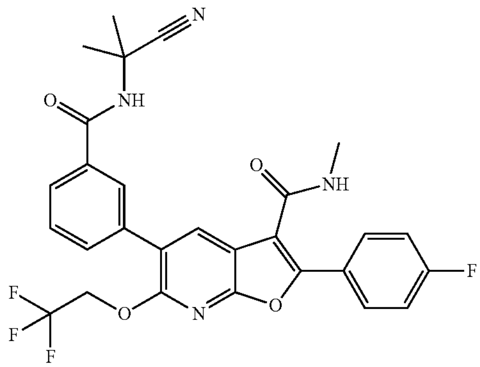 [SMILES: CNC(=O)c1c(-c2ccc(F)cc2)oc2nc(OCC(F)(F)F)c(-c3cccc(C(=O)NC(C)(C)C#N)c3)cc12] | 0.0177 uM (EC$_{50}$ for 1a instead) A |
| K10001 | 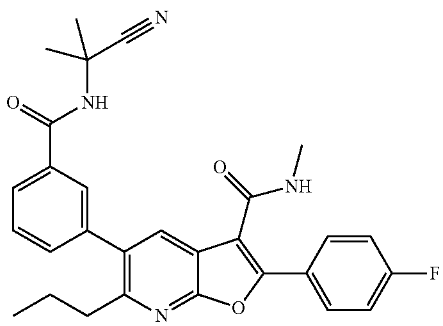 [SMILES: CCCc1nc2oc(-c3ccc(F)cc3)c(C(=O)NC)c2cc1-c1cccc(C(=O)NC(C)(C)C#N)c1] | A |
| K11001 | first eluting isomer | 0.0133 A |
| K11002 | second eluting isomer | 0.0044 A |

We claim:

1. A compound of Formula I, including pharmaceutically acceptable salts thereof:

[Structure of Formula I]

wherein
Z is C—R$^5$ or N;
R$^0$ is hydrogen;
R$^1$ is methyl;
R$^2$ is parafluorophenyl;
R$^3$ is hydrogen;
R$^4$, R$^5$, and R$^6$ are independently selected from the group of hydrogen, fluoro, alkoxy, and perdeuteroalkoxy;
R$^{7a}$ is selected from the group of hydrogen, methyl, fluoromethyl, and cyclopropyl;
R$^{7b}$ is selected from the group of hydrogen, methyl, fluoromethyl, cyclopropyl, and Ar$^1$;
or together R$^{7a}$ and R$^{7b}$ form a cyclopropyl or cyclobutyl ring;
R$^8$ is hydrogen,
Ar$^1$ is phenyl or pyrimidyl;
R$^9$ is R$^{201}$ or NR$^{203}$R$^{204}$;
R$^{201}$ is —CH$_2$CH$_2$CF$_3$ or vinyl;
R$^{202}$ is C$_1$-C$_3$ alkyl, or C$_1$-C$_3$ alkyl with between one to all of the hydrogens replaced by fluoro;
R$^{203}$ is hydrogen; and
R$^{204}$ is —CH$_2$CF$_3$, —CH$_2$CF$_2$—CF$_3$, or —CH$_2$CH$_2$OH.

2. A compound of claim 1 wherein R$^4$ is hydrogen, R$^5$ is hydrogen or fluoro, R$^{7b}$ is selected from the group of hydrogen, methyl, fluoromethyl, and cyclopropyl, or together R$^{7a}$ and R$^{7b}$ form a cyclopropyl or cyclobutyl ring; and
R$^{201}$ is —CH$_2$CH$_2$CF$_3$.

3. A compound of claim 1 wherein Z is N.

4. A compound of claim 1 wherein Z is CR$^5$.

5. A compound of claim 4 wherein R$^4$ is hydrogen and R$^6$ is —OCD$_3$.

6. A compound of claim 1 wherein R$^4$ is hydrogen, R$^5$ is hydrogen or fluoro R$^6$ is hydrogen, fluoro, or —OCH$_3$, R$^{7a}$ is selected from the group of hydrogen, methyl, fluoromethyl, and cyclopropyl, R$^{7b}$ is selected from hydrogen, methyl, fluoromethyl, or cyclopropyl, or together R$^{7a}$ and R$^{7b}$ form a cyclopropyl or cyclobutyl ring; and
R$^{201}$ is —CH$_2$CH$_2$CF$_3$.

7. A compound of claim 6 wherein R$^5$ is hydrogen, R$^6$ is fluoro, R$^{7a}$ is methyl, R$^{7b}$ is cyclopropyl, and R$^9$ is R$^{201}$.

8. The compound existing as a single enantiomer which is: (R)-5-(3-((1-cyano-1-cyclopropylethyl)carbamoyl)-4-fluorophenyl)-2-(4-fluorophenyl)-N-methyl-6-(3,3,3-trifluoropropyl)furo[2,3-b]pyridine-3-carboxamide.

9. The compound existing as a single enantiomer which is: (S)-5-(3-((1-cyano-1-cyclopropylethyl)carbamoyl)-4-fluorophenyl)-2-(4-fluorophenyl)-N-methyl-6-(3,3,3-trifluoropropyl)furo[2,3-b]pyridine-3-carboxamide.

10. A compound of claim 8 or claim 9, wherein said compound exists as the single enantiomer that exhibits a minus rotation when optical rotation is measured via standard methods in a polarimeter.

11. A compound, including pharmaceutically acceptable salts thereof, which is selected from the group of:

[Structures of compounds]

177
-continued
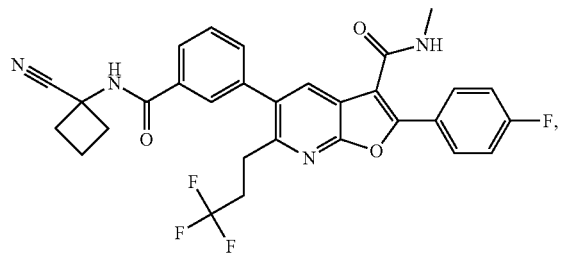
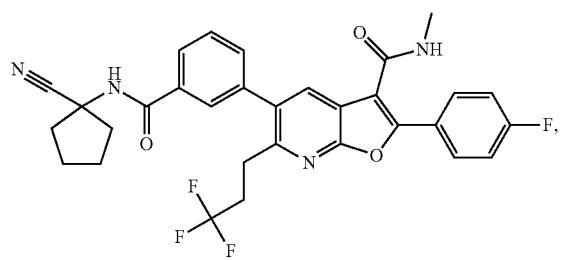
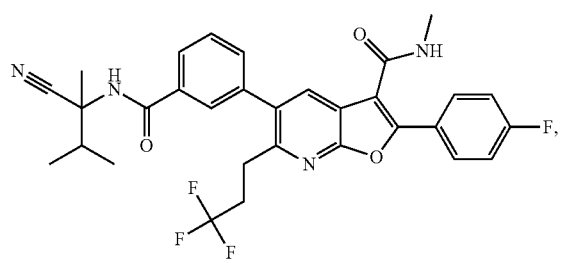
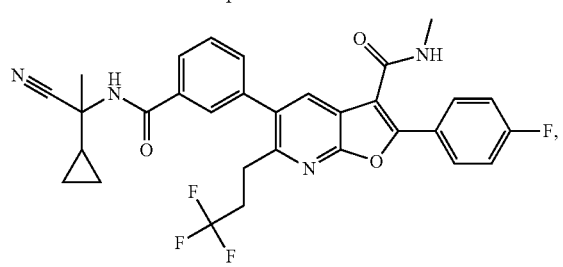
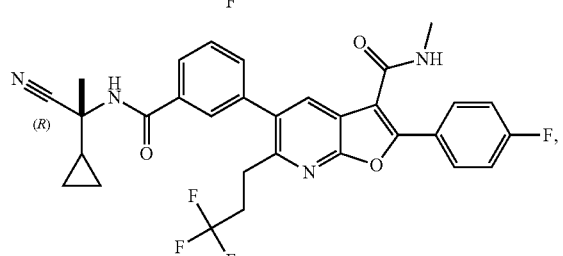
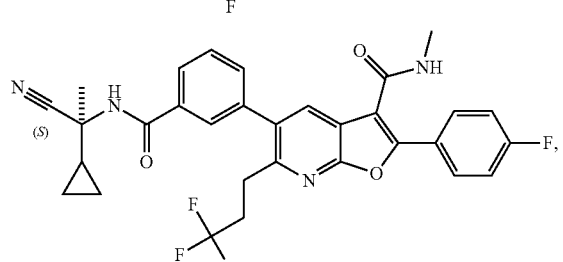
178
-continued
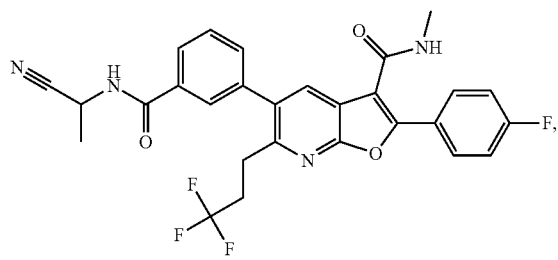
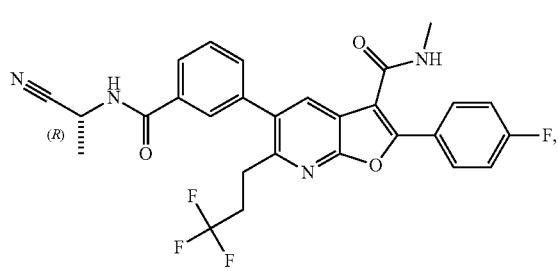
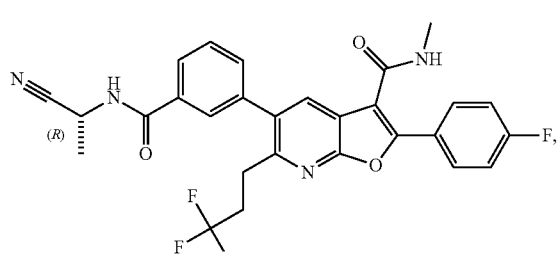
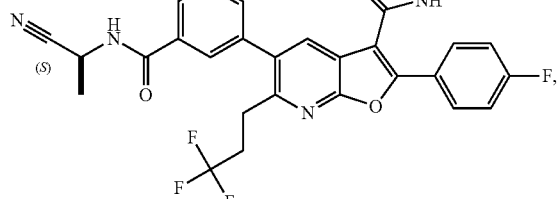
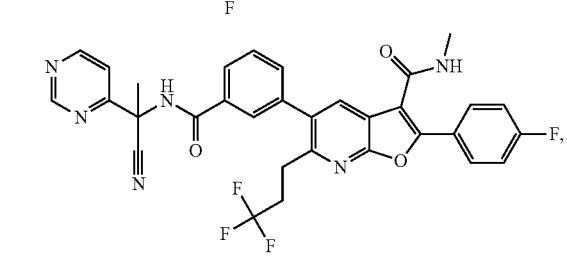
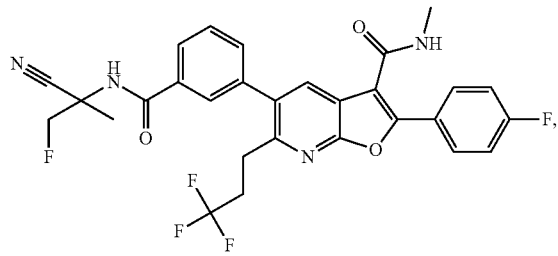
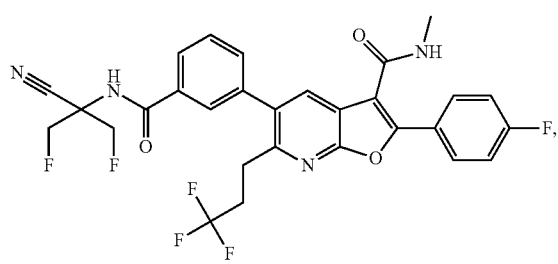

179
-continued
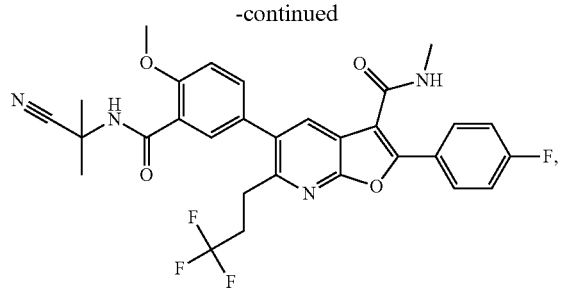
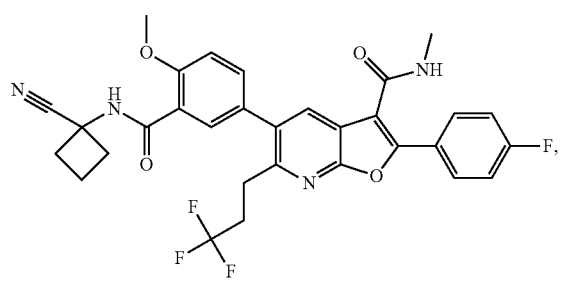
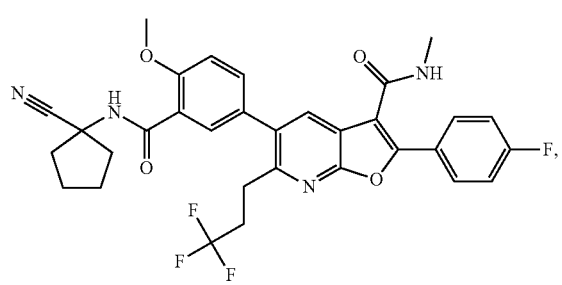
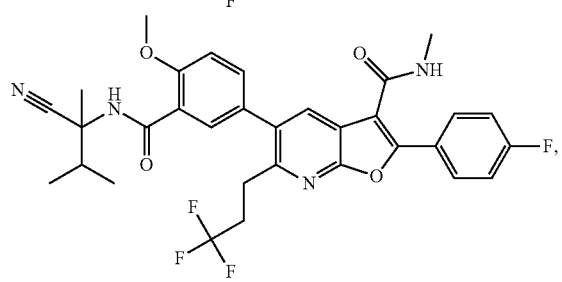
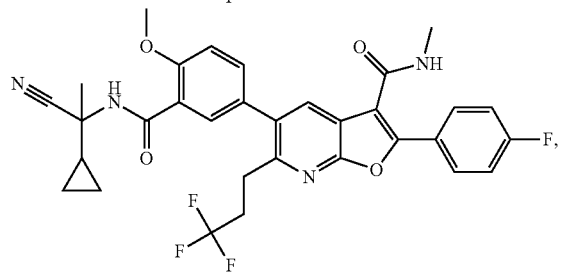
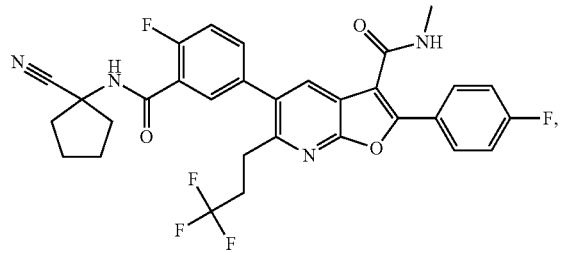
180
-continued
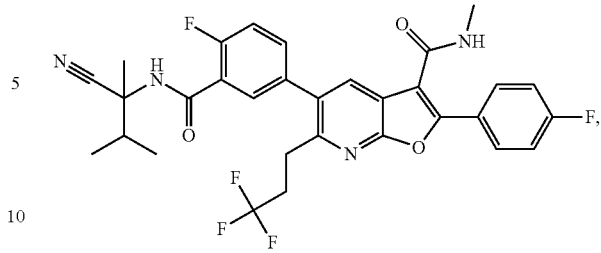
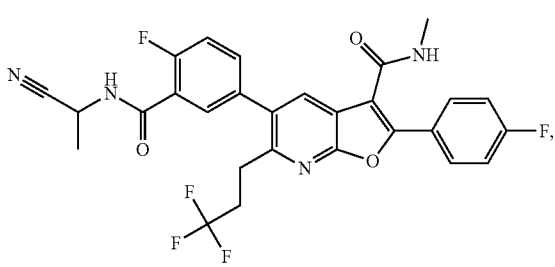
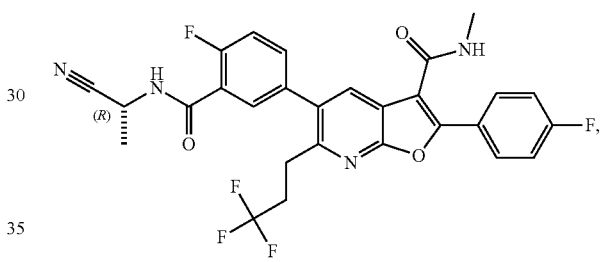
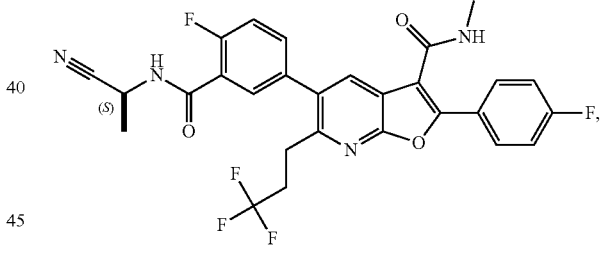
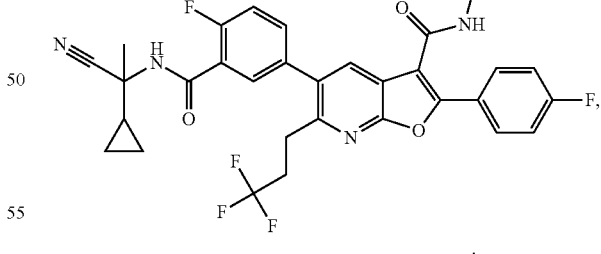
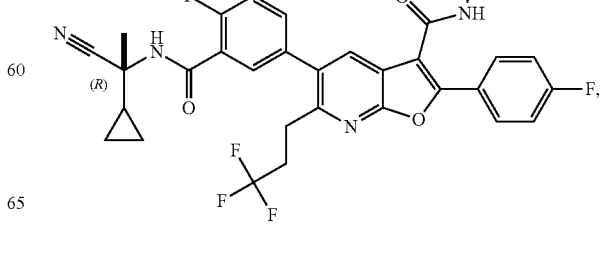

181
-continued
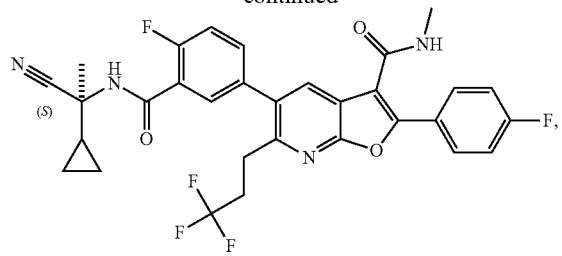
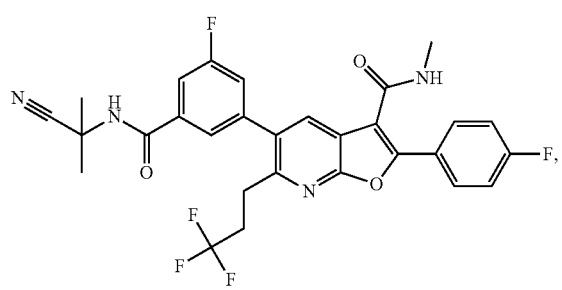
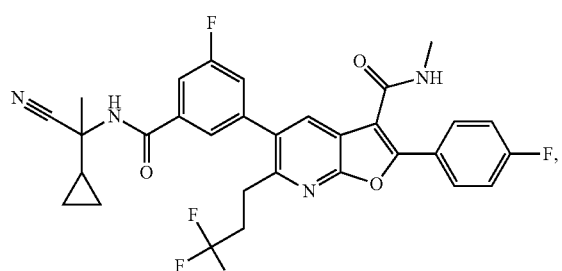
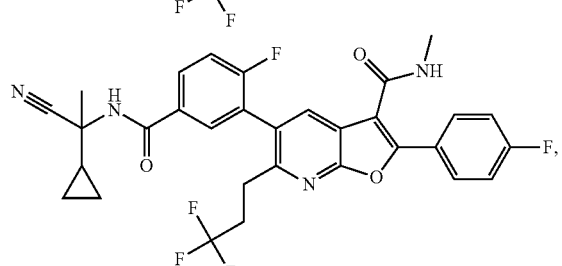
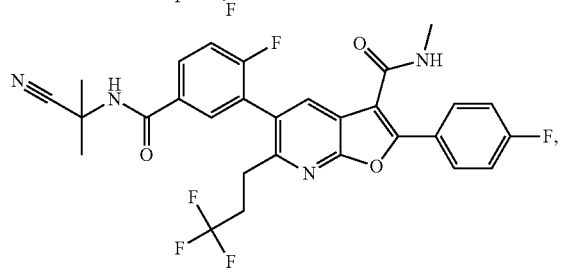
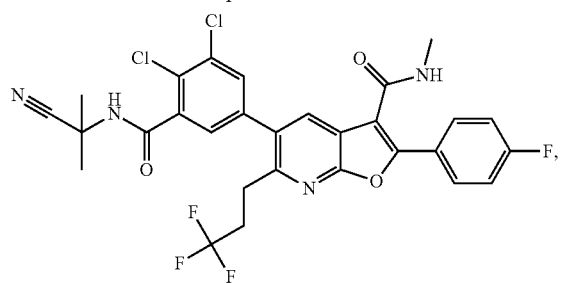
182
-continued
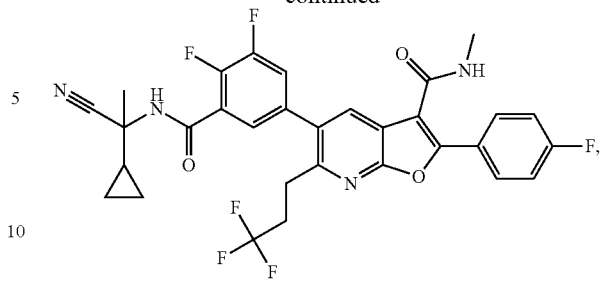
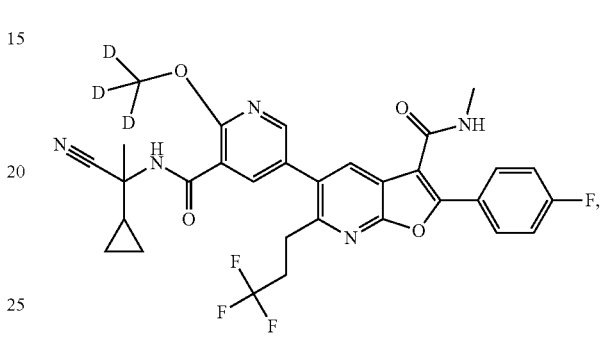
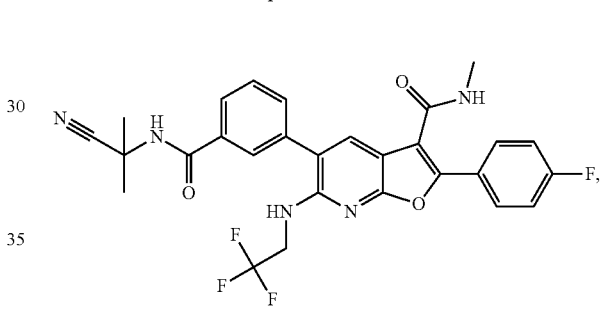
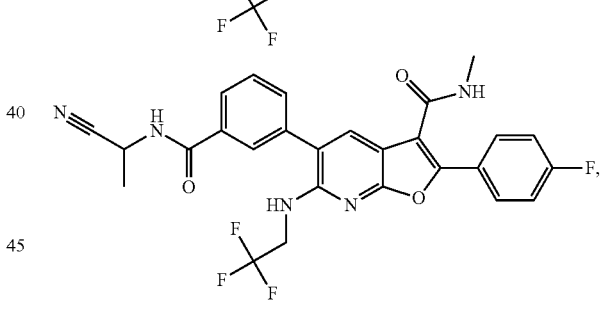
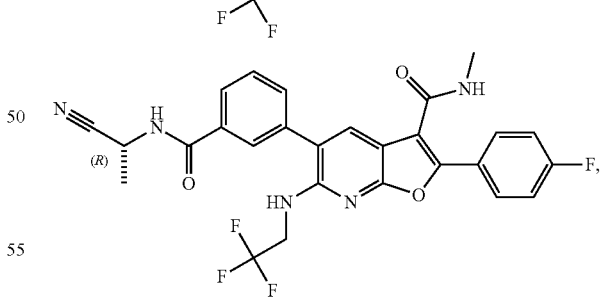
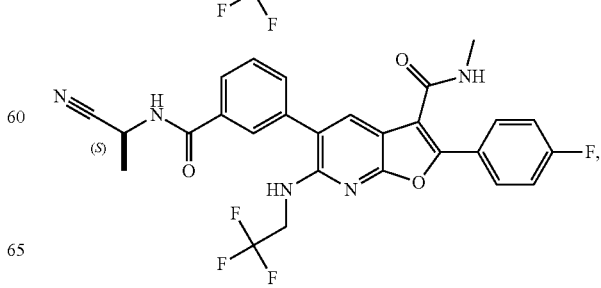

183
-continued
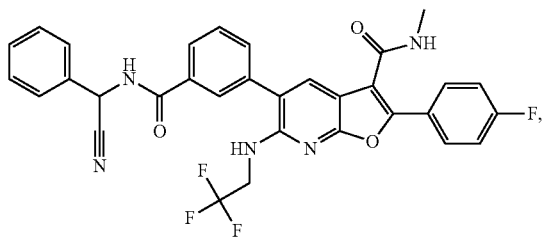
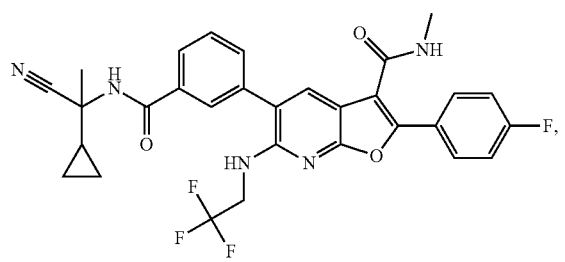
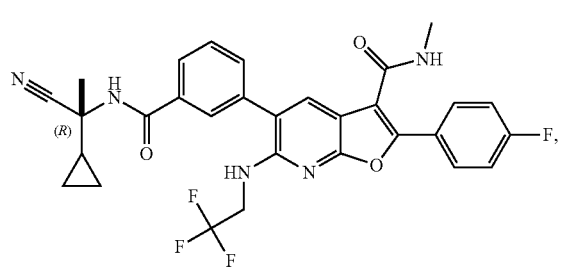
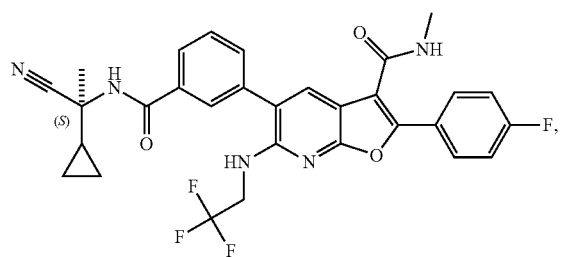
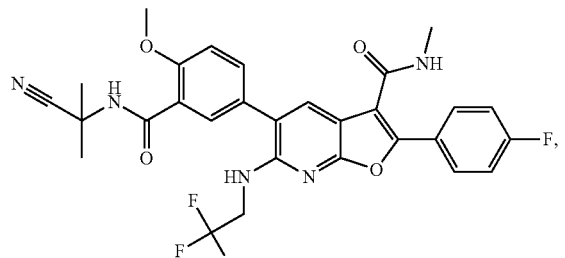
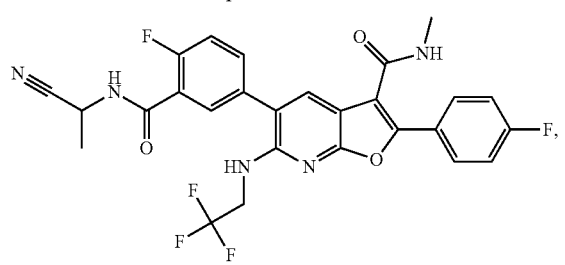
184
-continued
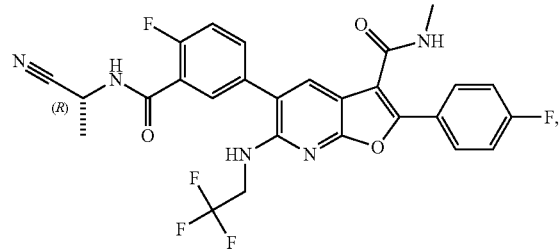
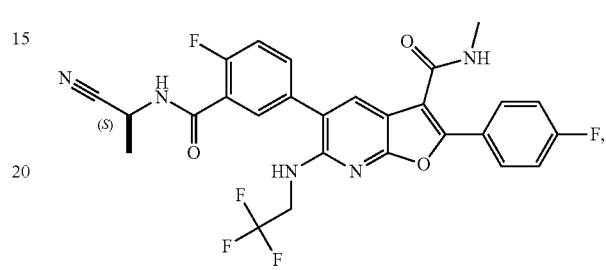
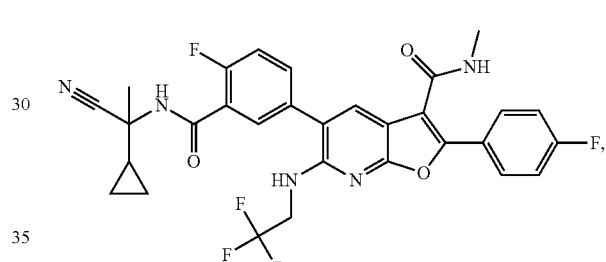
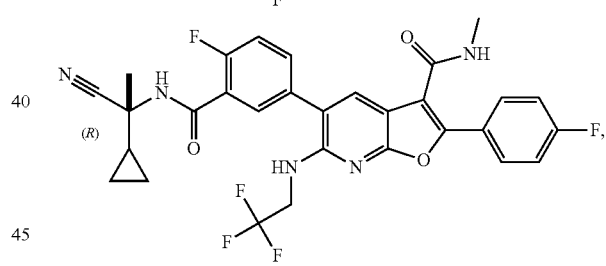
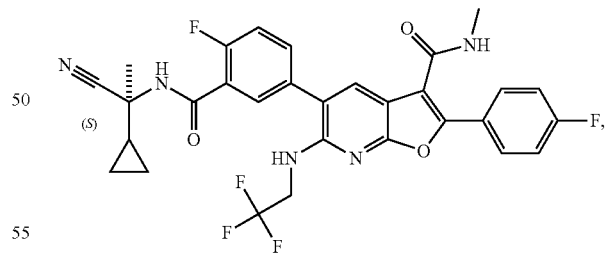
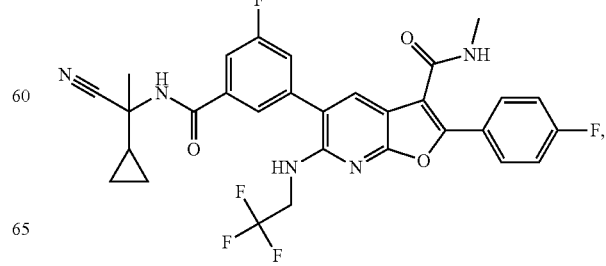

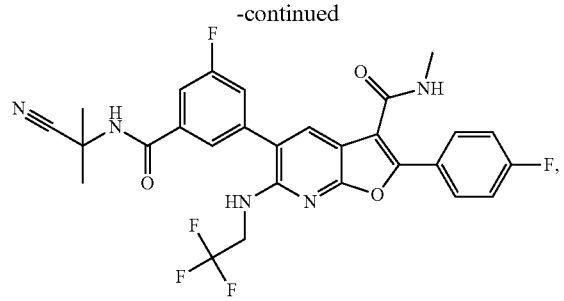
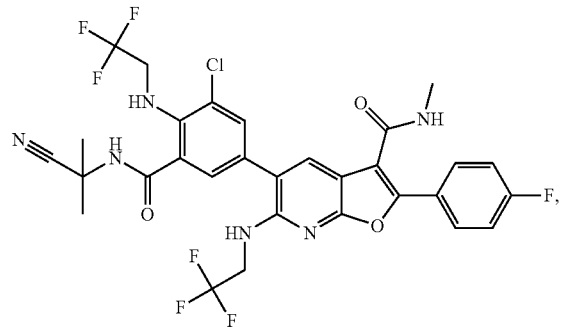
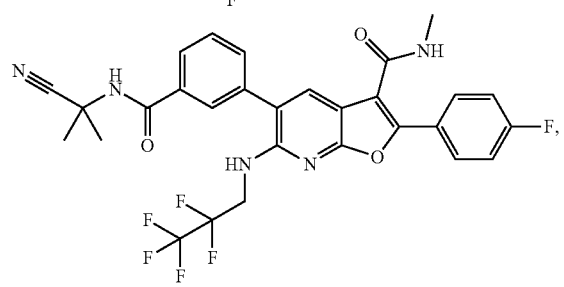
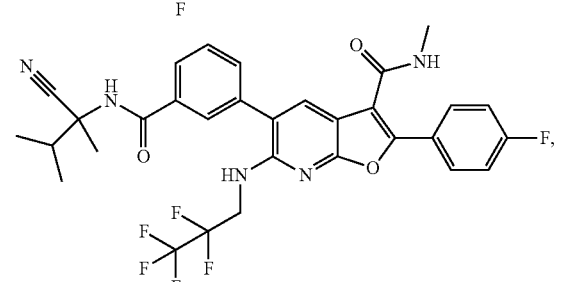
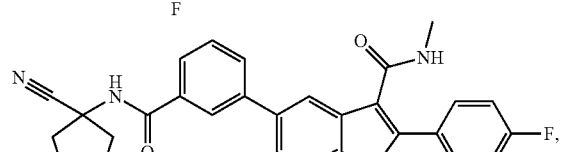
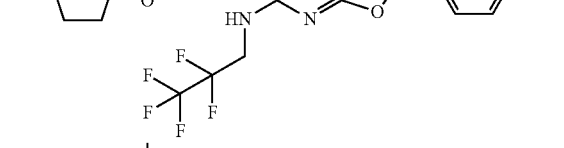
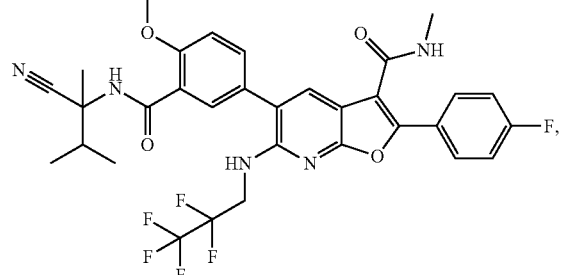
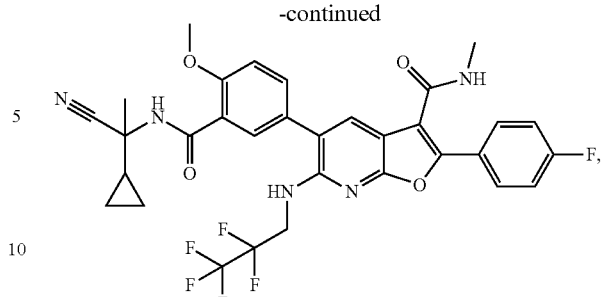
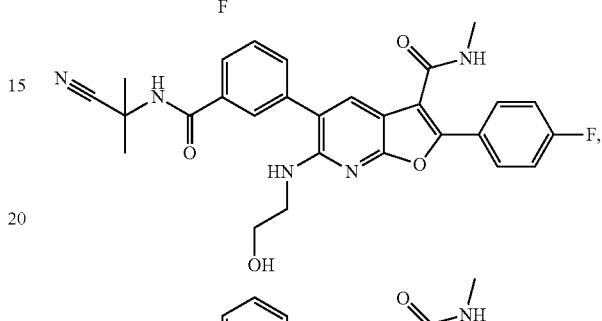
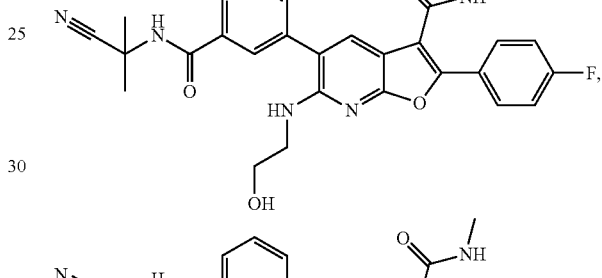
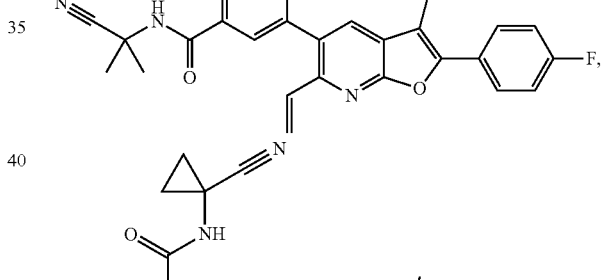
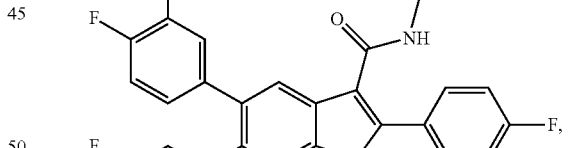
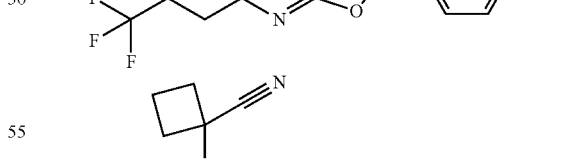
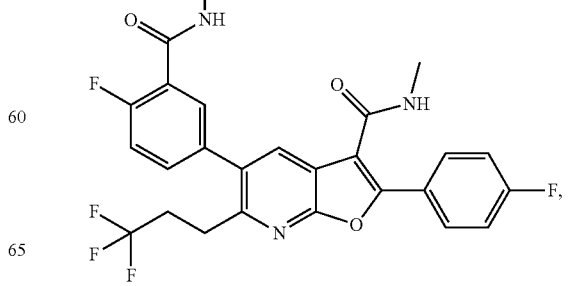

187
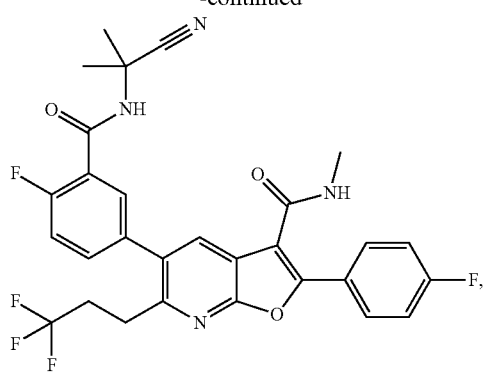
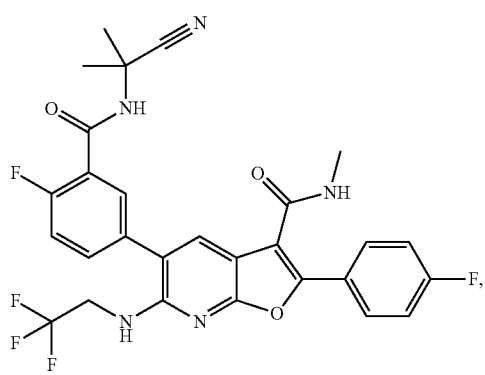
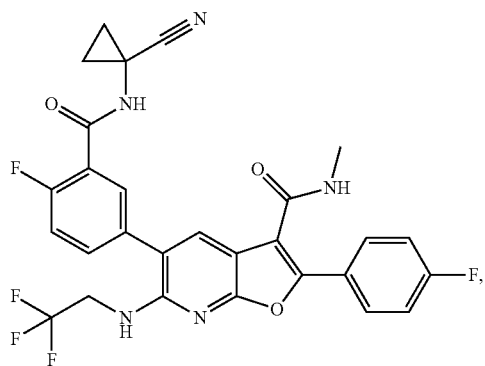
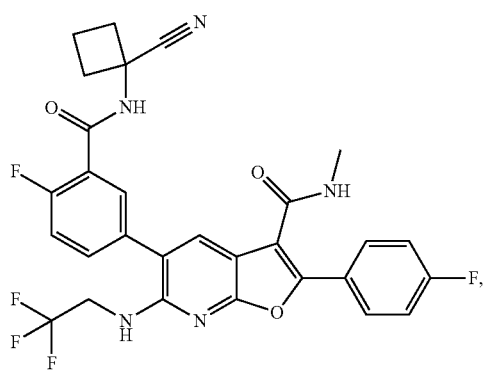
188
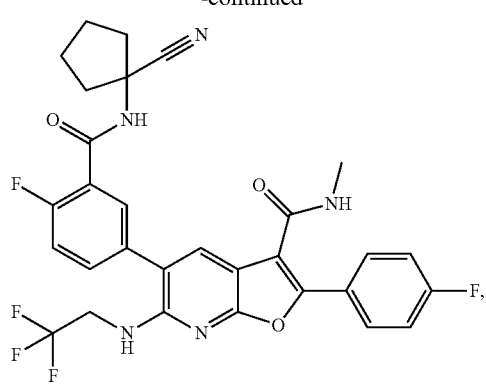
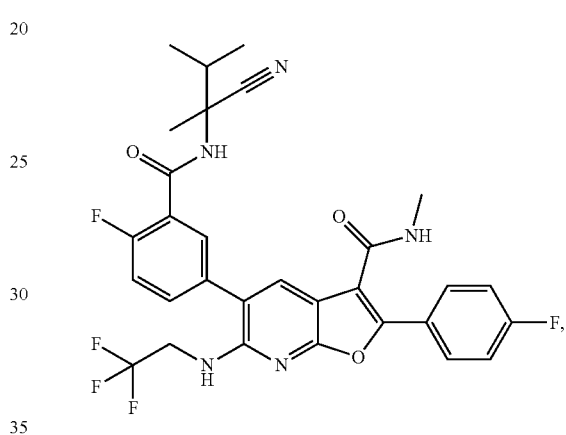
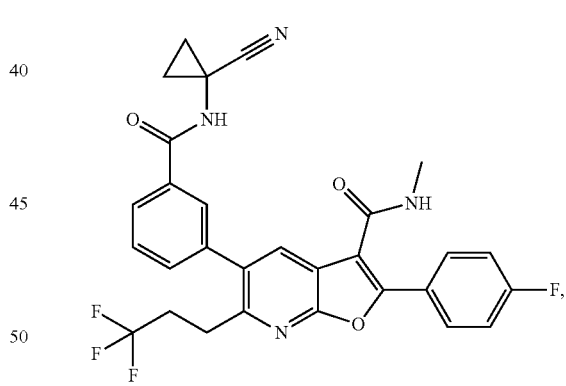
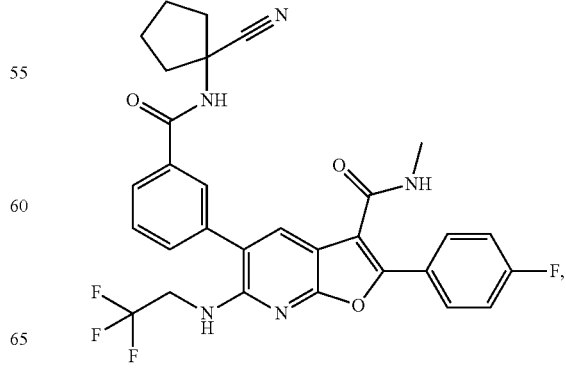

189
-continued
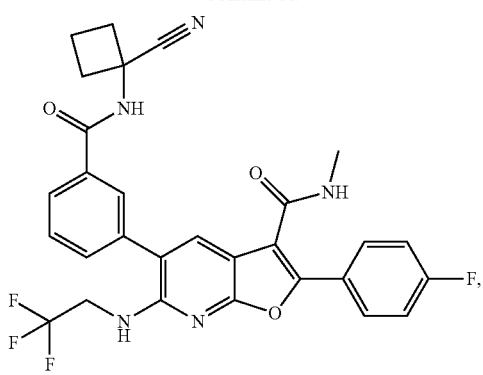
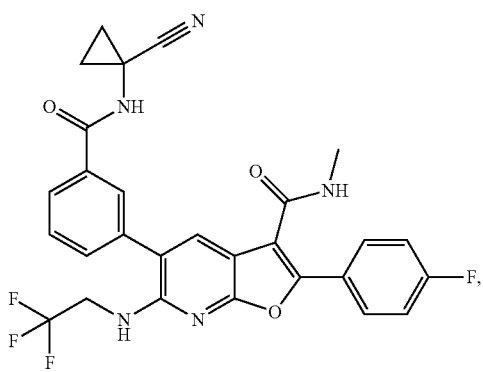
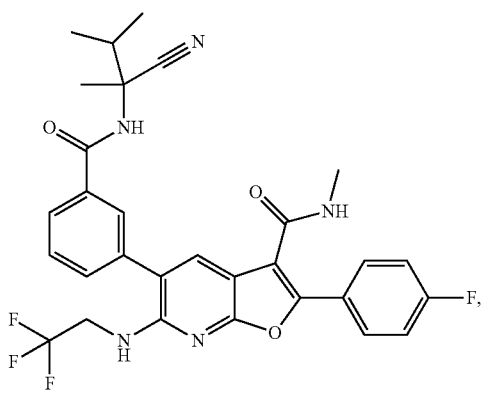
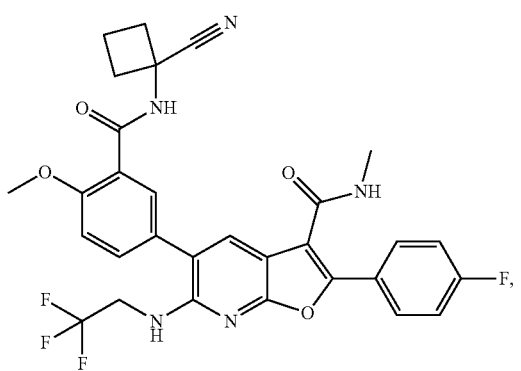
190
-continued
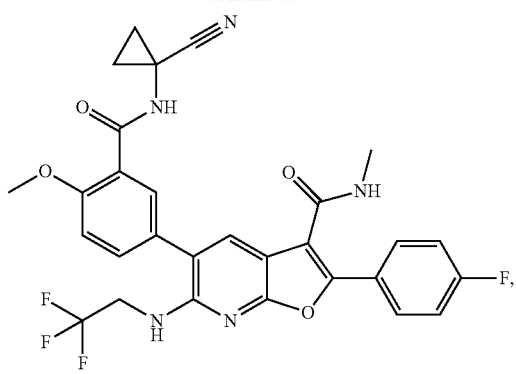
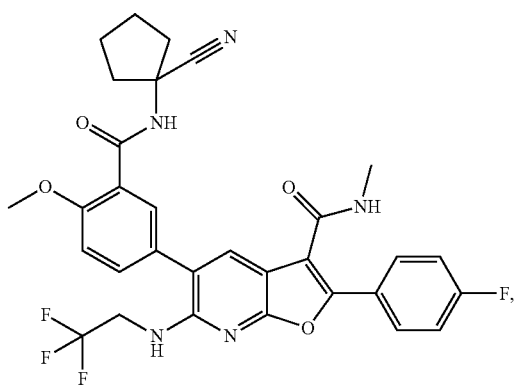
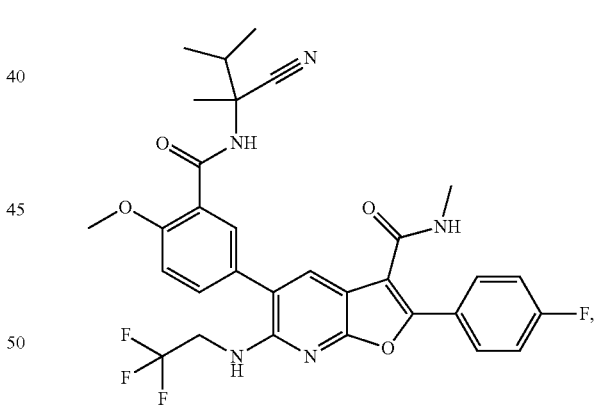
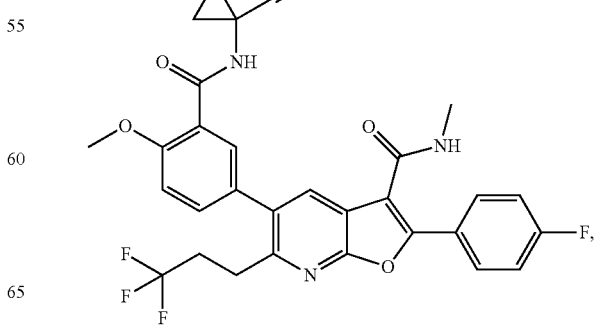

191
-continued
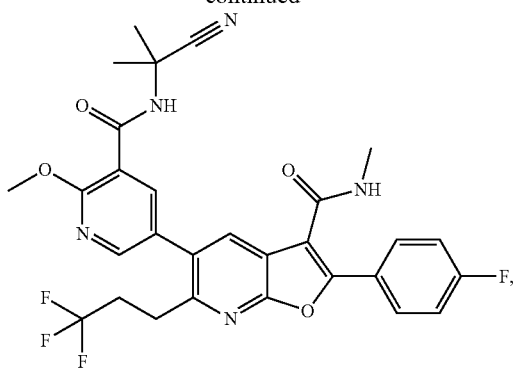
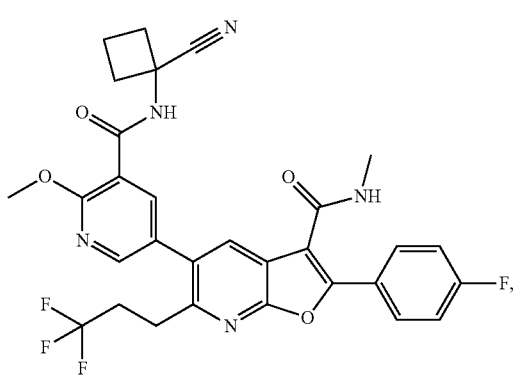
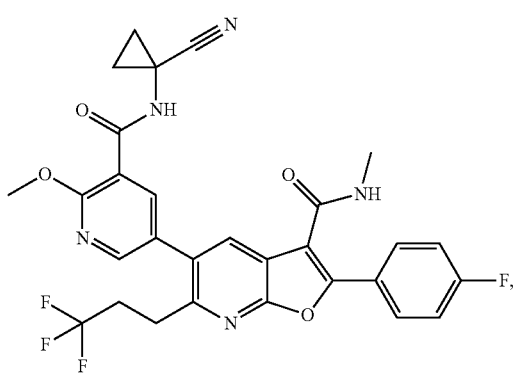
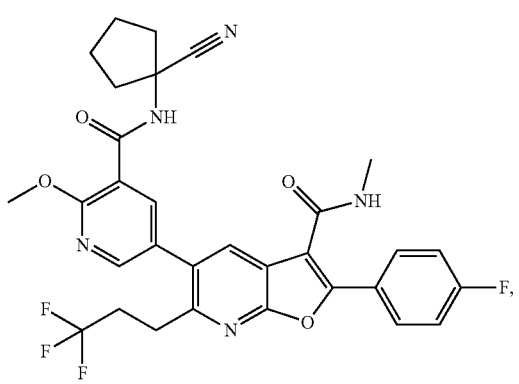
192
-continued
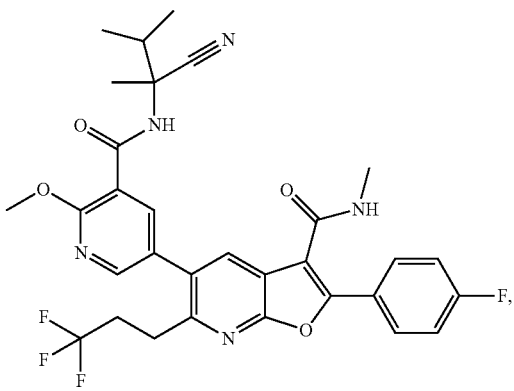
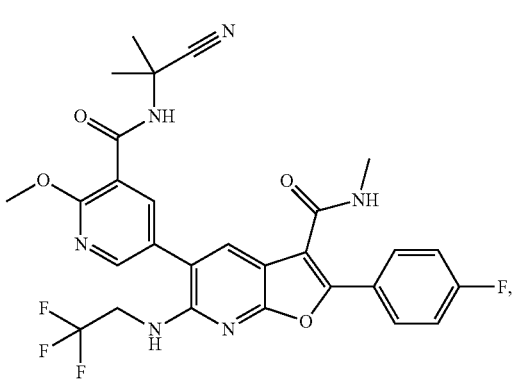
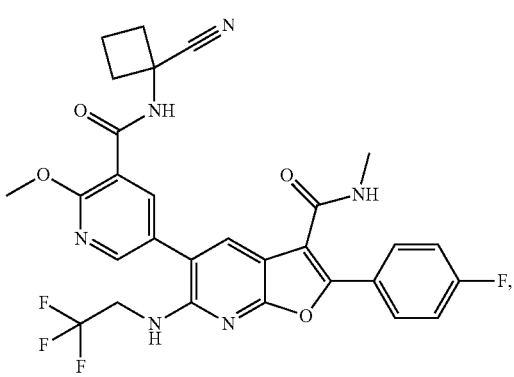
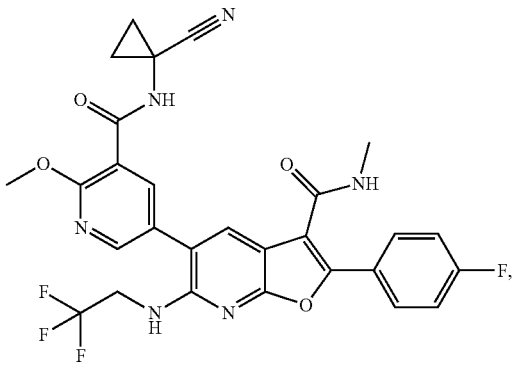

-continued
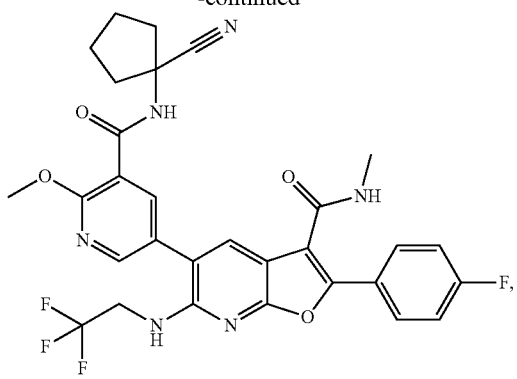
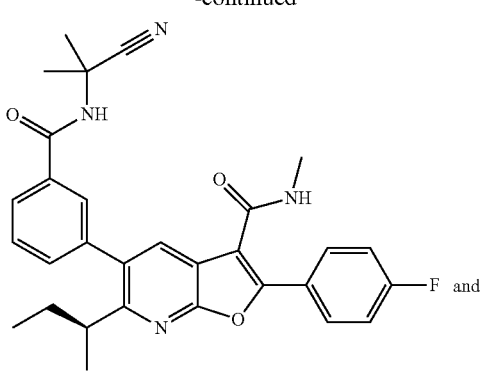
first eluting isomer
second eluting isomer
12. A compound, including pharmaceutically acceptable salts thereof, which is selected from the group of:

195
-continued
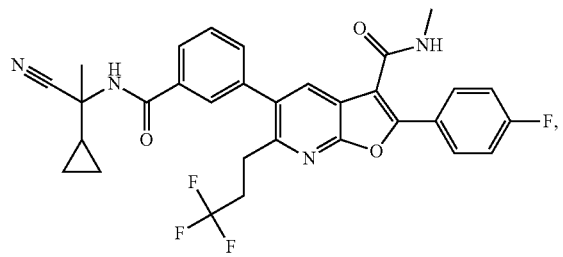
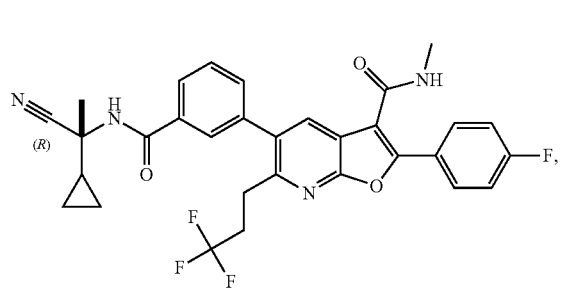
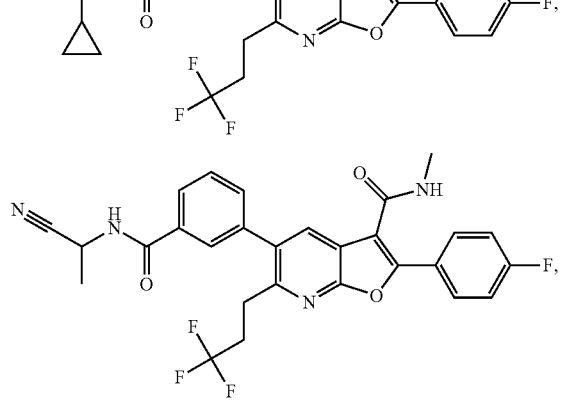
196
-continued
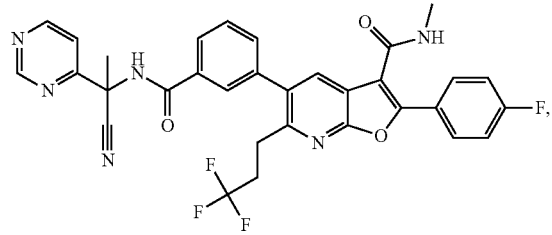
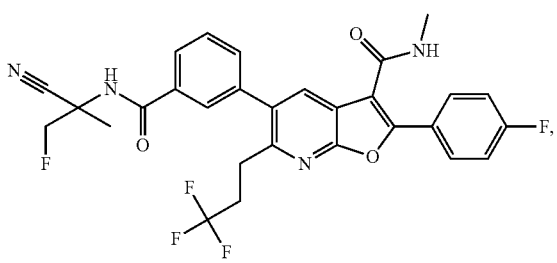
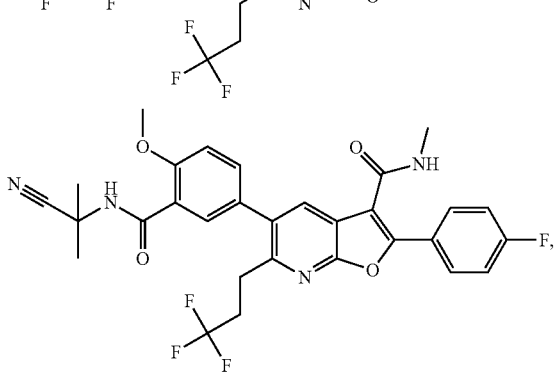
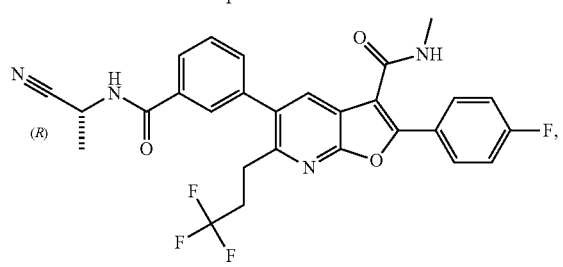
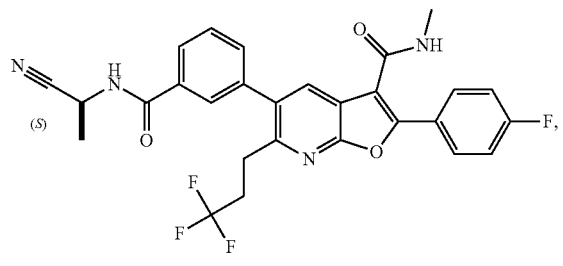
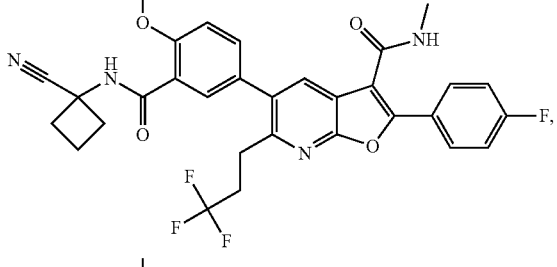
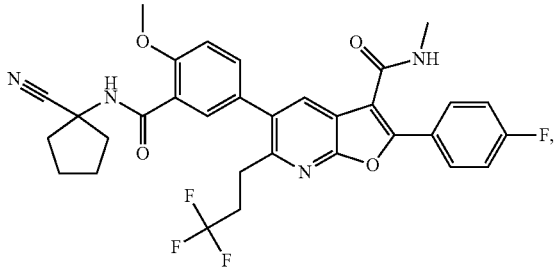

197
-continued
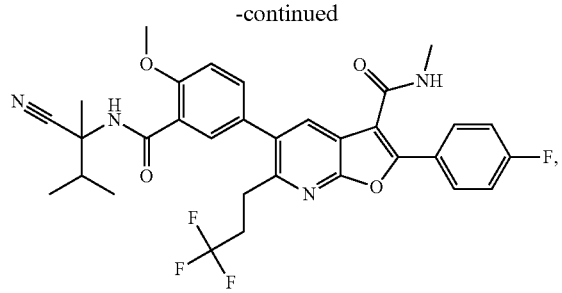
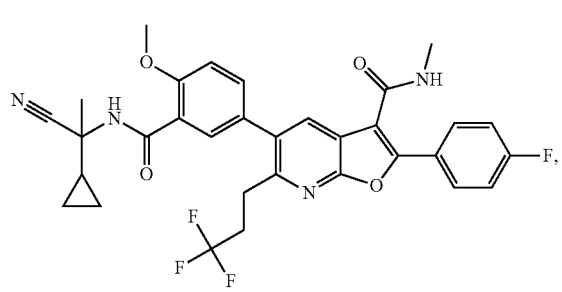
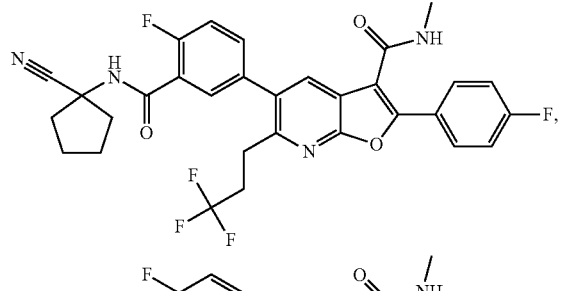
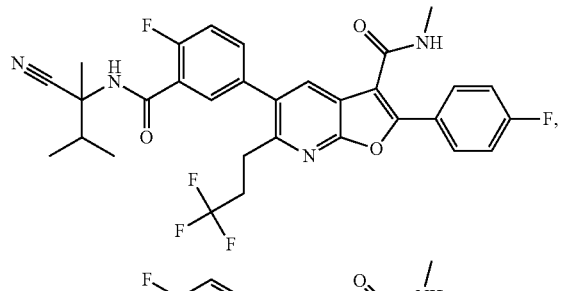
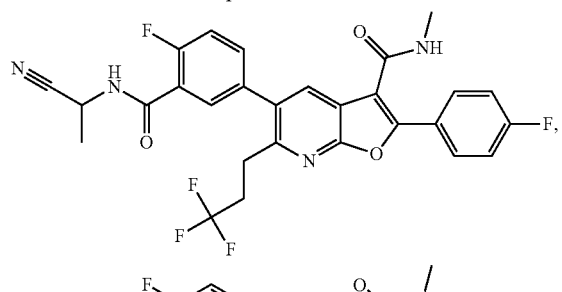
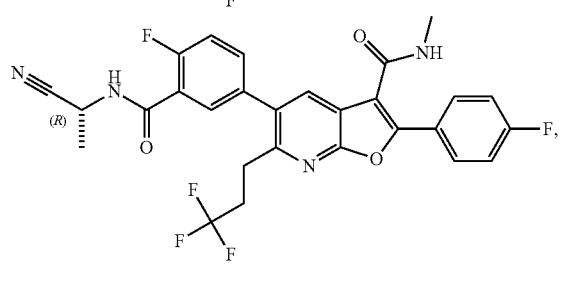
198
-continued
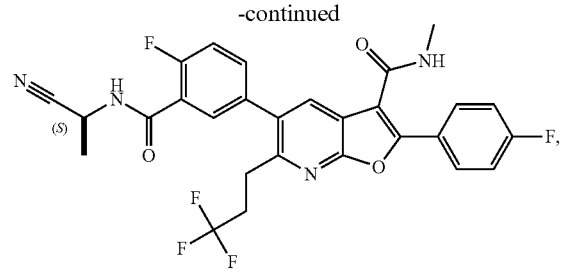
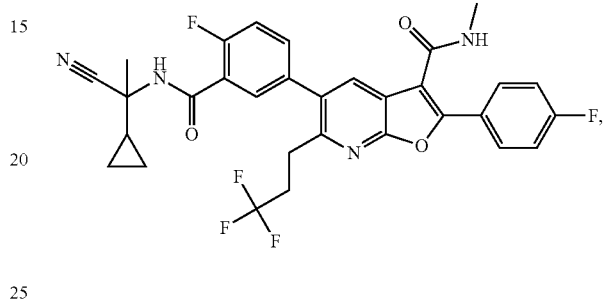
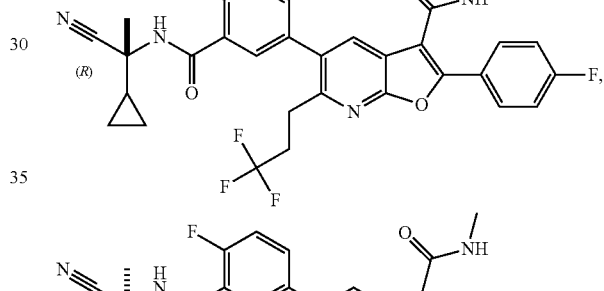
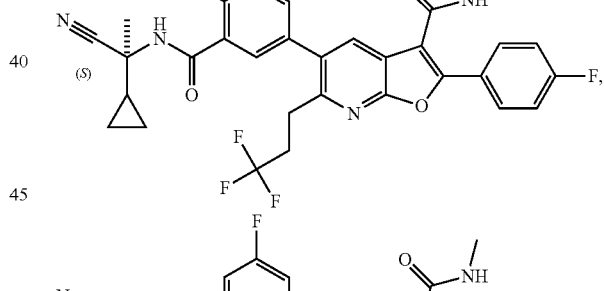
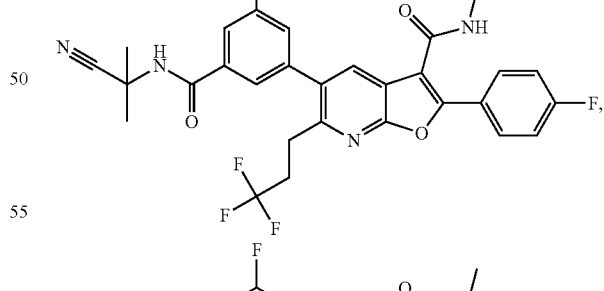
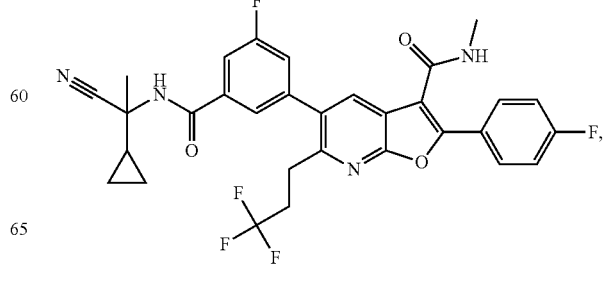

199
-continued

200
-continued

201
-continued
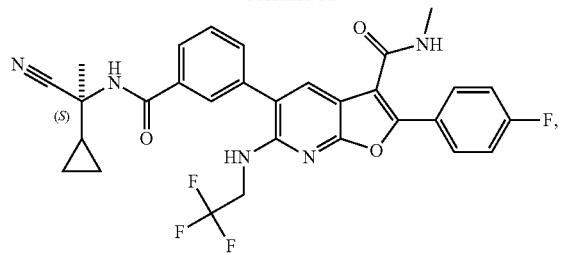
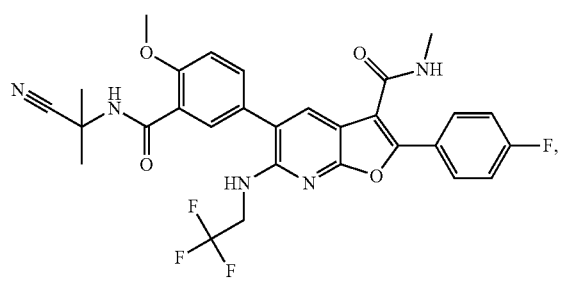
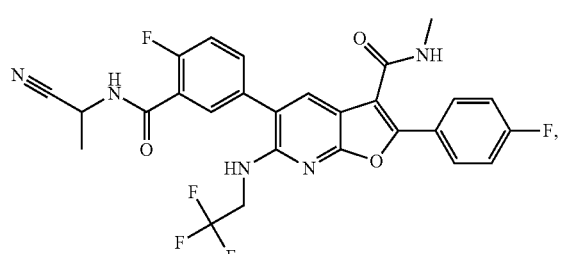
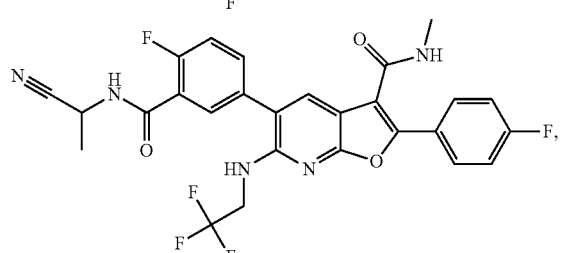
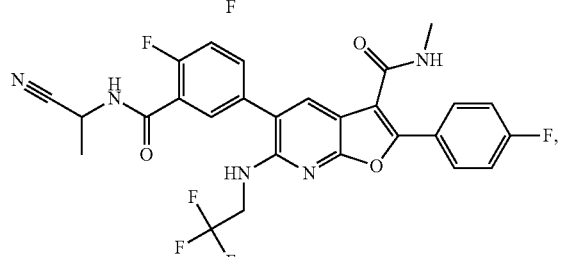
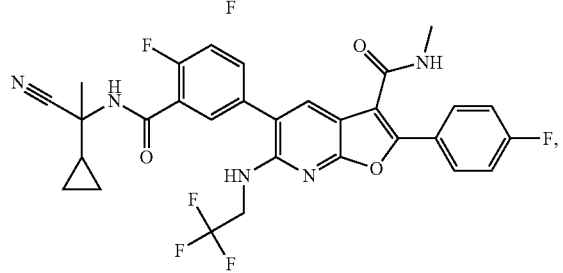
202
-continued
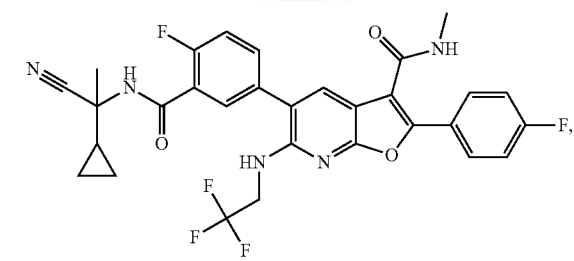
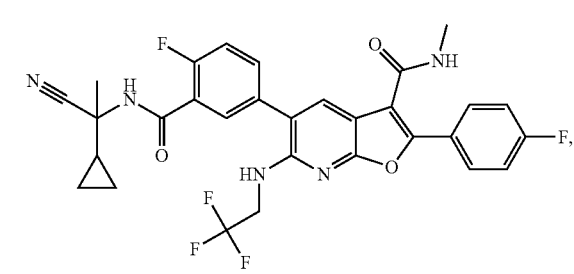
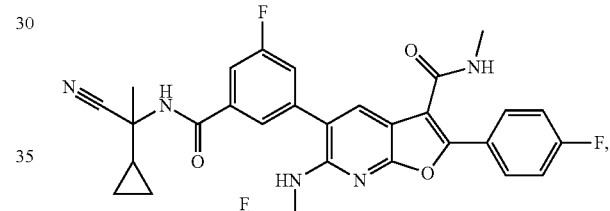
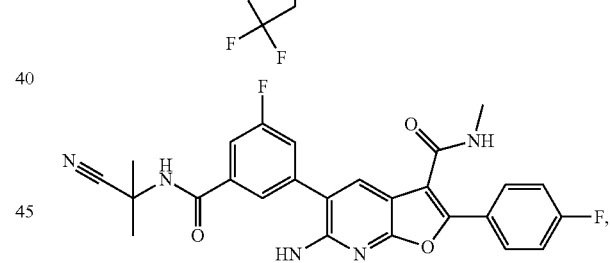
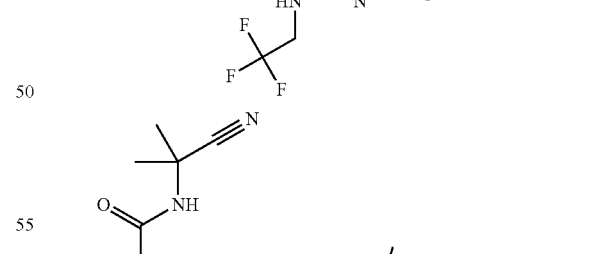
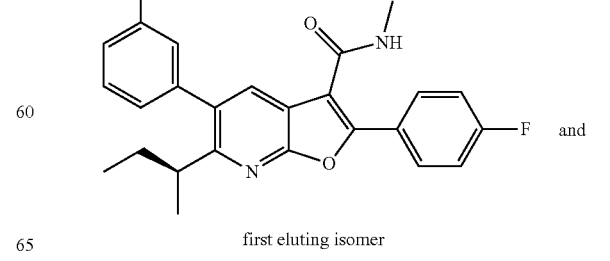
and
first eluting isomer

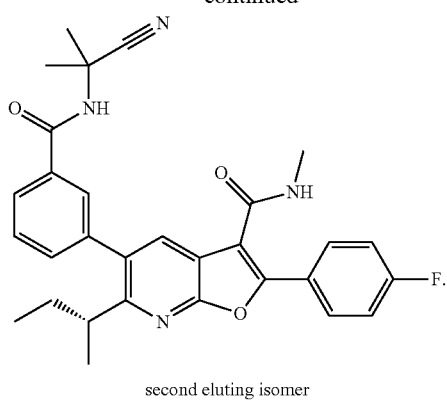
second eluting isomer
13. A compound, including pharmaceutically acceptable salts thereof, which is selected from the group of:
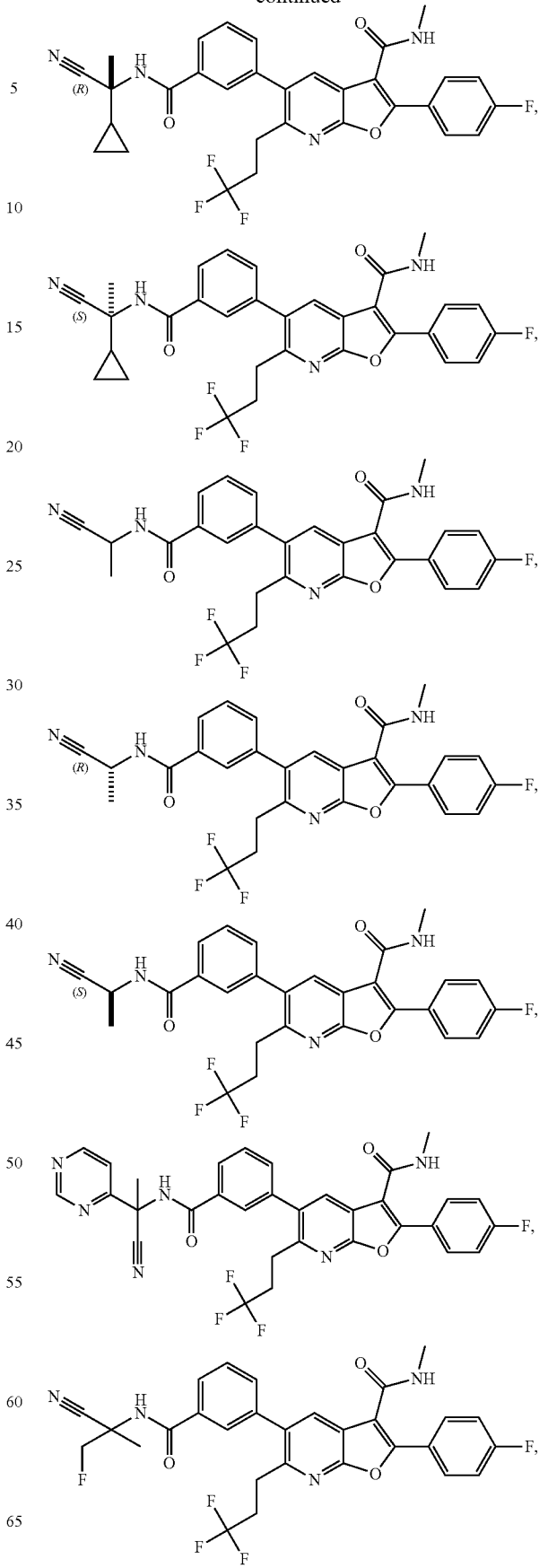

205
-continued
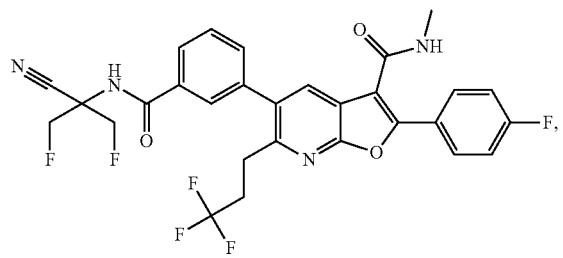
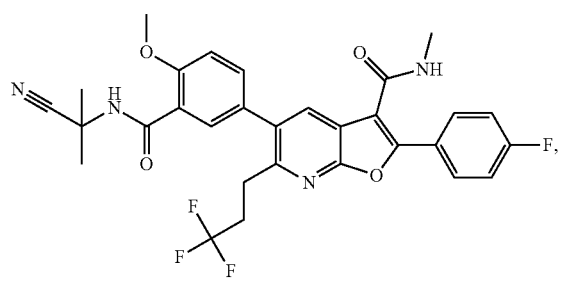
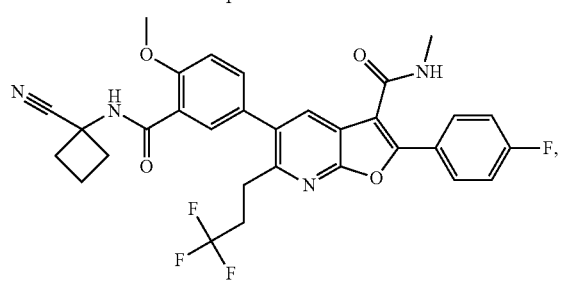
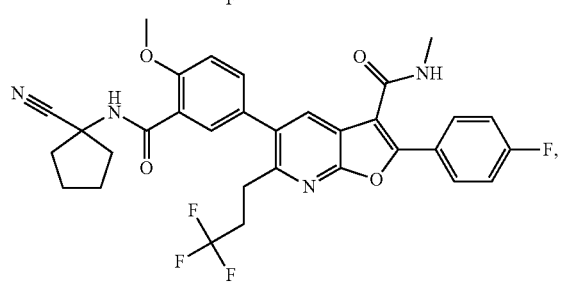
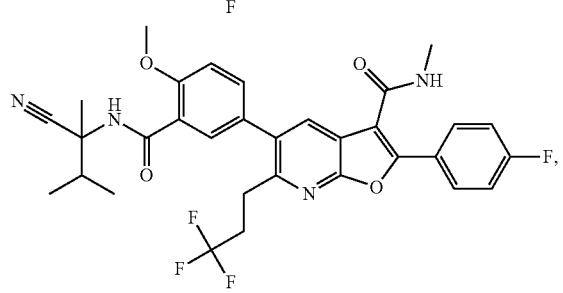
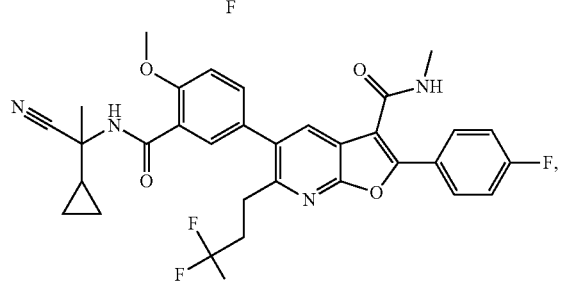
206
-continued
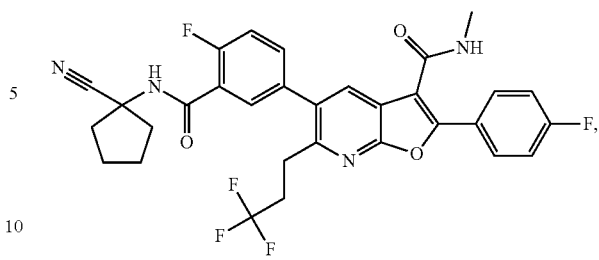
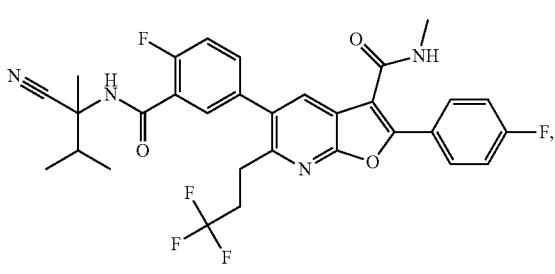
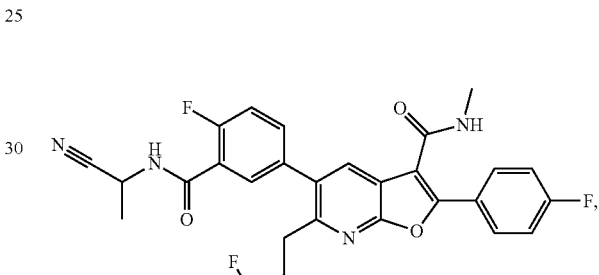
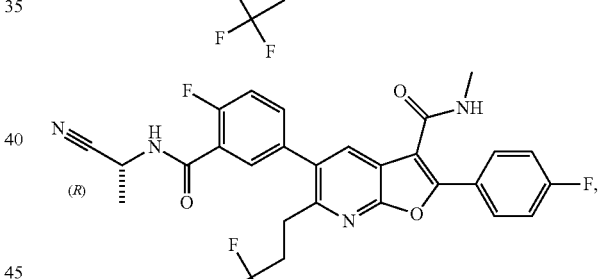
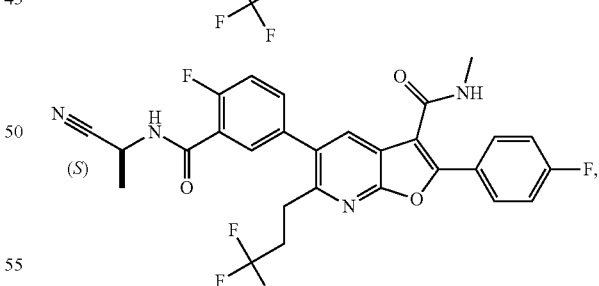
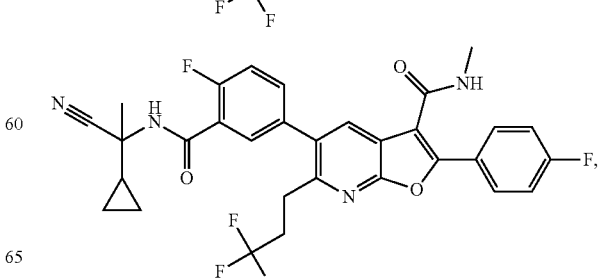

207
-continued
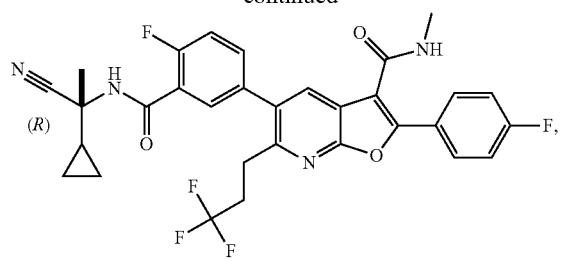
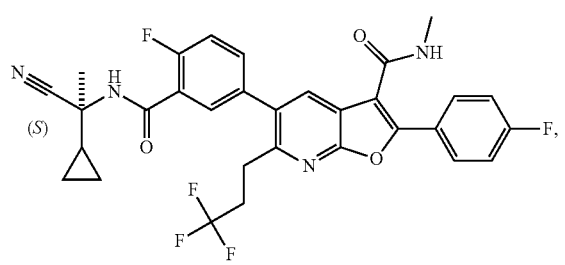
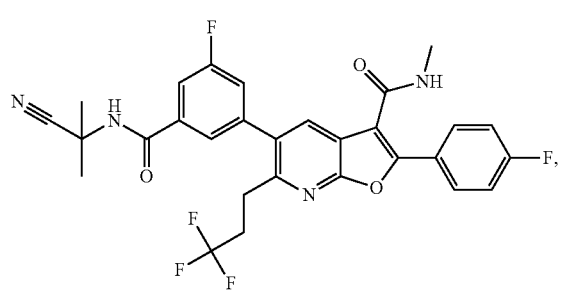
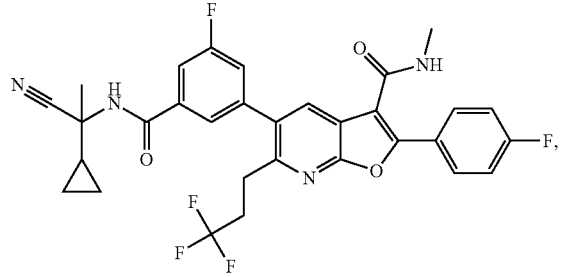
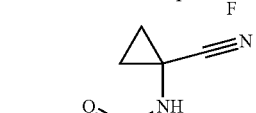
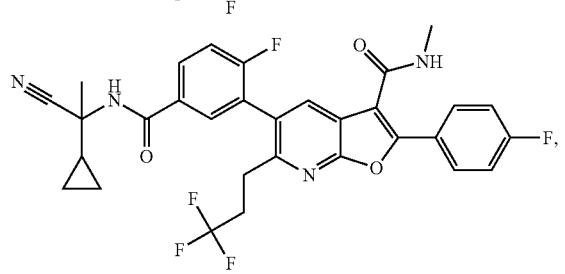
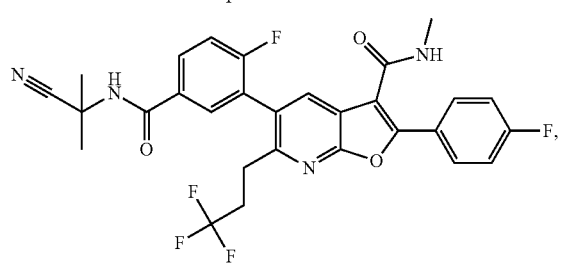
208
-continued
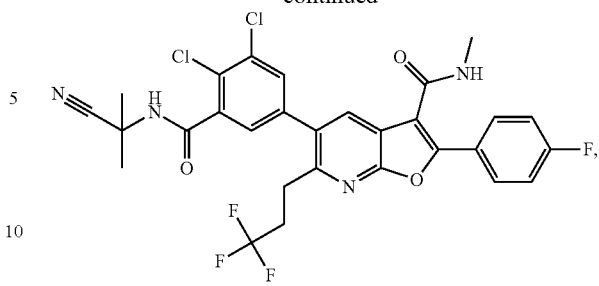
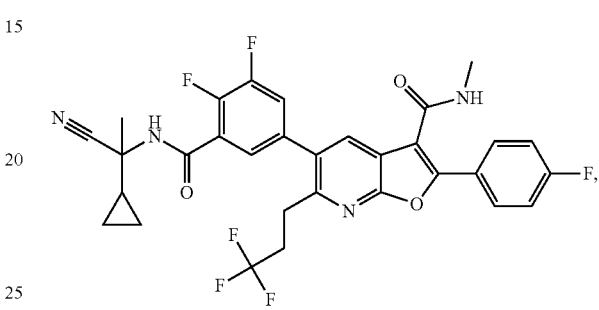
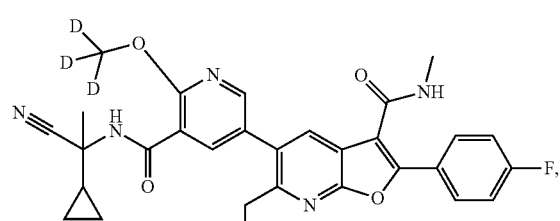
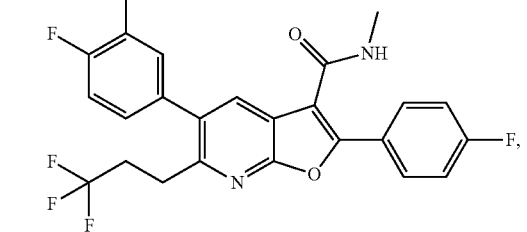
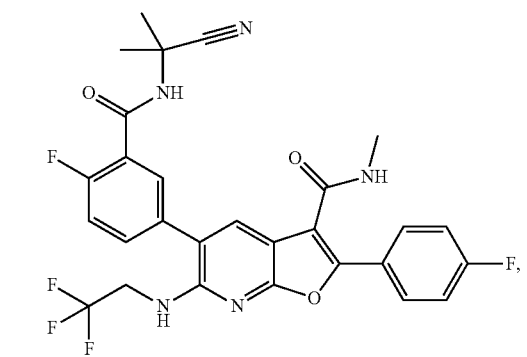

209
-continued
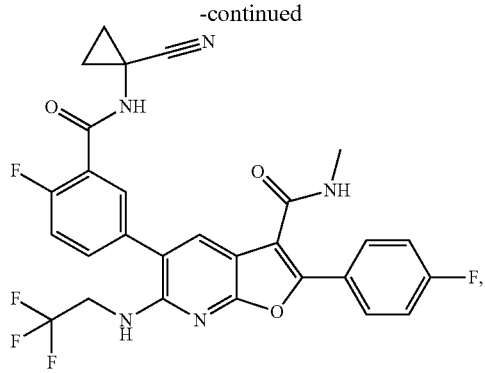
210
-continued
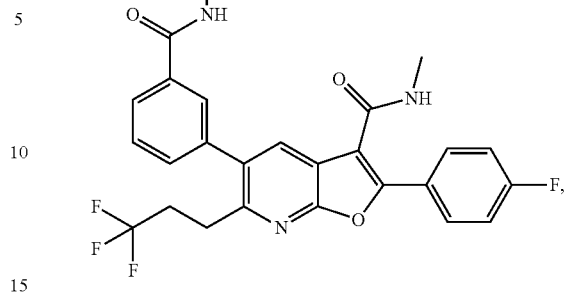
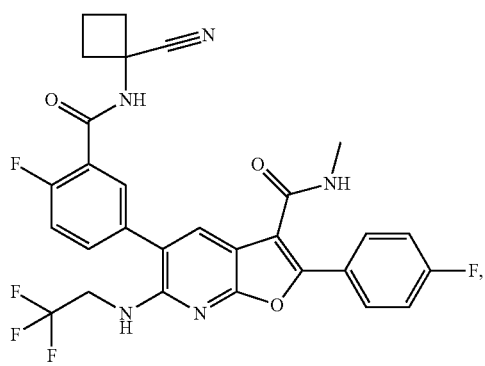
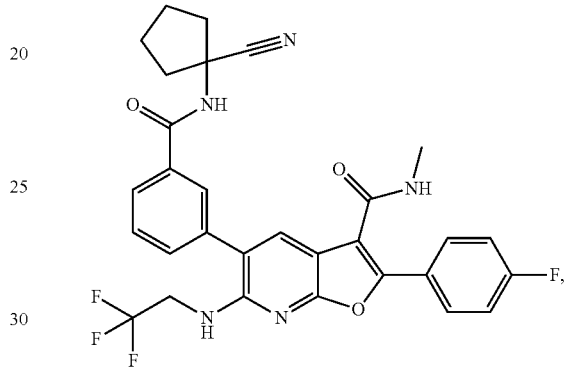
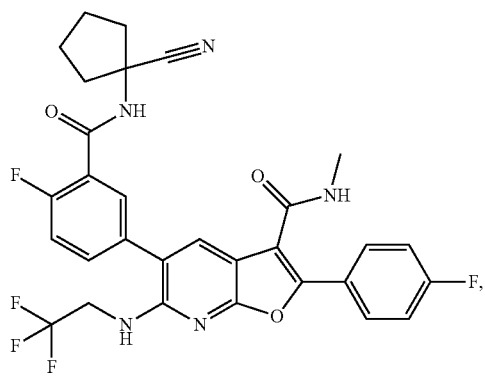
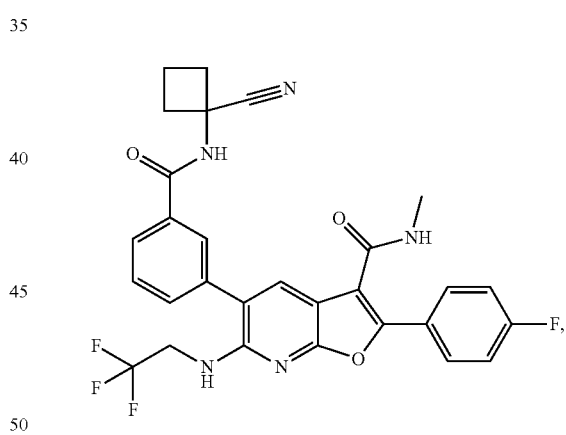
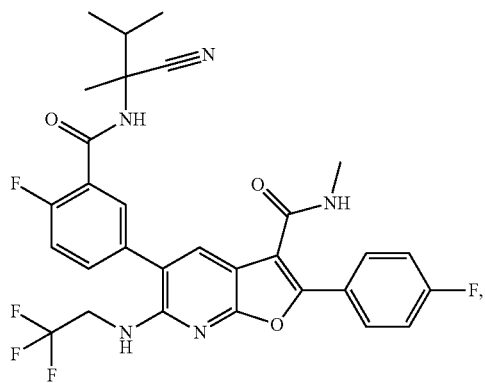
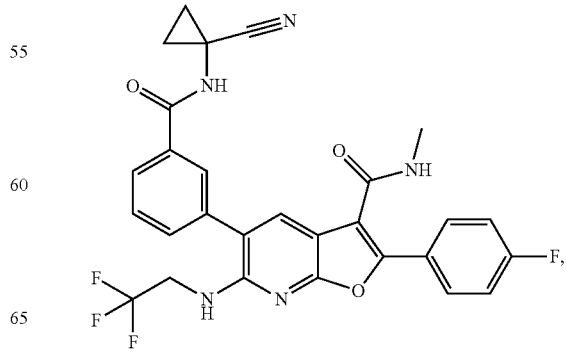

211
-continued
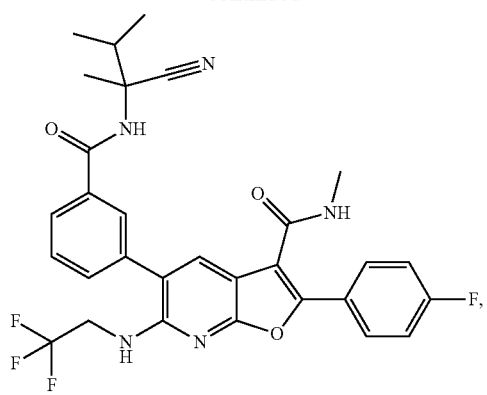
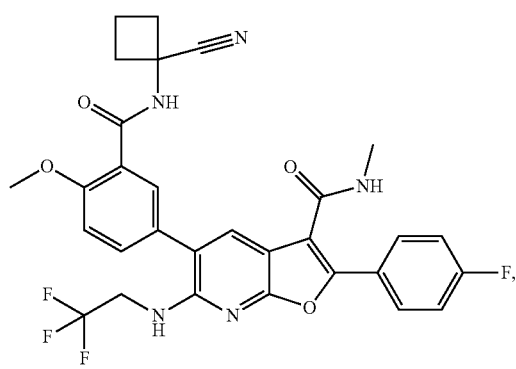
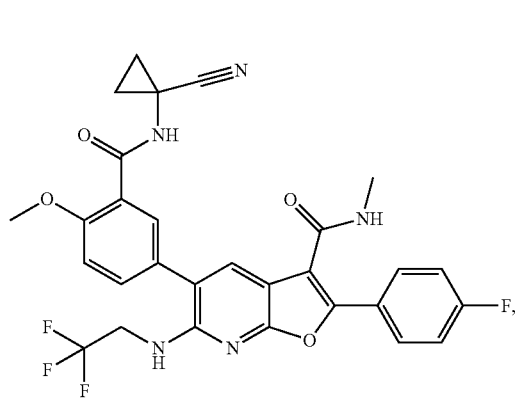
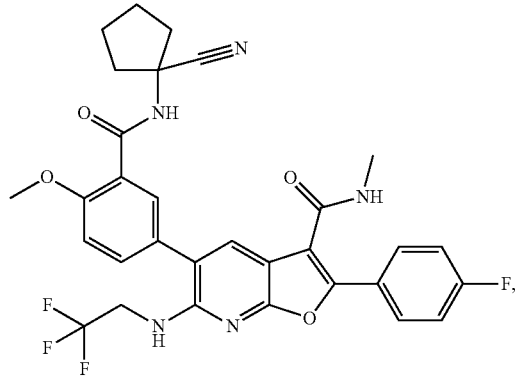
212
-continued
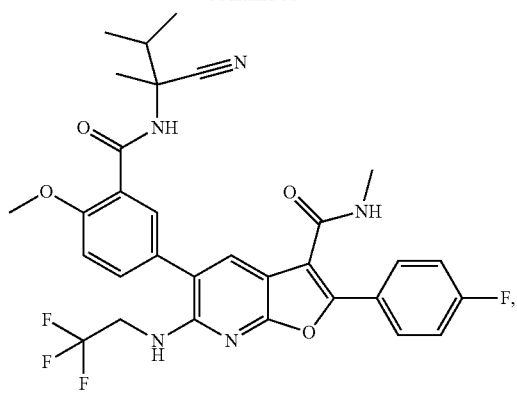
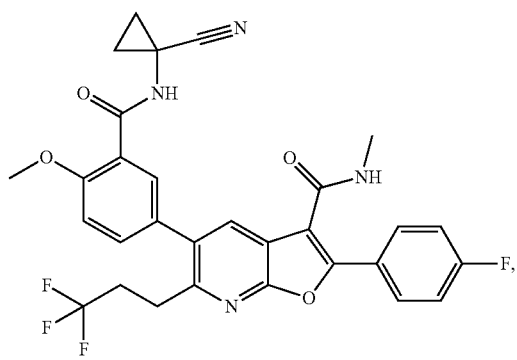
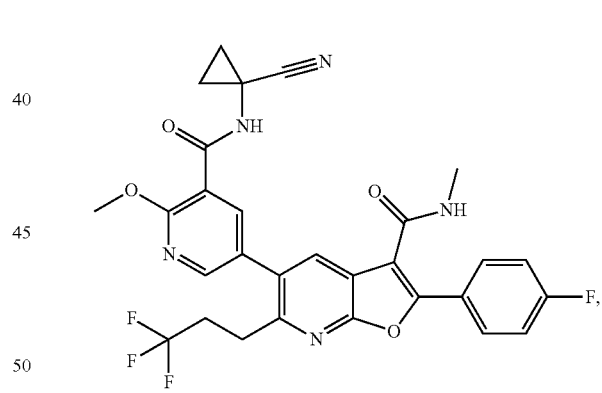
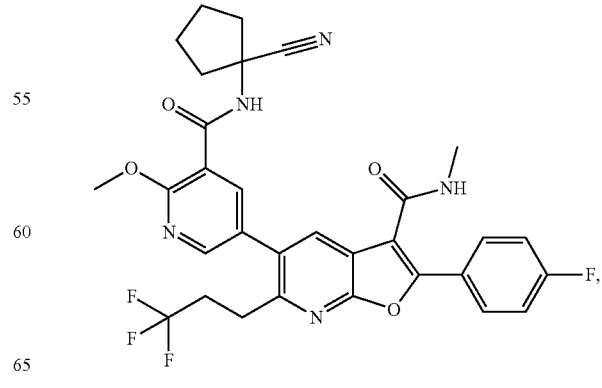

213
-continued
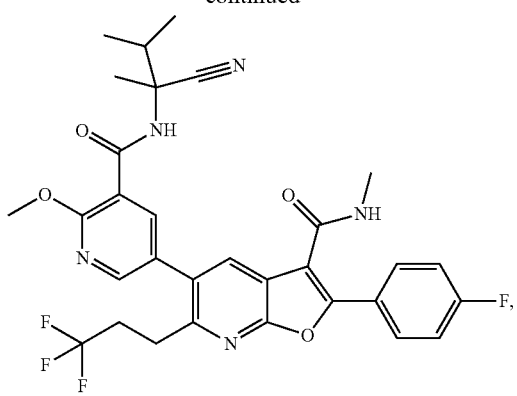
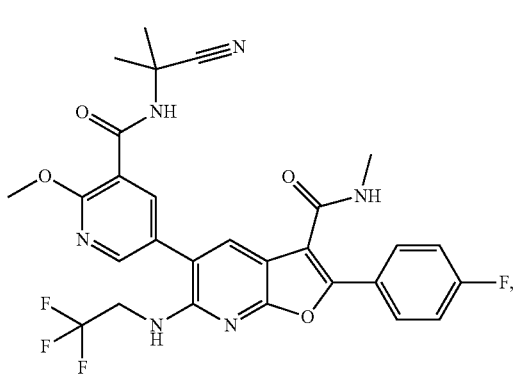
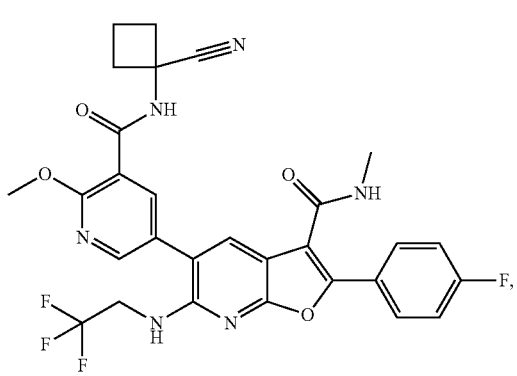
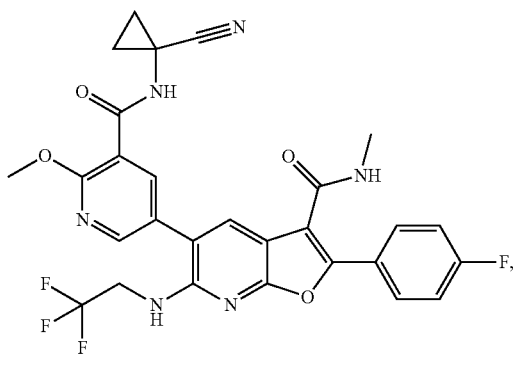
214
-continued
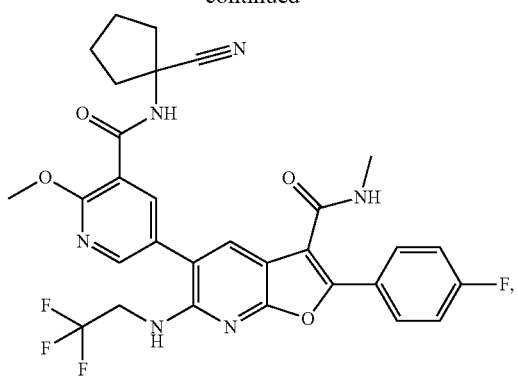
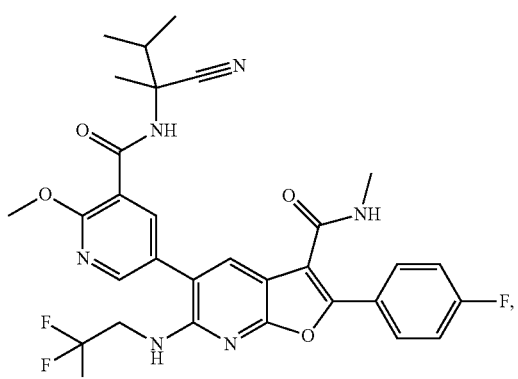
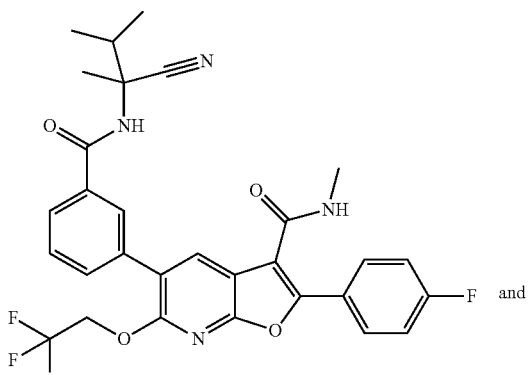 and
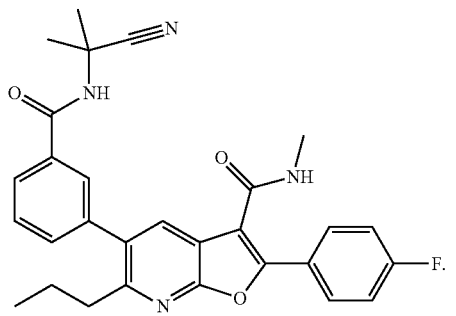
14. A compound, including pharmaceutically acceptable salts thereof, which is selected from the group of:

215
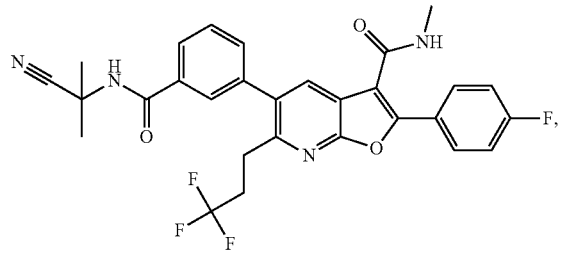
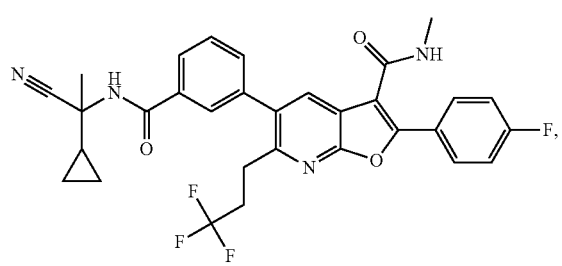
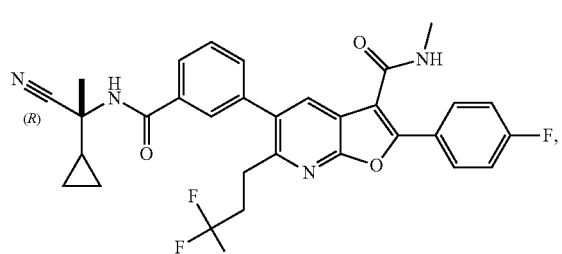
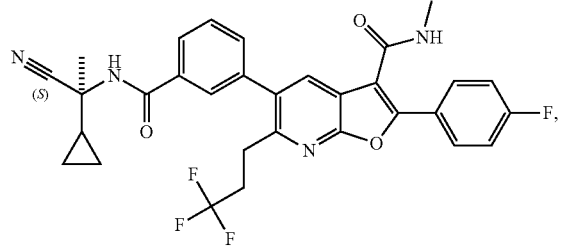
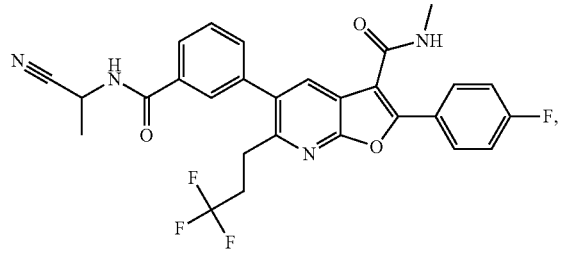
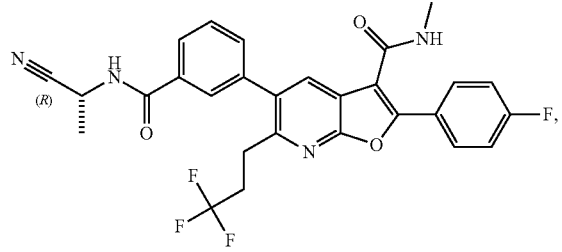
216
-continued
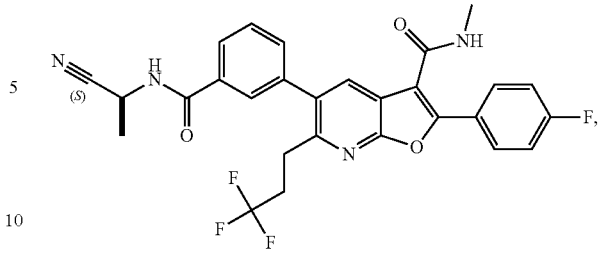
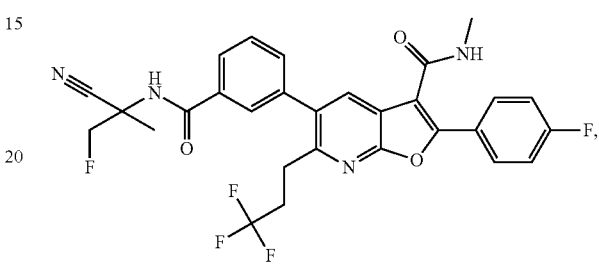
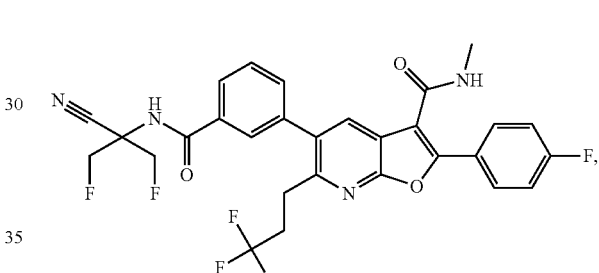
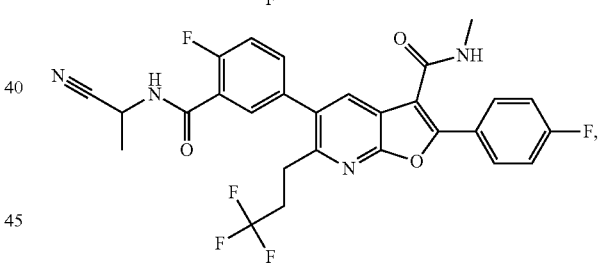
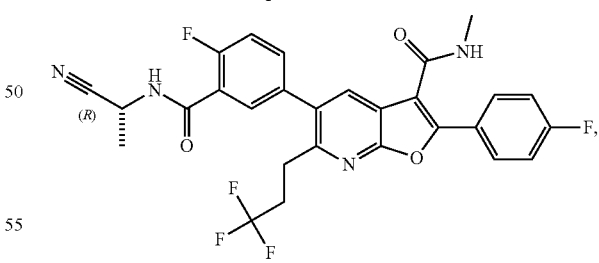
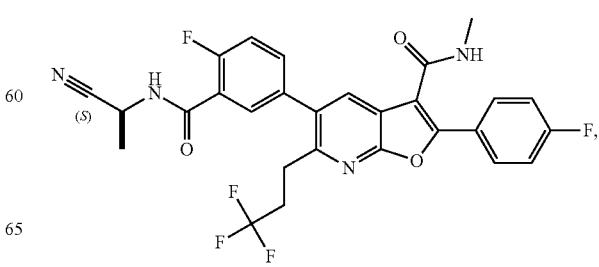

217
-continued
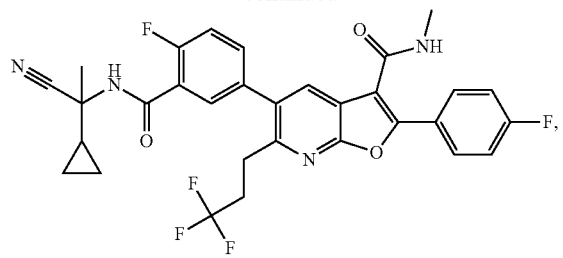
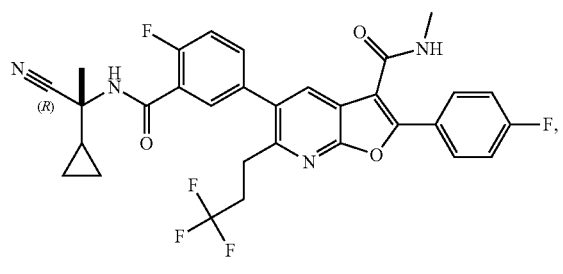
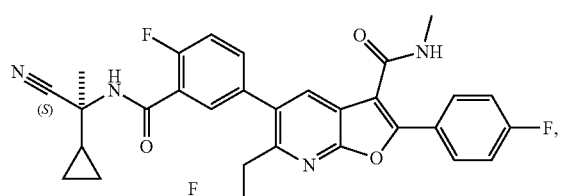
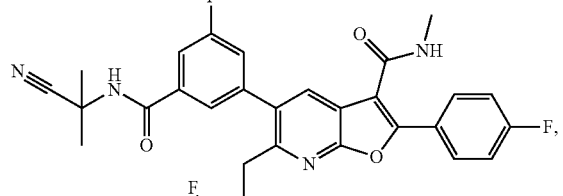
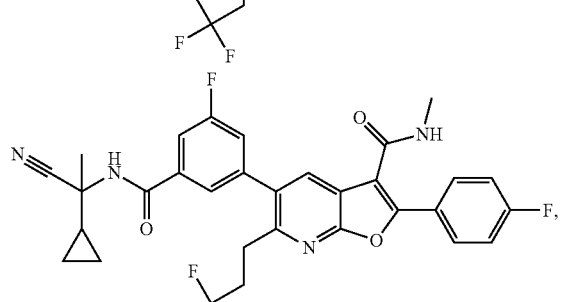
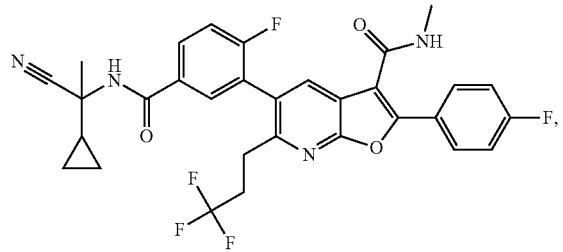
218
-continued
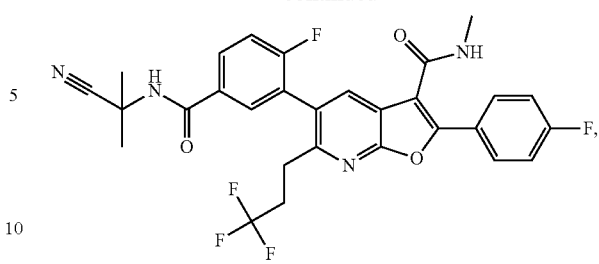
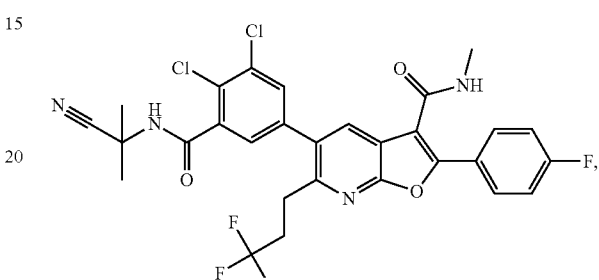
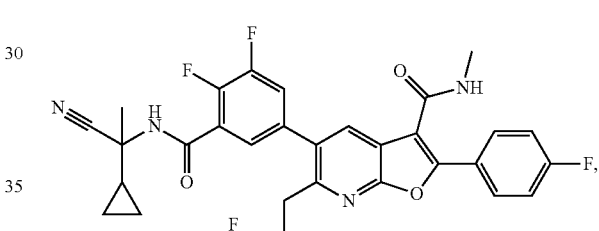
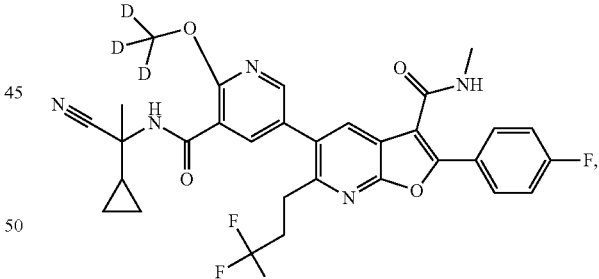
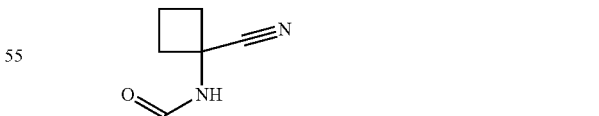
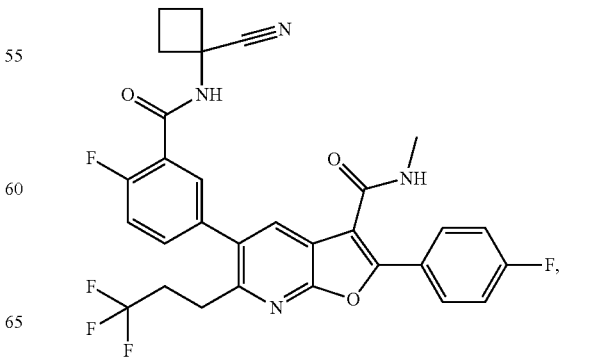

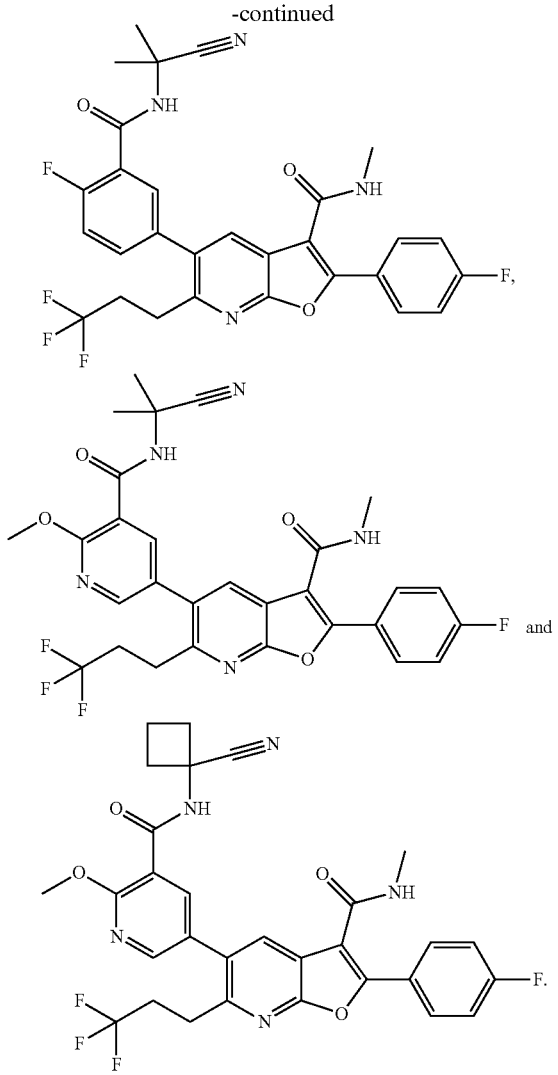

15. A compound, including pharmaceutically acceptable salts thereof, which is selected from the group of:

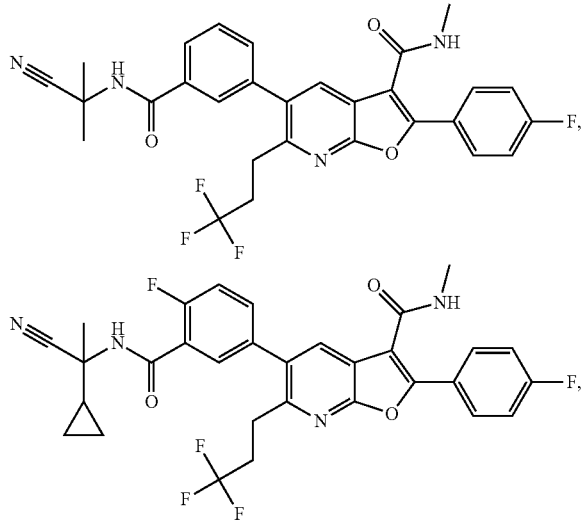

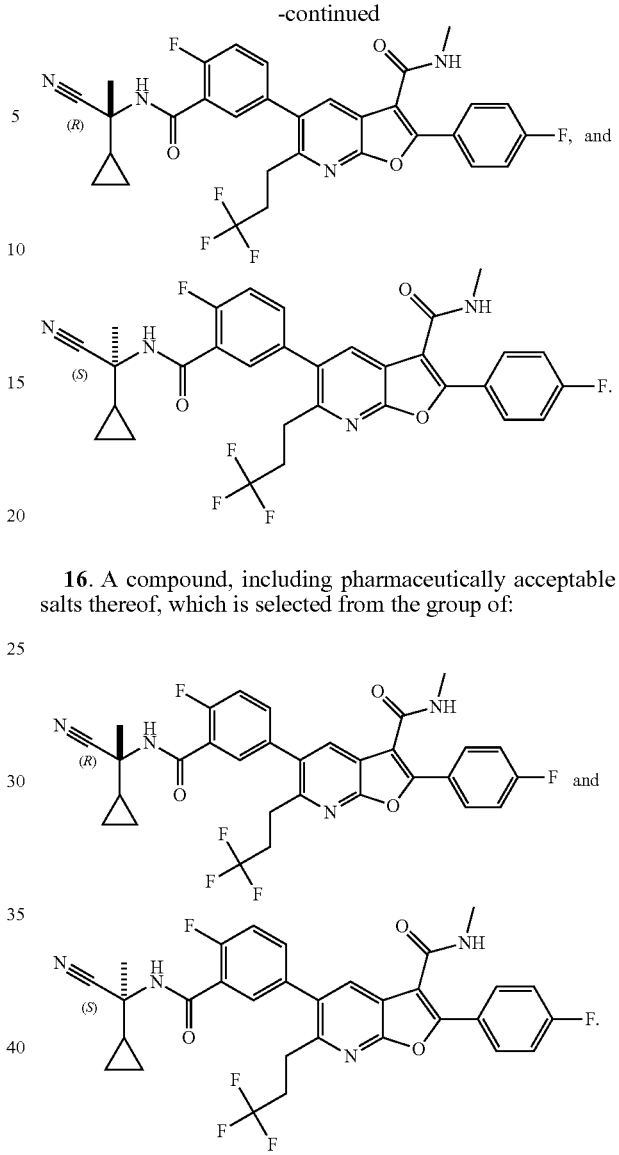

16. A compound, including pharmaceutically acceptable salts thereof, which is selected from the group of:

17. A composition comprising a compound of claim 1 and a pharmaceutically acceptable carrier, excipient and/or diluent.

18. A composition comprising a compound of claim 2 and a pharmaceutically acceptable carrier, excipient and/or diluent.

19. A composition comprising a compound of claim 11 and a pharmaceutically acceptable carrier, excipient and/or diluent.

20. A composition comprising a compound of claim 15 and a pharmaceutically acceptable carrier, excipient and/or diluent.

21. A composition comprising a compound of claim 7 and a pharmaceutically acceptable carrier, excipient and/or diluent.

22. A composition comprising a compound of claim 16 and a pharmaceutically acceptable carrier, excipient and/or diluents.

23. A method of treating hepatitis C infection comprising administering a therapeutically effective amount of a compound of claim 1 to a patient.

* * * * *